(12) United States Patent
Nichols et al.

(10) Patent No.: US 8,778,939 B2
(45) Date of Patent: Jul. 15, 2014

(54) COMPOUNDS

(75) Inventors: Paula Louise Nichols, Brentford (GB); Andrew John Eatherton, Brentford (GB); Paul Bamborough, Brentford (GB); Karamjit Singh Jandu, Brentford (GB); Oliver James Philps, Brentford (GB); Daniele Andreotti, Brentford (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/498,975

(22) PCT Filed: Sep. 27, 2010

(86) PCT No.: PCT/CN2010/001501
§ 371 (c)(1),
(2), (4) Date: Mar. 29, 2012

(87) PCT Pub. No.: WO2011/038572
PCT Pub. Date: Apr. 7, 2011

(65) Prior Publication Data
US 2012/0184553 A1    Jul. 19, 2012

Related U.S. Application Data

(60) Provisional application No. 61/246,550, filed on Sep. 29, 2009.

(30) Foreign Application Priority Data

Sep. 2, 2010 (WO) ................ PCT/CN2010/001334

(51) Int. Cl.
| | |
|---|---|
| A61K 31/5377 | (2006.01) |
| A61K 31/4406 | (2006.01) |
| C07C 235/56 | (2006.01) |
| A61K 31/167 | (2006.01) |
| C07D 237/20 | (2006.01) |
| A61K 31/50 | (2006.01) |
| A61K 31/4402 | (2006.01) |
| C07D 239/42 | (2006.01) |
| A61K 31/505 | (2006.01) |

(52) U.S. Cl.
USPC ........ 514/236.5; 514/352; 514/622; 514/247; 514/256; 544/224; 544/322; 546/309; 564/174

(58) Field of Classification Search
USPC ............... 514/236.5, 352, 622, 247, 256; 544/322; 546/309, 194; 564/174
See application file for complete search history.

(56) References Cited

U.S. PATENT DOCUMENTS

| | | | |
|---|---|---|---|
| 5,310,760 | A | 5/1994 | Washburn et al. |
| 6,001,879 | A | 12/1999 | Seitz et al. |
| 6,495,565 | B2 | 12/2002 | Duan et al. |
| 6,548,549 | B1 | 4/2003 | Seitz et al. |
| 6,960,685 | B2 | 11/2005 | Watkins et al. |
| 7,550,485 | B2 | 6/2009 | Mahaney et al. |
| 7,572,795 | B2 | 8/2009 | Liu et al. |
| 2002/0013341 | A1 | 1/2002 | Duan et al. |
| 2004/0198830 | A1 | 10/2004 | Watkins et al. |
| 2006/0014807 | A1 | 1/2006 | Lin |
| 2006/0235035 | A1 | 10/2006 | Hogberg et al. |
| 2006/0276496 | A1 | 12/2006 | Goldberg et al. |
| 2007/0213300 | A1 | 9/2007 | Liu et al. |
| 2008/0249137 | A1 | 10/2008 | Lin et al. |
| 2009/0156555 | A1 | 6/2009 | Liu et al. |
| 2009/0227790 | A1 | 9/2009 | Lin |
| 2011/0230536 | A1 | 9/2011 | Whitten et al. |

FOREIGN PATENT DOCUMENTS

| | | |
|---|---|---|
| JP | 2007176799 A | 7/2007 |
| WO | WO03047572 A1 | 6/2003 |
| WO | WO03087044 | 10/2003 |
| WO | WO2004099127 A1 | 11/2004 |
| WO | WO2005000309 | 1/2005 |
| WO | WO2006003923 A1 | 1/2006 |
| WO | WO2009/030270 | 3/2009 |
| WO | WO2009066060 A2 | 5/2009 |

Primary Examiner — San-Ming Hui
Assistant Examiner — Kathrien Cruz
(74) Attorney, Agent, or Firm — Fang Qian; James C. Kellerman

(57) ABSTRACT

The present invention relates to novel compounds that inhibit LRRK2 kinase activity, processes for their preparation, to compositions containing them and to their use in the treatment of diseases characterized by LRRK2 kinase activity, particularly Parkinson's disease and Alzheimer's disease.

13 Claims, No Drawings

COMPOUNDS

This application is a 371 of International Application No. PCT/CN2010/001501, filed 27 Sep. 2010, which claims the benefit of U.S. provisional application No. 61/246,550, filed 29 Sep. 2009 and International Application No. PCT/CN2010/001334, filed 2 Sep. 2010, the entire contents of both of which are incorporated herein by reference.

FIELD OF THE INVENTION

The present invention relates to novel compounds that inhibit LRRK2 kinase activity, processes for their preparation, to compositions containing them and to their use in the treatment of diseases characterised by LRRK2 kinase activity, particularly Parkinson's disease and Alzheimer's disease.

BACKGROUND OF THE INVENTION

Parkinson's disease is a neurodegenerative disorder characterised by selective degeneration and cell death of dopaminergic neurones in the substantia nigra region of the brainstem. Parkinson's disease is generally considered to be sporadic and of unknown etiology. Over the past five years however, a handful of mutations in the leucine rich repeat kinase 2 (LRRK2) gene have been linked to Parkinson's disease (WO2006068492 and WO2006045392). The G2019S mutation co-segregates with autosomal dominant parkinsonism and accounts for about 6% of familial Parkinson's disease cases and 3% of sporadic Parkinson's disease cases in Europe (Gilks et al., 2005, Lancet, 365: 415-416; Jaleel et al., 2007, Biochem J, 405: 307-317). LRRK2 is a member of the ROCO protein family and all members of this family share five conserved domains. The G2019S mutation occurs in the highly conserved kinase domain and it has therefore been postulated that the G2019S mutation may have an effect on kinase activity (WO2006068492). It has since been verified that this mutation increases the Vmax of LRRK2 for the non-natural, in vitro, substrates, moesin and the LRRKtide peptide (Jaleel et al., 2007, Biochem J, 405: 307-317). Amino acid substitutions at a second residue R1441 are also associated with Parkinson's Disease (reviewed in Paisan-Ruiz 2009, Hum. Mutat. 30: 1153-1160) and have also been shown to elevate LRRK2 kinase activity via decreasing the rate of GTP hydrolysis by the GTPase domain of LRRK2 (Guo et al., 2007 Exp Cell Res. 313: 3658-3670; West et al., 2007 Hum. Mal Gen. 16: 223-232). Over-expression of the mutant protein LRRK2 R1441G is reported to cause symptoms of Parkinson's disease and hyperphosphorylation of Tau in transgenic mouse models (Li, Y. et al. 2009, Nature Neuroscience 12: 826-828). This LRRK2 driven phenotype is also characterised by diminished dopamine release, suggesting that inhibitors of LRRK2 would be expected to positively regulate dopamine release. These data suggest that novel LRRK2 inhibitors of kinase catalytic activity could be useful for the treatment of Parkinson's disease, including idiopathic Parkinson's disease and familial Parkinson's disease, particularly familial Parkinson's disease in patients expressing LRRK2 kinase bearing the G2019S mutation or the R1441G mutation. In addition, LRRK2 inhibitors may have potential utility in treatment of other conditions characterised by diminished dopamine levels such as withdrawal symptoms/relapse associated with drug addiction (Rothman et al., 2008, Prog. Brain Res, 172: 385), and Tauopathy diseases characterised by hyperphosphorylation of Tau such as Alzheimer's disease, argyrophilic grain disease, Pick's disease, corticobasal degeneration, progressive supranuclear palsy and inherited frontotemporal dementia and parkinsonism linked to chromosome 17 (FTDP-17) (Goedert, M and Jakes, R (2005) Biochemica et Biophysica Acta 1739 240-250).

Two further mutations in LRRK2 have been identified that are clinically associated with the transition from mild cognitive impairment (MCI) to Alzheimer's disease (WO2007149798). These data provide further evidence that inhibitors of LRRK2 kinase activity could be useful for the treatment diseases such as Alzheimer's disease, other dementias and related neurodegenerative disorders.

In an experimental model of Parkinson's disease in marmosets an elevation of LRRK2 mRNA is observed in a manner that correlates with the level of L-Dopa induced dyskinesia (Hurley, M. J et al., 2007 Eur. J. Neurosci. 26: 171-177). This suggests that LRRK2 inhibitors may have utility in amelioration of such dyskinesias.

Evidence is also emerging of roles for LRRK2 in regulating neuronal progenitor differentiation in vitro (Milosevic, J. et al., 2009 Mol. Neurodegen. 4: 25), suggesting that inhibitors of LRRK2 may have utility in production of neuronal progenitor cells in vitro for consequent therapeutic application in cell based-treatment of CNS disorders.

Individuals bearing LRRK2 G2019S mutation have been reported to display increased frequency of non-skin cancers, including renal, breast, lung, prostate cancers as well as acute myelogenous leukemia (AML). Given that G2019S mutation in LRRK2 is reported to increase catalytic activity of the LRRK2 kinase domain, it is anticipated that there may be utility in small molecule inhibitors of LRRK2 for treatment of cancers, especially those of kidney, breast, lung, prostate (e.g. solid tumors) and blood (e.g. AML; Michael J. Fox Foundation for Parkinson's Research, LRRK2 Cohort Workshop, The Desmond Tutu Center, New York City, May 5-6, 2010).

EP1555018 (Institute of Medicinal Molecular Design, Inc.) discloses N-arylsalicylamide derivatives and hydroxyaryl derivatives which are inhibitors of NF-κB activation and AP-1 activation, and their use in the treatment of neurodegenerative diseases such as Alzheimer's disease. Liechti et al., (Eur. J. Med. Chem., 2004, 39: 11-26) discloses a series of salicylanilides and describes their inhibitory activity against tyrosine kinases. McKerrecher et al., (Bioorg. Med. Chem. Lett., 2005, 15(8): 2103-2106) and WO2003000267 (AstraZeneca AB) describe a series of benzamides that are reported to act as activators of glucokinase. WO2001064643 and WO2001064642 (Cor Therapeutics, Inc.) describe a series of benzamides which are stated to act as inhibitors of Factor Xa. JP51029464 (Microbial Chem Res Found) also discloses a series of benzamides. Jensen and Ingvorsen (Acta Chemica Scandinavica, 1952, 6: 161-165) describe the production of amides of 2-benzyloxy-4-nitrobenzoic acid. WO2003084949 describe a series of pyridinoylpiperidine compounds as 5-HT$_{1F}$ agonists, and their use in the treatment of dementia. WO2003078409 (Ono Pharm Co. Ltd) discloses a series of phenylacetic acid derivatives which are stated to be prostaglanding D2 DP receptor antagonists. EP796847 (Shiseido Co Ltd) disclose pyridine derivatives stated to be useful in the treatment of peptic ulcers. WO2006003923 and JP2007176799 (Sankyo Co Ltd) disclose substituted benzene compounds as liver X receptor modulators for use in treating a number of diseases including Alzheimer's disease. WO2007125103 (Novo Nordisk AS) discloses a series of benzamide compounds as glucokinase activators. WO2005000309 (Ionix Pharm Ltd) disclose a series of benzene derivatives as SNS-sodium channel inhibitors. WO2004099170 (Inst. Pharm Discovery LLC) discloses phenyl substituted carboxylic acid compounds as protein tyrosine phosphatase inhibitors. WO9948492 (Japan Tobacco Inc.) discloses amide derivatives as nociceptin antagonists. WO9850030 (Univ Pittsburgh) discloses substituted benzene compounds that are useful in the treatment or prophylaxis of restenosis, intimal hyperplasia associated with restenosis, atherosclerosis and cancer. WO9900121 (Eli Lilly & Co) disclose inhibitors of Factor Xa.

SUMMARY OF THE INVENTION

The present invention provides, in a first aspect, a compound of formula (I) or a pharmaceutically acceptable salt thereof for use as a medicament

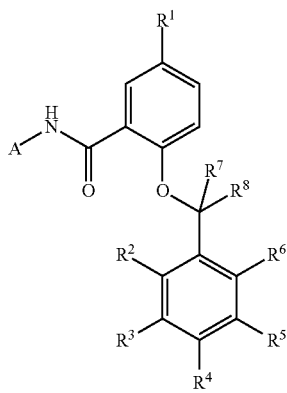

(I)

wherein:
A represents pyridin-2-yl, pyridin-3-yl, pyridazin-3-yl, pyridazin-4-yl, pyrimidin-5-yl, 1,3-oxazol-2-yl, 1H-pyrazol-4-yl or isoxazol-4-yl or a group of formula (a) wherein * represents the point of attachment:

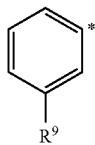

(a)

wherein when A represents pyridin-3-yl, the pyridinyl ring may optionally be substituted at the 2 position by fluoro, methoxy or $CH_2OH$, at the 4 position by methyl or $CH_2OH$, or at the 5 position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl;
$R^1$ represents halo, halo$C_{1-3}$alkyl, hydroxy, CN, —O(CH$_2$)$_2$—O—(CH$_2$)$_2$NH$_2$, —CNOH, (O)$_n$(CH$_2$)$_p$R$^{10}$, —(CO)R$^{10}$, R$^{13}$, —(SO$_2$)R$^{13}$, (C$_{1-3}$alkylene)(CO)$_q$R$^{14}$, (CH═CH)(CO)R$^{14}$, (C$_{1-3}$alkylene)NHCOR$^{14}$, —O-nitrogen containing monoheterocyclic ring with the proviso that the atom directly attached to the oxygen is not nitrogen, or a nitrogen containing heteroaryl ring, wherein the nitrogen containing monoheterocyclic ring is optionally substituted with one, two or three methyl groups and wherein the nitrogen containing heteroaryl ring is optionally substituted by one two or three groups selected from NH$_2$, (C$_{1-3}$alkylene)R$^{13}$, (C$_{1-3}$alkylene)(CO)$_q$R$^{14}$, C$_{1-3}$alkyl and halo;

n and q independently represent 0 or 1;
p represents 1, 2 or 3;
$R^2$, $R^3$, $R^4$, $R^5$ and $R^6$ independently represent hydrogen, halo, CN, C$_{1-3}$alkyl or C$_{1-3}$alkoxy;
$R^7$ and $R^8$ independently represent hydrogen or C$_{1-2}$ alkyl;
$R^9$ represents hydrogen, halo, C$_{1-2}$alkyl, —CH$_2$CO$_2$H or —CONHCH$_3$;
$R^{10}$ represents hydrogen, C$_{1-3}$alkyl, —NR$^{11}$R$^{12}$, or a nitrogen containing monoheterocyclic ring which ring is optionally substituted with one, two or three methyl groups;
$R^{11}$ and $R^{12}$ are independently selected from hydrogen and C$_{1-3}$ alkyl, wherein said C$_{1-3}$ alkyl group is optionally substituted with one, two or three halo, hydroxy, cyano or C$_{1-2}$alkoxy groups;
$R^{13}$ represents —NR$^{11}$R$^{12}$, or a nitrogen containing monoheterocyclic ring which ring is optionally substituted with one, two or three methyl groups and wherein the nitrogen containing monoheterocyclic ring is attached via a nitrogen atom; and
$R^{14}$ represents hydroxy or C$_{1-3}$alkoxy;
with the proviso that the compound of formula (I) is not:
2-[(phenylmethyl)oxy]-N-3-pyridinyl-5-(1-pyrrolidinylsulfonyl)benzamide; or
2-{[(3,4-difluorophenyl)methyl]oxy}-5-(1-hydroxyethyl)-N-4-pyridazinylbenzamide.
The term 'halo' as used herein refers to a fluoro, chloro, bromo or iodo group.
The term 'C$_{x-y}$ alkyl' as used herein as refers to a linear or branched saturated hydrocarbon group containing from x to y carbon atoms. Examples of C$_{1-3}$ alkyl groups include methyl, ethyl, n-propyl and isopropyl.
The term 'haloC$_{x-y}$ alkyl' as used herein refers to a C$_{x-y}$ alkyl group as defined herein wherein at least one hydrogen atom is replaced with halogen. Examples of such groups include fluoroethyl, trifluoromethyl or trifluoroethyl and the like.
The term C$_{x-y}$alkylene as used herein refers to a divalent linear or branched saturated hydrocarbon group containing from x to y carbon atoms. Examples of C$_{1-3}$ alkylene groups include, CH$_2$, CH$_2$CH$_2$, CH$_2$CH$_2$CH$_2$, CH(CH$_3$)CH$_2$, CH(CH$_3$)$_2$ and CH$_2$CH(CH$_3$).
The term 'C$_{x-y}$ alkoxy' as used herein refers to a group of formula —O—C$_{x-y}$ alkyl, wherein C$_{x-y}$ alkyl is defined as above. Examples of C$_{1-3}$ alkoxy groups include methoxy, ethoxy, n-propoxy, and isopropoxy.
The term 'nitrogen containing monoheterocyclic ring' as used herein refers to a 4-7 membered monocyclic ring which may be saturated or partially unsaturated, and which contains at least one nitrogen atom. Optionally, the ring may contain 1 to 3 other heteroatoms selected from oxygen, nitrogen or sulphur. Examples of nitrogen containing heterocyclyl groups include pyrrolidinyl, azetidinyl, pyrazolidinyl, oxazolidinyl, imidazolidinyl, piperidinyl, piperazinyl, morpholinyl, thiomorpholinyl, thiazolidinyl, hydantoinyl, valerolactamyl, tetrahydropyridinyl, tetrahydropyrimidinyl, diazepanyl, azepanyl and the like.
The term 'nitrogen containing heteroaryl ring' as used herein refers to a 5-6 membered monocyclic aromatic ring, which monocyclic aromatic ring contains at least one nitrogen atom and 1 to 3 further heteroatoms selected from oxygen, nitrogen and sulphur. Examples of such monocyclic aromatic rings include, furazanyl, pyrrolyl, triazolyl, tetrazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl, pyridinyl, triazinyl, tetrazinyl and the like.
In further aspects of the invention, the invention provides a compound of formula (I) or a salt thereof, and a pharmaceutical composition comprising the compound of formula (I) or a pharmaceutically acceptable salt thereof and a pharmaceutically acceptable carrier.

DETAILED DESCRIPTION OF THE INVENTION

As discussed above, in a first aspect, the invention provides a compound of formula (I) or a pharmaceutically acceptable salt thereof for use as a medicament

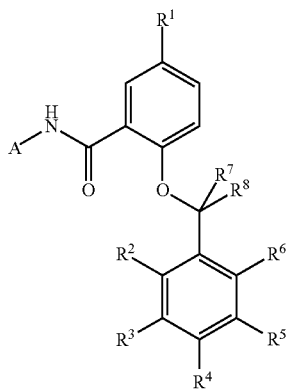

(I)

wherein:
A represents pyridin-2-yl, pyridin-3-yl, pyridazin-3-yl, pyridazin-4-yl, pyrimidin-5-yl, 1,3-oxazol-2-yl, 1H-1-pyrazol-4-yl or isoxazol-4-yl or a group of formula (a) wherein * represents the point of attachment:

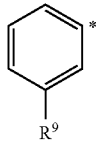

(a)

wherein when A represents pyridin-3-yl, the pyridinyl ring may optionally be substituted at the 2 position by fluoro, methoxy or CH$_2$OH, at the 4 position by methyl or CH$_2$OH, or at the 5 position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl;
$R^1$ represents halo, haloC$_{1-3}$alkyl, hydroxy, CN, —O(CH$_2$)$_2$—O—(CH$_2$)$_2$NH$_2$, —CNOH, (O)$_n$(CH$_2$)$_p$R$^{10}$, —(CO)R$^{10}$, R$^{13}$, —(SO$_2$)R$^{13}$, (C$_{1-3}$alkylene)(CO)$_q$R$^{14}$, (CH=CH)(CO)R$^{14}$, (C$_{1-3}$alkylene)NHCOR$^{14}$, —O-nitrogen containing monoheterocyclic ring with the proviso that the atom directly attached to the oxygen is not nitrogen, or a nitrogen containing heteroaryl ring, wherein the nitrogen containing monoheterocyclic ring is optionally substituted with one, two or three methyl groups and wherein the nitrogen containing heteroaryl ring is optionally substituted by one two or three groups selected from NH$_2$, C$_{1-3}$alkyleneR$^{13}$, (C$_{1-3}$alkylene)(CO)$_q$R$^{14}$, C$_{1-3}$alkyl and halo; n and q independently represent 0 or 1;
p represents 1, 2 or 3;
$R^2$, $R^3$, $R^4$, $R^5$ and $R^6$ independently represent hydrogen, halo, CN, C$_{1-3}$alkyl or C$_{1-3}$alkoxy;
$R^7$ and $R^8$ independently represent hydrogen or C$_{1-2}$ alkyl;
$R^9$ represents hydrogen, halo, C$_{1-2}$alkyl, C$_{1-2}$alkoxy, —CH$_2$CO$_2$H or —CONHCH$_3$;
$R^{10}$ represents hydrogen, C$_{1-3}$alkyl, —NR$^{11}$R$^{12}$, or a nitrogen containing monoheterocyclic ring which ring is optionally substituted with one, two or three methyl groups;
$R^{11}$ and $R^{12}$ are independently selected from hydrogen and C$_{1-3}$ alkyl, wherein said C$_{1-3}$ alkyl group is optionally substituted with one, two or three halo, hydroxy, cyano or C$_{1-2}$alkoxy groups;
$R^{13}$ represents —NR$^{11}$R$^{12}$, or a nitrogen containing monoheterocyclic ring which ring is optionally substituted with one, two or three methyl groups and wherein the nitrogen containing monoheterocyclic ring is attached via a nitrogen atom; and
$R^{14}$ represents hydroxy or C$_{1-3}$alkoxy;
with the proviso that the compound of formula (I) is not:
2-[(phenylmethyl)oxy]-N-3-pyridinyl-5-(1-pyrrolidinylsulfonyl)benzamide; or
2-{[(3,4-difluorophenyl)methyl]oxy}-5-(1-hydroxyethyl)-N-4-pyridazinylbenzamide.
In one embodiment, the compound of formula (I) is not 5-bromo-2-[(phenylmethyl)oxy]-N-2-pyridinylbenzamide.
In another embodiment, the compound of formula (I) is not 5-bromo-2-[(phenylmethyl)oxy]-N-2-pyridinylbenzamide, N-[2-(hydroxymethyl)-3-pyridinyl]-2-[(phenylmethyl)oxy]-5-(4-pyridinyl)benzamide, N-[4-(hydroxymethyl)-3-pyridinyl]-2-[(phenylmethyl)oxy]-5-(4-pyridinyl)benzamide, N-(5-methyl-4-isoxazolyl)-2-[(phenylmethyl)oxy]-5-(4-pyridinyl)benzamide, 5-(aminomethyl)-2-{[(3,4-difluorophenyl)methyl]oxy}-N-3-pyridinylbenzamide or methyl ({4-{[(3,4-difluorophenyl)methyl]oxy}-3-[(3-pyridinylamino)carbonyl]phenyl}methyl)carbamate.
In a further aspect, the invention provides a compound of formula (I) or a pharmaceutically acceptable salt thereof for use as a medicament wherein:
A represents pyridin-2-yl, pyridin-3-yl, pyridazin-3-yl, pyridazin-4-yl, pyrimidin-5-yl or a croup of formula (a) wherein * represents the point of attachment:

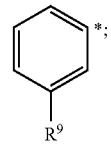

(a)

$R^1$ represents halo, hydroxy, CN, —R$^{10}$ or —OR$^{10}$;
$R^2$, $R^3$, $R^4$, $R^5$ and $R^6$ independently represent hydrogen, halo, CN, C$_{1-3}$alkyl or C$_{1-3}$alkoxy;
$R^7$ and $R^8$ independently represent hydrogen or C$_{1-2}$ alkyl;
$R^9$ represents hydrogen, halo, C$_{1-2}$alkyl, C$_{1-2}$alkoxy, —CH$_2$CO$_2$H or —CONHCH$_3$;
$R^{10}$ represents C$_{1-3}$alkyl optionally substituted with —NR$^{11}$R$^{12}$, or a nitrogen containing monoheterocyclic ring which is optionally substituted with one, two or three methyl groups; and
$R^{11}$ and $R^{12}$ are independently selected from hydrogen and C$_{1-3}$ alkyl, wherein said C$_{1-3}$ alkyl group is optionally substituted with one, two or three halo, hydroxy, cyano or C$_{1-2}$alkoxy groups.
In one embodiment, the compound of formula (I) is not 5-bromo-2-[(phenylmethyl)oxy]-N-2-pyridinylbenzamide.
In another embodiment, the compound of formula (I) is not 5-bromo-2-[(phenylmethyl)oxy]-N-2-pyridinylbenzamide or 5-(aminomethyl)-2-{[(3,4-difluorophenyl)methyl]oxy}-N-3-pyridinylbenzamide.

Compounds of formula (I) or pharmaceutically acceptable salts thereof are inhibitors of LRRK2 kinase activity and are thus believed to be of potential use in the treatment of neurological disorders including Parkinson's disease, Alzheimer's disease, dementia (including Lewy body dementia and vascular dementia), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), withdrawal symptoms/relapse associated with drug addiction, L-Dopa induced dyskinesia, and renal, breast, lung, prostate cancers as well as acute myelogenous leukemia (AML).

In the context of the present invention, treatment of Parkinson's disease refers to the treatment of idiopathic Parkinson's disease and familial Parkinson's disease. In one embodiment, familial Parkinson's disease includes patients expressing LRRK2 kinase bearing the G2019S mutation or the R1441G mutation. Treatment of Parkinson's disease may be symptomatic or may be disease modifying. In one embodiment, treatment of Parkinson's disease refers to symptomatic treatment.

Compounds of the present invention may also be useful in treating patients identified as susceptible to progression to severe Parkinsonism by means of one of more subtle features associated with disease progression such as family history, olfaction deficits, constipation, cognitive defects, gait or biological indicators of disease progression gained from molecular, biochemical, immunological or imaging technologies. In this context, treatment may be symptomatic or disease modifying.

In the context of the present invention, treatment of Alzheimer's disease refers to the treatment of idiopathic Alzheimer's disease and familial Alzheimer's disease. Treatment of Alzheimer's disease may be symptomatic or may be disease modifying. In one embodiment, treatment of Alzheimer's disease refers to symptomatic treatment. Similarly, treatment of dementia (including Lewy body dementia and vascular dementia), age related memory dysfunction, mild cognitive impairment argyrophilic grain disease, Pick's disease, corticobasal degeneration, progressive supranuclear palsy, inherited frontotemporal dementia and parkinsonism linked to chromosome 17 (FTDP-17) and renal, breast, lung, prostate cancers as well as acute myelogenous leukemia (AML) may be symptomatic or disease modifying. In one embodiment, treatment of dementia (including Lewy body dementia and vascular dementia), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), and renal, breast, lung, prostate cancers as well as acute myelogenous leukemia (AML) refers to symptomatic treatment.

In the context of the present invention, treatment of withdrawal symptoms/relapse associated with drug addiction and L-Dopa induced dyskinesia refers to symptomatic treatment.

Accordingly, in a second aspect, the invention provides a compound of formula (I) or a pharmaceutically acceptable salt thereof wherein A, n, p, q, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are as defined above for use in the treatment of the above disorders, and in particular Parkinson's disease and Alzheimer's disease. The invention also provides a compound of formula (I) or a pharmaceutically acceptable salt thereof wherein A, n, p, q, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are as defined above for use in the prophylaxis of Parkinson's disease, Alzheimer's disease, dementia (including Lewy body dementia and vascular dementia), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), and renal, breast, lung, prostate cancers as well as acute myelogenous leukemia (AML), particularly Parkinson's disease and Alzheimer's disease.

The invention further provides a method of treatment of the above disorders, particularly Parkinson's disease and Alzheimer's disease, in mammals including humans, which comprises administering to the sufferer a therapeutically effective amount of a compound of formula (I) or a pharmaceutically acceptable salt thereof wherein A, n, p, q, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are as defined above.

The invention also provides the use of the compound of formula (I) or a pharmaceutically acceptable salt thereof wherein A, n, p, q, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are as defined above in the manufacture of a medicament for use in the treatment of the above disorders, and particularly Parkinson's disease and Alzheimer's disease. The invention also provides the use of the compound of formula (I) or a pharmaceutically acceptable salt thereof wherein A, n, p, q, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are as defined above in the manufacture of a medicament for use in the prophylaxis of Parkinson's disease, Alzheimer's disease, dementia (including Lewy body dementia and vascular dementia), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), and renal, breast, lung, prostate cancers as well as acute myelogenous leukemia (AML), particularly Parkinson's disease and Alzheimer's disease.

The invention also provides the use of inhibitors of LRRK2 in the production of neuronal progenitor cells in vitro for consequent therapeutic application in cell based-treatment of CNS disorders.

In a third aspect, the invention provides a compound of formula (I) or a salt thereof

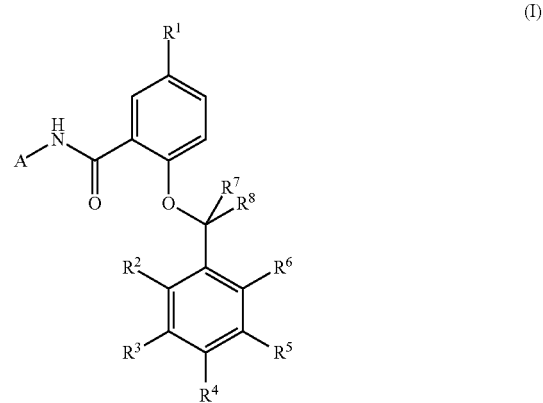

(I)

wherein:
A represents pyridin-2-yl, pyridin-3-yl, pyridazin-3-yl, pyridazin-4-yl, pyrimidin-5-yl, 1,3-oxazol-2-yl, 1H-pyrazol- 4-yl or isoxazol-4-yl or a group of formula (a) wherein * represents the point of attachment:

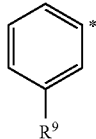

(a)

wherein when A represents pyridin-3-yl, the pyridinyl ring may optionally be substituted at the 2 position by fluoro, methoxy or CH$_2$OH, at the 4 position by methyl or CH$_2$OH, or at the 5 position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl;
R$^1$ represents halo, haloC$_{1-3}$alkyl, hydroxy, CN, —O(CH$_2$)$_2$—O—(CH$_2$)$_2$NH$_2$, —CNOH, (O)$_n$(CH$_2$)$_p$R$^{10}$, —(CO)R$^{10}$, R$^{13}$, —(SO$_2$)R$^{13}$, (C$_{1-3}$alkylene)(CO)$_q$R$^{14}$, (CH═CH)(CO)R$^{14}$, (C$_{1-3}$alkylene)NHCOR$^{14}$, —O-nitrogen containing monoheterocyclic ring with the proviso that the atom directly attached to the oxygen is not nitrogen, or a nitrogen containing heteroaryl ring, wherein the nitrogen containing monoheterocyclic ring is optionally substituted with one, two or three methyl groups and wherein the nitrogen containing heteroaryl ring is optionally substituted by one two or three groups selected from NH$_2$, (C$_{1-3}$alkylene)R$^{13}$, (C$_{1-3}$alkylene)(CO)$_q$R$^{14}$, C$_{1-3}$alkyl and halo;
n and q independently represent 0 or 1;
p represents 1, 2 or 3;
R$^2$, R$^3$, R$^4$, R$^5$ and R$^6$ independently represent hydrogen, halo, CN, C$_{1-3}$alkyl or C$_{1-3}$alkoxy;
R$^7$ and R$^8$ independently represent hydrogen or C$_{1-2}$ alkyl;
R$^9$ represents hydrogen, halo, C$_{1-2}$alkyl, C$_{1-2}$alkoxy, —CH$_2$CO$_2$H or —CONHCH$_3$;
R$^{10}$ represents hydrogen, C$_{1-3}$alkyl, —NR$^{11}$R$^{12}$, or a nitrogen containing monoheterocyclic ring which ring is optionally substituted with one, two or three methyl groups;
R$^{11}$ and R$^{12}$ are independently selected from hydrogen and C$_{1-3}$ alkyl, wherein said C$_{1-3}$ alkyl group is optionally substituted with one, two or three halo, hydroxy, cyano or C$_{1-2}$alkoxy groups;
R$^{13}$ represents —NR$^{11}$R$^{12}$, or a nitrogen containing monoheterocyclic ring which ring is optionally substituted with one, two or three methyl groups and wherein the nitrogen containing monoheterocyclic ring is attached via a nitrogen atom; and
R$^{14}$ represents hydroxy or C$_{1-3}$alkoxy;
with the proviso that the compound of formula (I) is not:
2-[(phenylmethyl)oxy]-N-3-pyridinyl-5-(1-pyrrolidinylsulfonyl)benzamide;
2-{[(3,4-difluorophenyl)methyl]oxy}-5-(1-hydroxyethyl)-N-4-pyridazinylbenzamide;
5-bromo-2-(2-chlorobenzyloxy)-N-(pyridin-3-yl)benzamide;
5-chloro-2-[(phenylmethyl)oxy]-N-3-pyridinylbenzamide;
5-bromo-N-{3-[(methylamino)carbonyl]phenyl}-2-[(phenylmethyl)oxy]benzamide; or
5-chloro-2-[(2-cyanophenyl)methoxy]-N-phenylbenzamide.
In one embodiment, the compound of formula (I) is not 5-bromo-2-[(phenylmethyl)oxy]-N-2-pyridinylbenzamide. In another embodiment, the compound of formula (I) is not 5-bromo-2-[(phenylmethyl)oxy]-N-2-pyridinylbenzamide, N-[2-(hydroxymethyl)-3-pyridinyl]-2-[(phenylmethyl)oxy]-5-(4-pyridinyl)benzamide, N-[4-(hydroxymethyl)-3-pyridinyl]-2-[(phenylmethyl)oxy]-5-(4-pyridinyl)benzamide, N-(5-methyl-4-isoxazolyl)-2-[(phenylmethyl)oxy]-5-(4-pyridinyl)benzamide, 5-(aminomethyl)-2-{[(3,4-difluorophenyl)methyl]oxy}-N-3-pyridinylbenzamide or methyl ({4-{[(3,4-difluorophenyl)methyl]oxy}-3-[(3-pyridinylamino)carbonyl]phenyl}methyl)carbamate.

In a further aspect, the invention provides a compound of formula (I) or a salt thereof.

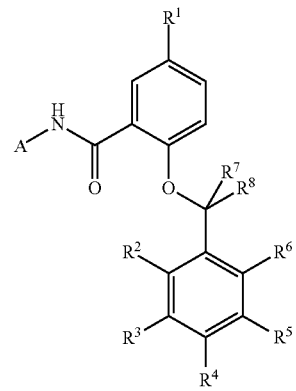

(I)

wherein:
A represents pyridin-2-yl, pyridin-3-yl, pyridazin-3-yl, pyridazin-4-yl, pyrimidin-5-yl or a group of formula (a) wherein * represents the point of attachment:

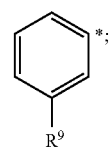

(a)

R$^1$ represents halo, hydroxy, CN, —R$^{10}$ or —OR$^{10}$;
R$^2$, R$^3$, R$^4$, R$^5$ and R$^6$ independently represent hydrogen, halo, CN, C$_{1-3}$alkyl or C$_{1-3}$alkoxy;
R$^7$ and R$^8$ independently represent hydrogen or C$_{1-2}$ alkyl;
R$^9$ represents hydrogen, halo, C$_{1-2}$alkyl, C$_{1-2}$alkoxy, —CH$_2$CO$_2$H or —CONHCH$_3$;
R$^{10}$ represents C$_{1-3}$alkyl optionally substituted with —NR$^{11}$R$^{12}$, or a nitrogen containing monoheterocyclic ring which is optionally substituted with one, two or three methyl groups; and
R$^{11}$ and R$^{12}$ are independently selected from hydrogen and C$_{1-3}$ alkyl, wherein said C$_{1-3}$ alkyl group is optionally substituted with one, two or three halo, hydroxy, cyano or C$_{1-2}$alkoxy groups;
with the proviso that the compound of formula (I) is not:
5-bromo-2-(2-chlorobenzyloxy)-N-(pyridin-3-yl)benzamide;
5-chloro-2-[(phenylmethyl)oxy]-N-3-pyridinylbenzamide;
5-bromo-N-{3-[(methylamino)carbonyl]phenyl}-2-[(phenylmethyl)oxy]benzamide; or
5-chloro-2-[(2-cyanophenyl)methoxy]-N-phenylbenzamide.
In one such embodiment, the compound of formula (I) is not 5-bromo-2-[(phenylmethyl)oxy]-N-2-pyridinylbenzamide. In another embodiment, the compound of formula (I) is not 5-bromo-2-[(phenylmethyl)oxy]-N-2-pyridinylbenzamide or 5-(aminomethyl)-2-{[(3,4-difluorophenyl)methyl]oxy}-N-3-pyridinylbenzamide.

In one embodiment of the compound of formula (I), $R^1$ represents:
—$(O)_n(CF_{12})_pR^{10}$; or
—$(CO)R^{10}$;
wherein $R^{10}$ represents hydrogen, $C_{1-3}$alkyl, —$NR^{11}R^{12}$, or a nitrogen containing monoheterocyclic ring which ring is optionally substituted with one, two or three methyl groups, wherein n represents 0 or 1 and wherein p represents 1, 2 or 3.

In a more particular embodiment, $R^1$ represents —$(CO)R^{10}$, wherein $R^{10}$ represents hydrogen, $C_{1-3}$alkyl, —$NR^{11}R^{12}$, or a nitrogen containing monoheterocyclic ring which ring is optionally substituted with one, two or three methyl groups. More particularly, $R^1$ represents —$(CO)R^{10}$, wherein $R^{10}$ represents hydrogen, $C_{1-3}$alkyl, —$NR^{11}R^{12}$, or a nitrogen containing monoheterocyclic ring which ring is optionally substituted with one, two or three methyl groups and which monocyclic ring is attached to the carbonyl group via a nitrogen atom.

In an alternative embodiment, $R^1$ represents —$(O)_n(CH_2)_pR^{10}$, wherein $R^{10}$ represents hydrogen, $C_{1-3}$alkyl, —$NR^{11}R^{12}$, or a nitrogen containing monoheterocyclic ring which ring is optionally substituted with one, two or three methyl groups, wherein n represents 0 or 1 and wherein p represents 1, 2 or 3. More particularly, $R^1$ represents —$(O)_n(CH_2)_pR^{10}$, wherein $R^{10}$ represents hydrogen, $C_{1-3}$alkyl, —$NR^{11}R^{12}$, or a nitrogen containing monoheterocyclic ring which ring is optionally substituted with one, two or three methyl groups, wherein n represents 0 or 1 and wherein p represents 1.

In certain embodiments where $R^1$ represents —$(O)_n(CH_2)_pR^{10}$ or —$(CO)R^{10}$, $R^{10}$ represents a nitrogen containing monoheterocyclic ring which ring is optionally substituted with one, two or three methyl groups. More particularly, $R^{10}$ represents a nitrogen containing monoheterocyclic ring selected from the group consisting of piperidinyl, piperazinyl pyrrolidinyl and morpholinyl, which ring is optionally substituted with one, two or three methyl groups.

Even more particularly, $R^{10}$ represents:
piperidinyl (e.g. piperidin-1-yl or piperidin-4-yl) which is optionally substituted with one, two or three methyl groups;
piperazinyl (e.g. piperazin-1-yl) which is optionally substituted with one, two or three methyl groups;
pyrrolidinyl (e.g. pyrrolidin-1-yl or pyrrolidin-2-yl) which is optionally substituted with one, two or three methyl groups; or
morpholinyl (e.g. morpholin-4-yl).

Most particularly, $R^{10}$ represents:
unsubstituted piperidin-1-yl;
piperidin-4-yl optionally substituted with one, two or three methyl groups (e.g. 1-methyl piperidin-4-yl);
piperazin-1-yl optionally substituted with one, two or three methyl groups (e.g. 4-methyl piperazin-1-yl);
unsubstituted pyrrolidin-1-yl;
pyrrolidin-2-yl optionally substituted with one, two or three methyl groups (e.g. 1-methylpyrrolidin-2-yl); or
unsubstituted morpholin-4-yl.

In embodiments in which $R^1$ represents —$(CO)R^{10}$, $R^{10}$ represents:
unsubstituted piperidin-1-yl;
piperidin-4-yl optionally substituted with one, two or three methyl groups (e.g. 1-methyl piperidin-4-yl);
piperazin-1-yl optionally substituted with one, two or three methyl groups (e.g. 4-methyl piperazin-1-yl);
unsubstituted pyrrolidin-1-yl; or
unsubstituted morpholin-4-yl.

In other embodiments in which $R^1$ represents —$(O)_n(CH_2)_pR^{10}$ or —$(CO)R^{10}$, $R^{10}$ represents —$NR^{11}R^{12}$, wherein $R^{11}$ and $R^{12}$ are independently selected from hydrogen and $C_{1-3}$ alkyl, wherein said $C_{1-3}$ alkyl group is optionally substituted with one, two or three halo, hydroxy, cyano or $C_{1-2}$alkoxy groups. More particularly, $R^{11}$ and $R^{12}$ are independently selected from hydrogen and $C_{1-3}$ alkyl. Most particularly, $R^{11}$ and $R^{12}$ are independently selected from hydrogen and methyl.

In a further embodiment, $R^1$ represents $R^{13}$ or —$(SO_2)R^{13}$ wherein $R^{13}$ represents —$NR^{11}R^{12}$, or a nitrogen containing monoheterocyclic ring which ring is optionally substituted with one, two or three methyl groups and wherein the nitrogen containing monoheterocyclic ring is attached to the sulphur via a nitrogen atom.

In a more particular embodiment, $R^1$ represents $R^{13}$, wherein $R^{13}$ represents —$NR^{11}R^{12}$ or a nitrogen containing monoheterocyclic ring which ring is optionally substituted with one, two or three methyl groups and wherein the nitrogen containing monoheterocyclic ring is attached via a nitrogen atom.

In an alternative embodiment, $R^1$ represents —$(SO_2)R^{13}$, wherein $R^{13}$ represents —$NR^{11}R^{12}$ or a nitrogen containing monoheterocyclic ring which ring is optionally substituted with one, two or three methyl groups and wherein the nitrogen containing monoheterocyclic ring is attached to the sulphur via a nitrogen atom.

In certain embodiments where $R^1$ represents $R^{13}$ or —$(SO_2)R^{13}$, $R^{13}$ represents a nitrogen containing monoheterocyclic ring which ring is optionally substituted with one, two or three methyl groups and wherein the nitrogen containing monoheterocyclic ring is attached via a nitrogen atom. More particularly, $R^{13}$ represents a nitrogen containing monoheterocyclic ring selected from the group consisting of piperidinyl, piperazinyl pyrrolidinyl and morpholinyl, which ring is optionally substituted with one, two or three methyl groups and wherein the nitrogen containing monoheterocyclic ring is attached via a nitrogen atom.

Even more particularly, $R^{13}$ represents:
piperidinyl (e.g. piperidin-1-yl or piperidin-4-yl) which is optionally substituted with one, two or three methyl groups;
piperazinyl (e.g. piperazin-1-yl) which is optionally substituted with one, two or three methyl groups;
pyrrolidinyl (e.g. pyrrolidin-1-yl) which is optionally substituted with one, two or three methyl groups; or
morpholinyl (e.g. morpholin-4-yl).

Most particularly, $R^{13}$ represents:
unsubstituted piperidin-1-yl;
piperidin-4-yl optionally substituted with one, two or three methyl groups (e.g. 1-methyl piperidin-4-yl);
piperazin-1-yl optionally substituted with one, two or three methyl groups (e.g. 4-methyl piperazin-1-yl);
unsubstituted pyrrolidin-1-yl; or
unsubstituted morpholin-4-yl.

In other embodiments in which $R^1$ represents $R^{13}$ or —$(SO_2)R^{13}$, $R^{13}$ represents —$NR^{11}R^{12}$, wherein $R^{11}$ and $R^{12}$ are independently selected from hydrogen and $C_{1-3}$ alkyl, wherein said $C_{1-3}$ alkyl group is optionally substituted with one, two or three halo, hydroxy, cyano or $C_{1-2}$alkoxy groups. More particularly, $R^{11}$ and $R^{12}$ are independently selected from hydrogen and $C_{1-3}$ alkyl. Most particularly, $R^{11}$ and $R^{12}$ are independently selected from hydrogen and methyl.

In an alternative embodiment, $R^1$ represents:
$(C_{1-3}$alkylene$)(CO)_pR^{14}$;
$(CH=CH)(CO)R^{14}$; or
$(C_{1-3}$alkylene$)NHCOR^{14}$;

wherein $R^{14}$ represents hydroxyl or $C_{1-3}$alkoxy and q represents 0 or 1.

In a further embodiment, $R^1$ represents a nitrogen containing heteroaryl ring, which nitrogen containing heteroaryl ring is optionally substituted by one, two or three groups selected from $NH_2$, $C_{1-3}$alkylene$R^{13}$, $(C_{1-3}$alkylene$)(CO)_qR^{14}$, $C_{1-3}$alkyl and halo. More particularly, $R^1$ represents a nitrogen containing heteroaryl ring, which nitrogen containing heteroaryl ring is optionally substituted by one group selected from $NH_2$, $(C_{1-3}$alkylene$)R^{13}$, $(C_{1-3}$alkylene$)(CO)_qR^{14}$, $C_{1-3}$alkyl and halo.

More particularly, $R^1$ represents pyridinyl or pyrazolyl, which pyridinyl or pyrazolyl group is optionally substituted by one, two or three groups selected from $NH_2$, $(C_{1-3}$alkylene$)R^{13}$, $(C_{1-3}$alkylene$)(CO)_qR^{14}$, $C_{1-3}$alkyl and halo. Even more particularly, $R^1$ represents pyridinyl or pyrazolyl, which pyridinyl or pyrazolyl group is optionally substituted by one group selected from $NH_2$, $C_{1-3}$alkylene$R^{13}$, $(C_{1-3}$alkylene$)(CO)_qR^{14}$, $C_{1-3}$alkyl and halo.

Most particularly, $R^1$ represents:
pyridin-4-yl optionally substituted by one $NH_2$ or halo group (e.g. 2-amino pyridin-4-yl, 2-fluoro pyridin-4-yl); unsubstituted pyridin-3-yl;
1H-pyrazol-4-yl optionally substituted by one group selected from 2-(4-morpholinyl)ethyl, 2-(methyloxy) ethyl or methyl (e.g. 1-[2-(4-morpholinyl)ethyl]-1H-pyrazol-4-yl, 1-[2-(methyloxy)ethyl]-1H-pyrazol-4-yl, 1 methyl-1H-pyrazol-4-yl); or
1H-pyrazol-5-yl optionally substituted by one methyl group (e.g. 1 methyl-1H-pyrazol-5-yl).

In another embodiment, $R^1$ represents —O-nitrogen containing monoheterocyclic ring, which ring is optionally substituted with one, two or three methyl groups with the proviso that the atom directly attached to the oxygen is not nitrogen. In a more particular embodiment, $R^1$ represents piperidinyloxy wherein the piperidine ring is optionally substituted with one, two or three methyl groups. More particularly, $R^1$ represents piperidinyloxy wherein the piperidine ring is optionally substituted with one methyl group (e.g. 1-methyl piperidin-4-yloxy).

In one embodiment of the compound of formula (I), $R^1$ represents:
halo (e.g. bromo, chloro, fluoro);
halo$C_{1-3}$alkyl (e.g. trifluoromethyl);
hydroxy;
CN;
—O(CH$_2$)$_2$—O—(CH$_2$)$_2$NH$_2$; or
—CNOH.

In a more particular embodiment, $R^1$ represents CN.

In a further embodiment, $R^1$ represents halo, more particularly bromo.

In another embodiment, $R^1$ represents halo$C_{1-3}$alkyl (e.g. trifluoromethyl).

In certain embodiments of the compound of formula (I), $R^1$ represents bromo, chloro, fluoro, CN, methyl, isopropyl, hydroxy, methoxy, ethoxy, piperidinyl, piperazinyl or piperidinyloxy, wherein said methoxy and ethyoxy group are optionally substituted with one dimethylamino group and wherein said piperidinyl, piperazinyl or piperidinyloxy groups are optionally substituted with one, two or three methyl groups.

In an alternative embodiment, $R^1$ represents $C_{1-3}$alkyl, more particularly isopropyl and methyl. In one embodiment, $R^1$ represents isopropyl.

In one embodiment, $R^1$ represents $C_{1-3}$alkoxy optionally substituted with one —NR$^{11}$R$^{12}$ group wherein R$^{11}$ and R$^{12}$ are independently selected from hydrogen and $C_{1-3}$ alkyl. In a more particular embodiment, $R^1$ represents $C_{1-3}$alkoxy optionally substituted with one —NR$^{11}$R$^{12}$ group wherein R$^{11}$ and R$^{12}$ each represent $C_{1-3}$ alkyl (e.g. methyl). Most particularly, $R^1$ represents methoxy or 2-(dimethylamino) ethoxy.

In another embodiment, $R^1$ represents a nitrogen containing monoheterocyclic ring (e.g. piperidinyl, piperazinyl) optionally substituted with one, two or three methyl groups. In a more particular embodiment $R^1$ represents a nitrogen containing monoheterocyclic ring (e.g. piperidinyl, piperazinyl) optionally substituted with one methyl group. Even more particularly, $R^1$ represents unsubstituted piperidin-1-yl, or piperazin-1-yl optionally substituted with one methyl group.

In a further embodiment, $R^1$ represents a nitrogen containing monoheterocyclyloxy group (e.g. piperidinyloxy) optionally substituted with one, two or three methyl groups. More particularly, $R^1$ represents a nitrogen containing monoheterocyclyloxy group (e.g. piperidinyloxy) optionally substituted with one methyl group. Even more particularly, $R^1$ represents piperidin-4-yloxy optionally substituted with one methyl group.

In another embodiment, $R^2$, $R^3$, $R^4$, $R^5$ and $R^6$ independently represent hydrogen, halo, CN, and $C_{1-3}$alkoxy. More particularly, $R^2$, $R^3$, $R^4$, $R^5$ and $R^6$ independently represent:
hydrogen;
halo (e.g. fluoro or chloro);
CN; or
$C_{1-3}$alkoxy (e.g. methoxy).

Even more particularly, $R^2$, $R^3$, $R^4$, $R^5$ and $R^6$ independently represent hydrogen or fluoro. In one embodiment, one or two of $R^2$, $R^3$, $R^4$, $R^5$ and $R^6$ represent fluoro and the remaining groups represent hydrogen.

In one embodiment, $R^2$, $R^3$, $R^4$, $R^5$ and $R^6$ each represent hydrogen. In an alternative embodiment, one of $R^2$, $R^3$, $R^4$, $R^5$ and $R^6$ represents halo, CN, $C_{1-3}$alkyl or $C_{1-3}$alkoxy and the remaining groups are each hydrogen.

In one embodiment, $R^3$, $R^4$, $R^5$ and $R^6$ each represent hydrogen and $R^2$ represents:
halo (e.g. fluoro or chloro);
CN; or
$C_{1-3}$alkoxy (e.g. methoxy).

In a more particular embodiment, $R^3$, $R^4$, $R^5$ and $R^6$ each represent hydrogen and $R^2$ represents chloro.

In an alternative embodiment, $R^3$, $R^4$, $R^5$ and $R^6$ each represent hydrogen and $R^2$ represents fluoro.

In a further embodiment, $R^2$, $R^4$, $R^5$ and $R^6$ each represent hydrogen and $R^3$ represents:
halo (e.g. fluoro chloro);
CN; or
$C_{1-3}$alkoxy (e.g. methoxy).

In a more particular embodiment $R^2$, $R^4$, $R^5$ and $R^6$ each represent hydrogen and $R^3$ represents chloro or CN.

In an alternative embodiment $R^2$, $R^4$, $R^5$ and $R^6$ each represent hydrogen and $R^3$ represents fluoro.

In yet another embodiment, $R^2$, $R^3$, $R^5$ and $R^6$ each represent hydrogen and $R^4$ represents:
halo (e.g. fluoro or chloro);
CN; or
$C_{1-3}$alkoxy (e.g. methoxy).

In a more particular embodiment $R^2$, $R^3$, $R^5$ and $R^6$ each represent hydrogen and $R^4$ represents chloro, CN or methoxy.

In an alternative embodiment $R^2$, $R^3$, $R^5$ and $R^6$ each represent hydrogen and $R^4$ represents fluoro.

In a further embodiment, $R^3$, $R^5$ and $R^6$ each represent hydrogen, and $R^2$ and $R^4$ each represent fluoro.

In a further embodiment, $R^2$, $R^5$ and $R^6$ each represent hydrogen, and $R^3$ and $R^4$ each represent fluoro.

In one embodiment, W and $R^8$ independently represent hydrogen or methyl. In a more particular embodiment, $R^7$ and $R^8$ each represent hydrogen.

In one embodiment, A represents:
pyridin-2-yl;
pyridin-3-yl, wherein the pyridinyl ring may optionally be substituted at the 2 position by fluoro, methoxy or $CH_2OH$, at the 4 position by methyl or $CH_2OH$, or at the 5 position by fluoro;
pyridazin-3-yl;
pyridazin-4-yl;
pyrimidin-5-yl;
1,3-oxazol-2-yl;
1H-pyrazol-4-yl, wherein the pyrazolyl ring may optionally be substituted at the 1 position by methyl;
isoxazol-4-yl, wherein the isoxazolyl ring may optionally be substituted at the 3 position by methyl or at the 5 position by methyl; or
a group of formula a).

In a more particular embodiment, A represents:
pyridin-3-yl, wherein the pyridinyl ring may optionally be substituted at the 2 position by fluoro;
pyridazin-4-yl;
1H-pyrazol-4-yl, wherein the pyrazolyl ring may optionally be substituted at the 1 position by methyl; or
isoxazol-4-yl, wherein the isoxazolyl ring may optionally be substituted at the 3 position by methyl or at the 5 position by methyl.

In one embodiment, A represents pyridin-2-yl, pyridin-3-yl, pyridazin-3-yl, pyridazin-4-yl, or a group of formula a). In a more particular embodiment, A represents pyridin-3-yl, pyridazin-3-yl, pyridazin-4-yl, or a group of formula (a).

In one embodiment, A represents pyridin-3-yl, pyridazin-3-yl or pyridazin-4-yl, more particularly, pyridin-3-yl.

In an alternative embodiment, A represents a group of formula (a).

In one embodiment, $R^9$ represents:
hydrogen;
halo (e.g. fluoro, chloro);
$C_{1-2}$alkyl (e.g. methyl, ethyl);
$C_{1-2}$alkoxy (e.g. methoxy);
—$CH_2CO_2H$; or
—$CONHCH_3$.

In a more particular embodiment, $R^9$ represents hydrogen, halo (e.g. fluoro chloro), $C_{1-2}$alkyl (e.g. methyl, ethyl) or $C_{1-2}$alkoxy (e.g. methoxy). More particularly, $R^9$ represents hydrogen, chloro, methyl and methoxy.

In one embodiment:
A represents pyridin-3-yl, pyridazin-4-yl, 1H-pyrazol-4-yl or isoxazol-4-yl, wherein when
A represents pyridin-3-yl, the pyridinyl ring may optionally be substituted at the 2 position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl;
$R^1$ represents —$(O)_n(CH_2)_pR^{10}$, —$(CO)R^{10}$, $R^{13}$, —$(SO_2)R^{13}$ or a nitrogen containing heteroaryl ring which nitrogen containing heteroaryl ring is optionally substituted by one, two or three groups selected from $NH_2$, $(C_{1-3}$alkylene$)R^{13}$, $(C_{1-3}$alkylene$)(CO)_qR^{14}$, $C_{1-3}$alkyl and halo;
$R^2$, $R^3$, $R^4$, $R^5$, $R^6$, independently represent hydrogen or fluoro;
$R^7$ and $R^8$ represent hydrogen;
$R^{10}$ represents hydrogen, $C_{1-3}$alkyl, —$NR^{11}R^{12}$, or a nitrogen containing monoheterocyclic ring which ring is optionally substituted with one, two or three methyl groups;
$R^{11}$ and $R^{12}$ independently represent hydrogen or $C_{1-3}$ alkyl;
$R^{13}$ represents —$NR^{11}R^{12}$, or a nitrogen containing monoheterocyclic ring which ring is optionally substituted with one, two or three methyl groups and wherein the nitrogen containing monoheterocyclic ring is attached via a nitrogen atom;
$R^{14}$ represents hydroxy or $C_{1-3}$alkoxy; and
n and q independently represent 0 or 1 and p represents 1, 2 or 3;
with the proviso that the compound of formula (I) is not 2-[(phenylmethyl)oxy]-N-3-pyridinyl-5-(1-pyrrolidinylsulfonyl)benzamide.

In a more particular embodiment, $R^1$ represents —$(CO)R^{10}$, wherein $R^{10}$ represents hydrogen, $C_{1-3}$alkyl, —$NR^{11}R^{12}$, or a nitrogen containing monoheterocyclic ring which ring is optionally substituted with one, two or three methyl groups. More particularly, $R^1$ represents —$(CO)R^{10}$, wherein $R^{10}$ represents hydrogen, $C_{1-3}$alkyl, —$NR^{11}R^{12}$, or a nitrogen containing monoheterocyclic ring which ring is optionally substituted with one, two or three methyl groups and which monocyclic ring is attached to the carbonyl group via a nitrogen atom.

In an alternative embodiment, $R^1$ represents —$(O)_n(CH_2)_pR^{10}$, wherein $R^{10}$ represents hydrogen, $C_{1-3}$alkyl, —$NR^{11}R^{12}$, or a nitrogen containing monoheterocyclic ring which ring is optionally substituted with one, two or three methyl groups, wherein n represents 0 or 1 and wherein p represents 1, 2 or 3. More particularly, $R^1$ represents —$(O)_n(CH_2)_pR^{10}$, wherein $R^{10}$ represents hydrogen, $C_{1-3}$alkyl, —$NR^{11}R^{12}$, or a nitrogen containing monoheterocyclic ring which ring is optionally substituted with one, two or three methyl groups, wherein n represents 0 or 1 and wherein p represents 1.

In certain embodiments where $R^1$ represents —$(O)_n(CH_2)_pR^{10}$ or —$(CO)R^{10}$, $R^{10}$ represents a nitrogen containing monoheterocyclic ring which ring is optionally substituted with one, two or three methyl groups. More particularly, $R^{10}$ represents a nitrogen containing monoheterocyclic ring selected from the group consisting of piperidinyl, piperazinyl pyrrolidinyl and morpholinyl, which ring is optionally substituted with one, two or three methyl groups.

Even more particularly, $R^{10}$ represents:
piperidinyl (e.g. piperidin-1-yl or piperidin-4-yl) which is optionally substituted with one, two or three methyl groups;
piperazinyl (e.g. piperazin-1-yl) which is optionally substituted with one, two or three methyl groups;
pyrrolidinyl (e.g. pyrrolidin-1-yl or pyrrolidin-2-yl) which is optionally substituted with one, two or three methyl groups; or
morpholinyl (e.g. morpholin-4-yl).
Most particularly, $R^{10}$ represents:
unsubstituted piperidin-1-yl;
piperidin-4-yl optionally substituted with one, two or three methyl groups (e.g. 1-methyl piperidin-4-yl);
piperazin-1-yl optionally substituted with one, two or three methyl groups (e.g. 4-methyl piperazin-1-yl);
unsubstituted pyrrolidin-1-yl;
pyrrolidin-2-yl optionally substituted with one, two or three methyl groups (e.g. 1-methylpyrrolidin-2-yl); or
unsubstituted morpholin-4-yl.
In embodiments in which $R^1$ represents —$(CO)R^{10}$, $R^{10}$ represents:
unsubstituted piperidin-1-yl;
piperidin-4-yl optionally substituted with one, two or three methyl groups (e.g. 1-methyl piperidin-4-yl);

piperazin-1-yl optionally substituted with one, two or three methyl groups (e.g. 4-methyl piperazin-1-yl);
unsubstituted pyrrolidin-1-yl; or
unsubstituted morpholin-4-yl.

In other embodiments in which $R^1$ represents —(O)$_n$(CH$_2$)$_p$R$^{10}$ or —(CO)R$^{10}$, R$^{10}$ represents —NR$^{11}$R$^{12}$, wherein $R^{11}$ and $R^{12}$ are independently selected from hydrogen and $C_{1-3}$ alkyl, wherein said $C_{1-3}$ alkyl group is optionally substituted with one, two or three halo, hydroxy, cyano or $C_{1-2}$alkoxy groups. More particularly, $R^{11}$ and $R^{12}$ are independently selected from hydrogen and $C_{1-3}$ alkyl. Most particularly, $R^{11}$ and $R^{12}$ are independently selected from hydrogen and methyl.

In a further embodiment, $R^1$ represents $R^{13}$ or —(SO$_2$)R$^{13}$ wherein $R^{13}$ represents —NR$^{11}$R$^{12}$, or a nitrogen containing monoheterocyclic ring which ring is optionally substituted with one, two or three methyl groups and wherein the nitrogen containing monoheterocyclic ring is attached to the sulphur via a nitrogen atom.

In a more particular embodiment, $R^1$ represents $R^{13}$, wherein $R^{13}$ represents —NR$^{11}$R$^{12}$ or a nitrogen containing monoheterocyclic ring which ring is optionally substituted with one, two or three methyl groups and wherein the nitrogen containing monoheterocyclic ring is attached via a nitrogen atom.

In an alternative embodiment, $R^1$ represents —(SO$_2$)R$^{13}$, wherein $R^{13}$ represents —NR$^{11}$R$^{12}$ or a nitrogen containing monoheterocyclic ring which ring is optionally substituted with one, two or three methyl groups and wherein the nitrogen containing monoheterocyclic ring is attached to the sulphur via a nitrogen atom.

In certain embodiments where $R^1$ represents $R^{13}$ or —(SO$_2$)R$^{13}$, $R^{13}$ represents a nitrogen containing monoheterocyclic ring which ring is optionally substituted with one, two or three methyl groups and wherein the nitrogen containing monoheterocyclic ring is attached via a nitrogen atom. More particularly, $R^{13}$ represents a nitrogen containing monoheterocyclic ring selected from the group consisting of piperidinyl, piperazinyl pyrrolidinyl and morpholinyl, which ring is optionally substituted with one, two or three methyl groups and wherein the nitrogen containing monoheterocyclic ring is attached via a nitrogen atom.

Even more particularly, $R^{13}$ represents:
piperidinyl (e.g. piperidin-1-yl or piperidin-4-yl) which is optionally substituted with one, two or three methyl groups;
piperazinyl (e.g. piperazin-1-yl) which is optionally substituted with one, two or three methyl groups;
pyrrolidinyl (e.g. pyrrolidin-1-yl) which is optionally substituted with one, two or three methyl groups; or
morpholinyl (e.g. morpholin-4-yl).
Most particularly, $R^{13}$ represents:
unsubstituted piperidin-1-yl;
piperidin-4-yl optionally substituted with one, two or three methyl groups (e.g. 1-methyl piperidin-4-yl);
piperazin-1-yl optionally substituted with one, two or three methyl groups (e.g. 4-methyl piperazin-1-yl);
unsubstituted pyrrolidin-1-yl; or
unsubstituted morpholin-4-yl.

In other embodiments in which $R^1$ represents $R^{13}$ or —(SO$_2$)R$^{13}$, $R^{13}$ represents —NR$^{11}$R$^{12}$, wherein $R^{11}$ and $R^{12}$ are independently selected from hydrogen and $C_{1-3}$ alkyl, wherein said $C_{1-3}$ alkyl group is optionally substituted with one, two or three halo, hydroxy, cyano or $C_{1-2}$alkoxy groups. More particularly, $R^{11}$ and $R^{12}$ are independently selected from hydrogen and $C_{1-3}$ alkyl. Most particularly, $R^{11}$ and $R^{12}$ are independently selected from hydrogen and methyl.

In a further embodiment, $R^1$ represents a nitrogen containing heteroaryl ring, which nitrogen containing heteroaryl ring is optionally substituted by one, two or three groups selected from NH$_2$, (C$_{1-3}$alkylene)R$^{13}$, (C$_{1-3}$alkylene)(CO)$_q$R$^{14}$, $C_{1-3}$alkyl and halo. More particularly, $R^1$ represents a nitrogen containing heteroaryl ring, which nitrogen containing heteroaryl ring is optionally substituted by one group selected from NH$_2$, C$_{1-3}$alkyleneR$^{13}$, (C$_{1-3}$alkylene)(CO)$_q$R$^{14}$, $C_{1-3}$alkyl and halo.

More particularly, $R^1$ represents pyridinyl or pyrazolyl, which pyridinyl or pyrazolyl group is optionally substituted by one, two or three groups selected from NH$_2$, C$_{1-3}$alkyleneR$^{13}$, (C$_{1-3}$alkylene)(CO)$_q$R$^{14}$, $C_{1-3}$alkyl and halo. Even more particularly, $R^1$ represents pyridinyl or pyrazolyl, which pyridinyl or pyrazolyl group is optionally substituted by one group selected from NH$_2$, (C$_{1-3}$alkylene)R$^{13}$, (C$_{1-3}$alkylene)(CO)$_q$R$^{14}$, $C_{1-3}$alkyl and halo.

Most particularly, $R^1$ represents:
pyridin-4-yl optionally substituted by one NH$_2$ or halo group (e.g. 2-amino pyridin-4-yl, 2-fluoro pyridin-4-yl);
unsubstituted pyridin-3-yl;
1H-pyrazol-4-yl optionally substituted by one group selected from 2-(4-morpholinyl)ethyl, 2-(methyloxy)ethyl or methyl (e.g. 1-[2-(4-morpholinyl)ethyl]-1H-pyrazol-4-yl, 1-[2-(methyloxy)ethyl]-1H-pyrazol-4-yl, 1 methyl-1H-pyrazol-4-yl); or
1H-pyrazol-5-yl optionally substituted by one methyl group (e.g. 1 methyl-1H-pyrazol-5-yl).

In certain embodiments, $R^2$, $R^3$, $R^4$, $R^5$ and $R^6$ each represent hydrogen.

In certain embodiments, $R^2$, $R^3$, $R^5$ and $R^6$ each represent hydrogen and $R^4$ represents fluoro.

In alternative embodiments, $R^3$, $R^5$ and $R^6$ each represent hydrogen, and $R^2$ and $R^4$ each represent fluoro.

In further embodiments, $R^2$, $R^5$ and $R^6$ each represent hydrogen, and $R^3$ and $R^4$ each represent fluoro.

Compounds of formula (I) or salts thereof include the compounds of examples 1-137 and their salts. In a more particular embodiment, compounds of formula (I) or salts thereof include the compounds of examples 1-21 and 23-137, and their salts. Even more particularly, compounds of formula (I) or salts thereof include the compounds of examples 1-21, 23-54, 57-61 and 63-137, and their salts In one embodiment, the compound of formula (I) or a salt thereof is:
2-{[(4-fluorophenyl)methyl]oxy}-5-(1-methyl-1H-pyrazol-4-yl)-N-3-pyridinylbenzamide;
2-{[(4-fluorophenyl)methyl]oxy}-5-(1-methyl-1H-pyrazol-4-yl)-N-4-pyridazinylbenzamide; or a salt thereof.
Other compounds of formula (I) or salts thereof include:
2-{[(4-fluorophenyl)methyl]oxy}-5-[3-(4-morpholinyl)propyl]-N-3-pyridinylbenzamide; or
2-{[(4-fluorophenyl)methyl]oxy}-5-{1-[2-(4-morpholinyl)ethyl]-1H-pyrazol-4-yl}-N-4-pyridazinylbenzamide;
or a salt thereof.

Certain compounds of formula (I) are capable of forming salts. Specifically, where A represents (optionally substituted) pyridin-2-yl, pyridin-3-yl, pyridazin-3-yl, pyridazin-4-yl, pyrimidin-5-yl or 1H-pyrazol-4-yl, where $R^1$ represents —O(CH$_2$)$_2$—O—(CH$_2$)$_2$NH$_2$, or certain (optionally substituted) nitrogen containing heteroaryl rings, or where $R^{10}$ represents a nitrogen containing monoheterocyclic ring or an —NR$^{11}$R$^{12}$ group, the compounds of formula (I) may form acid addition salts. Such salts can be formed by reaction with the appropriate acid, optionally in a suitable solvent such as an organic solvent, to give the salt which can be isolated for example by crystallisation and filtration. Where A represents a group of formula (a) and $R^9$ represents —$CH_2CO_2H$, or where $R^{14}$ represents hydroxy, the compounds of formula (I) may form basic salts. Such salts can be formed by reaction with the appropriate base, optionally in a suitable solvent such as an organic solvent, to give the salt which can be isolated for example by crystallisation and filtration.

Because of their potential use in medicine, the salts of the compound of formula (I) are preferably pharmaceutically acceptable.

Pharmaceutically acceptable acid addition salts of the compounds of formula (I) include hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salts.

Pharmaceutically acceptable base addition salts of the compounds of formula (I) include metal salts (such as sodium, potassium, aluminium, calcium, magnesium and zinc) and ammonium salts (such as isopropylamine, diethylamine, diethanolamine salts).

The invention includes within its scope all possible stoichiometric and non-stoichiometric forms of the salts of the compounds of formula (I).

Certain compounds of formula (I) or salts thereof may exist in the form of solvates (e.g. hydrates).

Certain compounds of formula (I) are capable of existing in stereoisomeric forms. It will be understood that the invention encompasses all geometric and optical isomers of these compounds and the mixtures thereof including racemates. The different stereoisomeric forms may be separated one from the other by methods known in the art (e.g. separation by chiral HPLC), or any given isomer may be obtained by stereospecific or asymmetric synthesis. The invention also extends to any tautomeric forms and mixtures thereof.

The invention also includes isotopically-labelled compounds and salts, which are identical to compounds of formula (I) or salts thereof, but for the fact that one or more atoms are replaced by an atom having an atomic mass or mass number different from the atomic mass or mass number most commonly found in nature. Examples of isotopes that can be incorporated into compounds of formula (I) or salts thereof isotopes of hydrogen, carbon, nitrogen, fluorine, such as $^3H$, $^{11}C$, $^{14}C$ and $^{18}F$. Such isotopically-labelled compound of formula (I) or salts thereof are useful in drug and/or substrate tissue distribution assays. For example, $^{11}C$ and $^{18}F$ isotopes are particularly useful in PET (positron emission tomography). PET is useful in brain imaging. Isotopically labelled compounds of formula (I) and salts thereof can generally be prepared by carrying out the procedures disclosed below, by substituting a readily available isotopically labelled reagent for a non-isotopically labelled reagent. In one embodiment, compounds of formula (I) or salts thereof are not isotopically labelled.

When used in therapy, a compound of formula (I) or pharmaceutically acceptable salt thereof is usually formulated in a standard pharmaceutical composition. Such compositions can be prepared using standard procedures.

The present invention further provides a pharmaceutical composition which comprises the compound of formula (I) or a pharmaceutically acceptable salt thereof and a pharmaceutically acceptable carrier.

When a compound of formula (I) or a pharmaceutically acceptable salt thereof is intended for use in the treatment of Parkinson's disease, it may be used in combination with medicaments claimed to be useful as symptomatic treatments of Parkinson's disease. Suitable examples of such other therapeutic agents include L-dopa, and dopamine agonists (e.g. pramipexole, ropinirole).

When a compound of formula (I) or a pharmaceutically acceptable salt thereof is intended for use in the treatment of Alzheimer's disease, it may be used in combination with medicaments claimed to be useful as either disease modifying or symptomatic treatments of Alzheimer's disease. Suitable examples of such other therapeutic agents may be symptomatic agents, for example those known to modify cholinergic transmission such as M1 muscarinic receptor agonists or allosteric modulators, M2 muscarinic antagonists, acetylcholinesterase inhibitors (such as tetrahydroaminoacridine, donepezil hydrochloride and rivastigmine), nicotinic receptor agonists or allosteric modulators (such as α7 agonists or allosteric modulators or α4β2 agonists or allosteric modulators), PPAR agonists (such as PPARγ agonists), 5-$HT_4$ receptor partial agonists, 5-$HT_6$ receptor antagonists or 5HT1A receptor antagonists and NMDA receptor antagonists or modulators, or disease modifying agents such as β- or γ-secretase inhibitors, mitochondrial stabilisers, microtubule stabilisers or modulators of Tau pathology such as Tau aggregation inhibitors (e.g. methylene blue and REMBER™).

When a compound of formula (I) or a pharmaceutically acceptable salt thereof is used in combination with other therapeutic agents, the compounds may be administered either sequentially or simultaneously by any convenient route.

The invention thus provides, in a further aspect, a combination comprising a compound of formula (I) or a pharmaceutically acceptable salt thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable salt thereof is used in combination with a second therapeutic agent active against the same disease state the dose of each compound may differ from that when the compound is used alone. Appropriate doses will be readily appreciated by those skilled in the art.

Pharmaceutical compositions can be administered to patients by any convenient route. For example, pharmaceutical compositions include those adapted for (1) oral administration such as tablets, capsules, caplets, pills lozenges, powders, syrups, elixirs, suspensions, solutions, emulsions, sachets and cachets; (2) parenteral administration such as sterile solutions, suspensions, implants and powders for reconstitution; (3) transdermal administration such as transdermal patches; (4) inhalation and intranasal such as dry powders, aerosols, suspensions and solutions (sprays and drops); (5) buccal and sublingual administration such as lozenges, patches, sprays, drops, chewing gums and tablets. Orally administrable pharmaceutical compositions are generally preferred.

The compounds of formula (I) or pharmaceutically acceptable salt thereof may be milled using known milling procedures such as wet milling to obtain a particle size appropriate for tablet formation and for other formulation types. Finely divided (nanoparticulate) preparations of the compounds of the invention may be prepared by processes known in the art, for example WO 02/00196.

Tablets and capsules for oral administration may be in unit dose form, and may contain conventional excipients, such as diluents, binding agents, lubricants, disintegrants, glidants, granulating agents, coating agents and wetting agents. The skilled artisan will appreciate that certain pharmaceutically acceptable excipients may serve more than one function and may serve alternative functions depending on how much of the excipient is present in the formulation and what other ingredients are present in the formulation. The tablets may be coated according to methods well known in normal pharmaceutical practice.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable compositions will contain 0.1 to 1000 mg, more suitably 0.1 to 200 mg and even more suitably 1.0 to 200 mg of the compound of formula (I) or a pharmaceutically acceptable salt thereof and 0.1 to 2 g of one or more pharmaceutically acceptable carriers. Such pharmaceutical compositions may be administered more than once a day, for example two or three a day. Such therapy may extend for a number of weeks, months or years.

The present invention also provides a process for the preparation of a compound of formula (I) or a salt thereof, which process comprises:

a) reacting a compound of formula (II) or a salt thereof:

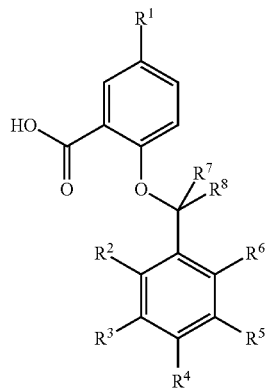

(II)

wherein $R^2$, $R^3$, $R^4$, $R^5$, $R^6$, $R^7$ and $R^8$ are as defined above, and wherein $R^1$ is as defined above with the proviso that $R^{14}$ is not hydroxy, with a A-$NH_2$ or a salt thereof; or b) reacting a compound of formula (VI) or a salt thereof:

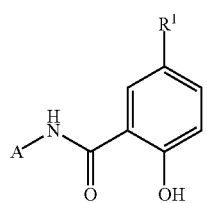

(VI)

wherein A is as defined above, wherein $R^1$ is as defined above with the proviso that $R^1$ is not hydroxy, with a compound of formula (IV) or a salt thereof:

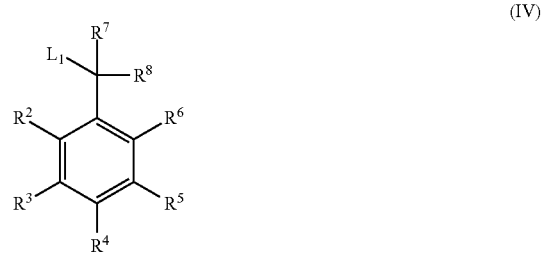

(IV)

wherein $R^2$, $R^3$, $R^4$, $R^5$, $R^6$, $R^7$ and $R^8$ are as defined above and wherein $L_1$ is a suitable leaving group, such as a halo group (e.g. bromo) or a hydroxy group;

c) reacting a compound of formula (VII) or a salt thereof:

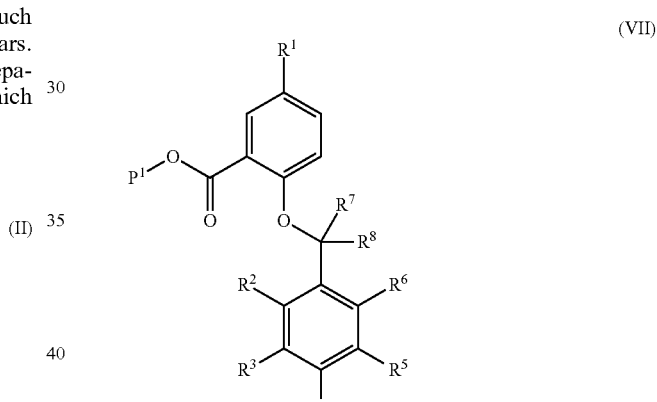

(VII)

wherein $R^2$, $R^3$, $R^4$, $R^5$, $R^6$, $R^7$ and $R^8$ are as defined above, wherein $R^1$ is as defined above with the proviso that $R^{14}$ is not hydroxyl, and wherein $P^1$ represents a suitable protecting group such as methyl, with A-$NH_2$ or a salt thereof; or d) interconversion of one compound of formula (I) or a salt thereof to another compound of formula (I), or a salt thereof; or e) deprotection of a compound of formula (I) or a salt thereof that is protected.

Process (a) typically utilises activating agents such as 1-(3-dimethylaminopropyl)-3-ethylcarbodiimide hydrochloride (EDC) together with 1-hydroxybenzotriazole (HOBT), or HATU, or CDI (N,N'-carbonyldiimidazole) in a suitable solvent at a suitable temperature. Where EDC/HOBT are used, the reaction may optionally take place in the presence of a base (e.g. triethylamine, diisopropylethylamine or N-ethyl morpholine). Suitable solvents for this reaction include dichloromethane (DCM) or dimethylformamide (DMF) and a suitable temperature would be e.g. between 15° C. and 40° C. Where CDI is used, a suitable solvent would be THF (tetrahydrofuran). The reaction is a two step process where the reaction of CDI with the acid is carried out at a suitable temperature such as room temperature, followed by addition of the amine with stirring at a suitable temperature e.g. reflux. Where HATU is used, the reaction may optionally take place in the presence of a base (e.g. diisopropylethylamine). Suitable solvents for this reaction include dimethylformamide (DMF) and a suitable temperature would be e.g. room temperature.

Alternatively, process (a) may comprise a step of converting the compound of formula (II) into the corresponding acyl chloride, followed by reaction with A-$NH_2$ or a salt thereof. The step of converting the compound of formula (II) to an acyl chloride typically comprises treatment of the compound of formula (II) with oxalyl chloride in a suitable solvent (e.g. DCM in the presence of a catalytic amount of DMF) at a suitable temperature (e.g. room temperature). The step of reacting the acyl chloride with A-$NH_2$ or a salt thereof optionally takes place in the presence of a base (e.g. diisopropylethylamine or triethylamine) in a suitable solvent such as DCM, at a suitable temperature e.g. between room temperature and 40° C.

When $L_1$ is a hydroxyl group, process (b) is a two step process. The first step is the formation of a basic salt by treatment of the compound of formula (VI) with a base (e.g. potassium hydroxide) in a suitable solvent (such as methanol), at a suitable temperature (such as room temperature). The second step involves the addition of the compound of formula (IV) and takes place in a suitable solvent (such as DMF) at a suitable temperature, such as reflux. Alternatively, when $L_1$ is a hydroxy group, process (b) may take place in the presence of coupling agents such as DEAD (diethyl azodicarboxylate) or DIAD (diisopropyl azodicarboxylate), and $Ph_3P$ (triphenyl phosphine). The reaction takes place in a suitable solvent such as toluene or DCM at a suitable temperature such as from 0° C. to room temperature.

When $L_1$ is halo (e.g. bromo), process (b) typically takes place in the presence of a base such as potassium carbonate or caesium carbonate, in a suitable solvent (e.g. DMF or acetone) at a suitable temperature (e.g. between room temperature and reflux).

Process (c) may be used where the acid is unstable and requires protection. For certain compounds of formula (VII), process (c) is a one step process that is conducted as described above for process (a). For other compounds, process (c) may be a two step process. The first step comprises treatment with potassium trimethylsilanolate. The second step comprises reaction with A-$NH_2$ or a salt thereof. This step may be conducted as described above for process (a).

Process (d) utilises standard chemical transformations known to a person of ordinary skill in the art.

Compounds of formula (I) where $R^1$ represents:
—O-nitrogen containing monoheterocyclic ring with the proviso that the atom directly attached to the oxygen is not nitrogen; or
—$(O)_n(CH_2)_pR^{10}$, where n represents 1, p represents 1, 2 or 3 and $R^{10}$ represents —$NR^{11}R^{12}$, or a nitrogen containing monoheterocyclic ring which ring is optionally substituted with one, two or three methyl groups;
may be prepared by reaction of the corresponding compound of formula (I) wherein $R^1$ represents hydroxy with the corresponding alcohol. This reaction typically takes place in the presence of coupling agents such as DIAD (diisopropyl azodicarboxylate) and $Ph_3P$ (triphenyl phosphine) in a suitable solvent such as toluene, at a suitable temperature such as 115° C.

Compounds of formula (I) where $R^1$ represents —$(O)_n(CH_2)_pR^{10}$, where n represents 0, p represents 1 and $R^{10}$ represents —$NR^{11}R^{12}$, or a nitrogen containing monoheterocyclic ring which ring is optionally substituted with one, two or three methyl groups and which ring is attached to the carbon by a nitrogen atom, can be prepared by reaction of the corresponding compound of formula (I) wherein $R^1$ represents $COR^{10}$, where $R^{10}$ represents hydrogen (i.e. formyl) by reductive alkylation of the corresponding amine. The reaction utilizes a reducing agent (e.g. sodium triacetoxyborohydride) optionally in the presence of an acid (e.g. acetic acid) in a suitable solvent such as DCE at a suitable temperature such as 50° C.

Compounds of formula (I) where $R^1$ represents —CNOH may be prepared from compounds of formula (I) wherein $R^1$ represents —$(CO)R^{10}$, wherein $R^{10}$ represents hydrogen (i.e. formyl) by reaction with hydroxylamine hydrochloride. This reaction typically takes place in the presence of a base (e.g. pyridine) in a suitable solvent (e.g. methanol) at a suitable temperature (e.g. room temperature).

Compounds of formula (I) where $R^1$ represents $R^{13}$ can be prepared by reaction of the corresponding compound of formula (I) wherein $R^1$ represents halo (e.g. bromo) with the corresponding amine in the presence of coupling agents such as 2,2'-bis(diphenylphosphino)-1,1'-binaphthyl and tris (dibenzylideneacetone)dipalladium(0). The reaction optionally takes place in the presence of a base such as cesium carbonate. The reaction takes place in a suitable solvent such as toluene, at a suitable temperature, such as reflux.

Compounds of formula (I) where $R^1$ represents a nitrogen containing heteroaryl ring, which nitrogen containing heteroaryl ring is optionally substituted by one, two or three groups selected from $NH_2$, $(C_{1-3}alkylene)R^{13}$, $(C_{1-3}alkylene)(CO)_qR^{14}$, $C_{1-4}alkyl$ and halo may be prepared by reaction of the corresponding compound of formula (I) wherein $R^1$ represents halo (e.g. bromo) with the corresponding boronic acid or dioxoborolane compound.

Where the boronic acid is used, the reaction takes place in the presence of a suitable coupling agent such as tetrakis (triphenylphosphine)palladium(0) or bis(triphenylphosphine)palladium(II) chloride optionally in the presence of a base, such as sodium carbonate. The reaction takes place in a suitable solvent (such as DME or 1,4-dioxane) and at a suitable temperature such as 100-140° C.

Where the corresponding dioxoborolane is used, the reaction takes place in the presence of a suitable coupling agent such as tetrakis(triphenylphosphine)palladium(0), optionally in the presence of a base, such as sodium carbonate or tripotassium phosphate. The reaction takes place in a suitable solvent (such as DME or 1,4-dioxane) at a suitable temperature such as 80-140° C.

The skilled person will also appreciate that where $R^1$ is pyrazol-4-yl or pyrazol-5-yl substituted by $(C_{1-3}alkylene)R^{13}$ or $(C_{1-3}alkylene)(CO)_qR^{14}$, these compounds may be prepared from the corresponding unsubstituted compound by reaction with a compound of formula Z—$(C_{1-3}alkylene)R^{13}$ or Z—$(C_{1-3}alkylene)(CO)_qR^{14}$ where Z is halo. The reaction typically takes place in the presence of a suitable base such as potassium carbonate at a suitable temperature, such as 50° C.

Compounds of formula (I) and salts thereof where $R^1$ represents:
(CH=CH)(CO)$R^{14}$ wherein $R^{14}$ represents $C_{1-3}alkoxy$;
$(C_{2-3}alkylene)(CO)_qR^{14}$ wherein the alkylene is a straight chain alkylene, q is 1 and $R^{14}$ represents hydroxy or $C_{1-3}alkoxy$;
$(C_{2-3}alkylene)(CO)_qR^{14}$ wherein the alkylene is a straight chain alkylene, q is 0 and $R^{14}$ represents hydroxy; or
$(C_{2-3}alkylene)NHCOR^{14}$ wherein the alkylene is a straight chain alkylene and $R^{14}$ represents $C_{1-3}alkoxy$;

may be prepared from compounds of formula (I) where $R^1$ represents halo in the same manner as described in Scheme 3 in relation to compounds of formula (VII).

Compounds of formula (I) of salts thereof wherein $R^1$ represents (CH=CH)$CO_2CH_2CH_3$ can alternatively be prepared by reaction of the corresponding compound of formula (I) wherein $R^1$ represents $COR^{10}$, wherein $R^{10}$ represents hydrogen (i.e. formyl) with KHMDS and triethyl phosphonoacetate The reaction takes place in a suitable solvent such as tetrahydrofuran, at a suitable temperature such as −78° C.

Compounds of formula (I) or salts thereof wherein $R^1$ is ($C_{1-3}$alkylene)(CO)$_q R^{14}$ wherein the alkylene group is $CH_2$, $CH(CH_3)$, $CH_2CH(CH_3)$ or $C(CH_3)_2$, wherein q is 0 or 1 and $R^{14}$ represents hydroxy may be prepared as described in steps (xiii) and (xiv) of Scheme 3 from the corresponding ester. Alternatively, compounds of formula (I) or salts thereof where $R^1$ represents $CH(CH_3)(CO)_q R^{14}$, q represents O and $R^{14}$ represents hydroxy may be prepared by reduction of the corresponding aldehyde (e.g. the corresponding compound of formula (I) wherein $R^1$ represents $COR^{10}$, wherein $R^{10}$ represents hydrogen (i.e. formyl)). Sodium borohydride may be used as a reducing agent in a suitable solvent such as ethanol at a suitable temperature such as room temperature. The reaction may optionally take place in the presence of an acid e.g. boric acid. Similarly, compounds of formula (I) or salts thereof where $R^1$ represents $C(CH_3)_2(CO)_q R^{14}$, q represents 0 and $R^{14}$ represents hydroxy may be prepared by reaction of the corresponding aldehyde (e.g. the corresponding compound of formula (I) wherein $R^1$ represents $COR^{10}$, wherein $R^{10}$ represents hydrogen (i.e. formyl)) with methylmagnesium bromide. The reaction takes place in a suitable solvent such as THF at a suitable temperature such as between 0° C. and room temperature.

Compounds of formula (I) or salts thereof wherein $R^1$ is ($C_{1-3}$alkylene)$NHCOR^{14}$ wherein the alkylene group $CH_2$, $CH(CH_3)$, $CH_2CH(CH_3)$ or $C(CH_3)_2$ and wherein $R^{14}$ represents $C_{1-3}$alkoxy may be prepared as described in steps (x) to (xii) from the corresponding ester. Alternatively, compounds of formula (I) where $R^1$ represents ($C_{1-3}$alkylene)$NHCOR^{14}$ wherein the alkylene is $CH_2$ and $R^{14}$ represents —$OC_{1-3}$alkyl may be prepared from compounds of formula (I) wherein $R^1$ represents —CNOH in a two step process. First, the amine is generated by treatment with zinc in the presence of acid (e.g. HCl). The reaction takes place in a suitable solvent e.g. THF at a suitable temperature e.g. 60° C. The amine is then reacted with a compound of formula $L_2$-$CO_2C_{1-3}$alkyl wherein $L_2$ is halo. The reaction takes place at a suitable temperature such as room temperature. Compounds of formula (I) wherein $R^1$ represents ($C_{1-3}$alkylene)$NHCOR^{14}$ wherein the alkylene is $CH(CH_3)$ and $R^{14}$ represents —$OC_{1-3}$alkyl may be prepared from corresponding compounds wherein $R^1$ represents —$C(CH_3)NOH$ in a similar fashion. The compounds wherein $R^1$ represents —$C(CH_3)NOH$ may be prepared from compounds of formula (I) wherein $R^1$ represents —$(CO)R^{10}$, wherein $R^{10}$ represents methyl by reaction with hydroxylamine hydrochloride. This reaction typically takes place in the presence of a base (e.g. pyridine) in a suitable solvent (e.g. methanol) at a suitable temperature (e.g. room temperature).

Compounds of formula (I) where $R^1$ represents ($C_{1-3}$alkylene)(CO)$_q R^{14}$, q represents 0 or 1 and $R^{14}$ represents hydroxy may be prepared by reaction of the corresponding compound of formula (I) where $R^1$ represents ($C_{1-3}$alkylene)(CO)$_q R^{14}$, q represents 1 and $R^{14}$ represents $OC_{1-3}$alkyl by treatment with lithium hydroxide in a suitable solvent such as a mixture of THF and water, at a suitable temperature such as room temperature.

Similarly, compounds of formula (I) where $R^1$ represents (CH=CH)(CO)$R^{14}$ or ($C_{1-3}$alkylene)$NHCOR^{14}$ wherein $R^{14}$ represents hydroxy may be prepared by reaction of the corresponding compound of formula (I) where $R^1$ represents (CH=CH)(CO)$R^{14}$ or ($C_{1-3}$alkylene)$NHCOR^{14}$, wherein $R^{14}$ represents $OC_{1-3}$alkyl by treatment with lithium hydroxide in a suitable solvent such as a mixture of THF and water, at a suitable temperature such as room temperature.

Compounds of formula (I) or salts thereof wherein $R^1$ represents —$(SO_2)R^{13}$ wherein $R^{13}$ represents —$NR^{11}R^{12}$, or a nitrogen containing monoheterocyclic ring which ring is optionally substituted with one, two or three methyl groups and wherein the nitrogen containing monoheterocyclic ring is attached to the sulphur via a nitrogen atom, may be prepared from compounds of formula (I) where $R^1$ represents halo in the same manner as described in steps (xviii) and (xix) of Scheme 5.

Compounds of formula (I) or salts thereof wherein $R^1$ represents —(CO)$R^{10}$ wherein $R^{10}$ represents —$NR^{11}R^{12}$, or a nitrogen containing monoheterocyclic ring which ring is optionally substituted with one, two or three methyl groups and which monocyclic ring is attached to the carbonyl group via a nitrogen atom may be prepared from the corresponding compounds in which $R^1$ is a carboxylic acid. This process may be carried out as described above for process (a). The carboxylic acid compounds can be prepared from the corresponding compounds of formula (I) wherein $R^1$ represents $COR^{10}$, wherein $R^{10}$ represents hydrogen (i.e. formyl) by treatment with potassium permanganate. This reaction takes place in a suitable solvent such as acetone at a suitable temperature such as room temperature.

Process (e) is a deprotection reaction and the nature of the reaction will depend upon the protecting group. When an amine is protected by a protecting group such as 1,1-dimethylethyl carboxylate, deprotection comprises treatment with trifluoroacetic acid in a suitable solvent (e.g. DCM) at a suitable temperature e.g. between room temperature and 30° C. When an acid group is protected by a protecting group such as methyl, deprotection may comprise treatment with lithium hydroxide in a suitable solvent such as a mixture of THF and water, at a suitable temperature such as room temperature.

Compounds of formula (II) or salts thereof, compounds of formula (VI) or salts thereof and compounds of formula (VII) or salts thereof where $R^1$ represents:
halo;
halo$C_{1-3}$alkyl;
—CN,
—(CO)$R^{10}$ wherein $R^{10}$ represents hydrogen, $C_{1-3}$alkyl, —$NR^{11}R^{12}$, or a nitrogen containing monoheterocyclic ring which ring is optionally substituted with one, two or three methyl groups;
—(O)$_n$(CH$_2$)$_p R^{10}$ wherein n represents 0 or 1, p represents 1, 2 or 3 and $R^{10}$ represents hydrogen or $C_{1-3}$alkyl; or
—(O)$_n$(CH$_2$)$_p R^{10}$ wherein n represents 0, p represents 1, 2 or 3 and $R^{10}$ represents —$NR^{11}R^{12}$, or a nitrogen containing monoheterocyclic ring which ring is optionally substituted with one, two or three methyl groups;

may be prepared in accordance with the following process:

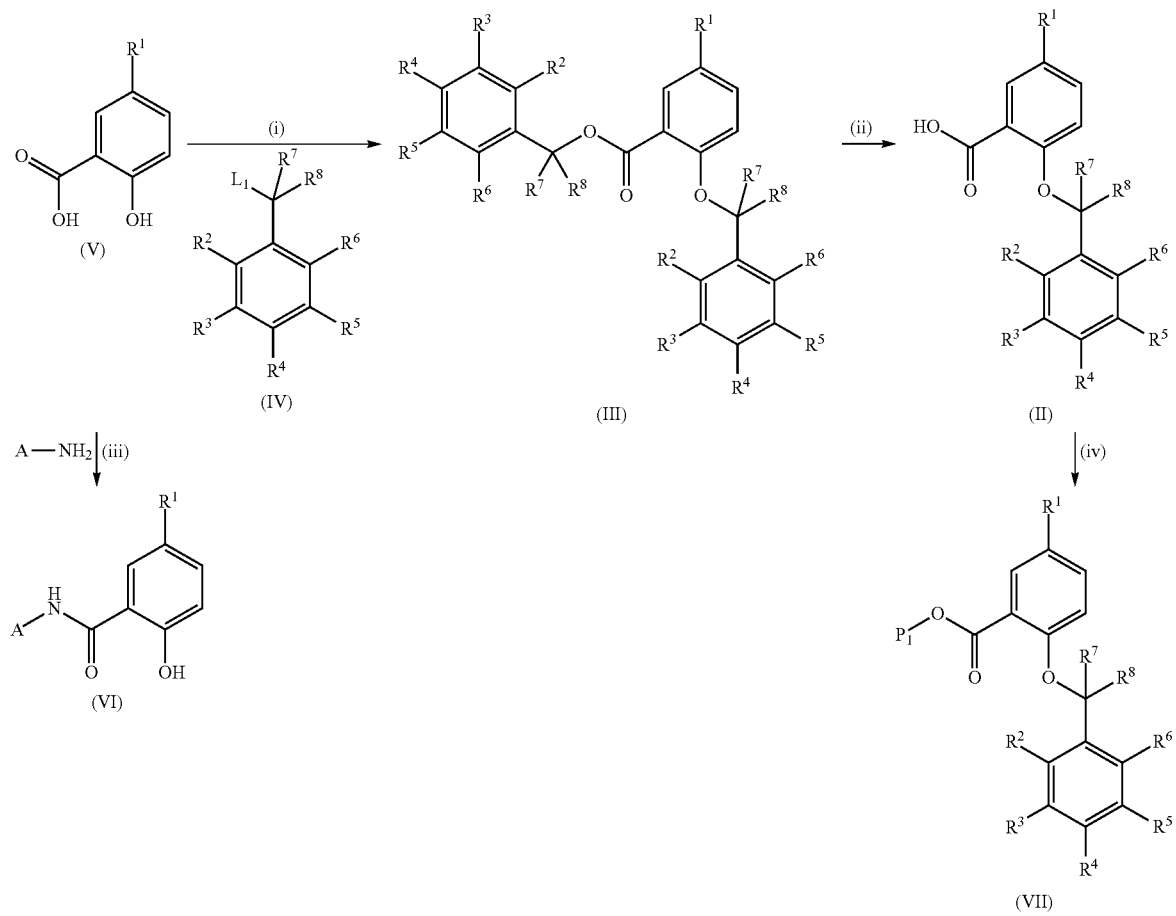

wherein $L_1$, A, $R^1$, $R^2$, $R^3$, $R^4$, $R^5$, $R^6$, $R^7$ and $R^8$ are as defined above and wherein $P_1$ represents a suitable protecting group, such as methyl.

Step (i) may be carried out as described above for process (b).

Step (ii) typically comprises treatment of a compound of formula (III) with lithium hydroxide in a suitable solvent, such as a mixture of THF (tetrahydrofuran) and water or a mixture of THF, methanol and water, at a suitable temperature such as between room temperature and reflux. Alternatively, step (ii) may comprise refluxing in a mixture of ethanol and 2M NaOH.

Step (iii) may be carried out as described above for process (a).

Step (iv) is a protection step. The nature of this reaction will depend upon the protecting group. Where $P_1$ represents methyl, this step comprises reaction with methanol, optionally in the presence of an acid (e.g. sulfuric acid).

Compounds of formula (VI) or salts thereof wherein $R^1$ is $(C_{1-3}\text{alkylene})(CO)_qR^{14}$ wherein q represents 0 or 1 and $R^{14}$ represents $C_{1-3}$alkoxy may additionally be prepared as described in step (iii) from the corresponding compound of formula (V). The compound of formula (V) may be prepared in accordance with the following process:

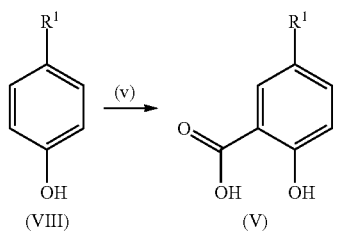

wherein $R^1$ is $(C_{1-3}\text{alkylene})(CO)_pR^{14}$, q represents 0 or 1 and $R^{14}$ represents $C_{1-3}$alkoxy.

Step (v) is a two step reaction. The first step comprises reaction with paraformaldehyde in the presence of a base such as triethylamine and a suitable solvent such as acetonitrile at a suitable temperature such as reflux. The second step comprises treatment with potassium permanganate Compounds of formula (III) where $R^1$ represents $-(O)_n(CH_2)_pR^{10}$, where n represents 0, p represents 1 and $R^{10}$ represents $-NR^{11}R^{12}$, or a nitrogen containing monoheterocyclic ring which ring is optionally substituted with one, two or three methyl groups and which ring is attached to the carbon by a nitrogen atom, can be prepared by reaction of the corresponding compound of formula (III) wherein $R^1$ represents $COR^{10}$, where $R^{10}$ represents hydrogen (i.e. formyl) by reductive alkylation of the corresponding amine. The reaction utilizes a reducing agent (e.g. sodium triacetoxyborohydride) optionally in the presence of an acid (e.g. acetic acid) in a suitable solvent such as DCE at a suitable temperature such as 50° C.

Compounds of formula (VII) where $R^1$ represents —$(O)_n$$(CH_2)_pR^{10}$, where n represents 0, p represents 3 and $R^{10}$ represents —$NR^{11}R^{12}$, or a nitrogen containing monoheterocyclic ring which ring is optionally substituted with one, two or three methyl groups and which ring is attached to the carbon by a nitrogen atom, can be prepared by reaction of the corresponding compound of formula (VII) wherein $R^1$ represents halo in a three step process. The first step comprises reaction with 3,3-bis(ethyloxy)-1-propene and takes place in the presence of a palladium acetate catalyst, optionally in the presence of a base such as potassium carbonate. A suitable solvent is DMF and a suitable temperature is 120° C. The second step comprises reductive alkylation of the corresponding amine. The reaction utilizes a reducing agent (e.g. sodium triacetoxyborohydride) optionally in the presence of an acid (e.g. acetic acid) in a suitable solvent such as DCE at a suitable temperature such as room temperature. The third step comprises hydrogenation of the double bond using hydrogen in the presence of Pd/C in methanol.

Compounds of formula (III) where $R^1$ represents —CNOH may be prepared from compounds of formula (III) wherein $R^1$ represents —$(CO)R^{10}$, wherein $R^{10}$ represents hydrogen (i.e. formyl) by reaction with hydroxylamine hydrochloride. This reaction typically takes place in the presence of a base (e.g. pyridine) in a suitable solvent (e.g. methanol) at a suitable temperature (e.g. room temperature).

Compounds of formula (III) where $R^1$ represents $R^{13}$ can be prepared by reaction of the corresponding compound of formula (III) wherein $R^1$ represents halo (e.g. bromo) with the corresponding amine in the presence of coupling agents such as 2,2'-bis(diphenylphosphino)-1,1-binaphthyl and tris(dibenzylideneacetone)dipalladium(0). The reaction optionally takes place in the presence of a base such as cesium carbonate. The reaction takes place in a suitable solvent such as toluene, at a suitable temperature, such as reflux.

Compounds of formula (III) where $R^1$ represents a nitrogen containing heteroaryl ring, which nitrogen containing heteroaryl ring is optionally substituted by one, two or three groups selected from $NH_2$, $(C_{1-3}alkylene)R^{13}$, $(C_{1-3}alkylene)(CO)_qR^{14}$, $C_{1-3}alkyl$ and halo may be prepared by reaction of the corresponding compound of formula (III) wherein $R^1$ represents halo (e.g. bromo) with the corresponding boronic acid or dioxoborolane compound.

Where the boronic acid is used, the reaction takes place in the presence of a suitable coupling agent such as tetrakis(triphenylphosphine)palladium(0) or bis(triphenylphosphine)palladium(II) chloride optionally in the presence of a base, such as sodium carbonate. The reaction takes place in a suitable solvent (such as DME or 1,4-dioxane) and at a suitable temperature such as 100-140° C.

Where the corresponding dioxoborolane is used, the reaction takes place in the presence of a suitable coupling agent such as tetrakis(triphenylphosphine)palladium(0), optionally in the presence of a base, such as sodium carbonate or tripotassium phosphate. The reaction takes place in a suitable solvent (such as DME or 1,4-dioxane) at a suitable temperature such as 80-140° C.

The skilled person will also appreciate that where $R^1$ is pyrazol-4-yl or pyrazol-5-yl substituted by $(C_{1-3}alkylene)R^{13}$ or $(C_{1-3}alkylene)(CO)_qR^{14}$, these compounds may be prepared from the corresponding unsubstituted compound by reaction with a compound of formula Z—$(C_{1-3}alkylene)R^{13}$ or Z—$(C_{1-3}alkylene)(CO)_qR^{14}$ where Z is halo. The reaction typically takes place in the presence of a suitable base such as potassium carbonate at a suitable temperature, such as 50° C.

Compounds of formula (III) or salts thereof wherein $R^1$ represents (CH=CH)$CO_2CH_2CH_3$ can alternatively be prepared by reaction of the corresponding compound of formula (III) wherein $R^1$ represents $COR^{10}$, wherein $R^{10}$ represents hydrogen (i.e. formyl) with KHMDS and triethyl phosphonoacetate The reaction takes place in a suitable solvent such as tetrahydrofuran, at a suitable temperature such as –78° C.

Compounds of formula (III) or salts thereof where $R^1$ represents $CH(CH_3)(CO)_qR^{14}$, q represents 0 and $R^{14}$ represents hydroxy may be prepared by reduction of the corresponding aldehyde (e.g. the corresponding compound of formula (III) wherein $R^1$ represents $COR^{10}$, wherein $R^{10}$ represents hydrogen (i.e. formyl)). Sodium borohydride may be used as a reducing agent in a suitable solvent such as ethanol at a suitable temperature such as room temperature. The reaction may optionally take place in the presence of an acid e.g. boric acid.

Compounds of formula (III) where $R^1$ represents $(C_{1-3}alkylene)NHCOR^{14}$ wherein the alkylene is $CH_2$ and $R^{14}$ represents —$OC_{1-3}alkyl$ may be prepared from compounds of formula (III) wherein $R^1$ represents —CNOH in a two step process. First, the amine is generated by treatment with zinc in the presence of acid (e.g. HCl). The reaction takes place in a suitable solvent e.g. THF at a suitable temperature e.g. 60° C. The amine is then reacted with a compound of formula $L_2$-$CO_2C_{1-3}alkyl$ wherein $L_2$ is halo. The reaction takes place at a suitable temperature such as room temperature. Compounds of formula (III) wherein $R^1$ represents $(C_{1-3}alkylene)NHCOR^{14}$ wherein the alkylene is $CH(CH_3)$ and $R^{14}$ represents —$OC_{1-3}alkyl$ may be prepared from corresponding compounds wherein $R^1$ represents —$C(CH_3)NOH$ in a similar fashion. The compounds wherein $R^1$ represents —$C(CH_3)NOH$ may be prepared from compounds of formula (III) wherein $R^1$ represents —$(CO)R^{10}$, wherein $R^{10}$ represents methyl by reaction with hydroxylamine hydrochloride. This reaction typically takes place in the presence of a base (e.g. pyridine) in a suitable solvent (e.g. methanol) at a suitable temperature (e.g. room temperature).

Compounds of formula (III) or salts thereof wherein $R^1$ represents —$(SO_2)R^{13}$ wherein $R^{13}$ represents —$NR^{11}R^{12}$, or a nitrogen containing monoheterocyclic ring which ring is optionally substituted with one, two or three methyl groups and wherein the nitrogen containing monoheterocyclic ring is attached to the sulphur via a nitrogen atom, may be prepared from compounds of formula (III) where $R^1$ represents halo in the same manner as described in steps (xviii) and (xix) of Scheme 5.

Compounds of formula (III) or salts thereof wherein $R^1$ represents —$(CO)R^{10}$ wherein $R^{10}$ represents —$NR^{11}R^{12}$, or a nitrogen containing monoheterocyclic ring which ring is optionally substituted with one, two or three methyl groups and which monocyclic ring is attached to the carbonyl group via a nitrogen atom may be prepared from the corresponding compounds in which $R^1$ is a carboxylic acid. This process may be carried out as described above for process (a). The carboxylic acid compounds can be prepared from the corresponding compounds of formula (III) wherein $R^1$ represents $COR^{10}$, wherein $R^{10}$ represents hydrogen (i.e. formyl) by treatment with potassium permanganate. This reaction takes place in a suitable solvent such as acetone at a suitable temperature such as room temperature.

Compounds of formula (VII) or salts thereof wherein $R^1$ represents:
(CH=CH)(CO)$R^{14}$ wherein $R^{14}$ represents $OC_{1-3}$alkyl;
($C_{2-3}$alkylene)(CO)$_q R^{14}$ wherein the alkylene is a straight chain alkylene, q is 1 and $R^{14}$ represents OH or $OC_{1-3}$alkyl;
($C_{2-3}$alkylene)(CO)$_q R^{14}$ wherein the alkylene is a straight chain alkylene, q is 0 and $R^{14}$ represents OH; or ($C_{2-3}$alkylene)NHCOR$^{14}$ wherein the alkylene is a straight chain alkylene and $R^{14}$ represents $OC_{1-3}$alkyl;

may be prepared from the corresponding compound of formula (VII) wherein $R^1$ represents halo in accordance with the following process:

Scheme 3

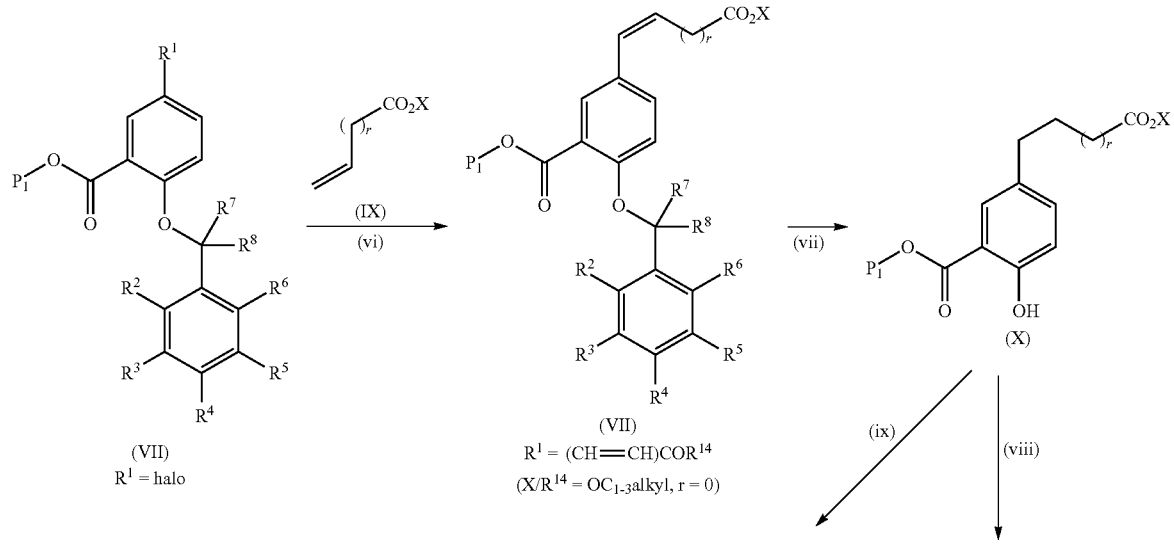

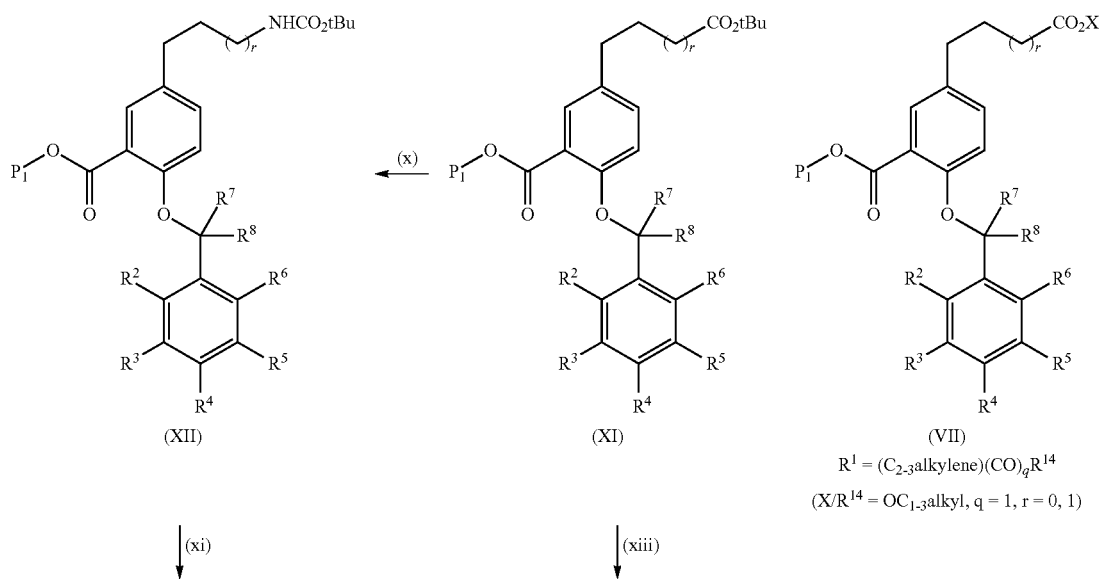

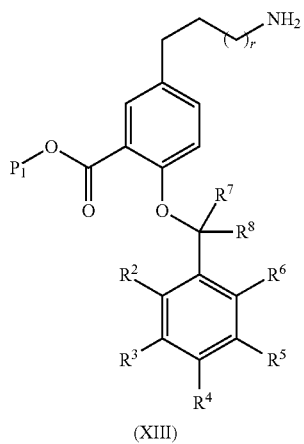

(XIII)

-continued

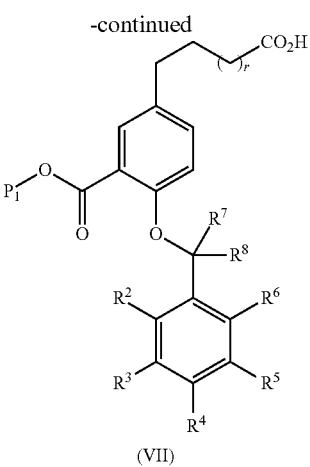

(VII)
$R^1 = (C_{2-3}\text{alkylene})(CO)_q R^{14}$
$(X/R^{14} = OH, q = 1, r = 0, 1)$

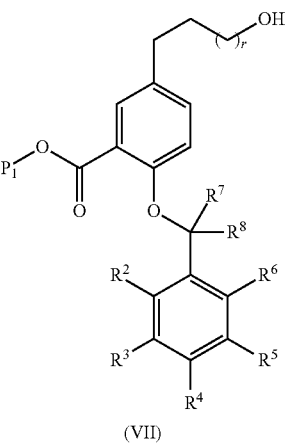

(VII)
$R^1 = (C_{2-3}\text{alkylene})(CO)_q R^{14}$
$(X/R^{14} = OH, q = 1, r = 0, 1)$

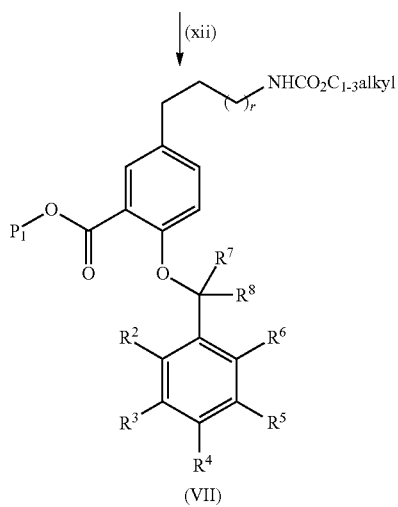

(VII)
$R^1 = (C_{2-3}\text{alkyleneNHCOR}^{14}$
$(R^{14} = OC_{1-3}\text{alkyl}, r = 0, 1)$ wherein $P_1$, A, $R^1$, $R^2$, $R^3$, $R^4$, $R^5$, $R^6$, $R^7$ and $R^8$ are as defined above, wherein X represents $C_{1-3}$alkyl or tert-butyl and wherein r represents 0 or 1.

Step (vi) comprises reaction with a compound of formula (IX). This step typically takes place in the presence of a palladium(0) catalyst such as palladium acetate and in the presence of a base such as potassium carbonate in a suitable solvent such as N,N-dimethylformamide at a suitable temperature such as 90° C.

Step (vii) comprises hydrogenation of the double bond and optionally substituted benzyl ether using hydrogen in the presence of Pd/C in methanol.

Steps (viii) and (ix) may be carried out as described above for process (b).

Step (x) is a Curtius reaction comprising reaction of the acid with diphenylphosphorylazide in the presence of base such as triethylamine in a suitable solvent such as a mixture of toluene/tert-butanol.

Step (xi) comprises deprotection of the tert-butyl ester by treatment with trifluoroacetic acid in a suitable solvent such as dichloromethane.

Step (xii) comprises reaction with the appropriate acid. This step may be carried out as described above for process (a).

Step (xiii) is a deprotection reaction and comprises treatment with trifluoroacetic acid in a suitable solvent (e.g. DCM) at a suitable temperature e.g. between room temperature and 30° C.

Step (xiv) comprises coupling the acid to give a mixed anhydride using isobutyl chloroformate in the presence of a base (N-methyl morpholine) in a suitable solvent such as tetrahydrofuran. The mixed anhydride is then reduced in situ using sodium borohydride.

Compounds of formula (VII) or salts thereof wherein $R^1$ is $(C_{1-3}\text{alkylene})(CO)_q R^{14}$ wherein the alkylene group $CH_2$, $CH(CH_3)$, $CH_2CH(CH_3)$ or $C(CH_3)_2$, wherein q is 0 or 1 and $R^{14}$ represents OH may be prepared as described in steps (xiii) and (xiv) from the corresponding compound of formula (XI).

Compounds of formula (VII) or salts thereof wherein $R^1$ is $(C_{1-3}\text{alkylene})NHCOR^{14}$ wherein the alkylene group $CH_2$, $CH(CH_3)$, $CH_2CH(CH_3)$ or $C(CH_3)_2$ and wherein $R^{14}$ represents $OC_{1-3}$alkyl may be prepared as described in steps (xi) to (xii) from the corresponding compound of formula (XII).

Compounds of formula (VII) where $R^1$ represents $(CH=CH)CO_2CH_2CH_3$ can alternatively be prepared by reaction of the corresponding compound of formula (VII)

wherein R¹ represents COR¹⁰, wherein R¹⁰ represents hydrogen (i.e. formyl) with KHMDS and triethyl phosphonoacetate. The reaction takes place in a suitable solvent such as tetrahydrofuran, at a suitable temperature such as −78° C.

Compounds of formula (II) or salts thereof wherein R¹ represents hydroxyl may be prepared in accordance with the following process:

Scheme 4

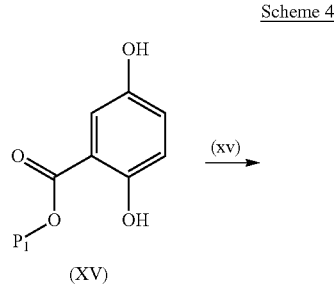

(XV)

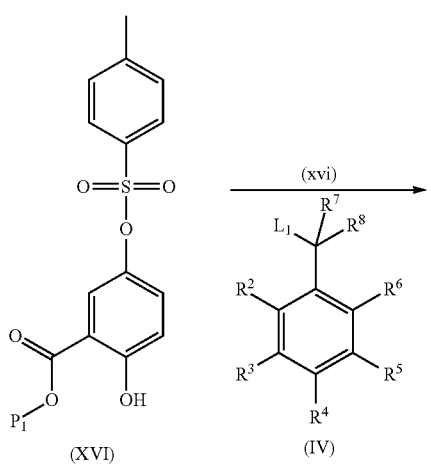

(XVI)

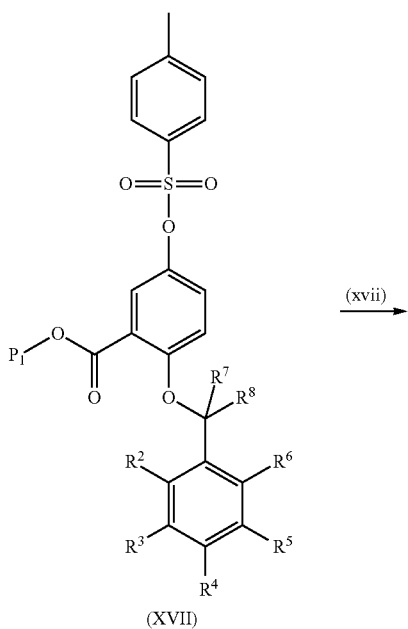

(XVII)

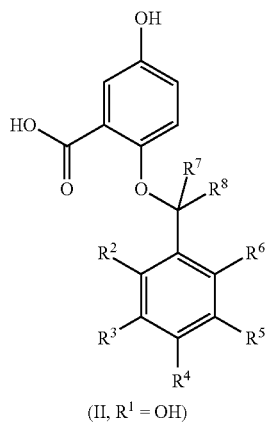

(II, R¹ = OH)

wherein $L_1$, $P_1$, $R^2$, $R^3$, $R^4$, $R^5$, $R^6$, $R^7$ and $R^8$ are as defined above.

Step (xv) comprises reaction with TsCl, optionally in the presence of a base such as potassium carbonate. The reaction takes place in a suitable solvent such as acetone, at a suitable temperature, such as reflux.

Step (xvi) may be carried out as described above for process (b).

Step (xvii) is a deprotection step and varies depending upon the nature of $P_1$. Where $P_1$ is methyl, this step may comprise boiling with potassium hydroxide in a suitable solvent e.g. mixture of ethanol and water.

Compounds of formula (II) where R¹ represents:
—O-nitrogen containing monoheterocyclic ring with the proviso that the atom directly attached to the oxygen is not nitrogen; or
—$(O)_n(CH_2)_pR^{10}$, where n represents 1, p represents 1, 2 or 3 and $R^{10}$ represents —$NR^{11}R^{12}$, or a nitrogen containing monoheterocyclic ring which ring is optionally substituted with one, two or three methyl groups;
may be prepared by reaction of the corresponding compound of formula (II) wherein R¹ represents hydroxy with the corresponding alcohol. This reaction typically takes place in the presence of coupling agents such as DIAD (diisopropyl azodicarboxylate) and Ph₃P (triphenyl phosphine) in a suitable solvent such as toluene, at a suitable temperature such as 115° C.

Compounds of formula (II) wherein R¹ represents hydroxyl can be used to prepare compounds of formula (II) where R¹ represents $(O)_n(CH_2)_pR^{10}$, where n represents 0, p represents 1, 2 or 3 and $R^{10}$ represents —$NR^{11}R^{12}$ or a nitrogen containing monoheterocyclic ring which ring is optionally substituted with one, two or three methyl groups. Where $R^{10}$ is not a tertiary amine, the nitrogen will need to be protected during the reaction with a suitable protecting group (e.g. 1,1-dimethylethyl carboxylate). The reaction is a two step process. In the first step, the compound of formula (II) wherein R¹ represents hydroxyl is treated with sodium hydride in a suitable solvent such as DMSO at a suitable temperature such as room temperature. The second step comprises reaction with $L_3$-$(CH_2)_pR^{10}$, wherein $R^{10}$ and p are as defined above and $L_3$ represents a suitable leaving group such as 4-methylbenzenesulfonate or 4-chlorophenyl)sulfonyl]oxy. This step takes place in a suitable solvent such as DMSO at a suitable temperature such as 75° C. Any protecting groups can be removed at this stage to generate a compound of formula (II), or following reaction with a compound of formula A-NH$_2$ (to generate a compound of formula (I)). Where the protecting group is 1,1-dimethylethyl carboxylate, this may be removed by treatment with trifluoroacetic acid.

Compounds of formula (II) wherein R$^1$ represents hydroxyl can be used to prepare compounds of formula (II) where R$^1$ represents —O(CH$_2$)$_2$—O—(CH$_2$)$_2$NH$_2$. The primary amine will need to be protected during the reaction with a suitable protecting group (e.g. 1,1-dimethylethyl carboxylate). The reaction is a two step process. In the first step, the compound of formula (II) wherein R$^1$ represents hydroxyl is treatment with 2,2-oxybis(ethane-2,1-diyl)bis(4-methylbenzenesulfonate). The reaction with 2,2-oxybis(ethane-2,1-diyl)bis(4-methylbenzenesulfonate) takes place in the presence of a suitable base such as potassium hydroxide in a suitable solvent such as methanol. The second step comprises reaction with the protected amine. The reaction with the protected amine takes place in the presence of a base such as cesium carbonate in a suitable solvent such as DMF at a suitable temperature such as 60° C. The protecting groups can be removed at this stage to generate a compound of formula (II), or following reaction with a compound of formula A-NH$_2$ (to generate a compound of formula (I)). Where the protecting group is 1,1-dimethylethyl carboxylate, this may be removed by treatment with trifluoroacetic acid.

Compounds of formula (II) or salts thereof wherein R$^1$ represents —(SO$_2$)R$^{13}$ wherein R$^{13}$ represents —NR$^{11}$R$^{12}$, or a nitrogen containing monoheterocyclic ring which ring is optionally substituted with one, two or three methyl groups and wherein the nitrogen containing monoheterocyclic ring is attached via a nitrogen atom, may be prepared in accordance with the following process:

Scheme 5

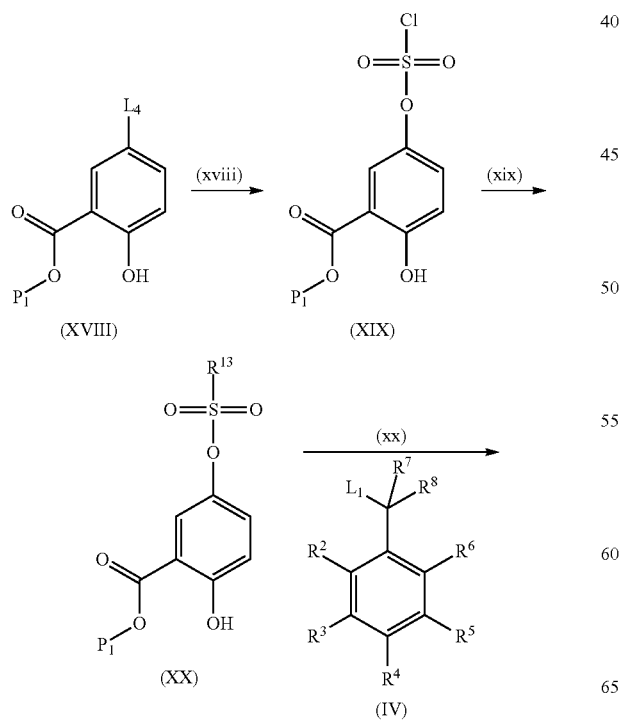

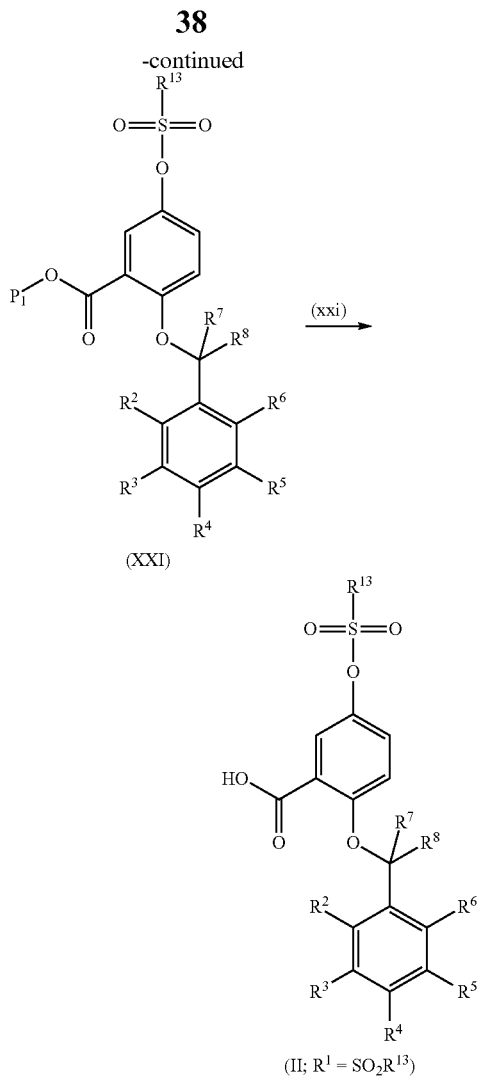

wherein L$_1$, P$_1$, R$^2$, R$^3$, R$^4$, R$^5$, R$^6$, R$^7$ and R$^8$ are as defined above and L$_4$ represents a suitable leaving groups such as a halo.

Step (xviii) comprises treatment with sulfurochloridic acid. The reaction takes place at a suitable temperature such as 0° C.

Step (xix) comprises reaction with the corresponding amine. This reaction takes place in a suitable solvent such as DCM at a suitable temperature such as room temperature.

Step (xx) may be carried out as described above for process (b).

Step (xxi) is a deprotection step and varies depending upon the nature of P$_1$. Where P$_1$ is methyl, this step may comprise boiling with potassium hydroxide in a suitable solvent e.g. mixture of ethanol and water.

Compounds of formula (II) or salts thereof wherein R$^1$ represents —(CO)R$^{10}$ wherein R$^{10}$ represents —NR$^{11}$R$^{12}$, or a nitrogen containing monoheterocyclic ring which ring is optionally substituted with one, two or three methyl groups and which monocyclic ring is attached to the carbonyl group via a nitrogen atom, may be prepared in accordance with the following process:

Scheme 6

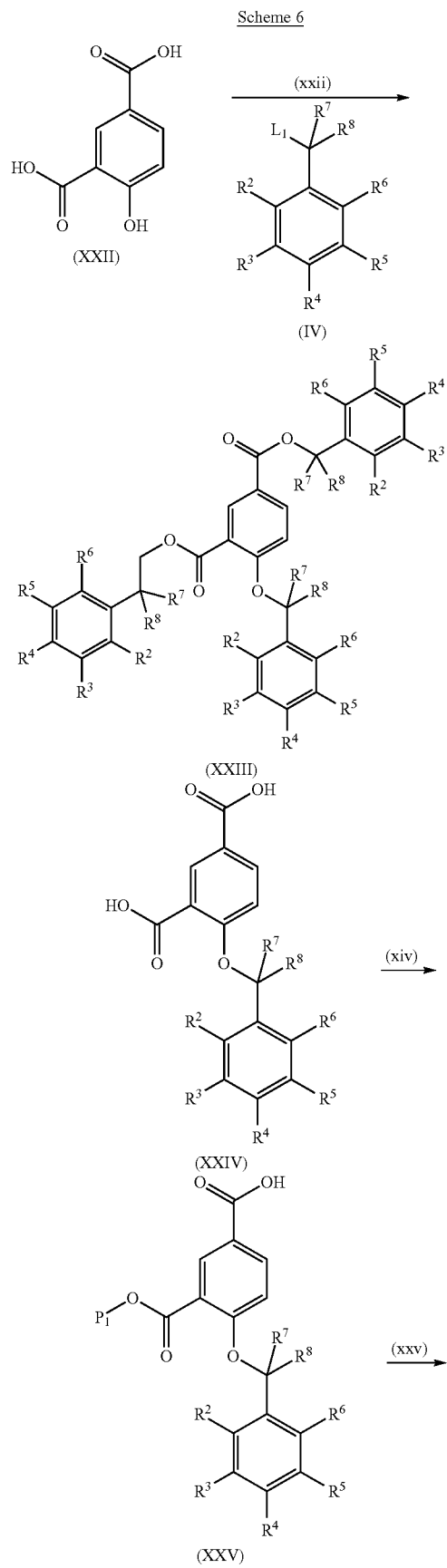

wherein $L_1$, $P_1$, $R^2$, $R^3$, $R^4$, $R^5$, $R^6$, $R^7$ and $R^8$ are as defined above.

Step (xxii) may be carried out as described above for process (b).

Step (xxiii) may be carried out as described above for step (ii).

Step (xxiv) is a protection step. The nature of this reaction will depend upon the protecting group. Where $P_1$ represents methyl, this step comprises reaction with methanol, optionally in the presence of an acid (e.g. sulfuric acid).

Step (xxv) may be carried out as described above for process (a).

Step (xxvi) is a deprotection step and varies depending upon the nature of $P_1$. Where $P_1$ is methyl, this step comprises treatment lithium hydroxide in a suitable solvent, such as a mixture of THF (tetrahydrofuran) and water, at a suitable temperature such as between room temperature and reflux.

Compounds of formula (IV), (V), (VIII), (XV), (XVIII), (XXII) and compounds of formula A-NH$_2$, (CH=CH)(CH$_2$)$_r$CO$_2$X, L$_2$-CO$_2$C$_{1-3}$alkyl and L$_3$-(CH$_2$)$_p$R$^{10}$ are either commercially available or may be readily prepared from commercially available compounds using procedures known to a person of ordinary skill in the art.

Certain compounds of formula (I) are also commercially available, including 5-bromo-2-(2-chlorobenzyloxy)-N-(pyridin-3-yl)benzamide, 5-chloro-2-[(phenylmethyl)oxy]-N-3-pyridinylbenzamide, 5-bromo-N-{3-[(methylamino)carbonyl]phenyl}-2-[phenylmethyl)oxy]benzamide and 5-chloro-2-[(2-cyanophenyl)methoxy]-N-phenylbenzamide.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

ABBREVIATIONS

BINAP 2,2'-Bis(diphenylphosphino)-1,1'-binaphthyl
CDI N,N'-Carbonyldiimidazole
DCE Dichloroethane
DCM Dichloromethane
DEAD Diethyl azodicarboxylate
DIAD Diisopropyl azodicarboxylate
DIPEA Diisopropylethylamine
DME 1,2-Dimethoxyethane
DMF N,N'-Dimethylformamide
DMSO Dimethyl sulfoxide
EDC/EDAC 1-(3-Dimethylaminopropyl)-3-ethylcarbodiimide hydrochloride
HATU O-(7-Azabenzotriazole-1-yl)-1,1,3,3-tetramethyluronium hexafluorophosphate
HOBT 1-Hydroxybenzotriazole
HPLC High performance liquid chromatography
KHMDS Potassium hexamethyldisilazane
MDAP Mass directed autopreparation
Pd/C Palladium on carbon
$PdCl_2$(dppf) 1,1'-Bis(diphenylphosphino)ferrocene-palladium(II) dichloride
$Pd_2$(dba)$_3$ Tris(dibenzylideneacetone)dipalladium(0)
$PdOAc_2$ Palladium acetate
Pd(PPh$_3$)$_4$ Tetrakis(triphenylphosphine)palladium(0)
Ph$_3$P Triphenyl phosphine
SCX Strong-cation exchanger
Tetrakis Tetrakis(triphenylphosphine)palladium(0)
THF Tetrahydrofuran
TLC Thin layer chromatography
TsCl 4-Toluenesulfonyl chloride

Description 1

2-Hydroxy-5-(1-methylethyl)benzoic acid (D1)

4-Isopropylphenol (2.7 g, 19.83 mmol) and $K_2CO_3$ (5.48 g, 39.7 mmol) were heated to 150° C. under an atmosphere of carbon dioxide. The cooled residue was suspended in ethyl acetate and acidified with 2N hydrochloric acid. The organic layer was separated and the combined extracts were dried ($MgSO_4$) and evaporated under reduced pressure to yield the title compound which was used in the next step without further purification. 2.0 g.
MS (electrospray): m/z [M+H]$^+$=181

Description 2

Phenylmethyl 5-(1-methylethyl)-2-[(phenylmethyl)oxy]benzoate (D2)

$K_2CO_3$ (3.83 g, 27.7 mmol) was added to a stirred solution of 2-hydroxy-5-(1-methylethyl)benzoic acid (may be prepared as described in Description 1; 2.0 g, 11.10 mmol) in acetone (80 ml), followed by the addition of (bromomethyl)benzene (4.75 g, 27.7 mmol). The mixture was refluxed for 12 h and then cooled to room temperature. The mixture was filtered and the filtrate was concentrated to a yellow solid. Flash chromatography over silica gel, using 1:10 ethyl acetate-petroleum ether yielded the title compound as a yellow oil. 1.0 g.
MS (electrospray): m/z [M+H]$^+$=361

Description 3

5-(1-Methylethyl)-2-[(phenylmethyl)oxy]benzoic acid (D3)

LiOH.H$_2$O (0.70 g, 16.65 mmol) was added to a stirred solution of phenylmethyl 5-(1-methylethyl)-2-[(phenylmethyl)oxy]benzoate (may be prepared as described in Description 2; 1.5 g, 4.16 mmol) in a 3:1 mixture of THF:H$_2$O (40 ml). The mixture was heated to reflux for 12 h and then diluted with ethyl acetate (50 ml). 10% aqueous HCl was added to the mixture to adjust the pH to 2. The organic phase was isolated, washed with brine, dried over $MgSO_4$, and concentrated to give a yellow oil. 700 mg.

Description 4

Phenylmethyl 5-bromo-2-[(phenylmethyl)oxy]benzoate (D4)

Method A
$K_2CO_3$ (701 mg, 5.00 mmol) was added to a stirred solution of 5-bromo-2-hydroxybenzoic acid (434 mg, 2.00 mmol) in acetone (30 ml), followed by the addition of (bromomethyl)benzene (855 mg, 5.00 mmol). The mixture was refluxed for 12 h and then cooled to room temperature. The mixture was filtered and the filtrate was concentrated to a yellow solid. Flash chromatography over silica gel, using 1:10 ethyl acetate-petroleum ether yielded the title compound as a pure, white powder. 700 mg.
MS (electrospray): m/z [M+Na]$^+$=419, 421
Method B
Solid potassium carbonate (2.76 g, 20 mmol) was added to a solution of 5-bromo-2-hydroxybenzoic acid (1.74 g, 8 mmol) in acetone (20 ml) and the reaction mixture was stirred at 20° C. for 10 mins. (Bromomethyl)benzene (3.42 g, 20 mmol) was added dropwise. The reaction mixture was stirred at 71° C. for 10 h. After cooling to room temperature, the mixture was filtered and the filtrate was concentrated to give a colourless oil. The crude product was purified on a silica gel column, eluting with hexane:ethyl acetate (100:5) to yield the title compound as a white solid. 3 g.
MS (electrospray): m/z MH$^+$=397; [M+Na]$^+$=419
Method C
Neat (bromomethyl)benzene (17.10 g, 100 mmol) was added to a stirred suspension of 5-bromo-2-hydroxybenzoic acid (8.68 g, 40.0 mmol) and potassium carbonate (13.82 g, 100 mmol) in acetone (150 ml) at 20° C. over 1 min. The reaction mixture was refluxed overnight. After filtration, the filtrate was evaporated to yield the title compound as an oil which was used in the next step without further purification. 15 g.
Method D
(Bromomethyl)benzene (34.2 ml, 288 mmol) was added over 5 minutes to a stirred suspension of 5-bromo-2-hydroxybenzoic acid (28.4 g, 131 mmol) and potassium carbonate (45.2 g, 327 mmol) in acetone (300 ml) in air at room temperature. The reaction mixture was stirred at 70° C. overnight. After filtering, the filtrate was evaporated to give a light yellow oil, dried in a vacuum to give yellow solid, which was washed by petroleum ether (300 ml×2), filtered and dried in vacuum to yield the title compound as a white solid. 48.2 g.

MS (electrospray): m/z [M+H]$^+$=397.

Description 5

5-Bromo-2-[(phenylmethyl)oxy]benzoic acid (D5)

Method A

LiOH.H$_2$O (222 mg, 5.29 mmol) was added to a stirred solution of phenylmethyl 5-bromo-2-[(phenylmethyl)oxy] benzoate (may be prepared as described in Description 4, method A; 700 mg, 1.76 mmol) in THF (15 ml) and water (5.00 ml). The mixture was refluxed for 12 h and then diluted with ethyl acetate (50 ml). 10% aqueous HCl was added to the mixture to adjust the pH to 2. The organic phase was isolated, washed with brine, dried over MgSO$_4$, and concentrated to yield the title compound as a yellow solid. 400 mg.

MS (electrospray): m/z [M+1-1]$^+$=307, 309

Method B

Solid LiOH (1.01 g, 42.1 mmol) was added in a single charge to a stirred solution of phenylmethyl 5-bromo-2-[(phenylmethyl)oxy]benzoate (may be prepared as described in Description 4, method B; 3 g, 7.55 mmol) in a 3:1 mixture of THF and water (40 ml) at 20° C. The reaction mixture was stirred at 71° C. for 16 h. After cooling to room temperature, it was diluted with ethyl acetate (200 ml). 10% aqueous HCl was added to the mixture to adjust the pH to 2. The organic phase was isolated, washed with brine, dried over Na$_2$SO$_4$, and concentrated to give a white solid. The crude product was purified by silica gel chromatography eluting with hexane: ethyl acetate (3:1) to yield the title compound as white solid. 2.1 g.

MS (electrospray): m/z [M+H]$^+$=307; [M+Na]$^+$=329, 331

Method C

Solid LiOH (5.04 g, 210 mmol) was added to a stirred solution of phenylmethyl 5-bromo-2-[(phenylmethyl)oxy] benzoate (may be prepared as described in Description 4, method C, 15 g, 37.8 mmol) in THF (150 ml) and water (50.0 ml) at 20° C. The reaction mixture was stirred at 71° C. overnight. After cooling to room temperature, the reaction mixture was diluted with ethyl acetate (200 ml). 10% aqueous HCl was added to the mixture to adjust the pH to 2. The organic phase was isolated, washed with brine, dried over Na$_2$SO$_4$ and concentrated to give a white solid. The crude product was purified by silica gel chromatography eluting with hexane:ethyl acetate (3:1) to yield the title compound. 6.1 g.

MS (electrospray): m/z [M+Na]$^+$=329, 331

Method D

Solid LiOH (0.53 g, 12.59 mmol) was added to a stirred solution of phenylmethyl 5-bromo-2-[(phenylmethyl)oxy] benzoate (may be prepared as described in Description 4; 1 g, 2.52 mmol) in tetrahydrofuran (20 ml) and water (4.00 ml) in air at room temperature. The reaction mixture was stirred at 70° C. overnight. After cooling to room temperature, the solvent was removed to obtain a white solid, which was dissolved in water (100 ml) and stirred in ice-water bath. 1N HCl (aq) was added to adjust the pH to 4. The white solid was filtered and dried in vacuum to yield the title compound as a white solid. 0.78 g.

MS (electrospray): m/z [M+Na]$^+$=328.8

Description 6

Phenylmethyl 5-(methyloxy)-2-[(phenylmethyl)oxy]benzoate (D6)

Potassium carbonate (690 mg, 5.00 mmol) was added to a stirred solution of 2-hydroxy-5-(methyloxy)benzoic acid (336 mg, 2.00 mmol) in acetone (20 ml) followed by the addition of ((bromomethyl)benzene (854 mg, 5.00 mmol). The mixture was refluxed for 12 h and then cooled to room temperature. The mixture was filtered and the filtrate was concentrated to a yellow solid. Flash chromatography over silica gel eluting with 1:10 ethyl acetate:petroleum ether yielded the title compound as a pure, white powder. 500 mg.

MS (electrospray): m/z [M+H]$^+$=349

Description 7

5-(Methyloxy)-2-[(phenylmethyl)oxy]benzoic acid (D7)

LiOH.H$_2$O (181 mg, 4.31 mmol) was added to a stirred solution of phenylmethyl 5-(methyloxy)-2-[(phenylmethyl) oxy]benzoate (may be prepared as described in Description 6; 500 mg, 1.44 mmol) in a 3:1 mixture of THF:H$_2$O (40 ml). The mixture was refluxed for 12 h and then diluted with ethyl acetate (50 ml). 10% aqueous HCl was added to the mixture to adjust the pH to 2. The organic phase was isolated, washed with brine, dried over MgSO$_4$, and concentrated to yield the title compound as a yellow solid. 280 mg.

MS (electrospray): m/z [M+1-1]$^+$=259

Description 8

Phenylmethyl 5-methyl-2-[(phenylmethyl)oxy]benzoate (D8)

K$_2$CO$_3$ (1379 mg, 9.99 mmol) was added to a stirred solution of 2-hydroxy-5-methylbenzoic acid (608 mg, 4.00 mmol) in acetone (10 ml), followed by the addition of (bromomethyl)benzene (1709 mg, 9.99 mmol). The mixture was refluxed for 12 h and then cooled to room temperature. The mixture was filtered and the filtrate was concentrated to a yellow solid. The crude product was purified by Flash chromatography over silica gel, eluting with 1:10 ethyl acetate-petroleum ether to yield the title compound as a white powder. 1.0 g.

MS (electrospray): m/z [M-1-H]$^+$=333

Description 9

5-Methyl-2-[(phenylmethyl)oxy]benzoic acid (D9)

LiOH.H$_2$O (0.379 g, 9.03 mmol) was added to a stirred solution of phenylmethyl 5-methyl-2-[(phenylmethyl)oxy] benzoate (may be prepared as described in Description 8; 1.0 g, 3.01 mmol) in a 3:1 mixture of THF:H$_2$O (40 ml). The mixture was refluxed for 12 h and then diluted with ethyl acetate (50 ml). 10% aqueous HCl was added to the mixture to adjust the pH to 2. The organic phase was isolated, washed with brine, dried over MgSO$_4$, and concentrated to yield the title compound as a yellow solid. 500 mg.

MS (electrospray): m/z [M+H]$^+$=243

Description 10

3,5-Dichloro-4-pyridazinamine and 5,6-dichloro-4-pyridazinamine (D10)

A solution of 3,4,5-trichloropyridazine (470 mg, 2.56 mmol) in ethanol (30 ml) was cooled to 0° C. and saturated with ammonia gas and stirred at room temperature for 4 days. The reaction mixture was then purged with nitrogen for 2 h, and filtered to remove ammonium chloride. The filter cake was washed with anhydrous ethanol, the filtrate and washes were used directly in the next step.

MS (electrospray): m/z [M+H]$^+$=164, 165, 166, 167, 168, 169

Description 11

4-Pyridazinamine (D11)

A solution of 3,5-dichloro-4-pyridazinamine and 5,6-dichloro-4-pyridazinamine (may be prepared as described in Description 10; 419.8 mg, 2.56 mmol), sodium hydroxide (246 mg, 6.14 mmol) and Pd/C (136 mg, 0.128 mmol) in ethanol (20 nil) was hydrogenated overnight. The reaction mixture was purged with nitrogen and filtered. The filtrate was concentrated to a residue and triturated with ethyl acetate. The mixture was filtered again to collect a solid which was dried to yield the title compound as a yellow solid. 98 mg.

MS (electrospray): m/z [M+H]$^+$=96

Description 12

Methyl 5-cyano-2-hydroxybenzoate (D12)

A suspension of methyl 5-bromo-2-hydroxybenzoate (2 g, 8.66 mmol) and copper cyanide (1.861 g, 20.78 mmol) in DMF (30 ml) was stirred under nitrogen at 140° C. for 20 h. The reaction mixture was then cooled, quenched with water (120 ml) and extracted with ethyl acetate (3×80 ml). The organic phase was washed with saturated brine (50 ml), dried over sodium sulphate and evaporated in vacuo to yield the title compound as a white solid. 1 g.

MS (electrospray): m/z, [M+H]$^+$=178

Description 13

Methyl 5-cyano-2-[(phenylmethyl)oxy]benzoate (D13)

A suspension of methyl 5-cyano-2-hydroxybenzoate (may be prepared as described in Description 12; 531 mg, 3 mmol), potassium carbonate (1037 mg, 7.50 mmol) and (bromomethyl)benzene (1026 mg, 6.00 mmol) in acetone (60 ml) was stirred at 50° C. overnight. The mixture was cooled and filtered. The filtrate was concentrated. The crude product was purified by silica gel chromatography eluting with hexane:ethyl acetate (10:1) to yield the title compound as a white solid. 480 mg.

MS (electrospray): m/z, [M+H]$^+$=268

Description 14

5-Cyano-2-[(phenylmethyl)oxy]benzoic acid (D14)

To a stirred solution of methyl 5-cyano-2-[(phenylmethyl)oxy]benzoate (may be prepared as described in Description 13; 200 mg, 0.75 mmol) in THF (2 ml) was added a solution of lithium hydroxide (94 mg, 2.25 mmol) in water (8 ml). The reaction mixture was stirred at room temperature overnight. The THF was removed and the mixture was adjusted to pH 7 with 2N HCl. The mixture was filtered and the residue dried to yield the title compound as a yellow solid. 160 mg.

MS (electrospray): m/z, [M+H]$^+$=254

Description 15

(4-Chlorophenyl)methyl 5-bromo-2-{[(4-chlorophenyl)methyl]oxy}benzoate (D15)

1-(Bromomethyl)-4-chlorobenzene (592 mg, 2.88 mmol) was added in a single charge to a stirred suspension of 5-bromo-2-hydroxybenzoic acid (250 mg, 1.15 mmol) and potassium carbonate (478 mg, 3.46 mmol) in acetone (40 ml) under nitrogen at 20° C. The reaction mixture was stirred at 55° C. for 18 h. The organic phase was evaporated and the residue was washed with water (25 ml), extracted with ethyl acetate (30×3 ml) and evaporated in vacuo to yield the title compound as an off-white solid. 320 mg.

MS (electrospray): m/z [M+Na]$^+$=487, 489, 491

Description 16

5-Bromo-2-{[(4-chlorophenyl)methyl]oxy}benzoic acid (D16)

A solution of lithium hydroxide (164 mg, 6.86 mmol) in water (20.00 mL) was added dropwise to a stirred solution of (4-chlorophenyl)methyl 5-bromo-2-{[(4-chlorophenyl)methyl]oxy}benzoate (may be prepared as described in Description 15; 320 mg, 0.69 mmol) in THF (20 ml) over 5 min. The reaction mixture was then stirred at 20° C. for 16 h. The organic phase was evaporated and the residual aqueous phase (20 ml) was extracted with ethyl acetate (20 ml). The aqueous phase (20 ml) was adjusted to pH 2 with 2M hydrochloric acid (1 ml) and was extracted with ethyl acetate (3×20 ml). The organic phase was evaporated in vacuo to give the title compound as a light yellow solid. 180 mg.

MS (electrospray): m/z [M+Na]$^+$=363, 365, 367

Description 17

[4-(Methyloxy)phenyl]methyl 5-bromo-2-({[4-(methyloxy)phenyl]methyl}oxy)benzoate (D17)

1-(Bromomethyl)-4-methoxybenzene (510 mg, 2.53 mmol) was added in a single charge to a stirred suspension of 5-bromo-2-hydroxybenzoic acid (250 mg, 1.15 mmol) and potassium carbonate (318 mg, 2.30 mmol) in acetone (40 ml) over 1 min under nitrogen. The reaction mixture was stirred at 55° C. for 16 h. The organic phase was evaporated and the residue was washed with water (25 ml), extracted with ethyl acetate (3×30 ml) and evaporated in vacuo to yield the title compound as a light yellow solid. 400 mg.

MS (electrospray): m/z [M+Na]$^+$=479, 481

Description D18

5-Bromo-2-({[4-(methyloxy)phenyl]methyl}oxy)benzoic acid (D18)

A solution of lithium hydroxide (367 mg, 8.75 mmol) in water (20 ml) was added dropwise to a stirred solution of [4-(methyloxy)phenyl]methyl 5-bromo-2-({[4-(methyloxy)phenyl]methyl}oxy)benzoate (may be prepared as described in Description 17; 400 mg, 0.875 mmol) in THF over 1 min. The reaction mixture was stirred at 20° C. for 16 h. The organic phase was evaporated and the aqueous phase (20 ml) was extracted with ethyl acetate (20 ml). The aqueous phase (20 ml) was adjusted to pH 2 with 2M hydrochloric acid (1 ml) and was extracted with ethyl acetate (3×20 ml). The organic phase was evaporated in vacuo to yield the title compound as a light yellow solid. 200 mg.

MS (electrospray): m/z [M+Na]$^+$=359, 361

Description 19

Phenylmethyl 5-fluoro-2-[(phenylmethyl)oxy]benzoate (D19)

A suspension of 5-fluoro-2-hydroxybenzoic acid (468 mg, 3 mmol), potassium carbonate (1037 mg, 7.50 mmol) and (bromomethyl)benzene (1283 mg, 7.50 mmol) in acetone (60 ml) was stirred at 50° C. overnight. The mixture was cooled and filtered. The filtrate was concentrated and the crude product was purified by silica gel chromatography, eluting with hexane:ethyl acetate (10:1) to yield the title compound as a colourless oil. 860 mg.

MS (electrospray): m/z [M+Na]$^+$=359

Description 20

5-Fluoro-2-[(phenylmethyl)oxy]benzoic acid (D20)

A solution of lithium hydroxide (71.9 mg, 3.00 mmol) in water (12 ml) was added to a stirred solution of phenylmethyl 5-fluoro-2-[(phenylmethyl)oxy]benzoate (may be prepared as described in Description 19, 336 mg, 1 mmol) in THF (3 ml). The reaction mixture was stirred at room temperature overnight. The THF was removed, the mixture was adjusted to pH 7 with 2N HCl. The mixture was filtered and the residue was dried to yield the title compound as a white solid. 180 mg.

MS (electrospray): m/z [M+Na]$^+$=269

Description 21

(3-Chlorophenyl)methyl 5-bromo-2-{[(3-chlorophenyl)methyl]oxy}benzoate (D21)

3-Chlorobenzyl bromide (568 mg, 2.76 mmol) was added dropwise to a stirred suspension of 5-bromo-2-hydroxybenzoic acid (200 mg, 0.92 mmol) and potassium carbonate (255 mg, 1.84 mmol) in acetone (40 ml) over 1 min. The reaction mixture was stirred at 56° C. for 24 h. The organic phase was evaporated and the residue was washed with water (25 ml), extracted with ethyl acetate (3×30 ml) and evaporated in vacuo to yield the title compound as an off white solid. 427 mg.

MS (electrospray): m/z [M+H]$^+$=465, 467, 469, 471

Description 22

5-Bromo-2-{[(3-chlorophenyl)methyl]oxy}benzoic acid (D22)

A solution of lithium hydroxide (384 mg, 9.16 mmol) in water (20 ml) was added dropwise to a stirred solution of (3-chlorophenyl)methyl 5-bromo-2-([(3-chlorophenyl)methyl]oxy)benzoate (may be prepared as described in Description 21; 427 mg, 0.92 mmol) in THF (20 ml) over 1 min. The reaction mixture was stirred at 20° C. for 16 h. The organic phase was evaporated and the aqueous phase (20 ml) was extracted with ethyl acetate (20 ml). The aqueous phase (20 ml) was adjusted to pH 2 with 2M hydrochloric acid (1 ml). The aqueous phase was then extracted with ethyl acetate (3×20 ml). The organic phase was evaporated in vacuo to yield the title compound as a white solid. 200 mg.

MS (electrospray): m/z [M+Na]$^+$=363, 365, 367

Description 23

(4-Cyanophenyl)methyl 5-bromo-2-{[(4-cyanophenyl)methyl]oxy}benzoate (D23)

4-(Bromomethyl)benzonitrile (318 mg, 1.622 mmol) was added in a single charge to a stirred suspension of 5-bromo-2-hydroxybenzoic acid (160 mg, 0.74 mmol) and potassium carbonate (204 mg, 1.48 mmol) in acetone (40 ml) at 20° C. The reaction mixture was stirred at 55° C. for 18 h. The organic phase was evaporated and the residue was washed with water (25 ml), extracted with ethyl acetate (3×30 ml) and evaporated in vacuo to yield the title compound as an off-white solid. 300 mg.

MS (electrospray): m/z [M+H]$^+$=447, 449; [M+Na]$^+$=469, 471

Description 24

5-Bromo-2-{[(4-cyanophenyl)methyl]oxy}benzoic acid (D24)

Lithium hydroxide (281 mg, 6.71 mmol) in water (20 ml) was added dropwise to a stirred solution of (4-cyanophenyl)methyl 5-bromo-2-{[(4-cyanophenyl)methyl]oxy}benzoate (may be prepared as described in Description 23; 300 mg, 0.67 mmol) in THF (20 ml) over 5 min. The reaction mixture was stirred at 20° C. for 16 h. The organic phase was evaporated and the aqueous phase (20 ml) was extracted with ethyl acetate (20 ml). The aqueous phase (20 ml) was adjusted to pH 2 with 2M hydrochloric acid (1 ml). The aqueous phase was then extracted with ethyl acetate (3×20 ml). The organic phase was then evaporated in vacuo to yield the title compound as a light yellow solid. 145 mg.

MS (electrospray): m/z [M+H]$^+$=332, 334; [M+Na]$^+$=354, 356

Description 25

(3-Cyanophenyl)methyl 5-bromo-2-{[(3-cyanophenyl)methyl]oxy}benzoate (D25)

3-Cyanobenzylbromide (542 mg, 2.76 mmol) was added dropwise to a stirred suspension of 5-bromo-2-hydroxybenzoic acid (200 mg, 0.92 mmol) and potassium carbonate (255 mg, 1.84 mmol) in acetone (40 ml) over 1 min. The reaction mixture was then stirred at 56° C. for 24 h. The organic phase was evaporated and the residue was washed with water (25 ml), extracted with ethyl acetate (100 ml) and evaporated in vacuo to yield the title compound as an off white solid. 411 mg.

Description 26

5-Bromo-2-{[(3-cyanophenyl)methyl]oxy}benzoic acid (D26)

A solution of lithium hydroxide (386 mg, 9.19 mmol) in water (20.00 mL) was added dropwise to a stirred solution of (3-cyanophenyl)methyl 5-bromo-2-{[(3-cyanophenyl)methyl]oxy}benzoate (may be prepared as described in Description 25; 411 mg, 0.92 mmol) in THF (20 ml) over 1 min. The reaction mixture was stirred at 20° C. for 16 h. The organic phase was evaporated and the aqueous phase (20 ml) was extracted by ethyl acetate (20 ml). The aqueous phase (20 ml) was adjusted to pH 2 with 2M hydrochloric acid (1 ml). The aqueous phase was then extracted with ethyl acetate (3×20 ml). The organic phase was evaporated in vacuo to yield the title compound as an off-white solid. 200 mg.

MS (electrospray): m/z [M+H]+=332, 334

Description 27

(2-Chlorophenyl)methyl 5-bromo-2-{[(2-chlorophenyl)methyl]oxy}benzoate (D27)

1-(Bromomethyl)-2-chlorobenzene (833 mg, 4.05 mmol) was added dropwise to a stirred suspension of 5-bromo-2-hydroxybenzoic acid (400 mg, 1.84 mmol) and potassium carbonate (509 mg, 3.69 mmol) in acetone (50 ml) over 1 min under nitrogen. The reaction mixture was stirred at 55° C. for 16 h. The organic phase was evaporated and the residue was washed with water (25 ml), extracted by ethyl acetate (3×30 ml) and evaporated in vacuo to yield the title compound as a light yellow solid. 520 mg.

MS (electrospray): m/z [M+Na]+=487, 489, 491, 493

Description 28

5-Bromo-2-{[(2-chlorophenyl)methyl]oxy}benzoic acid (D28)

A solution of lithium hydroxide (468 mg, 11.16 mmol) in water (25 m) was added dropwise to a stirred solution of (2-chlorophenyl)methyl 5-bromo-2-{[(2-chlorophenyl)methyl]oxy}benzoate (may be prepared as described in Description 27; 520 mg, 1.12 mmol) in THF (25 ml) over 1 min. The reaction mixture was stirred at 20° C. for 16 hours. The organic phase was evaporated and the aqueous phase (25 ml) was adjusted to pH 2 with 2M hydrochloric acid (1 ml) and was extracted by ethyl acetate (3×20 ml). The organic phase was evaporated in vacuo to yield the title compound as a light yellow solid. 350 mg.

MS (electrospray): m/z [M+H]+=341, 343

Description 29

[3-(Methyloxy)phenyl]methyl 5-bromo-2-({[3-(methyloxy)phenyl]methyl}oxy)benzoate (D29)

Neat 1-(bromomethyl)-3-methoxybenzene (510 mg, 2.53 mmol) was added in one charge to a stirred suspension of 5-bromo-2-hydroxybenzoic acid (250 mg, 1.15 mmol) and potassium carbonate (318 mg, 2.304 mmol) in acetone (40 ml) under nitrogen at 20° C. The reaction mixture was stirred at 55° C. for 16 h. The organic phase was evaporated and the residue was washed with water (25 ml), extracted by ethyl acetate (3×30 ml) and evaporated in vacuo to yield the title compound as an off-white solid. 430 mg.

MS (electrospray): m/z [M+Na]+=479, 481

Description 30

5-Bromo-2-({[3-(methyloxy)phenyl]methyl}oxy) benzoic acid (D30)

A solution of lithium hydroxide (395 mg, 9.40 mmol) in water (20 ml) was added dropwise to a stirred solution of [3-(methyloxy)phenyl]methyl 5-bromo-2-({[3-(methyloxy)phenyl]methyl}oxy)benzoate (may be prepared as described in Description 29; 430 mg, 0.94 mmol) in THF (20 ml) over 1 min. The reaction mixture was stirred at 20° C. for 16 h. The organic phase was evaporated and the aqueous phase (20 ml) was extracted with ethyl acetate (20 ml). The aqueous phase (20 ml) was adjusted to pH 2 with 2M hydrochloric acid (1 ml). The aqueous phase was then extracted with ethyl acetate (3×20 ml). The organic phase was evaporated in vacuo to yield the title compound as a light yellow solid. 275 mg.

MS (electrospray): m/z [M+Na]+=359, 361

Description 31

[2-(Methyloxy)phenyl]methyl 5-bromo-2-({[2-(methyloxy)phenyl]methyl}oxy)benzoate (D31)

Neat 1-(chloromethyl)-2-methoxybenzene (397 mg, 2.53 mmol) was added in one charge to a stirred suspension of 5-bromo-2-hydroxybenzoic acid (250 mg, 1.15 mmol) and cesium carbonate (751 mg, 2.30 mmol) in acetone (40 ml) under nitrogen at 20° C. The reaction mixture was stirred at 55° C. for 16 h. The organic phase was evaporated and the residue was washed with water (25 ml), extracted with ethyl acetate (3×30 ml) and evaporated in vacuo to yield the title compound as a light yellow liquid. 420 mg.

MS (electrospray): m/z [M+Na]+=479, 481

Description 32

5-Bromo-2-({[2-(methyloxy)phenyl]methyl}oxy) benzoic acid (D32)

A solution of lithium hydroxide (385 mg, 9.18 mmol) in water (20 ml) was added dropwise to a stirred solution of [2-(methyloxy)phenyl]methyl 5-bromo-2-({[2-(methyloxy)phenyl]methyl}oxy)benzoate (may be prepared as described in Description 31; 420 mg, 0.92 mmol) in THF (20 ml) over 5 min. The reaction mixture was stirred at 20° C. for 16 h. The organic phase was evaporated and the aqueous phase (20 ml) was extracted with ethyl acetate (20 ml). The aqueous phase (20 ml) was adjusted to pH 2 with 2M hydrochloric acid (1 ml). The aqueous phase was then extracted with ethyl acetate (3×20 ml). The organic phase was then evaporated in vacuo to yield the title compound as a light yellow solid. 280 mg.

MS (electrospray): m/z [M+Na]+=359, 361

Description 33

(2-Cyanophenyl)methyl 5-bromo-2-{[(2-cyanophenyl)methyl]oxy}benzoate (D33)

2-(Bromomethyl)benzonitrile (397 mg, 2.027 mmol) was added in one charge to a stirred suspension of 5-bromo-2-hydroxybenzoic acid (200 mg, 0.92 mmol) and potassium carbonate (255 mg, 1.84 mmol) in acetone (40 ml) under nitrogen at 20° C. The reaction mixture was stirred at 55° C. for 16 h. The organic phase was evaporated and the residue was washed with water (25 ml), extracted with ethyl acetate (100 ml) and evaporated in vacuo to yield the title compound as an off-white solid. 350 mg.

MS (electrospray): m/z [M+H]+=447, 449; [M+Na]+=469, 471

Description 34

5-Bromo-2-{[(2-cyanophenyl)methyl]oxy}benzoic acid (D34)

A solution of lithium hydroxide (328 mg, 7.83 mmol) in water (20 m) was added dropwise to a stirred solution of (2-cyanophenyl)methyl 5-bromo-2-{[(2-cyanophenyl)methyl]oxy}benzoate (may be prepared as described in Description 34; 350 mg, 0.78 mmol) in THF (20 ml) over 1 min. The reaction mixture was stirred at 20° C. for 18 h. The organic phase was evaporated and the aqueous phase (20 ml) was extracted with ethyl acetate (20 ml). The aqueous phase (20 ml) was adjusted to pH 2 with 2M hydrochloric acid (1 ml). The residual water phase was extracted with ethyl acetate (3×20 ml). The organic phase was then evaporated in vacuo to yield the title compound as a light yellow solid. 160 mg.

MS (electrospray): m/z [M+H]$^+$=332, 334

Description 35

5-Bromo-2-hydroxy-N-3-pyridinylbenzamide (D35)

A solution of 5-bromo-2-hydroxybenzoic acid (5.2 g, 23.96 mmol), 3-pyridinamine (2.26 g, 23.96 mmol), EDC (4.59 g, 23.96 mmol), HOBT (3.67 g, 23.96 mmol) and triethylamine (3.34 ml, 23.96 mmol) in DMF (80 ml) was stirred for 3 h. The reaction mixture was filtered. 150 ml water was added to the filtrate to yield a white solid. This was filtered and dried to yield the title compound. 2.8 g.

MS (electrospray): m/z [M+H]$^+$=293, 295

Description 36

Methyl 2-hydroxy-5-{[(4-methylphenyl)sulfonyl]oxy}benzoate (D36)

A mixture of methyl 2,5-dihydroxybenzoate (1.5 g, 8.92 mmol), potassium carbonate (7.50 g, 54.2 mmol), and dry acetone (100 ml) was stirred at room temperature for 30 min. To the mixture was added TsCl (1.72 g, 9.00 mmol) portionwise and the mixture was refluxed for 7 h. The reaction mixture was used in the next step directly.

MS (electrospray): m/z [M+H]$^+$=323

Description 37

Methyl 5-{[(4-methylphenyl)sulfonyl]oxy}-2-[(phenylmethyl)oxy]benzoate (D37)

Method A (Bromomethyl)benzene (3.81 g, 22.26 mmol) was added to methyl 2-hydroxy-5-{[(4-methylphenyl)sulfonyl]oxy}benzoate (may be prepared as described in Description 36; 2.87 g, 8.90 mmol) and the resulting mixture was refluxed overnight. After cooling, the resulting precipitate was filtered and the filtrate was evaporated. The crude product was purified by silica gel chromatography, eluting with a 4:1 mixture of hexane:ethyl acetate to yield the title compound as a colourless oil. 2.7 g.

MS (electrospray): m/z, [M+H]$^+$=413

Method B

A mixture of methyl 2,5-dihydroxybenzoate (2.5 g, 14.87 mmol), potassium carbonate (25 g, 181 mmol), and dry acetone (150 ml) was stirred at room temperature for 30 min. 4-Methylbenzenesulfonyl chloride (2.86 g, 15.00 mmol) was added portionwise and the mixture was refluxed for 7 h. (Bromomethyl)benzene (6.35 g, 37.2 mmol) was added and the resulting mixture was refluxed overnight. After cooling, the precipitate was filtered, and the filtrate was evaporated. The residue was loaded onto a silica gel column, and was eluted with petroleum ether:ethyl acetate=4:1 to yield the title compound as a white solid. 2.6 g.

MS (electrospray): m/z [M+H]$^+$=413.0.

Method C

A mixture of methyl 2,5-dihydroxybenzoate (10 g, 59.5 mmol), potassium carbonate (50.0 g, 362 mmol), and dry acetone (450 ml) was stirred at room temperature for 30 min. 4-Methylbenzenesulfonyl chloride (11.44 g, 60.0 mmol) was added portionwise and the mixture was refluxed for 7 h. (Bromomethyl)benzene (25.4 g, 149 mmol) was added and the resulting mixture was refluxed overnight. After cooling, the precipitate was filtered, and the filtrate was evaporated. The residue was loaded onto a silica gel column and was eluted with hexane/ethyl acetate=4:1 to yield the title compound as a yellow solid. 22 g.

MS (electrospray): m/z [M+H]$^+$=413

Description 38

5-Hydroxy-2-[(phenylmethyl)oxy]benzoic acid (D38)

Method A

Methyl 5-{[(4-methylphenyl)sulfonyl]oxy}-2-[(phenylmethyl)oxy]benzoate (may be prepared as described in Description 37; 2.5 g, 6.06 mmol) was boiled with potassium hydroxide (2.38 g, 42.4 mmol) in a mixture of ethanol (60 ml) and water (15 ml) for 4 h. After the ethanol had been evaporated, the aqueous solution was washed with ethyl acetate (20 ml) and acidified with concentrated HCl. The mixture was extracted with ethyl acetate (3×30 ml). The organic phase was washed with saturated brine (25 ml), dried over sodium sulphate and evaporated in vacuo to yield the title compound as a yellow oil. 1.35 g.

MS (electrospray): m/z [M+H]$^+$=245; [M+Na]$^+$=267

Method B

Methyl 5-{[(4-methylphenyl)sulfonyl]oxy}-2-[(phenylmethyl)oxy]benzoate (may be prepared as described in Description 75; 9.0 g, 21.82 mmol) was boiled with potassium hydroxide (8.57 g, 153 mmol) in a mixture of ethanol (160 ml) and water (40 ml) for 3 h. After the ethanol had been evaporated, the aqueous solution was washed with ethyl acetate (250 ml), and then acidified with concentrated HCl. The mixture was extracted with ethyl acetate. The organic phase was washed with saturated brine, dried over Na$_2$SO$_4$, and evaporated in vacuo to yield the title compound as a yellow oil. 5.2 g.

MS (electrospray): m/z [M+H]$^+$=244.9.

Method C

Methyl 5-{[(4-methylphenyl)sulfonyl]oxy}-2-[(phenylmethyl)oxy]benzoate (may be prepared as described in Description 75; 22.0 g, 53.3 mmol) was boiled with potassium hydroxide (20.95 g, 373 mmol) in a mixture of ethanol (320 ml) and water (80 ml) overnight. After the ethanol had been evaporated, the aqueous solution was washed with ethyl acetate (500 ml), and then acidified with concentrated HCl. The mixture was extracted with ethyl acetate. The organic phase was washed with saturated brine, dried over sodium sulfate, and evaporated in vacuo to yield the title compound as a yellow oil. 14 g.

MS (electrospray): m/z [MH+23]$^+$=267

Description 39

Phenylmethyl 5-(4-methyl-1-piperazinyl)-2-[(phenylmethyl)oxy]benzoate (D39)

Caesium carbonate (574 mg, 1.76 mmol) was finely ground in a nitrogen-filled glovebox and weighed into an oven-dried Schlenk flask. The flask was quickly capped with a rubber septum and purged with argon. $Pd_2(dba)_3$ (2.88 mg, 3.15 μmol) and BINAP (5.88 mg, 9.44 μmol) were added into the flask, followed by benzyl 2-(benzyloxy)-5-bromobenzoate (may be prepared as described in Description 4; 500 mg, 1.26 mmol), 1-methylpiperazine (126 mg, 1.26 mmol), and toluene (10 ml). The solution was refluxed for 10 h. The solution was then cooled to room temperature, diluted with ether, filtered, and concentrated in vacuo to yield the title compound which was not further purified. 100 mg.

MS (electrospray): m/z $[M+H]^+$=417

Description 40

5-(4-Methyl-1-piperazinyl)-2-[(phenylmethyl)oxy] benzoic acid (D40)

Lithium hydroxide (17.25 mg, 0.72 mmol) was added to a stirred solution of phenylmethyl 5-(4-methyl-1-piperazinyl)-2-[(phenylmethyl)oxy]benzoate (may be prepared as described in Description 39; 100 mg, 0.24 mmol) in a mixture of THF:water (3:1, 10 ml). The mixture was heated to reflux for 12 h and then diluted with ethyl acetate (50 ml). 10% aqueous HCl was added to the mixture to adjust the pH to 2. The organic phase was isolated, washed with brine, dried over magnesium sulphate, and concentrated to give a white solid. The product was purified using Comflash to yield the title compound. 50 mg.

MS (electrospray): m/z $[M+H]^+$=327

Description 41

Phenylmethyl 2-[(phenylmethyl)oxy]-5-(1-piperidinyl)benzoate (D41)

Caesium carbonate (689 mg, 2.11 mmol) was finely ground in a nitrogen-filled glovebox and weighed into an oven-dried Schlenk flask. The flask was quickly capped with a rubber septum and purged with argon. $Pd_2(dba)_3$ (3.46 mg, 3.78 μmol) and BINAP (7.05 mg, 0.01 mmol) were added into the flask, followed by benzyl 2-(benzyloxy)-5-bromobenzoate (may be prepared as described in Description 4; 600 mg, 1.51 mmol), piperidine (129 mg, 1.510 mmol), and toluene (10 ml). The solution was refluxed for 10 h. The solution was then cooled to room temperature, diluted with ether, filtered, and concentrated in vacuo to yield the title compound.

MS (electrospray): m/z $[M+H]^+$=402

Description 42

2-[(Phenylmethyl)oxy]-5-(1-piperidinyl)benzoic acid (D42)

LiOH (1.25 mL, 3.74 mmol) was added to a stirred solution of phenylmethyl 2-[(phenylmethyl)oxy]-5-(1-piperidinyl) benzoate (may be prepared as described in Description 41; 150 mg, 0.37 mmol) in a mixture of THF:water (3:1, 10 ml). The mixture was heated to reflux for 12 h and then diluted with ethyl acetate (50 ml). 10% aqueous HCl was added to the mixture to adjust the pH to 2. The organic phase was isolated, washed with brine, dried over magnesium sulphate, and concentrated to give a yellow oil. The crude product was purified using Comflash to yield the title compound. 80 mg.

Description 43

Phenylmethyl 5-chloro-2-[(phenylmethyl)oxy]benzoate (D43)

A mixture of 5-chloro-2-hydroxybenzoic acid (2.03 g, 11.8 mmol), benzyl bromide (2.79 ml, 23.5 mmol) and potassium carbonate (4.87 g, 35.3 mmol) in DMF (20 ml) was stirred at room temperature overnight then heated at 60° C. for 1 hour. Cooled, diluted with water (150 ml) and extracted with ethyl acetate (×3). The organics were washed with water (×2) and brine, dried ($MgSO_4$), and concentrated in vacuo to yield the crude title compound as a yellow oil which was used immediately without further purification.

Description 44

Methyl (3-aminophenyl)acetate (D44)

A mixture of (3-aminophenyl)acetic acid (5.0 g, 33 mmol), methanol (150 ml), and c.$H_2SO_4$ (10 ml) was heated at reflux overnight. The solvent was evaporated in vacuo and the residue taken up in water (50 ml) and ethyl acetate (200 ml). Solid $Na_2CO_3$ was added until the solution was pH 10. The layers were separated and the aqueous layer was extracted again with ethyl acetate (250 ml). The organic layers were combined, washed with brine, dried ($MgSO_4$) and evaporated in vacuo to give the title compound as a brown oil. 5.0 g.

MS (electrospray): m/z $[M+H]^+$=166

Description 45

5-Chloro-2-[(phenylmethyl)oxy]benzoic acid (D45)

Phenylmethyl 5-chloro-2-[(phenylmethyl)oxy]benzoate (may be prepared as described in Description 43; 4.16 g, 11.8 mmol), in ethanol (40 ml) and 2M NaOH (20 ml) was heated at reflux for two hours. The mixture was cooled, concentrated in vacuo, acidified with 2M HCl and extracted with ethyl acetate (×3). The organics were washed with brine, dried ($MgSO_4$), and concentrated to give a yellow oil. Purified using biotage chromatography (C18 cartridge, $CH_3CN/H_2O$) to give the title compound as a white solid. 1.9 g.

MS (electrospray): m/z $[M+Na]^+$=285, 287

Description 46

Methyl {3-[({5-chloro-2-[(phenylmethyl)oxy] phenyl}carbonyl)amino]phenyl}acetate (D46)

A mixture of 5-chloro-2-[(phenylmethyl)oxy]benzoic acid (may be prepared as described in Description 45; 50 mg, 0.19 mmol), methyl (3-aminophenyl)acetate (may be prepared as described in Description 44; 48 mg, 0.29 mmol), EDAC (56 mg, 0.29 mmol), and dichloromethane (3 ml) was heated in the microwave at 60° C. for 40 minutes. DIPEA (53 μl, 0.3 mmol) was added and the mixture was heated at 60° C. in the microwave for another 20 minutes. The reaction mixture was purified by SCX cartridge, eluting with methanol. The fractions were combined and evaporated to give the title compound as an off-white solid. 35 mg.

MS (electrospray): m/z $[M+H]^+$=410, 412

Description 47

Bis(phenylmethyl) 4-[(phenylmethyl)oxy]-1,3-benzenedicarboxylate (D47)

To a suspension of 4-hydroxy-1,3-benzenedicarboxylic acid (5 g, 27.5 mmol) and $K_2CO_3$ (13.66 g, 99 mmol) in acetone (180 ml) stirred at room temperature was added bromomethyl)benzene (16.90 g, 99 mmol) dropwise. The reaction mixture was stirred at 50° C. overnight. The mixture was cooled to room temperature, and filtered. The filtrate was concentrated to afford the crude product, which was added to a silica gel column (100 g) and was eluted with hexanes/ethyl acetate=10:1 (2 L) to yield the title compound as a colourless oil. 6.6 g.

MS (electrospray): m/z [M+Na]$^+$=474.9

Description 48

4-[(Phenylmethyl)oxy]-1,3-benzenedicarboxylic acid (D48)

A solution of LiOH (6.12 g, 146 mmol) in water (100 ml) was added to a stirred solution of bis(phenylmethyl) 4-[(phenylmethyl)oxy]-1,3-benzenedicarboxylate (may be prepared as described in Description 47; 6.6 g, 14.59 mmol) in tetrahydrofuran (25 ml) at room temperature. The mixture was stirred at room temperature overnight. The reaction mixture was acidified with concentrated HCl. The white precipitate was collected by filtration, and dried to yield the title compound as a white solid. 3.8 g.

MS (electrospray): m/z [M+Na]$^+$=294.9

Description 49

3-[(Methyloxy)carbonyl]-4-[(phenylmethyl)oxy]benzoic acid (D49)

$H_2SO_4$ (0.8 ml, 11.02 mmol) was added dropwise to a solution of 4-[(phenylmethyl)oxy]-1,3-benzenedicarboxylic acid (may be prepared as described in Description 48; 3 g, 11.02 mmol) in methanol (40 ml). The mixture was stirred at room temperature for 3 h before being poured into ice-water (40 ml). The precipitate was collected and added to a saturated $NaHCO_3$ solution. The mixture was filtered to remove the insoluble residue and the pH of the filtrate was adjusted to pH=4.8 by HCl (6 mol/L). The precipitate was collected to afford crude product. The crude product was added to a silica gel column (300 g), and was eluted with dichloromethane/methanol=100:1 (3 L) to afford a mixture of 5-[(methyloxy)carbonyl]-2-[(phenylmethyl)oxy]benzoic acid and the title compound as a white solid. 1 g.

MS (electrospray): m/z [M+Na]$^+$=309.0

Description 50

Methyl 5-[(4-methyl-1-piperazinyl)carbonyl]-2-[(phenylmethyl)oxy]benzoate (D50)

Oxalyl chloride (0.46 ml, 5.24 mmol) was added dropwise to a stirred solution of 3-[methyloxy)carbonyl]-4-[(phenylmethyl)oxy]benzoic acid (may be prepared as described in Description 49; 300 mg, 1.05 mmol) in dichloromethane (10 ml) and dimethyl formamide (3 drops) at room temperature. The mixture was stirred at room temperature for 1 h, and then concentrated to dryness. The residue was dissolved in dichloromethane (5 ml), and then was added to a solution of 1-methylpiperazine (525 mg, 5.24 mmol) in dichloromethane (5 ml). The mixture was stirred at room temperature for 2 h. Water (60 ml) was added and the mixture was extracted with dichloromethane (3×60 ml). The organic phase was washed with saturated brine (50 ml), dried over sodium sulfate, and evaporated in vacuo to give crude product. The crude product was added to a silica gel column and was eluted with dichloromethane/methanol=10:1 to yield the title compound as a colourless oil. 345 mg.

MS (electrospray): m/z [M+H]$^+$=369.1

Description 51

5-[(4-Methyl-1-piperazinyl)carbonyl]-2-[(phenylmethyl)oxy]benzoic acid (D51)

A solution of LiOH (393 mg, 9.36 mmol) in water (10 ml) was added to a stirred solution of methyl 5-[(4-methyl-1-piperazinyl)carbonyl]-2-[(phenylmethyl)oxy]benzoate (may be prepared as described in Description 50; 345 mg, 0.94 mmol) in tetrahydrofuran (2.5 ml) at room temperature. The mixture was stirred at room temperature for 3 h. The mixture was acidified by HCl (6 mol/L). The solvent was evaporated in vacuo to afford the crude product. The crude product was used directly in the next step without further purification.

MS (electrospray): m/z [M+H]$^+$=355.0

Description 52

Methyl 2-[(phenylmethyl)oxy]-5-(1-piperidinylcarbonyl)benzoate (D52)

Oxalyl chloride (0.61 ml, 6.99 mmol) was added dropwise to a stirred solution of 3-[(methyloxy)carbonyl]-4-[(phenylmethyl)oxy]benzoic acid (may be prepared as described in Description 49; 400 mg, 1.40 mmol) in dichloromethane (10 ml) and dimethylformamide (3 drops) at room temperature. The mixture was stirred at room temperature for 1 h. The solvent was then removed and the residue was dissolved in dichloromethane (5 ml). This mixture was added to a solution of 1-methylpiperazine (525 mg, 5.24 mmol) in dichloromethane (5 ml). The mixture was stirred at room temperature for 2 h. Water (60 ml) was added to the mixture, which was then extracted with dichloromethane (3×60 ml). The organic phase was washed with saturated brine (50 ml), dried over sodium sulfate and evaporated in vacuo to give the crude product. The crude product was loaded onto a silica gel (200 g) column and eluted with dichloromethane/methanol=50:1 to yield the title compound as a colourless oil. 450 mg.

MS (electrospray): m/z [M+H]$^+$=354

Description 53

2-[(Phenylmethyl)oxy]-5-(1-piperidinylcarbonyl)benzoic acid (D53)

A solution of LiOH (534 mg, 12.73 mmol) in water (8 ml) was added to a stirred solution of methyl 2-[(phenylmethyl)oxy]-5-(1-piperidinylcarbonyl)benzoate (may be prepared as described in Description 52; 450 mg, 1.27 mmol) in tetrahydrofuran (2 ml) at room temperature. The mixture was stirred at room temperature for 3 h. The mixture was then acidified by 6N HCl and the precipitate was collected and dried to yield the title compound as a white solid. 400 mg.

MS (electrospray): m/z [M+H]$^+$=340

Description 54

Methyl 2-[(phenylmethyl)oxy]-5-(1-pyrrolidinylcarbonyl)benzoate (D54)

Oxalyl chloride (0.61 ml, 6.99 mmol) was added dropwise to a stirred solution of 3-[(methyloxy)carbonyl]-4-[(phenylmethyl)oxy]benzoic acid (may be prepared as described in Description 49; 400 mg, 1.40 mmol) in dichloromethane (10 ml) and dimethylformamide (3 drops) at room temperature. The mixture was stirred at room temperature for 1 h. The solvent was removed, and the residue was dissolved in dichloromethane (5 ml). This mixture was added to a solution of pyrrolidine (497 mg, 6.99 mmol) in dichloromethane (5 ml) and the mixture was stirred at room temperature for 2 h. Water (60 ml) was added, and the mixture was extracted with dichloromethane (3×60 ml). The organic phase was washed with saturated brine (50 ml), dried over sodium sulfate, and evaporated in vacuo to give the crude product. The crude product was loaded onto a silica gel column (200 g), and was eluted with dichloromethane/methanol=50:1 to yield the title compound as a colourless oil. 400 mg.

MS (electrospray): m/z [M+H]$^+$=340

Description 55

2-[(Phenylmethyl)oxy]-5-(1-pyrrolidinylcarbonyl)benzoic acid (D55)

A solution of LiOH (495 mg, 11.79 mmol) in water (8 ml) was added to a stirred solution of methyl 2-[(phenylmethyl)oxy]-5-(1-pyrrolidinylcarbonyl)benzoate (may be prepared as described in Description 54; 400 mg, 1.18 mmol) in tetrahydrofuran (2 ml) at room temperature. The mixture was stirred at room temperature for 3 h. The mixture was acidified by HCl (6 mol/l). The precipitate was collected and dried to yield the title compound as a white solid. 300 mg.

MS (electrospray): m/z [M+H]$^+$=326

Description 56

Methyl 5-(4-morpholinylcarbonyl)-2-[(phenylmethyl)oxy]benzoate (D56)

Oxalyl chloride (0.61 ml, 6.99 mmol) was added dropwise to a stirred solution of 3-[(methyloxy)carbonyl]-4-[(phenylmethyl)oxy]benzoic acid (may be prepared as described in Description 49; 400 mg, 1.40 mmol) in dichloromethane (10 ml) and dimethylformamide (3 drops) at room temperature. The mixture was stirred at room temperature for 1 h. The solvent was removed. The residue was dissolved in dichloromethane (5 ml). This mixture was added to a solution of morpholine (609 mg, 6.99 mmol) in dichloromethane (5 ml). The mixture was stirred at room temperature for 2 h. Water (60 ml) was added and the mixture was extracted with dichloromethane (3×60 ml). The organic phase was washed with saturated brine (50 ml), dried over sodium sulfate, and evaporated in vacuo to give the crude product as colourless oil. The crude product was loaded onto a silica gel column and was eluted with dichloromethane/methanol=20:1 to yield the title compound as a colourless oil. 450 mg.

MS (electrospray): m/z [M+H]$^+$=356

Description 57

5-(4-Morpholinylcarbonyl)-2-[(phenylmethyl)oxy]benzoic acid (D57)

A solution of LiOH (420 mg, 10 mmol) in water (8 ml) was added to a stirred solution of methyl 5-(4-morpholinylcarbonyl)-2-[(phenylmethyl)oxy]benzoate (may be prepared as described in Description 56; 450 mg, 1.27 mmol) in tetrahydrofuran (2 ml) at room temperature. The mixture was stirred at room temperature for 3 h. The mixture was acidified with HCl (6 mol/l), extracted with ethyl acetate (3×40 ml). The organic phase was washed with saturated brine (25 ml), dried over sodium sulfate, and evaporated in vacuo to give crude title compound as a white solid. 400 mg.

MS (electrospray): m/z [M+H]$^+$=342

Description 58

Methyl 5-[(dimethylamino)carbonyl]-2-[(phenylmethyl)oxy]benzoate (D58)

Oxalyl chloride (0.46 ml, 5.24 mmol) was added dropwise to a stirred solution of 3-[(methyloxy)carbonyl]-4-[(phenylmethyl)oxy]benzoic acid (may be prepared as described in Description 49; 300 mg, 1.05 mmol) in dichloromethane (10 ml) and dimethylformamide (3 drops) at room temperature. The mixture was stirred at room temperature for 1 h. The solvent was removed, and the residue was dissolved in dichloromethane (5 ml). This mixture was added to a solution of dimethylamine (716 mg, 5.24 mmol) in dichloromethane (5 ml). The mixture was stirred at room temperature for 2 h. Water (40 ml) was added and the mixture was extracted with dichloromethane (3×60 ml). The organic phase was washed with saturated brine (25 ml), dried over sodium sulfate, and evaporated in vacuo to give the crude product as colourless oil. The crude product was used directly in the next step without further purification.

MS (electrospray): m/z [M+H]$^+$=314

Description 59

5-[(Dimethylamino)carbonyl]-2-[(phenylmethyl)oxy]benzoic acid (D59)

A solution of LiOH (585 mg, 13.95 mmol) in water (8 ml) was added to a stirred solution of methyl 5-[(dimethylamino)carbonyl]-2-[(phenylmethyl)oxy]benzoate (may be prepared as described in Description 58; 437 mg, 1.40 mmol) in tetrahydrofuran (2 ml) at room temperature. The mixture was stirred at room temperature for 3 h. The mixture was acidified with HCl (6 mol/l) and extracted with ethyl acetate (3×40 ml). The organic phase was washed with saturated brine (25 ml), dried over sodium sulfate, and evaporated in vacuo to give the crude product as a white solid. 350 mg.

MS (electrospray): m/z [M+H]$^+$=300

Description 60

Methyl 5-(chlorosulfonyl)-2-hydroxybenzoate (D60)

Sulfurochloridic acid (38.3 g, 329 mmol) at 0° C. was added to methyl 2-hydroxybenzoate (10 g, 65.7 mmol) in small portions and the mixture was then stirred at 0° C. for 1 h. The mixture was added dropwise to 10 ml ice-water with stirring and stirring continued for an additional 0.5 h. The ensuing white crystals were collected by filtration, washed three times with water, and then dried to yield the title compound. 12 g.

Description 61

Methyl 5-[(dimethylamino)sulfonyl]-2-hydroxybenzoate (D61)

A 33% solution of dimethylamine (1.53 ml, 9.97 mmol) in water was added dropwise to methyl 5-(chlorosulfonyl)-2-hydroxybenzoate (may be prepared as described in Description 60; 500 mg, 2.00 mmol) in dichloromethane (20 ml) at 25° C., and the mixture was allowed to stir at 25° C. for 2 h. The mixture was then concentrated in vacuo to give the yield the title compound as a crude product. 260 mg.

MS (electrospray): m/z [M+H]$^+$=260

Description 62

Methyl 5-[(dimethylamino)sulfonyl]-2-[(phenylmethyl)oxy]benzoate (D62)

K$_2$CO$_3$ (139 mg, 1.00 mmol) was added to a stirred solution of methyl 5-[(dimethylamino)sulfonyl]-2-hydroxybenzoate (may be prepared as described in Description 61; 260 mg, 1.00 mmol) in acetone (30 ml), followed by the addition of (bromomethyl)benzene (172 mg, 1.00 mmol). The mixture was heated to reflux for 16 h, and then cooled to room temperature. The mixture was filtered, and the filtrate was concentrated to yield the title compound as a colourless oil. 300 mg.

MS (electrospray): m/z [M+H]$^+$=350

Description 63

5-[(Dimethylamino)sulfonyl]-2-[(phenylmethyl)oxy]benzoic acid (D63)

LiOH (20.56 mg, 0.86 mmol) was added to a stirred solution of methyl 5-[(dimethylamino) sulfonyl]-2-[(phenylmethyl)oxy]benzoate (may be prepared as described in Description 62; 300 mg, 0.86 mmol) in a mixture of tetrahydrofuran and water (3:1, 40 ml). The mixture was heated at 50° C. for 6 h, and then diluted with ethyl acetate (50 ml). 10% Aqueous HCl was added to the mixture to adjust pH to 2. The organic phase was isolated, washed with brine, dried over MgSO$_4$, and concentrated to yield the title compound as a white solid. 230 mg.

MS (electrospray): m/z [M+H]$^+$=336

Description 64

Methyl 2-hydroxy-5-(4-morpholinylsulfonyl)benzoate (D64)

Morpholine (174 mg, 2.00 mmol) was added dropwise to methyl 5-(chlorosulfonyl)-2-hydroxybenzoate (may be prepared as described in Description 63; 500 mg, 2.00 mmol) in dichloromethane (20 ml) at 25° C., and the mixture was allowed to stir at 25° C. for 2 h. The mixture was then concentrated in vacuo to yield the crude title compound. 350 mg.

MS (electrospray): m/z [M+H]$^+$=302

Description 65

Methyl 5-(4-morpholinylsulfonyl)-2-[(phenylmethyl)oxy]benzoate (D65)

K$_2$CO$_3$ (138 mg, 1.00 mmol) was added to a stirred solution of methyl 2-hydroxy-5-(4-morpholinylsulfonyl)benzoate (may be prepared as described in Description 64; 300 mg, 1.00 mmol) in acetone (20 ml), followed by the addition of (bromomethyl)benzene (170 mg, 1.00 mmol). The mixture was heated to reflux for 16 h, and then cooled to room temperature. The mixture was filtered, and the filtrate was concentrated to yield the title compound as a colourless oil. 380 mg.

MS (electrospray): m/z [M+H]$^+$=392

Description 66

5-(4-Morpholinylsulfonyl)-2-[(phenylmethyl)oxy]benzoic acid (D66)

LiOH (23.25 mg, 0.97 mmol) was added to a stirred solution of methyl 5-(4-morpholinylsulfonyl)-2-[(phenylmethyl)oxy]benzoate (may be prepared as described in Description 65; 380 mg, 0.97 mmol) in a mixture of tetrahydrofuran and water (3:1, 40 ml). The mixture was heated at 50° C. for 6 h, and then diluted with ethyl acetate (50 m). 10% Aqueous HCl was added to the mixture to adjust pH to 2. The organic phase was isolated, washed with brine, dried over MgSO$_4$, and concentrated to yield the title compound as a white solid. 250 mg.

MS (electrospray): m/z [M+H]$^+$=378

Description 67

Methyl 2-hydroxy-5-(1-piperidinylsulfonyl)benzoate (D67)

Piperidine (849 mg, 9.97 mmol) was added dropwise to methyl 5-(chlorosulfonyl)-2-hydroxybenzoate (may be prepared as described in Description 60; 500 mg, 2.00 mmol) in dichloromethane (20 ml) at 25° C., and the mixture was allowed to stir at 25° C. for 2 h. The mixture was then concentrated in vacuo to yield the title compound as a crude product. 430 mg.

MS (electrospray): m/z [M+H]$^+$=300

Description 68

Methyl 2-[(phenylmethyl)oxy]-5-(1-piperidinylsulfonyl)benzoate (D68)

K$_2$CO$_3$ (203 mg, 1.47 mmol) was added to a stirred solution of methyl 2-hydroxy-5-(1-piperidinylsulfonyl)benzoate (may be prepared as described in Description 67; 400 mg, 1.34 mmol) in acetone (20 ml), followed by the addition of (bromomethyl)benzene (251 mg, 1.47 mmol). The mixture was heated at reflux for 16 h, and then cooled to room temperature. The mixture was filtered, and the filtrate was concentrated to yield the title compound as a colourless oil. 300 mg.

MS (electrospray): m/z=390

Description 69

2-[(Phenylmethyl)oxy]-5-(1-piperidinylsulfonyl) benzoic acid (D69)

LiOH (20.29 mg, 0.847 mmol) was added to a stirred solution of methyl 2-[(phenylmethyl)oxy]-5-(1-piperidinylsulfonyl)benzoate (may be prepared as described in Description 68; 330 mg, 0.85 mmol) in a mixture of tetrahydrofuran and water (3:1, 40 ml). The mixture was heated at 50° C. for 6 h, and then diluted with ethyl acetate (50 ml). 10% Aqueous HCl was added to the mixture to adjust pH to 2. The organic phase was isolated, washed with brine, dried over MgSO$_4$, and concentrated to yield the title compound as a white solid. 220 mg.

MS (electrospray): m/z [M+H]$^+$=376

Description 70

Methyl 2-hydroxy-5-[(4-methyl-1-piperazinyl)sulfonyl]benzoate (D70)

Methyl 5-(chlorosulfonyl)-2-hydroxybenzoate (may be prepared as described in Description 60; 500 mg, 1.995 mmol) was added to a stirred solution of 1-methylpiperazine (200 mg, 2.00 mmol) in dichloromethane (20 ml). The mixture was stirred for 0.5 h, and then concentrated under reduced pressure to yield the title compound as a colourless oil. 430 mg.

MS (electrospray): m/z [M+H]$^+$=315

Description 71

Methyl 5-[(4-methyl-1-piperazinyl)sulfonyl]-2-[(phenylmethyl)oxy]benzoate (D71)

DEAD (0.24 ml, 1.51 mmol) was slowly added to a mixture of methyl 2-hydroxy-5-[(4-methyl-1-piperazinyl)sulfonyl] benzoate (may be prepared as described in Description 70; 430 mg, 1.37 mmol), Ph$_3$P (395 mg, 1.51 mmol) and phenylmethanol (163 mg, 1.505 mmol) in toluene (15 ml) cooled in an ice bath at 0° C. The mixture was stirred for 2 h at room temperature. Ether was added to the mixture and the mixture was filtered. The filtrate was evaporated to yield the title compound. 260 mg.

MS (electrospray): m/z [M+H]$^+$=405

Description 72

5-[(4-Methyl-1-piperazinyl)sulfonyl]-2-[(phenylmethyl)oxy]benzoic acid (D72)

LiOH (15.39 mg, 0.64 mmol) was added to a stirred solution of methyl 5-[(4-methyl-1-piperazinyl) sulfonyl]-2-[(phenylmethyl)oxy]benzoate (may be prepared as described in Description 71; 260 mg, 0.64 mmol) in a mixture of tetrahydrofuran and water (3:1, 40 ml). The mixture was heated at 50° C. for 6 h and then diluted with ethyl acetate (50 nil). 10% Aqueous HCl was added to the mixture to adjust pH to 2. The organic phase was isolated, washed with brine, dried over MgSO$_4$, and concentrated to yield the title compound as a white solid. 120 mg.

MS (electrospray): m/z [M+H]$^+$=391

Description 73

1,1-Dimethylethyl (2R)-2-[({4-[(phenylmethyl)oxy]-3-[(3-pyridinylamino)carbonyl]phenyl}oxy)methyl]-1-pyrrolidinecarboxylate (D73)

Sodium hydride (44.9 mg, 1.87 mmol) was added to a solution of 5-hydroxy-2-[(phenylmethyl)oxy]-N-3-pyridinylbenzamide (may be prepared as described in Example 29; 500 mg, 1.56 mmol) in dimethylsulfoxide (8 ml) at 0° C., and the mixture was stirred at room temperature for 1 h. 1,1-Dimethylethyl (2R)-2-({[(4-chlorophenyl)sulfonyl]oxy}methyl)-1-pyrrolidinecarboxylate (555 mg, 1.56 mmol) in dimethylsulfoxide (7 ml) was added dropwise, and the mixture was stirred at 75° C. for 18 h. The mixture was poured into water (100 ml) and extracted with ethyl acetate. The organic layer was dried, and concentrated to obtain a crude product, which was purified by chromatography on silica gel (dichloromethane/methanol=50:1) to yield the title compound as a yellow oil. 0.55 g.

MS (electrospray): m/z [M+H]$^+$=504.0.

Description 74

1,1-Dimethylethyl (2S)-2-[({4-[(phenylmethyl)oxy]-3-[(3-pyridinylamino)carbonyl]phenyl}oxy)methyl]-1-pyrrolidinecarboxylate (D74)

Sodium hydride (36.0 mg, 1.50 mmol) was added to a solution of 5-hydroxy-2-[(phenylmethyl)oxy]-N-3-pyridinylbenzamide (may be prepared as described in Example 29; 400 mg, 1.25 mmol) in dimethylsulfoxide (8 ml) at 0° C., and the mixture was stirred at room temperature for 1 h. 1,1-Dimethylethyl (2S)-2-({[(4-chlorophenyl)sulfonyl]oxy}methyl)-1-pyrrolidinecarboxylate (444 mg, 1.25 mmol) in dimethylsulfoxide (7 ml) was added to the solution dropwise, and the mixture was stirred at 75° C. for 18 h. The mixture was poured into water (100 ml), extracted thoroughly with ethyl acetate. The organic layer was dried, and concentrated to obtain a crude product, which was purified by chromatography on silica gel (dichloromethane/methanol=50:1) to yield the title compound as a yellow oil. 0.60 g.

MS (electrospray): m/z [M+H]$^+$=504.1.

Description 75

1,1-Dimethylethyl methyl[2-({4-[(phenylmethyl)oxy]-3-[(3-pyridinylamino)carbonyl]phenyl}oxy)ethyl]carbamate (D75)

To a solution of 5-hydroxy-2-[(phenylmethyl)oxy]-N-3-pyridinylbenzamide (may be prepared as described in Example 44; 200 mg, 0.62 mmol) in dimethylsulfoxide (8 ml) was added sodium hydride (17.98 mg, 0.75 mmol) at 0° C., and the mixture was stirred at room temperature for 1 h. 2-[{[(1,1-Dimethylethyl)oxy]carbonyl}(methyl)amino] ethyl 4-methylbenzenesulfonate (247 mg, 0.75 mmol) in dimethylsulfoxide (8 ml) was added to the solution dropwise, and the mixture was stirred at 75° C. for 18 h. The mixture was poured into water (100 ml), extracted thoroughly with ethyl acetate. The organic layer was dried, and concentrated to obtain a crude product. The crude product was purified by chromatography on silica gel (dichloromethane/methanol=15:1) to yield the title compound as a yellow oil. 140 mg.

MS (electrospray): m/z [M+H]$^+$=478.2.

Description 76

2-{[(2-({4-[(Phenylmethyl)oxy]-3-[(3-pyridinylamino)carbonyl]phenyl}oxy)ethyl]oxy}ethyl 4-methylbenzenesulfonate (D76)

Potassium hydroxide (0.15 g, 2.62 mmol) was added to a solution of 5-hydroxy-2-[(phenylmethyl)oxy]-N-3-pyridinylbenzamide (may be prepared as described in Example 44; 0.7 g, 2.19 mmol) in methanol. The mixture was stirred for 0.5 h. The mixture was evaporated and the residue was dissolved in dimethylformamide. 2,2'-Oxybis(ethane-2,1-diyl)bis(4-methylbenzenesulfonate) (1.36 g, 3.28 mmol) was slowly added and the mixture was stirred overnight. The solvent was evaporated to yield the title compound as a crude product. 420 mg.

MS (electrospray): m/z $[M+H]^+=563$

Description 77

Bis(1,1-dimethylethyl) (2-{[2-({4-[(phenylmethyl)oxy]-3-[(3-pyridinylamino)carbonyl]phenyl}oxy)ethyl]oxy}ethyl)imidodicarbonate (D77)

2-{[2-({4-[(Phenylmethyl)oxy]-3-[(3-pyridinylamino)carbonyl]phenyl}oxy)ethyl]oxy}ethyl 4-methylbenzenesulfonate (may be prepared as described in Description 76; 500 mg, 0.89 mmol) was dissolved in N,N-dimethylformamide (10 ml). Di-tert-butyl iminodicarbonate (193 mg, 0.89 mmol) and $Cs_2CO_3$ (290 mg, 0.89 mmol) were added. The reaction mixture was heated at 60° C. for 3 h. After cooling to room temperature, the reaction mixture was diluted with water and extracted with ethyl acetate. The combined organic extracts were washed with water, brine, dried over $Na_2SO_4$, and concentrated under reduced pressure to yield the title compound as an oil. 360 mg.

MS (electrospray): m/z $[MH-100]^+=508$

Description 78

Phenylmethyl 2-[(phenylmethyl)oxy]-5-(4-pyridinyl)benzoate (D78)

$Na_2CO_3$ (0.53 g, 5.00 mmol), followed by pyridin-4-ylboronic acid (0.34 g, 2.75 mmol) and $Pd(Ph3P)_4$ (0.144 g, 0.125 mmol) were added to a mixture of benzyl 2-(benzyloxy)-5-bromobenzoate (may be prepared as described in Description 4; 1.0 g, 2.50 mmol) in 1,4-dioxane (25 ml) and water (5 ml) under nitrogen. After addition, the mixture was stirred at 90° C. for 4 hours. The reaction mixture was evaporated to give brown crude product, which was purified by chromatography (silica gel, 40 g, eluent: ethyl acetate/petroleum ether=1:2, 1.2 L) to yield the title compound as a white solid. 0.81 g.

MS (electrospray): m/z $[M+H]^+=396$

Description 79

2-[(Phenylmethyl)oxy]-5-(4-pyridinyl)benzoic acid (D79)

Solid LiOH (0.79 g, 18.77 mmol) was added to a stirred solution of phenylmethyl 2-[(phenylmethyl)oxy]-5-(4-pyridinyl)benzoate (may be prepared as described in Description 78; 0.81 g, 1.88 mmol) in tetrahydrofuran (50 ml) and water (10 ml) in air at room temperature. The reaction mixture was stirred at 70° C. overnight. After the reaction mixture was cooled to room temperature, the solvent was removed and the residue was dissolved in water (100 ml) and stirred in an ice-water bath. 1N HCl (aq) was added to adjust the pH to 4. The solid was filtered, and dissolved in ethyl acetate (80 ml). The solution was dried over $Na_2SO_4$, filtered, and concentrated under reduced pressure to yield the title compound as a white solid, 486 mg.

MS (electrospray): m/z $[M+H]^+=305.9$

Description 80

(3-Aminopyridin-2-yl)methanol (D80)

3-Aminopicolinic acid (145 mg, 1.05 mmol) was carefully added in 3 aliquots to a slurry of $LiAlH_4$ (143 mg, 3.78 mmol) in dry tetrahydrofuran (6 ml). The resulting mixture was stirred at 15° C. overnight. After cooling in an ice bath, the reaction mixture was quenched with careful addition of water (1 ml) dropwise, followed by 15% aqueous NaOH (1 ml), and then water (3 ml). The resulting solid was filtered and washed several times with tetrahydrofuran. The filtrate was concentrated. The residue was purified by flash chromatography on silica gel using 5% $CH_3OH(NH_3)$/ethyl acetate as eluent to yield the title compound as a yellow oil. 110 mg.

MS (electrospray): m/z $[M+H]^+=125$

Description 81

(3-Aminopyridin-4-yl)methanol (D81)

3-Aminoisonicotinic acid (1 g, 7.24 mmol) was carefully added in 3 aliquots to a slurry of $LiAlH_4$ (0.99 g, 26.1 mmol) in dry tetrahydrofuran (40 ml). The resulting mixture was stirred at 15° C. overnight. After cooling in an ice bath, the reaction mixture was quenched with careful addition of water (1 ml) dropwise, followed by 15% aqueous NaOH (1 ml), and then water (3 ml). The resulting solid was filtered, and washed several times with tetrahydrofuran. The filtrate was concentrated to give oil, which was purified by flash chromatography on silica gel using 5% $CH_3OH(NH_3)$/ethyl acetate as eluent to yield the title compound as a yellow oil. 610 mg.

MS (electrospray): m/z $[M+H]^+=125$

Description 82

(3-Fluorophenyl)methyl 5-bromo-2-{[(3-fluorophenyl)methyl]oxy}benzoate (D82)

Solid potassium carbonate (2.76 g, 20 mmol) was added to a stirred solution of 5-bromo-2-hydroxybenzoic acid (1 g, 4.61 mmol) in acetone (20 ml) at 20° C. The reaction mixture was stirred at 20° C. for 10 min, and then 1-(bromomethyl)-3-fluorobenzene (1.92 g, 10.14 mmol) was added dropwise. The reaction mixture was stirred at 71° C. for 18 h. After cooling to room temperature, the mixture was filtered. The filtrate was concentrated to give a colourless oil. The crude product was added to a silica gel column and was eluted with hexane/ethyl acetate (100:5 then 20:1) to yield the title compound as a white solid. 1.65 g.

MS (electrospray): m/z $[M+Na]^+=454.8, 456.8$

Description 83

5-Bromo-2-{[(3-fluorophenyl)methyl]oxy}benzoic acid (D83)

Solid LiOH (0.50 g, 20.95 mmol) was added in one charge to a stirred solution of (3-fluorophenyl)methyl 5-bromo-2-{

[(3-fluorophenyl)methyl]oxy}benzoate (may be prepared as described in Description 82; 1.65 g, 3.81 mmol) in tetrahydrofuran (15 ml) and water (5 ml) in air at 20° C. The reaction mixture was stirred at 71° C. for 16 h. After cooling to room temperature, the reaction mixture was diluted with ethyl acetate (200 ml). 10% Aqueous HCl was added to the mixture to adjust pH to 2. The organic phase was isolated, washed with brine, dried over $Na_2SO_4$, and concentrated to yield the title compound as a white solid. 1.5 g.

MS (electrospray): m/z $[M+H]^+$=324.8, 326.8,

Description 84

(2-Fluorophenyl)methyl 5-bromo-2-{[(2-fluorophenyl)methyl]oxy}benzoate (D84)

Neat 1-(bromomethyl)-2-fluorobenzene (1533 mg, 8.11 mmol) was added over 1 min to a stirred suspension of 5-bromo-2-hydroxybenzoic acid (800 mg, 3.69 mmol) and potassium carbonate (1274 mg, 9.22 mmol) in acetone (60 ml) in air at room temperature. The reaction mixture was stirred at 70° C. overnight. The reaction mixture was filtered. The filtrate was evaporated and the residue was dissolved in diethyl ether (30 ml) and evaporated again. The residue was dried in vacuo to yield the title compound as a white solid. 1.74 g.

MS (electrospray): m/z $[M+H]^+$=433, $[M+Na]^+$=455

Description 85

5-Bromo-2-{[(2-fluorophenyl)methyl]oxy}benzoic acid (D85)

Solid LiOH (0.24 g, 10.16 mmol) was added to a stirred solution of (2-fluorophenyl)methyl 5-bromo-2-{[(2-fluorophenyl)methyl]oxy}benzoate (may be prepared as described in Description 84; 1 g, 2.03 mmol) in tetrahydrofuran (30 ml) and water (10 ml) in air at room temperature. The reaction mixture was stirred at 70° C. overnight. After cooled to room temperature, the solvent was removed to obtain a solid, which was dissolved in water (20 ml) and stirred in ice-water bath. 1 M HCl (aq) was added to adjust the pH to 4. The solid was filtered and dried in vacuum to yield the title compound as a white solid. 695 mg.

MS (electrospray): m/z $[M+Na]^+$=347.0, 348.9

Description 86

(4-Fluorophenyl)methyl 5-bromo-2-{[(4-fluorophenyl)methyl]oxy}benzoate (D86)

Method A
Neat 1-(bromomethyl)-4-fluorobenzene (1533 mg, 8.11 mmol) was added over 1 min to a stirred suspension of 5-bromo-2-hydroxybenzoic acid (800 mg, 3.69 mmol) and potassium carbonate (1274 mg, 9.22 mmol) in acetone (60 ml) in air at room temperature. The reaction mixture was stirred at 70° C. overnight. After filtering, the filtrate was evaporated to give a solid, which was dried in vacuo to yield the title compound as a white solid. 1.56 g.

MS (electrospray): m/z $[M+Na]^+$=455
Method B
Cesium carbonate (7.51 g, 23.04 mmol) and 4-fluorobenzyl bromide (2.51 ml, 20.27 mmol) were added to a solution of 5-bromosalicyclic acid (2 g, 9.22 mmol) in acetone (50 ml). The mixture was stirred for 2 hours, the solvent removed in vacuo and the residue redissolved in water (20 ml) and ethyl acetate (50 ml). The organic layer was separated, dried ($MgSO_4$) and the solvent removed in vacuo to give a solid. Trituration with 3:1 hexane/ethyl acetate yielded the title compound as a white solid. 2.62 g.

MS (electrospray): m/z $[M+Na]^+$=457

Description 87

5-Bromo-2-{[(4-fluorophenyl)methyl]oxy}benzoic acid (D87)

Solid LiOH (0.23 g, 9.58 mmol) was added to a stirred solution of (4-fluorophenyl)methyl 5-bromo-2-{[(4-fluorophenyl)methyl]oxy}benzoate (may be prepared as described in Description 86; 1 g, 1.92 mmol) in tetrahydrofuran (30 ml) and water (10 ml) in air at room temperature. The reaction mixture was stirred at 70° C. overnight. After cooling to room temperature, the solvent was removed to obtain a solid, which was dissolved in water (20 ml) and stirred in an ice-water bath. 1N HCl (aq) was added to adjust the pH to 4. The solid was filtered, and dried in vacuo to yield the title compound as a grey solid. 674 mg.

MS (electrospray): m/z $[M+Na]^+$=347.0, 348.9
Method B
Lithium hydroxide (0.43 g, 18.14 mmol) was added to a solution of (4-fluorophenyl)methyl 5-bromo-2-{[(4-fluorophenyl)methyl]oxy}benzoate (may be prepared as described in Description 86) (2.62 g, 6.05 mmol) in water (5 ml) and tetrahydrofuran (20 ml). The mixture was stirred overnight and the solvent removed in vacuo. The residue was redissolved in water (30 ml) and acidified to pH=2 using 1N HCl and then extracted with ethyl acetate (3×25 ml). The combined organic layers were dried ($MgSO_4$) and the solvent removed in vacuo to yield the titled compound as a white solid. 1.97 g.

MS (electrospray): m/z $[M+H]^+$=324/326

Description 88

(3,4-Difluorophenyl)methyl 5-bromo-2-{[(3,4-difluorophenyl)methyl]oxy}benzoate (D88)

Neat 4-(bromomethyl)-1,2-difluorobenzene (1526 mg, 7.37 mmol) was added over 1 min to a stirred suspension of 5-bromo-2-hydroxybenzoic acid (800 mg, 3.69 mmol) and potassium carbonate (1274 mg, 9.22 mmol) in acetone (60 ml) in air at room temperature. The reaction mixture was stirred at 70° C. overnight. After filtering, the filtrate was evaporated to give a solid, which was dried in vacuo to yield the title compound as a white solid. 2.0 g.

MS (electrospray): m/z $[M+Na]^+$=491
Method B
To a stirred solution of 5-bromo-2-hydroxybenzoic acid (1.8 g, 8.29 mmol) in acetone (50 ml) at room temperature was added potassium carbonate (2.87 g, 20.74 mmol) followed by 4-(bromomethyl)-1,2-difluorobenzene (2.34 ml, 18.25 mmol). The mixture was stirred at room temperature for 30 min and then heated to reflux for 15 hr. The solid was filtered off and washed with acetone (3×50 ml). The organic layer was evaporated under reduced pressure and the oil was purified by chromatography using a silica cartridge, eluting with 0-15% ethyl acetate/isohexane to give a clear oil, which solidified on standing to yield the title compound. 3.9 g.

MS (electrospray): m/z $[M+H]^+$ no mass ion observed.

Description 89

5-Bromo-2-{[(3,4-difluorophenyl)methyl]oxy}benzoic acid (D89)

Solid LiOH (0.26 g, 10.86 mmol) was added to a stirred solution of (3,4-difluorophenyl)methyl 5-bromo-2-{[(3,4-difluorophenyl)methyl]oxy}benzoate (may be prepared as described in Description 88; 1.2 g, 2.17 mmol) in tetrahydrofuran (30 ml) and water (10 ml) in air at room temperature. The reaction mixture was stirred at 70° C. overnight. After cooling to room temperature, the solvent was removed. The residue was dissolved in water (20 ml) and stirred in ice-water bath. 1N HCl (aq) was added to the mixture to adjust the pH to 4. The solid was filtered, and dried in vacuo to yield the title compound as a white solid. 730 mg.

MS (electrospray): m/z [M+Na]$^+$=365

Method B

Water (50 ml) and lithium hydroxide (0.60 g, 24.93 mmol) were added to a solution of (3,4-difluorophenyl)methyl 5-bromo-2-{[(3,4-difluorophenyl)methyl]oxy}benzoate (may be prepared by Description 88; 3.9 g, 8.31 mmol) in tetrahydrofuran (150 ml). The mixture was heated to reflux for 2 hours. The mixture was allowed to cool and diluted with ethyl acetate (200 ml) and this mixture was then acidified to pH=1 using 2M aqueous HCl. The organics were separated and the aqueous layer was extracted with ethyl acetate (100 ml). The organics were combined, dried (MgSO$_4$) and evaporated under reduced pressure to yield the title compound as a white solid. 2.9 g. The residue contains some benzyl alcohol.

MS (electrospray): m/z [M+H]$^+$=343

Description 90

1,1-Dimethylethyl (3-methyl-4-isoxazolyl)carbamate (D90)

Diphenyl phosphorazidate (1083 mg, 3.93 mmol) and triethylamine (0.55 ml, 3.93 mmol) were added to a stirred solution of 3-methylisoxazole-4-carboxylic acid (500 mg, 3.93 mmol) in tert-butanol (30 ml) at 50° C. After addition, the solution was heated at 90° C. for 6 hours. The reaction mixture was evaporated to remove solvent and the residue was purified by chromatography column (silica gel, 40 g, eluent: dichloromethane/methanol=50:1, 500 ml) to yield the title compound as a white solid. 517 mg.

MS (electrospray): m/z [M+H]$^+$=199

Description 91

3-Methyl-4-isoxazolamine (D91)

HCl gas in ethanol (10 ml, 13 mmol) was carefully added 1,1-dimethylethyl (3-methyl-4-isoxazolyl)carbamate (may be prepared as described in Description 90; 517 mg, 2.07 mmol) in an ice-water bath. After addition, the solution was stirred at room temperature for 2 hours. The reaction mixture was concentrated to obtain colourless gum, which was dissolved in water (10 ml), then aqueous ammonia solution (30%) was added to adjust the pH to 9. The solution was concentrated to yield crude title compound as a yellow solid. 560 mg.

Description 92

1,1-Dimethylethyl (5-methyl-4-isoxazolyl)carbamate (D92)

Diphenyl phosphorazidate (1083 mg, 3.93 mmol) and triethylamine (0.55 ml, 3.93 mmol) was added to a stirred solution of 5-methylisoxazole-4-carboxylic acid (500 mg, 3.93 mmol) in tert-butanol (30 ml) at 50° C. After addition, the solution was heated at 90° C. for 6 hours. The reaction mixture was diluted with saturated NaHCO$_3$ solution (50 ml) and then extracted with ethyl acetate (60 ml×5). The combined organic phases were dried over anhydrous MgSO$_4$, and concentrated. The residue was purified by column chromatography column (silica gel, 40 g, eluent: dichloromethane/methanol=100:1, 1.3 L) to yield the title compound as a white solid. 161 mg, MS (electrospray): m/z [M+H]$^+$=199.0

Description 93

5-Methyl-4-isoxazolamine (D93)

HCl gas in ethanol (5 ml, 6.50 mmol) was added into 1,1-dimethylethyl (5-methyl-4-isoxazolyl)carbamate (may be prepared as described in Description 92; 161 mg, 0.81 mmol) carefully in ice-water bath. The solution was stirred at room temperature for 2 hours. The reaction mixture was concentrated to and the residue was dissolved in water (10 ml). 30% Aqueous ammonia solution was added to adjust the pH to 9. The solution was then concentrated to yield the title compound as a yellow solid. 142 mg.

Description 94

4-Nitroisoxazole (D94)

Isoxazole (4.64 ml, 72.4 mmol) was dissolved in trifluoroacetic anhydride (30 ml) and ammonium nitrate (6.37 g, 80 mmol) was added in 0.5 g portions, keeping the reaction temperature between 25° C.~30° C. Another batch of ammonium nitrate (3.6 g) was then added. About one third of the reaction solution was poured onto ice water, and extracted with dichloromethane (60 ml×4). The extracts were combined, washed with water (80 ml×3), dried over anhydrous MgSO$_4$, and concentrated to yield the title compound as a yellow solid. 0.9 g.

Description 95

4-Isoxazolamine (D95)

4-Nitroisoxazole (may be prepared as described in Description 94; 850 mg, 7.45 mmol) was added to a solution of ammonium chloride (9169 mg, 171 mmol) in water (60 ml). The resultant suspension was cooled to 0° C., and zinc (4142 mg, 63.3 mmol) was added in portions whilst keeping the temperature below 5° C. After the addition, the mixture was stirred at 0-5° C. for 2 hours. The reaction mixture was then filtered, and the filtrate was extracted with ethyl acetate (100 ml×4). The organic phase was washed by water (100 ml×2), dried over anhydrous MgSO$_4$, and concentrated to yield the title compound as a brown oil. 535 mg.

Description 96

Phenylmethyl 5-formyl-2-[(phenylmethyl)oxy]benzoate (D96)

Cesium carbonate (14.71 g, 45.1 mmol) and benzyl bromide (4.47 ml, 37.6 mmol) were added dropwise to a solution of 5-formyl-2-hydroxybenzoic acid (2.5 g, 15.05 mmol) in dimethylformamide (40 ml). The mixture was stirred for 24 hours. The dimethylformamide was removed in vacuo and the residue was redissolved in ethyl acetate (150 ml), washed with water (3×30 ml), dried (MgSO$_4$) and the solvent removed in vacuo to give a off white solid. Trituration with 6:1 isohexane/ethyl acetate yielded the title compound as a white solid. 4.20 g.

MS (electrospray): m/z [M+H]$^+$=347

Description 97

5-Formyl-2-[(phenylmethyl)oxy]benzoic acid (D97)

Lithium hydroxide (207 mg, 8.66 mmol) and water (2.5 ml) were added to a solution of phenylmethyl 5-formyl-2-[(phenylmethyl)oxy]benzoate (may be prepared as described in description 96) (1 g, 2.89 mmol) in tetrahydrofuran (10 ml) and methanol (2.5 ml). The mixture was stirred overnight. The tetrahydrofuran/methanol was removed in vacuo and the remaining aqueous solution was acidified to pH=1 and extracted with ethyl acetate (3×20 ml). The solvent was removed in vacuo to yield the title compound as a white solid. 1.1 g.

MS (electrospray): m/z [M−H]$^+$=255

Description 98

Ethyl 3-{4-hydroxy-3-[(3-pyridinylamino)carbonyl]phenyl}propanoate (D98)

To a suspension of ethyl (2Z)-3-{4-[(phenylmethyl)oxy]-3-[(3-pyridinylamino)carbonyl]phenyl}-2-propenoate (may be prepared as described in Example 68; 160 mg, 0.40 mmol) in methanol (10 ml) was added Pd/C (20 mg). The mixture was put under a hydrogen atmosphere for 5 hours. The catalyst was removed by filtration through Celite and the solvent removed in vacuo to yield the title compound as a pale yellow solid. 119 mg.

MS (electrospray): m/z [M+H]$^+$=314

Description 99

Methyl 5-bromo-2-{[(1S)-1-phenylethyl]oxy}benzoate (D99)

(1R)-1-Phenylethanol (3.33 g, 27.30 mmol) and Ph$_3$P (7.15 g, 27.3 mmol) was added to a solution of methyl 4-bromo-2-hydroxybenzoate (3 g, 12.98 mmol) in dichloromethane (50 ml). The solution was cooled to 0° C. then DIAD (5.30 ml, 27.30 mmol) was added. The mixture was allowed to warm to room temperature and was then stirred overnight. The solvent was removed in vacuo and purified by column chromatography (5% ethyl acetate/hexane to 20% ethyl acetate/hexane) to yield the title compound as a colourless oil. 4.56 g. It contained trace ethyl acetate and Ph$_3$P by NMR.

MS (electrospray): m/z [M+H]$^+$=357/359

Description 100

(3,4-Difluorophenyl)methyl 2-{[(3,4-difluorophenyl)methyl]oxy}-5-formylbenzoate (D100)

Cesium carbonate (17.65 g, 54.2 mmol) and 4-(bromomethyl)-1,2-difluorobenzene (5.78 ml, 45.1 mmol) were added to a solution of 5-formyl-2-hydroxybenzoic acid (3 g, 18.06 mmol) in dimethylformamide (100 ml) was added) at room temperature. The mixture was stirred at room temperature overnight. The mixture was then filtered, the dimethylformamide was evaporated and the residue was diluted with ethyl acetate (100 ml) and washed with water (3×50 ml). The organic layer was dried (MgSO$_4$) and evaporated under reduced pressure to give an oil which solidified on standing solidified. The solid was triturated with an 8:1 mixture of hexane/ethyl acetate. The solid was filtered and dried in air under vacuum to yield the title compound as a white solid. 7 g.

MS (electrospray): m/z [M+H]$^+$=419

Description 101

2-{[(3,4-Difluorophenyl)methyl]oxy}-5-formylbenzoic acid (D101)

To a solution of (3,4-difluorophenyl)methyl 2-{[(3,4-difluorophenyl)methyl]oxy}-5-formylbenzoate (may be prepared by Description 100; 7 g, 16.73 mmol) in tetrahydrofuran (50 ml) was added lithium hydroxide (1.202 g, 50.2 mmol) followed by methanol (12.50 ml) and water (12.5 ml). The mixture was stirred at room temperature overnight. The mixture was then evaporated under reduced pressure to one third volume. The mixture was diluted with water (50 ml) and acidified to pH=1 using 2M aqueous HCl. The solid formed was filtered off, washed with water and air dried under vacuum to give a white solid. 4.85 g.

MS (electrospray): m/z [M+H]$^+$=293

Description 102

(2,4-Difluorophenyl)methyl 5-bromo-2-{[(2,4-difluorophenyl)methyl]oxy}benzoate (D102)

To a solution of 5-bromo-2-hydroxybenzoic acid (2.5 g, 11.52 mmol) in acetone (100 ml) was added potassium carbonate (3.98 g, 28.8 mmol) and 1-(bromomethyl)-2,4-difluorobenzene (3.25 ml, 25.3 mmol). The mixture was heated to reflux for 4 hours. On cooling the mixture was filtered to remove the carbonate, the solid was washed with acetone (50 ml). The organics were evaporated under reduced pressure to give a white solid 5.39 g. No attempt was made to purify this compound it was taken on as is.

MS (electrospray): m/z [M+H]$^+$=470

Description 103

5-Bromo-2-{[(2,4-difluorophenyl)methyl]oxy}benzoic acid (D103)

Lithium hydroxide (0.83 g, 34.5 mmol) and water (50 ml) were added to a solution of (2,4-difluorophenyl)methyl 5-bromo-2-{[(2,4-difluorophenyl)methyl]oxy}benzoate (may be prepared by Description 102; 5.39 g, 11.49 mmol) in tetrahydrofuran (200 ml). The mixture was heated to reflux for 2 hrs. The tetrahydrofuran was then removed on a buchi and the aqueous mixture was acidified to pH=1 using 2M aqueous HCl. The solid formed was filtered off, washed with water (2×50 ml) and dried in air under vacuum. The solid was triturated with diethyl ether to give a white solid. 3.1 g.

MS (electrospray): m/z [M+H]$^+$=344

Description 104

(4-Fluorophenyl)methyl 2-{[(4-fluorophenyl)methyl]oxy}-5-formylbenzoate (D104)

Cesium carbonate (11.77 g, 36.1 mmol) and 1-(bromomethyl)-4-fluorobenzene (1.50 ml, 12.04 mmol) were added to a solution of 5-formyl-2-hydroxybenzoic acid (2 g, 12.04 mmol) in dimethylformamide (100 m) at room temperature. The mixture was stirred at room temperature overnight. The mixture was filtered, the dimethylformamide was evaporated and the residue was diluted with ethyl acetate (100 ml) and washed with water (3×50 ml). The organic layer was dried (MgSO$_4$) and evaporated under reduced pressure to give an oil which solidified on standing. The solid was triturated with an 8:1 mixture of hexane/ethyl acetate. The solid was filtered and dried in air under vacuum to yield the title compound as a white solid. 4.09 g.

MS (electrospray): m/z [M+H]$^+$=383

Description 105

2-{[(4-Fluorophenyl)methyl]oxy}-5-formylbenzoic acid (D105)

Lithium hydroxide (0.75 g, 31.4 mmol), methanol (25 ml) and water (25 ml) were added to a solution of (4-fluorophenyl)methyl 2-{[(4-fluorophenyl)methyl]oxy}-5-formylbenzoate (may be prepared as described in Description 104; 4 g, 10.46 mmol) in tetrahydrofuran (100 ml). The mixture was stirred at room temperature overnight. The mixture was evaporated to half volume, diluted with water (100 ml) and acidified with 1M aqueous hydrochloric acid to adjust the pH to 1. The mixture was stirred at room temperature and the solid formed was filtered, washed with water (50 ml) and air dried under vacuum to yield the title compound as a white solid. 2.85 g.

MS (electrospray): m/z [M+H]$^+$=273

Description 106

Methyl 5-formyl-2-hydroxybenzoate (D106)

To a solution of 5-formyl-2-hydroxybenzoic acid (3 g, 18.06 mmol) in methanol (10 ml) was added H$_2$SO$_4$ (0.5 ml, 9.38 mmol). The solution was heated at 50° C. for 18 hours. The solution was cooled, and DCM (30 ml) and water (20 ml) were added. The organic layer was separated, washed with NaHCO$_3$ (10 ml), dried (MgSO$_4$) and the solvent removed in vacuo to yield the title compound as a yellow solid. 3.1 g.

MS (electrospray): m/z, [M+H]$^+$=181

Description 107

4-Hydroxy-3-[(methyloxy)carbonyl]benzoic acid (D107)

Sulfamic acid (1.83 g, 18.87 mmol) and 2-methyl-1-butene (1.20 ml, 11.10 mmol) were added to a solution of methyl 5-formyl-2-hydroxybenzoate (may be prepared as described in Description 106; 1 g, 5.55 mmol) in tetrahydrofuran (20 ml), water (20 ml) and dimethyl sulfoxide (20 ml). The solution was cooled to 0° C. and sodium chlorite (1.51 g, 16.65 mmol) in water (5 ml) was added. After 45 minutes at 0° C. the reaction the mixture was quenched with saturated Na$_2$S$_2$O$_3$ solution (20 ml) and extracted with ethyl acetate (3×30 ml). The organic layer was dried (MgSO$_4$) and the solvent removed in vacuo to yield the title compound as a solid. 1.09 g (damp with DMSO/H$_2$O).

MS (electrospray): m/z, [M+H]$^+$=197

Description 108

Methyl 2-hydroxy-5-(4-morpholinylcarbonyl)benzoate (D108)

To a solution of 4-hydroxy-3-[(methyloxy)carbonyl]benzoic acid (may be prepared as described in Description 107, 1.31 g, 6.68 mmol) in N,N-dimethylformamide (10 ml) was added diisopropylethylamine (2.33 ml, 13.36 mmol), morpholine (1.75 ml, 20.03 mmol), HOBT (1.33 g, 8.68 mmol) and EDC (2.56 g, 13.36 mmol). The solution was stirred at room temperature for 18 hours then another equivalent of EDC was added (1.28 g, 13.38 mmol). The solution was stirred for another 6 hours then ethyl acetate (20 ml) and water were added. The organic layer was separated, washed with water (3×10 ml), dried (MgSO$_4$) and the solvent removed in vacuo to give a gum. Purification by MDAP yielded the title compound as a gum. 560 mg.

MS (electrospray): m/z, [M+H]$^+$=266

Description 109

Methyl 2-{[(4-fluorophenyl)methyl]oxy}-5-(4-morpholinylcarbonyl)benzoate (D109)

To a solution of methyl 2-hydroxy-5-(4-morpholinylcarbonyl)benzoate (may be prepared as described in Description 108, 270 mg, 1.02 mmol) in acetone (3 ml) was added cesium carbonate (663 mg, 2.04 mmol) and 4-fluorobenzyl bromide (0.16 ml, 1.32 mmol). The mixture was heated at 50° C. for 2 hours. The solvent was removed in vacuo and the residue partitioned between ethyl acetate (15 ml) and water (5 ml). The organic layer was dried and the solvent removed in vacuo and the residue purified by column chromatography (silicon, 4:1 ethyl acetate/cyclohexane) to give the title compound as a yellow gum. 96 mg.

MS (electrospray): m/z, [M+H]$^+$=374

Description 110

Methyl 2-{[(2,4-difluorophenyl)methyl]oxy}-5-(4-morpholinylcarbonyl)benzoate (D110)

To a stirred solution of methyl 2-hydroxy-5-(4-morpholinylcarbonyl)benzoate (may be prepared as described in Description 108, 270 mg, 1.02 mmol) in acetone (3 ml) was added cesium carbonate (663 mg, 2.04 mmol) and 1-(bromomethyl)-2,4-difluorobenzene (0.17 ml, 1.32 mmol). The mixture was heated at 50° C. for 2 hours, cooled and the solvent removed in vacuo. The residue was partitioned between water (5 ml) and ethyl acetate (10 ml). The organic layer was dried (MgSO$_4$) and the solvent removed in vacuo to give a residue. Purification by column chromatography (silicon, 4:1 ethyl acetate/cyclohexane) yielded the title compound as a yellow gum. 100 mg.

MS (electrospray): m/z, [M+H]$^+$=392

Description 111

4-{[(4-Fluorophenyl)methyl]oxy}-3-[(3-pyridinylamino)carbonyl]benzoic acid (D111)

To a solution of 2-{[(4-fluorophenyl)methyl]oxy}-5-formyl-N-3-pyridinylbenzamide (may be prepared as described in Example 82; 100 mg, 0.29 mmol) in acetone (10 ml) was added potassium permanganate (67.7 mg, 0.43 mmol) as a solution in 10 ml of water. The mixture was stirred at room temperature overnight. The mixture was quenched by adding 10 ml of 5% sodium sulfite solution. The solution was filtered through celite and mixed with 1 ml of acetic acid. The mixture was evaporated to a third volume, water (20 ml) was added and the mixture was filtered to yield the title compound as a white solid. This contains about 10% starting material and was used directly without further purification. 63 mg.

MS (electrospray): m/z [M+H]$^+$=367

Description 112

Methyl 2-{[(4-fluorophenyl)methyl]oxy}-5-iodobenzoate (D112)

To a solution of methyl 2-hydroxy-5-iodobenzoate (15 g, 53.9 mmol) in acetone (200 ml) was added 1-(bromomethyl)-4-fluorobenzene (9.95 ml, 81 mmol), potassium carbonate (14.91 g, 108 mmol) and the mixture was refluxed overnight. The mixture was allowed to cool and then filtered to remove the potassium carbonate. The solid potassium carbonate was washed with acetone (100 ml). The organics were combined and evaporated under reduced pressure on a buchi to give a solid. The solid was taken up into ethyl acetate (500 ml) and the organic phase was washed with water (2×200 ml), dried (MgSO$_4$) and evaporated under reduced pressure on a buchi. The solid obtained was recrystallised from cyclohexane to yield the title compound as a white solid. 18.2 g.

MS (electrospray): m/z [M+H]$^-$=385

Description 113

Methyl 2-{[(4-fluorophenyl)methyl]oxy}-5-{1-[2-(4-morpholinyl)ethyl]-1H-pyrazol-4-yl}benzoate (D113)

To a microwave vial was added methyl 2-{[(4-fluorophenyl)methyl]oxy}-5-iodobenzoate (may be prepared as described in Description 112; 0.5 g, 1.30 mmol), 4-{2-[4-(4,4,5,5-tetramethyl-1,3,2-dioxoborolan-2-yl)-1H-pyrazol-1-yl]ethyl}morpholine (0.60 g, 1.94 mmol), 1,2-dimethoxyethane (10 ml), tripotassium phosphate (0.55 g, 2.59 mmol) and PdCl$_2$(dppf) (0.08 g, 0.10 mmol). The mixture was sealed and heated to 120° C. for 30 min under microwave conditions. The mixture was evaporated under reduced pressure on a buchi. The residue was taken up into ethyl acetate (50 ml) and washed with water (2×25 ml). The organic phase was evaporated and purified by chromatography using a Flashmaster, eluting with 0-25% methanol/dichloromethane to yield the title compound as the major compound. This was used directly without further purification. 372 mg.

MS (electrospray): m/z [M+H]$^+$=440

Description 114

2-{[(4-Fluorophenyl)methyl]oxy}-5-{1-[2-(4-morpholinyl)ethyl]-1H-pyrazol-4-yl}benzoic acid (D114)

To a solution of methyl 2-{[(4-fluorophenyl)methyl]oxy}-5-{1-[2-(4-morpholinyl)ethyl]-1H-pyrazol-4-yl}benzoate (may be prepared as described in Description 113; 372 mg, 0.85 mmol) in tetrahydrofuran (25 ml) was added lithium hydroxide (60.8 mg, 2.54 mmol), water (5 ml) and the mixture was refluxed for 4 hours. The mixture was evaporated under reduced pressure on a buchi. The residue was taken up into water (10 ml) and acidified using 2M aqueous HCl to pH 1. The solid formed was filtered, washed with water and dried in air under vacuum to yield the title compound as a light brown solid. 170 mg.

MS (electrospray): m/z [M+H]$^+$=426

Description 115

Methyl 2-{[(4-fluorophenyl)methyl]oxy}-5-(1H-pyrazol-4-yl)benzoate (D115)

To a solution of methyl 2-{[(4-fluorophenyl)methyl]oxy}-5-iodobenzoate (may be prepared as described in Description 112; 1.4 g, 3.63 mmol) in 1,2-dimethoxyethane (40 ml) was added 1,1-dimethylethyl 4-(4,4,5,5-tetramethyl-1,3,2-dioxaborolan-2-yl)-1H-pyrazole-1-carboxylate (3.20 g, 10.88 mmol), tripotassium phosphate (1.54 g, 7.25 mmol), PdCl$_2$(dppf) (0.16 g, 0.22 mmol) and the mixture was heated to 80° C. for 6 hours. The temperature was raised to 90° C. for 2 hours. Further catalyst was added and the mixture was divided into two. One 20 ml portion was subjected to 120° C. for 30 min under microwave conditions. The second portion of 20 ml was heated to reflux for 12 hrs. The 1,1-dimethylethyl carboxylate protected products were deprotected. The products were then combined and evaporated under reduced pressure on a buchi. The mixture was taken up into dichloromethane (20 ml), treated with trifluoroacetic acid (10 ml) and stirred at room temperature for 1 hour. The mixture was evaporated and purified using the Flashmaster eluting with 0-25% methanol/dichloromethane to yield the title compound. 1.15 g.

MS (electrospray): m/z [M+H]$^+$=327

Description 116

Methyl 2-{[(4-fluorophenyl)methyl]oxy}-5-{1-[2-(methyloxy)ethyl]-1H-pyrazol-4-yl}benzoate (D116)

To a solution of methyl 2-{[(4-fluorophenyl)methyl]oxy}-5-(1H-pyrazol-4-yl)benzoate (may be prepared as described in Description 115; 200 mg, 0.61 mmol) was added 2-bromoethyl methyl ether (0.10 ml, 1.23 mmol), potassium carbonate (254 mg, 1.84 mmol) and the reaction mixture was stirred at room temperature. The reaction mixture was then warmed to 50° C. for 5 hours. The reaction was filtered to remove the potassium carbonate, and the organics were evaporated on a buchi under reduced pressure. The solid was taken up into ethyl acetate (50 ml) and this was washed with water (1×25 ml). The organics were dried (MgSO$_4$) and evaporated under reduced pressure on a buchi to yield the title compound. The crude product was used directly without further purification. 240 mg.

MS (electrospray): m/z [M+H]$^+$=385

Description 117

2-Hydroxy-5-(trifluoromethyl)benzoic acid (D117)

Iodocyclohexane (29.4 ml, 227 mmol) was added to a solution of 2-(methyloxy)-5-(trifluoromethyl)benzoic acid (5 g, 22.71 mmol) in N,N-dimethylformamide (25 ml), and the mixture was heated under reflux for 4 hours. After cooling, the reaction was evaporated under reduced pressure on a buchi. The residue was triturated with cyclohexane, and the solid obtained was filtered, washed with cyclohexane and dried in air under vacuum. 4.2 g MS (electrospray): m/z [M+H]$^-$=205

Description 118

(4-Fluorophenyl)methyl 2-{[(4-fluorophenyl)methyl]
oxy}-5-(trifluoromethyl)benzoate (D118)

To a solution of 2-hydroxy-5-(trifluoromethyl)benzoic acid (may be prepared as described in Description 117; 2 g, 9.70 mmol) in acetone (50 ml) was added 1-(bromomethyl)-4-fluorobenzene (4.04 g, 21.35 mmol), potassium carbonate (4.02 g, 29.1 mmol) and the reaction was heated to reflux overnight. The mixture was filtered to remove the solid potassium carbonate. The solid was washed with acetone (50 ml). The organics were combined and evaporated under reduced pressure on a buchi to yield the title compound. The crude yellow oil was used directly without further purification. 4.1 g.

MS (electrospray): m/z $[M+H]^+$=423

Description 119

2-{[(4-Fluorophenyl)methyl]oxy}-5-(trifluoromethyl)benzoic acid (D119)

Lithium hydroxide (0.70 g, 29.1 mmol) and water (20 ml) were added to a solution of (4-fluorophenyl)methyl 2-{[(4-fluorophenyl)methyl]oxy}-5-(trifluoromethyl)benzoate (may be prepared as described in Description 118; 4.1 g, 9.71 mmol) in tetrahydrofuran (100 ml) and the mixture was heated to reflux for 2 hours. The mixture was evaporated under reduced pressure on a buchi. Water (100) ml was added and the mixture was acidified to pH=1 using 2M aqueous hydrochloric acid. The precipitate was filtered and washed with water (2×50 ml). The solid was dried in air, under vacuum to yield the title compound as a white solid. 2.39 g MS (electrospray): m/z $[M+H]^+$=315

Description 120

(4-Fluorophenyl)methyl 2-{[(4-fluorophenyl)methyl]
oxy}-5-(1-methyl-1H-pyrazol-4-yl)benzoate (D120)

A mixture of (4-fluorophenyl)methyl 5-bromo-2-{[(4-fluorophenyl)methyl]oxy}benzoate (420 mg, 0.97 mmol), 1-methyl-4-(4,4,5,5-tetramethyl-1,3,2-dioxaborolan-2-yl)-1H-pyrazole (208 mg, 1.00 mmol), tetrakis(triphenylphosphine)palladium(0) (34.7 mg, 0.03 mmol) and $K_2CO_3$ (414 mg, 3 mmol) in 1,4-dioxane (10 ml) and water (2 ml) was stirred under nitrogen and heated at 90° C. for 16 hours. The solvent was removed, and the residue was dissolved in ethyl acetate (100 ml) and filtered. The filtrate was washed with water (50 ml) and brine (50 ml), dried over $Na_2SO_4$, and concentrated to give the crude product. The crude product was purified by a silica gel column (eluting with dichloromethane/methanol=50:1) yield the title compound as a white solid. 360 mg.

LCMS: MH+=435.0

Description 121

2-{[(4-Fluorophenyl)methyl]oxy}-5-(1-methyl-1H-pyrazol-4-yl)benzoic acid (D121)

(4-Fluorophenyl)methyl 2-{[(4-fluorophenyl)methyl]oxy}-5-(1-methyl-1H-pyrazol-4-yl)benzoate (may be prepared as described in Description 120; 360 mg, 0.83 mmol) was dissolved in tetrahydrofuran (20 ml) and water (5 ml). Then LiOH (99 mg, 4.14 mmol) was added. The resultant mixture was stirred at room temperature for 16 hours. The solvent was removed. The residue was dissolved in water (20 ml). The solution was acidified by 1N HCl to pH<5. The precipitate was filtered, washed with ether, and dried in vacuo to yield the title compound as a white solid. 260 mg.

LCMS: MH+=326.9

Description 122

Methyl 2-{[(4-fluorophenyl)methyl]oxy}-5-[(1Z)-3-oxo-1-propen-1-yl]benzoate (D122)

To a suspension of methyl 2-{[(4-fluorophenyl)methyl]oxy}-5-iodobenzoate (may be prepared as described in Description 112; 740 mg, 1.92 mmol) in N,N-dimethylformamide (5 ml) was added 3,3-bis(ethyloxy)-1-propene (0.88 ml, 5.8 mmol), potassium carbonate (397 mg, 2.87 mmol) and $PdOAc_2$ (25.8 mg, 0.115 mmol). The reaction was heated in the microwave at 120° C. for 40 minutes, cooled and then 2M HCl (5 ml) was added and the mixture stirred for 20 minutes. The mixture was extracted with diethyl ether (2×10 ml), the organic layer dried ($MgSO_4$), and the solvent removed in vacuo. Purification by column (Si, (solute, 6:1 cyclohexane/ethyl acetate) yielded the title compound. 163 mg.

MS (electrospray): m/z $[M+H]^+$ No mass seen but NMR consistent with product.

Description 123

Methyl 2-{[(4-fluorophenyl)methyl]oxy}-5-[(1Z)-3-(4-morpholinyl)-1-propen-1-yl]benzoate (D123)

To a solution of methyl 2-{[(4-fluorophenyl)methyl]oxy}-5-[(1Z)-3-oxo-1-propen-1-yl]benzoate (may be prepared as described in Description 122; 163 mg, 0.52 mmol) in 1,2-dichloroethane (10 ml) was added morpholine (0.05 ml, 0.52 mmol) and acetic acid (0.03 ml, 0.52 mmol). The solution was stirred for 3 hours then sodium triacetoxyborohydride (165 mg, 0.78 mmol) was added and stirred for one hour. Saturated $NaHCO_3$ solution (10 ml) was added and the mixture was stirred for 15 minutes. Dichloromethane (10 ml) was added and the organic layer was separated, dried ($MgSO_4$) and the solvent removed in vacuo to yield the title compound as a yellow gum. 197 mg.

MS (electrospray): m/z $[M+H]^+$ 386

Description 124

Methyl 2-{[(4-fluorophenyl)methyl]oxy}-5-[3-(4-morpholinyl)propyl]benzoate (D124)

2-{[(4-fluorophenyl)methyl]oxy}-5-[(1Z/E)-3-(4-morpholinyl)-1-propen-1-yl]-N-3-pyridinylbenzamide (may be prepared as described in Description 123; 197 mg, 0.51 mmol) was redissolved in methanol (10 ml) and added to Pd/C (40 mg, 0.38 mmol). The mixture was put under one atmosphere of hydrogen for 3 hours, filtered through Celite and the solvent removed in vacuo to yield the title compound as an oil. 166 mg.

MS (electrospray): m/z $[M+H]^+$ 388

Example 1

5-(1-Methylethyl)-2-[(phenylmethyl)oxy]-N-3-pyridinylbenzamide (E1)

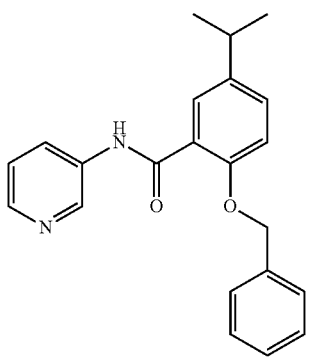 [SMILES: CC(C)c1ccc(OCc2ccccc2)c(C(=O)Nc2cccnc2)c1]

A solution of 5-(1-methylethyl)-2-[(phenylmethyl)oxy]benzoic acid (may be prepared as described in Description 3; 300 mg, 1.11 mmol), pyridin-3-amine (157 mg, 1.67 mmol), EDC (319 mg, 1.67 mmol) and HOBT (255 mg, 1.665 mmol) in DMF (5 mL) was stirred at room temperature overnight. The reaction mixture was poured into water (20 ml), filtered and the solid was washed with water and dried to yield a white solid. The crude product was purified by silica gel chromatography, eluting with petroleum ether:ethyl acetate (3:1) to yield the title compound as a white solid. 140 mg.

MS (electrospray): m/z [M+H]$^+$=347

$^1$H NMR (DMSO-d6): 1.21 (6H, d, J=7.2 Hz), 2.93 (1H, m), 5.23 (2H, s), 7.21-7.23 (1H, d, J=3.2, J=8.8 Hz), 7.33-7.42 (5H, m), 7.52-7.56 (3H, m), 8.10 (1H, d, J=8.8 Hz), 8.27 (1H, dd, J=1.2 Hz J=4.8 Hz), 8.67 (1H, d, J=2.4 Hz), 10.35 (1H, s).

Example 2

5-Bromo-2-[(phenylmethyl)oxy]-N-3-Pyridinylbenzamide (E2)

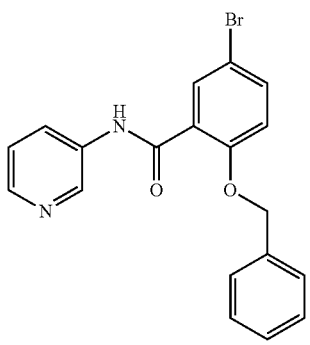 [SMILES: O=C(Nc1cccnc1)c1cc(Br)ccc1OCc1ccccc1]

3-Pyridinamine (123 mg, 1.30 mmol) in DCM (15 ml) was added to a stirred solution of 5-bromo-2-[(phenylmethyl)oxy]benzoic acid (may be prepared as described in Description 5, method A; 200 mg, 0.65 mmol), HOBT (150 mg, 0.98 mmol) and EDC (187 mg, 0.98 mmol) in DCM (15 ml) under nitrogen at room temperature. The reaction mixture was stirred at 20° C. overnight. The reaction mixture was partitioned between DCM (50 ml) and water (25 ml). The organic phase was washed with saturated brine (25 ml), dried over sodium sulphate and evaporated in vacuo to give the crude product as a yellow solid. The crude product was added to a Biotage column and was eluted with petroleum ether:ethyl acetate (3:1) to yield the title compound as a white solid. 75 mg. MS (electrospray): m/z [M+H]$^+$=383

$^1$H NMR (DMSO-d6): 5.25 (2H, s), 7.28 (1H, d, J=8.8 Hz), 7.33-7.39 (4H, m), 7.51 (2H, m), 7.71 (1H, dd, J=8.8 Hz, J=2.4 Hz), 7.79 (1H, d, J=2.4 Hz), 8.09 (1H, m), 8.30 (1H, dd, J=4.8 Hz, J=1.6 Hz), 8.70 (1H, d, J=2.4 Hz), 10.44 (1H, s).

Example 3

5-(Methyloxy)-2-[(phenylmethyl)oxy]-N-3-pyridinylbenzamide (E3)

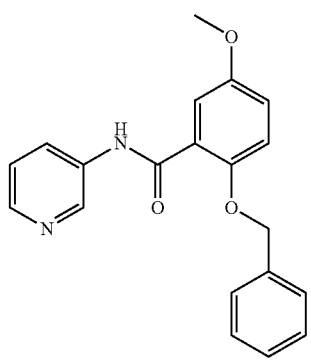 [SMILES: COc1ccc(OCc2ccccc2)c(C(=O)Nc2cccnc2)c1]

A solution of 5-(methyloxy)-2-[(phenylmethyl)oxy]benzoic acid (may be prepared as described in Description 7; 280 mg, 1.08 mmol), 3-pyridinamine (204 mg, 2.17 mmol), EDC (312 mg, 1.63 mmol) and HOBT (249 mg, 1.626 mmol) in DMF (5 ml) was stirred under nitrogen at 25° C. overnight. The reaction mixture was then poured into water (20 ml), filtered and the solid was washed with water and dried to yield the title compound as a white solid. 150 mg.

MS (electrospray): m/z [M+H]$^+$=335

$^1$H NMR (DMSO-d6): 3.83 (3H, s), 5.26 (2H, s), 7.16 (1H, dd, J=2.8 Hz, J=8.8 Hz), 7.29-7.33 (2H, m), 7.38-7.44 (4H, m), 7.56-7.58 (2H, d, J=6.4 Hz), 8.14 (1H, d, J=8.8 Hz), 8.33 (1H, dd, J=1.2 Hz, J=4.8 Hz), 8.71 (1H, d, J=2.0 Hz), 10.44 (1H, s).

Example 4

5-Methyl-2-[(phenylmethyl)oxy]-N-3-pyridinylbenzamide (E4)

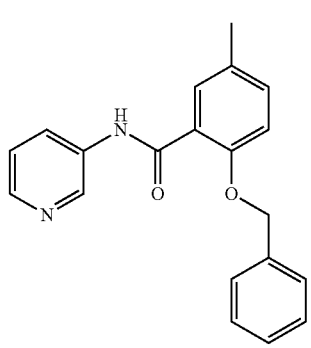 [SMILES: Cc1ccc(OCc2ccccc2)c(C(=O)Nc2cccnc2)c1]

A solution of 5-methyl-2-[(phenylmethyl)oxy]benzoic acid (may be prepared as described in Description 9; 400 mg, 1.65 mmol), 3-pyridinamine (311 mg, 3.30 mmol), HOBT (379 mg, 2.48 mmol) and EDC (475 mg, 2.48 mmol) in DMF (5 ml) was stirred at room temperature overnight. The reaction mixture was poured into water (20 ml), filtered and the solid was washed by water and dried to yield the title compound as a white solid. 220 mg.

MS (electrospray): m/z [M+H]⁺=319

¹H NMR (DMSO-d6): 2.30 (3H, s), 5.22 (2H, s), 7.18-7.20 (1H, d, J=8.4 Hz), 7.31-7.39 (5H, m), 7.52-7.54 (3H, m), 8.09 (1H, m), 8.27 (1H, dd, J=4.8 Hz, J=1.2 Hz), 8.66 (1H, d, J=2.4 Hz), 10.34 (1H, s).

Example 5

5-Bromo-N-(3-methylphenyl)-2-[(phenylmethyl)oxy]benzamide (E5)

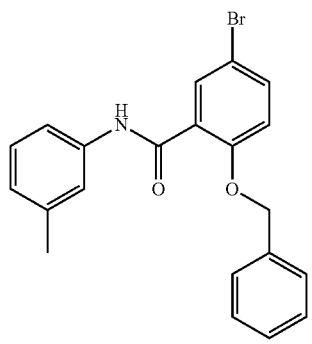 [SMILES: Cc1cccc(NC(=O)c2cc(Br)ccc2OCc2ccccc2)c1]

Solid 5-bromo-2-[(phenylmethyl)oxy]benzoic acid (may be prepared as described in Description 5, method B; 200 mg, 0.651 mmol) was added to a stirred suspension of CDI (106 mg, 0.651 mmol) in THF (6 ml) under nitrogen at 20° C. The reaction mixture was stirred at room temperature for 10 min and m-toluidine (69.8 mg, 0.65 mmol) was added dropwise. After refluxing for 14 h, the reaction mixture was concentrated to obtain crude product. The crude product was dissolved in 20 ml of CH₂Cl₂ and the organic phase was washed with 2M hydrochloric acid (5 ml), water (5×2 ml), dried over sodium sulphate and evaporated in vacuo to give yellow solid. The crude product was further purified by silica gel chromatography eluting with hexane:ethyl acetate (10:1) to yield the title compound. 120 mg.

MS (electrospray): m/z [M+H]⁺=396, 398.

Example 6

5-Bromo-2-[(phenylmethyl)oxy]-N-4-pyridazinylbenzamide (E6)

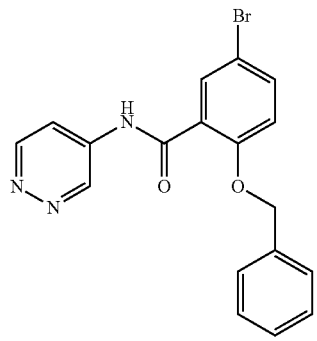 [SMILES: O=C(Nc1ccnnc1)c1cc(Br)ccc1OCc1ccccc1]

Solid 5-bromo-2-[(phenylmethyl)oxy]benzoic acid (may be prepared as described in Description 5, method C; 200 mg, 0.651 mmol) was added to a stirred suspension of CDI (106 mg, 0.651 mmol) in THF (10 ml) under nitrogen at 20° C. The reaction mixture was stirred at room temperature for 10 min and 4-pyridazinamine (may be prepared as described in Description 11; 61.9 mg, 0.65 mmol) was added dropwise. After refluxing for 14 h, the reaction mixture was concentrated. Water was added to the residue and the mixture was extracted with ethyl acetate (3×50 ml). The organic phase was washed with saturated brine (25 ml), dried over sodium sulphate and evaporated in vacuo. The residue was washed with methanol to yield the title compound as a white solid. 95 mg.

MS (electrospray): m/z [H+H]⁺=384

¹H NMR (DMSO-d6): 5.29 (2H, s), 7.32-7.40 (4H, m), 7.52 (1H, s), 7.53 (1H, s), 7.76 (1H, dd, J=2.8 Hz, J=9.2 Hz), 7.83 (1H, d, J=2.8 Hz), 8.05 (1H, dd, J=2.4 Hz, J=6 Hz), 9.11 (1H, d, J=6 Hz), 9.30 (1H, d, J=2.4 Hz), 10.90 (1H, s)

Example 7

5-Bromo-N-(3-chlorophenyl)-2-[(phenylmethyl)oxy]benzamide (E7)

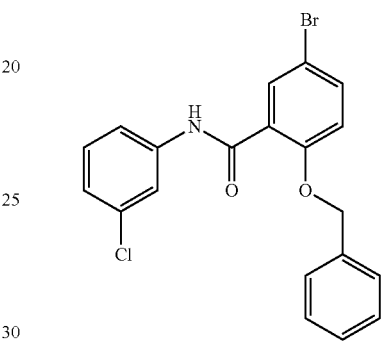

Solid 5-bromo-2-[(phenylmethyl)oxy]benzoic acid (may be prepared as described in Description 5, method B; 200 mg, 0.65 mmol) was added to a stirred suspension of CDI (106 mg, 0.65 mmol) in THF (6 ml) under nitrogen at 20° C. The reaction mixture was stirred at room temperature for 10 min. 3-Chlorobenzenamine (83 mg, 0.65 mmol) was then added dropwise. After refluxing for 14 h, the reaction mixture was concentrated to obtain crude product. The crude product was purified by silica gel chromatography eluting with hexane: ethyl acetate (10:1) to yield the title compound. 110 mg.

MS (electrospray): m/z [M+H]⁺=416, 418

Example 8

5-Cyano-2-[(phenylmethyl)oxy]-N-3-pyridinylbenzamide (E8)

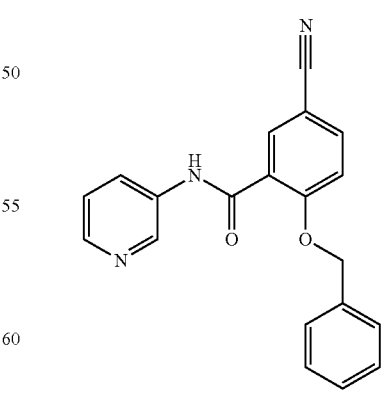

A solution of 5-cyano-2-[(phenylmethyl)oxy]benzoic acid (may be prepared as described in Description 14; 160 mg, 0.63 mmol), 3-pyridinamine (65.4 mg, 0.70 mmol), HOBT (116 mg, 0.76 mmol) and EDC (145 mg, 0.76 mmol) in DMF (10 ml) was stirred at room temperature overnight. Water (30 ml) was added and the mixture was then filtered. The residue was dried to yield the title compound as a white solid. 90 mg.

MS (electrospray): m/z, [M+H]$^+$=330

$^1$H NMR (DMSO-d6): 5.31 (2H, s), 7.31-7.35 (4H, m), 7.42-7.49 (3H, m), 7.97 (1H, dd, J=2 Hz, J=8.4 Hz), 8.04 (1H, d, J=2 Hz), 8.07 (2H, m), 8.28 (1H, s), 8.72 (1H, bs), 10.49 (1H, s)

Example 9

5-Bromo-2-{[(4-chlorophenyl)methyl]oxy}-N-3-pyridinylbenzamide (E9)

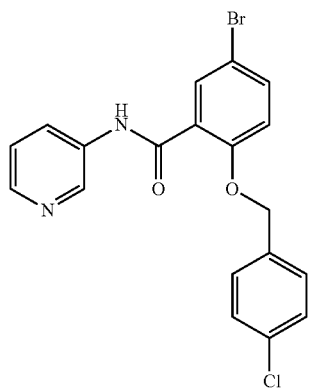 [SMILES: O=C(Nc1cccnc1)c1cc(Br)ccc1OCc1ccc(Cl)cc1]

Solid pyridin-3-amine (99 mg, 1.05 mmol) was added in one charge to a stirred solution of 5-bromo-2-(4-chlorobenzyloxy)benzoic acid (may be prepared as described in Description 16, 180 mg, 0.53 mmol), 1-(3-Dimethylaminopropyl)-3-ethylcarbodiimide hydrochloride (121 mg, 0.63 mmol) and 1-Hydroxybenzotriazole (85 mg, 0.63 mmol) in DMF (15 ml) under nitrogen at 20° C. The reaction mixture was stirred at 20° C. for 16 h. The organic phase was washed with water (25 ml), extracted with ethyl acetate (3×30 ml), dried over sodium sulphate, evaporated in vacuo and purified by column chromatography (petroleum ether:ethyl acetate=1.5:1) to yield the title compound as a white solid. 200 mg.

MS (electrospray): m/z, [M+H]$^+$=417, 419

$^1$H NMR (CDCl$_3$): 5.23 (2H, s), 7.03 (1H, d, J=8.8 Hz), 7.25 (1H, dd, J=8.4 Hz, J=4.8 Hz), 7.49 (4H, m), 7.64 (1H, dd, J=8.8 Hz, J=2.4 Hz), 8.06 (1H, d, J=8.4 Hz), 8.25 (1H, d, J=2.4 Hz), 8.34 (1H, d, J=4.8 Hz), 8.45 (1H, d, J=2.4 Hz), 9.81 (1H, s).

Example 10

5-Bromo-2-[(phenylmethyl)oxy]-N-3-pyridazinylbenzamide (E10)

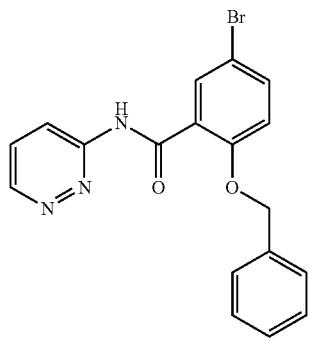 [SMILES: O=C(Nc1cccnn1)c1cc(Br)ccc1OCc1ccccc1]

Solid 5-bromo-2-[(phenylmethyl)oxy]benzoic acid (may be prepared as described in Description 5, method C; 200 mg, 0.651 mmol) was added to a stirred suspension of CD (106 mg, 0.651 mmol) in THF (6 ml) under nitrogen at 20° C. The reaction mixture was stirred at room temperature for 10 min and pyridazin-3-amine (61.9 mg, 0.651 mmol) was added dropwise. After refluxing for 14 h, the reaction mixture was concentrated to obtain crude product. The crude product was purified by silica gel chromatography, eluting with hexane: ethyl acetate (4:1) to yield the title compound. 183 mg.

MS (electrospray): m/z, [M+H]$^+$=384, 386

Example 11

5-Bromo-2-({[4-(methyloxy)phenyl]methyl}oxy)-N-3-pyridinylbenzamide (E11)

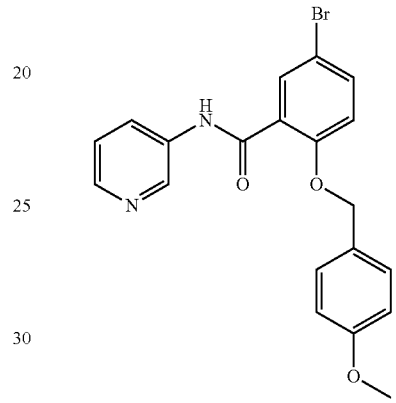

Solid pyridin-3-amine (112 mg, 1.19 mmol) was added in one charge to a stirred solution of 5-bromo-2-({[4-(methyloxy)phenyl]methyl}oxy)benzoic acid (may be prepared as described in Description 18; 200 mg, 0.59 mmol), 1-(3-Dimethylaminopropyl)-3-ethylcarbodiimide hydrochloride (136 mg, 0.71 mmol) and 1-Hydroxybenzotriazole (96 mg, 0.71 mmol) in DMF (20 ml) under nitrogen at 20° C. The reaction mixture was stirred at 20° C. for 16 h. The organic phase was washed with water (25 ml), extracted with ethyl acetate (3×30 ml), dried over sodium sulphate, evaporated in vacuo and purified by column chromatography (petroleum ether:ethyl acetate=2:1) to yield the title compound as a white solid. 200 mg.

MS (electrospray): m/z, [M+H]$^+$=413, 415

Example 12

5-Fluoro-2-[(phenylmethyl)oxy]-N-3-pyridinylbenzamide (E12)

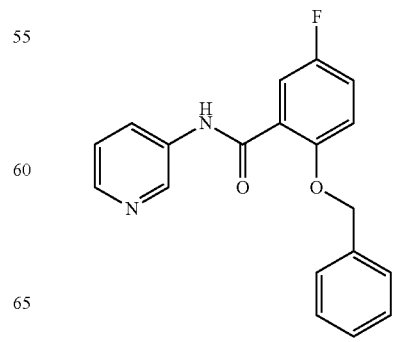

A solution of 5-fluoro-2-[(phenylmethyl)oxy]benzoic acid (may be prepared as described in Description 20, 180 mg, 0.73 mmol), 3-pyridinamine (68.8 mg, 0.73 mmol), HOBT (134 mg, 0.88 mmol) and EDC (168 mg, 0.88 mmol) in DMF (10 ml) was stirred at room temperature overnight. Water (30 ml) was added and the mixture was filtered. The residue was dried to yield the title compound as a white solid. 100 mg.

MS (electrospray): m/z [M+H]$^+$=323

Example 13

5-Bromo-2-{[(3-chlorophenyl)methyl]oxy}-N-3-pyridinylbenzamide (E13)

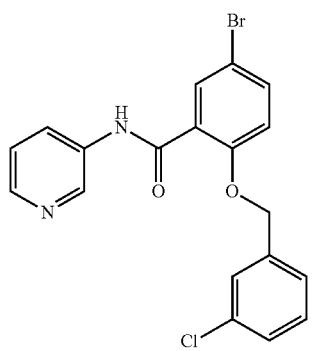 [SMILES: O=C(Nc1cccnc1)c1cc(Br)ccc1OCc1cccc(Cl)c1]

Solid pyridin-3-amine (110 mg, 1.17 mmol) was added in one charge to a stirred solution of 5-bromo-2-{[(3-chlorophenyl)methyl]oxy}benzoic acid (may be prepared as described in Description 22; 200 mg, 0.59 mmol), 1-(3-Dimethylaminopropyl)-3-ethylcarbodiimide hydrochloride (135 mg, 0.70 mmol) and 1-Hydroxybenzotriazole (95 mg, 0.70 mmol) in DMF (20 ml) under nitrogen at 20° C. The reaction mixture was stirred at 20° C. for 16 h. The organic phase was washed with water (25 ml), extracted with ethyl acetate (3×30 ml), dried over sodium sulphate, evaporated in vacuo and purified by column chromatography (petroleum ether:ethyl acetate=2:1) to yield the title compound as a white solid. 70 mg.

MS (electrospray): m/z [M+H]$^+$=417, 419

Example 14

5-Bromo-2-{[(4-cyanophenyl)methyl]oxy}-N-3-pyridinylbenzamide (E14)

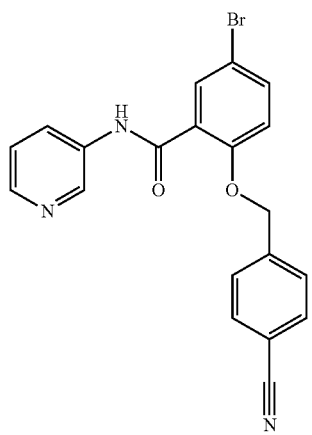 [SMILES: N#Cc1ccc(COc2ccc(Br)cc2C(=O)Nc2cccnc2)cc1]

Solid pyridin-3-amine (82 mg, 0.873 mmol) was added in one charge to a stirred solution of 5-bromo-2-{[(4-cyanophenyl)methyl]oxy}benzoic acid (may be prepared as described in Description 24; 145 mg, 0.44 mmol), 1-(3-Dimethylaminopropyl)-3-ethylcarbodiimide hydrochloride (100 mg, 0.52 mmol) and 1-Hydroxybenzotriazole (70.8 mg, 0.52 mmol) in DMF (15 ml) under nitrogen at 20° C. The reaction mixture was stirred at 20° C. for 16 h. The organic phase was washed with water (25 ml), extracted with ethyl acetate (3×30 ml), dried over sodium sulphate, evaporated in vacuo and purified by column chromatography (petroleum ether:ethyl acetate=2:1) to yield the title compound as a white solid. 100 mg.

MS (electrospray): m/z [M+H]$^+$=408, 410

Example 15

5-Bromo-2-{[(3-cyanophenyl)methyl]oxy}-N-3-pyridinylbenzamide (E15)

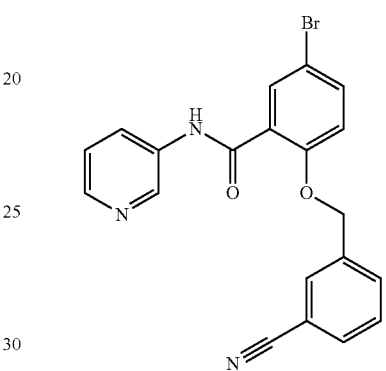

Solid pyridin-3-amine (113 mg, 1.20 mmol) was added in one charge to a stirred solution of 5-bromo-2-{[(3-cyanophenyl)methyl]oxy}benzoic acid (may be prepared as described in Description 26; 200 mg, 0.60 mmol), 1-(3-Dimethylaminopropyl)-3-ethylcarbodiimide hydrochloride (139 mg, 0.72 mmol) and 1-Hydroxybenzotriazole (98 mg, 0.72 mmol) in DMF (20 ml) sunder nitrogen at 20° C. The reaction mixture was stirred at 20° C. for 16 h. The organic phase was washed with water (25 ml), extracted with ethyl acetate (3×30 ml), dried over sodium sulphate, evaporated in vacuo and purified by column chromatography (petroleum ether:ethyl acetate=2:1) to yield the title compound as a white solid. 170 mg.

MS (electrospray): m/z [M+H]$^+$=408, 410

Example 16

5-Bromo-2-{[(2-chlorophenyl)methyl]oxy}-N-3-pyridinylbenzamide (E16)

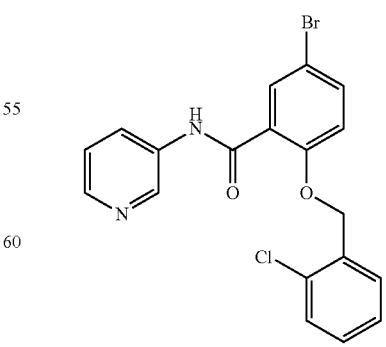

Solid pyridin-3-amine (212 mg, 2.25 mmol) was added in one charge to a stirred solution of 5-bromo-2-{[(2-chlorophenyl)methyl]oxy}benzoic acid (may be prepared as described in Description 28; 350 mg, 1.03 mmol), 1-(3-Dimethylaminopropyl)-3-ethylcarbodiimide hydrochloride (236 mg, 1.23 mmol) and 1-Hydroxybenzotriazole (166 mg, 1.23 mmol) in DMF (20 ml) under nitrogen at 20° C. The reaction mixture was stirred at 20° C. for 16 h. Water (50 ml) was added to the mixture and the mixture was filtered to yield the title compound as a white solid. 400 mg.

MS (electrospray): m/z [M+H]$^+$=417, 419, 421

Example 17

5-Bromo-N-[3-(methyloxy)phenyl]-2-[(phenylmethyl)oxy]benzamide (E17)

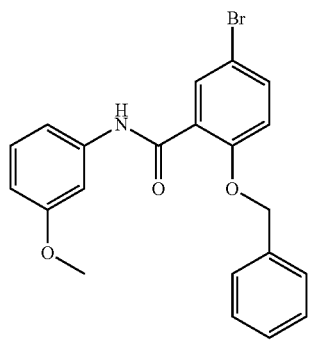 [SMILES: COc1cccc(NC(=O)c2cc(Br)ccc2OCc2ccccc2)c1]

Solid 5-bromo-2-[(phenylmethyl)oxy]benzoic acid (may be prepared as described in Description 5, method B; 200 mg, 0.65 mmol) was added to a stirred suspension of CDI (106 mg, 0.65 mmol) in THE (6 ml) under nitrogen at 20° C. The reaction mixture was stirred at room temperature for 10 min and 3-methoxybenzenamine (80 mg, 0.65 mmol) was added dropwise. After refluxing for 14 h, the reaction mixture was concentrated to obtain crude product. The crude product was purified by silica gel chromatography eluting with hexane:ethyl acetate (10:1). The crude product was added to a silica gel column and was eluted with DCM:hexane (2:1). The crude product was then added to a preparative HPLC column and was eluted with 0.05% trifluoroacetic acid, water/acetonitrile to yield the title compound. 110 mg.

MS (electrospray): m/z [M+H]$^+$=412, 414

Example 18

5-Bromo-2-({[3-(methyloxy)phenyl]methyl}oxy)-N-3-pyridinylbenzamide (E18)

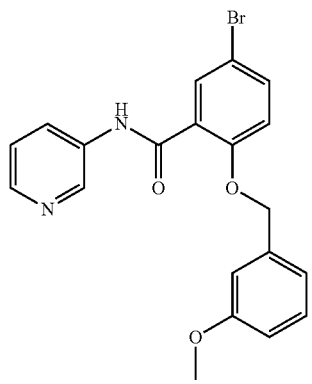 [SMILES: COc1cccc(COc2ccc(Br)cc2C(=O)Nc2cccnc2)c1]

Solid pyridin-3-amine (154 mg, 1.63 mmol) was added in one charge to a stirred solution of 5-bromo-2-({[3-(methyloxy)phenyl]methyl}oxy)benzoic acid (may be prepared as described in Description 30; 275 mg, 0.82 mmol), 1-(3-Dimethylaminopropyl)-3-ethylcarbodiimide hydrochloride (188 mg, 0.98 mmol) and 1-Hydroxybenzotriazole (132 mg, 0.98 mmol) in DMF (20 ml) under nitrogen at 20° C. The reaction mixture was stirred at 20° C. for 16 h. The organic phase was washed with water (25 ml), extracted with ethyl acetate (3×30 ml), dried over sodium sulphate, evaporated in vacuo and purified by column chromatography (petroleum ether:ethyl acetate=2:1) to yield the title compound as a white solid. 270 mg.

MS (electrospray): m/z [M+H]$^+$=413, 415

Example 19

5-Bromo-N-(3-fluorophenyl)-2-[(phenylmethyl)oxy]benzamide (E19)

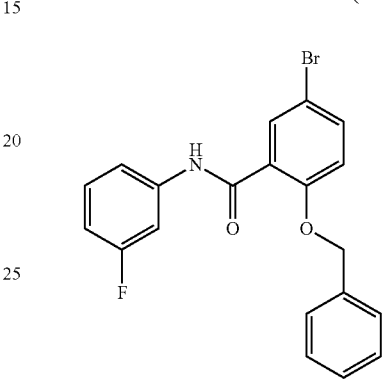

Solid 5-bromo-2-[(phenylmethyl)oxy]benzoic acid (may be prepared as described in Description 5, method C; 200 mg, 0.65 mmol) was added to a stirred suspension of CDI (106 mg, 0.65 mmol) in THF (6 ml) under nitrogen at 20° C. The reaction mixture was stirred at room temperature for 10 min and 3-fluorobenzenamine (72.4 mg, 0.65 mmol) was added dropwise. After refluxing for 14 h, the reaction mixture was concentrated to obtain crude product. The crude product was purified by silica gel chromatography eluting with hexane:ethyl acetate (10:1). The product was then purified by preparative HPLC (A: 0.05% trifluoroacetic acid/water B: dichloromethane) to yield the title compound. 73 mg.

MS (electrospray): m/z [M+H]$^+$=400, 402; MNa$^+$=422, 424

Example 20

5-Bromo-N-(3-ethylphenyl)-2-[(phenylmethyl)oxy]benzamide (E20)

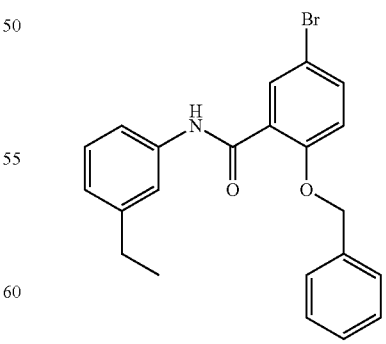

Solid 5-bromo-2-[(phenylmethyl)oxy]benzoic acid (may be prepared as described in Description 5, method B; 200 mg, 0.65 mmol) was added to a stirred suspension of CDI (106 mg, 0.65 mmol) in THF (6 ml) under nitrogen at 20° C. The reaction mixture was stirred at room temperature for 10 min and 3-ethylbenzenamine (79 mg, 0.65 mmol) was added dropwise. After refluxing for 14 h, the reaction mixture was concentrated to obtain crude product. The crude product was purified by silica gel chromatography eluting with hexane:ethyl acetate (10:1) to yield the title compound. 80 mg.

MS (electrospray): m/z [M-f-H]⁺=410, 412

Example 21

5-Bromo-2-({[2-(methyloxy)phenyl]methyl}oxy)-N-3-pyridinylbenzamide (E21)

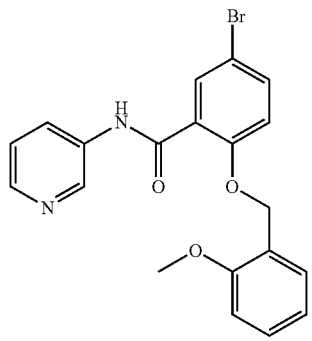 [SMILES: COc1ccccc1COc1ccc(Br)cc1C(=O)Nc1cccnc1]

Solid pyridin-3-amine (156 mg, 1.66 mmol) was added in one charge to a stirred solution of 5-bromo-2-({[2-(methyloxy)phenyl]methyl}oxy)benzoic acid (may be prepared as described in Description 32; 280 mg, 0.83 mmol), 1-(3-Dimethylaminopropyl)-3-ethylcarbodiimide hydrochloride (191 mg, 1.00 mmol) and 1-Hydroxybenzotriazole (135 mg, 1.00 mmol) in DMF (20 ml) under nitrogen at 20° C. The reaction mixture was stirred at 20° C. for 16 h. The organic phase was washed with water (25 ml), extracted with ethyl acetate (3×30 ml), dried over sodium sulphate, evaporated in vacuo and purified by column chromatography (petroleum ether:ethyl acetate=2:1) to yield the title compound as a white solid. 270 mg.

MS (electrospray): m/z [M+H]⁺=413, 415

Example 22

5-Bromo-2-[(phenylmethyl)oxy]-N-2-pyridinylbenzamide (E22)

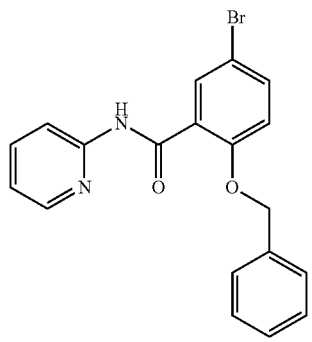 [SMILES: O=C(Nc1ccccn1)c1cc(Br)ccc1OCc1ccccc1]

Neat triethylamine (0.27 ml, 1.95 mmol) and pyridin-2-amine (61.3 mg, 0.65 mmol) were added to a stirred suspension of 5-bromo-2-[(phenylmethyl)oxy]benzoic acid (may be prepared as described in Description 5, method C; 200 mg, 0.65 mmol), EDC (250 mg, 1.30 mmol) and HOBT (199 mg, 1.30 mmol) in DMF (3 ml) at 20° C. The reaction mixture was stirred at 20° C. overnight and was then poured into 15 ml water and filtered. The residue was washed with methanol (10 ml) to yield the title compound. The mother liquid was evaporated and the solid was purified by preparative HPLC, (A: 10 mmol ammonium carbonate/water B: acetonitrile) to yield the title compound. The two batches of product were mixed. 47 mg.

MS (electrospray): m/z [M+H]⁺=383, 385

Example 23

5-Bromo-2-{[(2-cyanophenyl)methyl]oxy}-N-3-pyridinylbenzamide (E23)

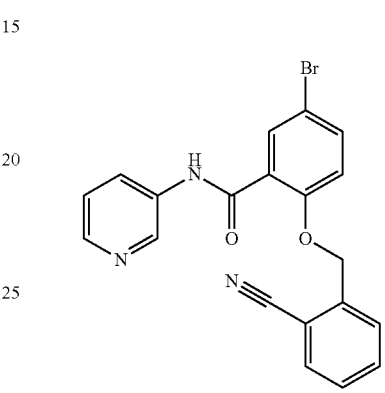

Solid pyridin-3-amine (91 mg, 0.96 mmol) was added in one charge to a stirred solution of 5-bromo-2-{[(2-cyanophenyl)methyl]oxy}benzoic acid (may be prepared as described in Description 34; 160 mg, 0.48 mmol), 1-(3-Dimethylaminopropyl)-3-ethylcarbodiimide hydrochloride (111 mg, 0.58 mmol) and 1-Hydroxybenzotriazole (78 mg, 0.58 mmol) in DMF (15 ml) under nitrogen at 20° C. The reaction mixture was stirred at 20° C. for 16 h. The organic phase was washed with water (25 ml), and extracted with ethyl acetate (3×30 ml), dried over sodium sulphate, evaporated in vacuo and purified by column chromatography (petroleum ether:ethyl acetate=2:1) to yield the title compound as a white solid. 180 mg.

MS (electrospray): m/z [M+H]⁺=408, 410

Example 24

5-Bromo-2-[(phenylmethyl)oxy]-N-5-pyrimidinylbenzamide (E24)

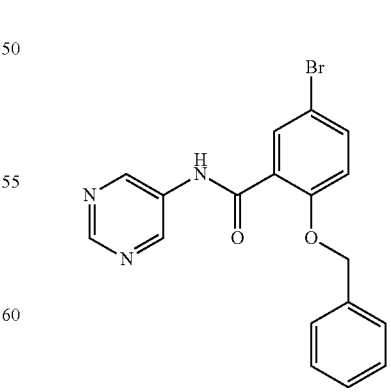

Solid 5-bromo-2-[(phenylmethyl)oxy]benzoic acid (may be prepared as described in Description 5, method C; 200 mg, 0.65 mmol) was added to a stirred suspension of CDI (106 mg, 0.65 mmol) in THF (3 ml) under nitrogen at 20° C. The reaction mixture was stirred at room temperature for 10 min and pyrimidin-5-amine (61.9 mg, 0.65 mmol) was added dropwise. After refluxing for 14 h, the reaction mixture was concentrated to obtain crude product. The crude product was purified by silica gel chromatography eluting with hexane: ethyl acetate:triethylamine (4:1:0.01) to yield the title compound. 150 mg.

MS (electrospray): m/z [M+H]$^+$=384, 386

Example 25

{3-[({5-Chloro-2-[(phenylmethyl)oxy]phenyl}carbonyl)amino]phenyl}acetic acid

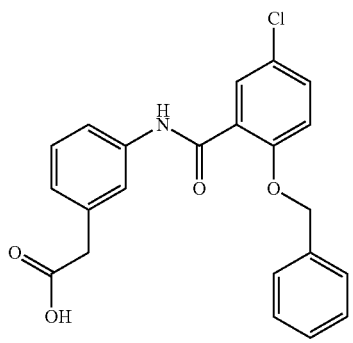 [SMILES: O=C(O)Cc1cccc(NC(=O)c2cc(Cl)ccc2OCc2ccccc2)c1]

A mixture of methyl {3-[({5-chloro-2-[(phenylmethyl)oxy]phenyl}carbonyl)amino]phenyl}acetate (may be prepared as described in Description 46, 160 mg, 0.39 mmol), 2M HCl (3 ml) and acetic acid (3 ml) was heated at 90° C. for 4 hours and then cooled to room temperature. Water was added and the mixture was filtered to give a white solid. The crude product was purified by MDAP to yield the title compound as a white solid. 53 mg.

MS (electrospray): m/z [M+H]$^+$=396, 398

Example 26

5-Chloro-2-[(phenylmethyl)oxy]-N-3-pyridinylbenzamide (E26)

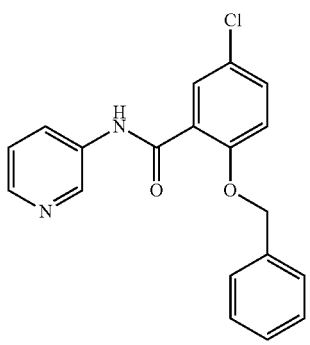

This compound is commercially available.

Example 27

5-Bromo-N-{3-[(methylamino)carbonyl]phenyl}-2-[(phenylmethyl)oxy]benzamide (E27)

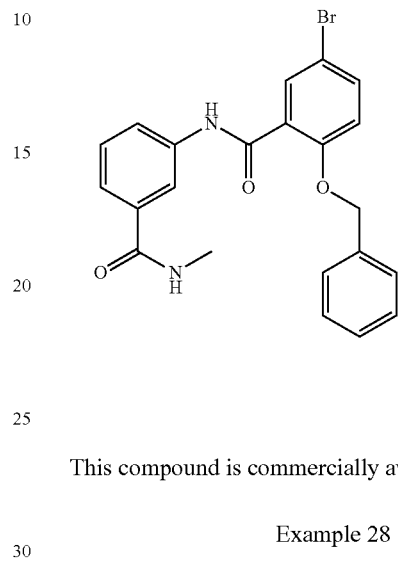

This compound is commercially available.

Example 28

5-Bromo-2-[(1-phenylethyl)oxy]-N-3-pyridinylbenzamide (E28)

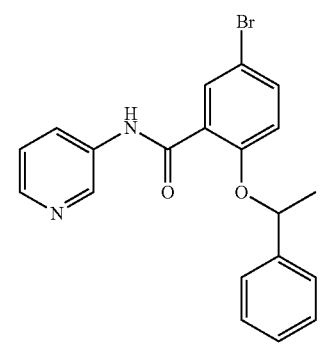 [SMILES: CC(Oc1ccc(Br)cc1C(=O)Nc1cccnc1)c1ccccc1]

The compound 5-bromo-2-hydroxy-N-3-pyridinylbenzamide (may be prepared as described in Description 35; 300 mg, 1.02 mmol) was added to a solution of potassium hydroxide (57.4 mg, 1.02 mmol) in methanol (2 ml, 49.4 mmol). The mixture was then stirred at room temperature for 15 min and the solvent was removed in vacuo. To the potassium salt was added DMF (10 ml) and (1-bromoethyl)benzene (189 mg, 1.023 mmol), The reaction mixture was then heated under reflux for 2 h. The mixture was cooled, diluted with water (20 ml) and the precipitate was collected, and finally crystallized from ethyl acetate to yield the title compound. 63 mg.

MS (electrospray): m/z [M+H]$^+$=397, 399

Example 28A

5-Bromo-2-{[(1S)-1-phenylethyl]oxy}-N-3-pyridinylbenzamide (E28A)

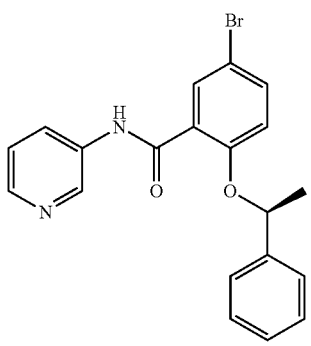 [SMILES: C[C@H](Oc1ccc(Br)cc1C(=O)Nc1cccnc1)c1ccccc1]

To a solution of methyl 5-bromo-2-{[(1S)-1-phenylethyl]oxy}benzoate (may be prepared as described in Description 99; 100 mg, 0.30 mmol) in THF (2 ml) was added potassium trimethylsilanolate (115 mg, 0.90 mmol). The mixture was stirred for 45 minutes. The solvent was removed and the residue redissolved in DMF (2 ml). To the solution was added DIPEA (0.13 ml, 0.75 mmol), 3-aminopyridine (56 mg, 0.60 mmol) and HATU (170 mg, 0.45 mmol). The solution was stirred for 18 hours. The solvent was removed in vacuo and purified by MDAP to give the titled example as a colourless gum. 73 mg.

MS (electrospray): m/z $[M+H]^+=397/399$
$^1$H NMR (DMSO-$d_6$): 1.58 (3H, d, J=6.36 Hz), 5.63 (1H, q, J=6.21 Hz), 7.00 (1H, d, J=8.99 Hz), 7.14-7.62 (8H, m), 7.73 (1H, d, J=2.63 Hz), 8.10-8.25 (1H, m), 8.33 (1H, dd, J=4.60, 1.32 Hz), 8.84 (1H, d, J=2.19 Hz), 10.46 (1H, s)

Example 28B

5-Bromo-2-{[(1R)-1-phenylethyl]oxy}-N-3-pyridinylbenzamide (E28B)

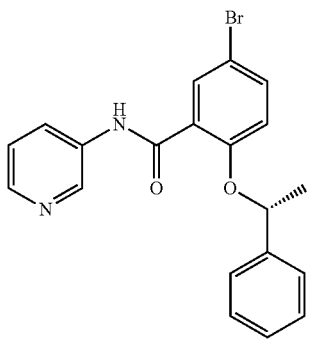 [SMILES: C[C@@H](Oc1ccc(Br)cc1C(=O)Nc1cccnc1)c1ccccc1]

5-Bromo-2-hydroxy-N-3-pyridinylbenzamide (may be prepared as described in Description 35; 300 mg, 1.023 mmol) was added to a solution of KOH (57.4 mg, 1.02 mmol) in methanol (2 ml, 49.4 mmol). The mixture was then stirred at room temperature for 15 min and the solvent was removed in vacuo. To the potassium salt was added N,N-dimethylformamide (10 ml) and (1-bromoethyl)benzene (189 mg, 1.02 mmol). The reaction mixture was then heated at 80° C. for 2 h. The mixture was cooled, diluted with water (20 ml) and the precipitate was collected. Recrystallisation from ethyl acetate gave the racemic compound (63 mg). The racemic material was chirally resolved (ChiralPak IA 250 mm×4.6 mm, heptane/ethanol (70/30)) to yield the title compound. 9 mg.

MS (electrospray): m/z $[M+H]^+=397/399$
$^1$H NMR (DMSO-$d_6$): 1.58 (3H, d, J=6.36 Hz), 5.63 (1H, q, J=6.14 Hz), 7.00 (1H, d, J=8.99 Hz), 7.20-7.48 (6H, m), 7.54 (1H, dd, J=8.99, 2.63 Hz), 7.73 (1H, d, J=2.41 Hz), 8.07-8.25 (1H, m), 8.33 (1H, dd, J=4.71, 1.43 Hz), 8.84 (1H, d, J=2.19 Hz), 10.46 (1H, s)

Example 29

5-Hydroxy-2-[(phenylmethyl)oxy]-N-3-pyridinylbenzamide (E29)

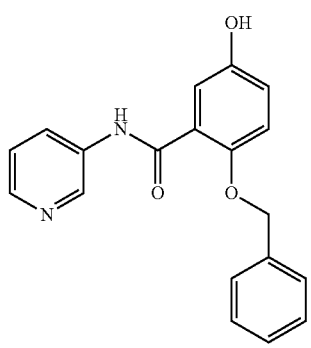 [SMILES: O=C(Nc1cccnc1)c1cc(O)ccc1OCc1ccccc1]

Solid HOBT (552 mg, 3.60 mmol) was added in one charge to a stirred solution of 5-hydroxy-2-[(phenylmethyl)oxy]benzoic acid (may be prepared as described in Description 38; 800 mg, 3.28 mmol), 3-pyridinamine (339 mg, 3.60 mmol) and EDC (691 mg, 3.60 mmol) in DMF (30 mL) at room temp. The reaction mixture was stirred at room temperature for 4 h. After 4 h, water was added to the reaction mixture. The reaction mixture was filtered and the residue was washed with ethyl acetate to yield the title compound as a white solid. 500 mg.

MS (electrospray): m/z $[M+H]^+=321$
$^1$H NMR (DMSO-d6): 5.17 (2H, s), 6.91 (1H, dd, J=3.2 Hz, J=9.2 Hz), 7.14 (1H, d, J=4.4 Hz), 7.16 (1H, s), 7.34 (4H, m), 7.51 (2H, dd, J=1.6 Hz, J=8.0 Hz), 8.04 (1H, d, J=5.2 Hz), 8.25 (1H, dd, J=1.6 Hz, J=5.2 Hz), 8.6 (1H, d, J=2.4 Hz), 9.38 (1N, s), 10.33 (1H, s)

Method B

3-Pyridinamine (2.20 g, 23.42 mmol) was added to a stirred solution of 5-hydroxy-2-[(phenylmethyl)oxy]benzoic acid (may be prepared as described in Description 76; 5.2 g, 21.29 mmol), HOBT (3.59 g, 23.4 mmol) and EDC (4.49 g, 23.42 mmol) in dimethylformamide (100 ml) at room temperature. The reaction mixture was stirred at 25° C. overnight. Water was added, the solid was filtered and washed with ethyl acetate to yield the title compound as a white solid. 3.7 g.

MS (electrospray): m/z $[M+H]^+=321.3$.

Method C

Oxalyl chloride (1.08 ml, 12.28 mmol) was added to a mixture of 5-hydroxy-2-[(phenylmethyl)oxy]benzoic acid (1 g, 4.09 mmol) dissolved in dichloromethane. The mixture was stirred for 2 h, and then concentrated. The residue was dissolved in dichloromethane, and then added to a mixture of pyridin-3-amine (0.39 g, 4.09 mmol) and triethylamine (1.14 ml, 8.19 mmol) in dichloromethane. The mixture was stirred at 40° C. for 3 h. The mixture was filtered, and the filtrate was added to water (10 ml) and extracted with ethyl acetate (30 ml). The organic phase was concentrated to yield the title compound as a crude solid product. 0.72 g.

MS (electrospray): m/z $[M+H]^+=321$

Example 30

5-{[2-(Dimethylamino)ethyl]oxy}-2-[(phenylmethyl)oxy]-N-3-pyridinylbenzamide (E30)

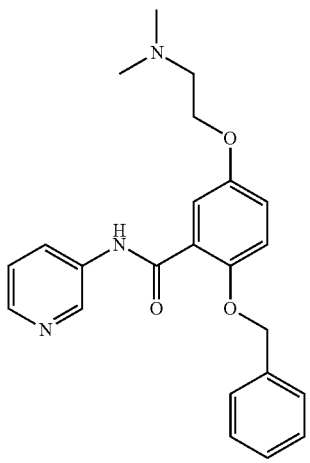 [SMILES: CN(C)CCOc1ccc(OCc2ccccc2)c(C(=O)Nc2cccnc2)c1]

A solution of DIAD (252 mg, 1.249 mmol) in toluene (1 ml) was added dropwise to a stirred solution of 5-hydroxy-2-[(phenylmethyl)oxy]-N-3-pyridinylbenzamide (may be prepared as described in Example 29; 160 mg, 0.50 mmol), 2-(dimethylamino)ethanol (49.0 mg, 0.549 mmol) and Ph$_3$P (328 mg, 1.25 mmol) in toluene (4 ml) under nitrogen at 0° C. The reaction mixture was stirred at 115° C. overnight. The mixture was then cooled and concentrated. The residue was added to water and extracted with ethyl acetate (3×60 ml). The organic phase was washed with saturated brine (30 ml), dried over sodium sulphate and evaporated in vacuo to give crude product. The crude product was added to a silica gel column (40 g) and was eluted with a 20:1 mixture of DCM/methanol (2 l) to yield the title compound as a yellow solid. 50 mg.

MS (electrospray): m/z [M+H]$^+$=392

1H NMR (CDCl3): 2.54 (6H, s), 2.97 (2H, t, J=4.8 Hz), 4.25 (2H, t, J=4.8 Hz), 5.19 (2H, s), 7.00-7.20 (3H, m), 7.50 (5H, m), 7.85 (1H, d, J=3.2 Hz), 7.99 (1H, s), 8.07 (1H, d, J=8 Hz), 8.26 (1H, d, J=4.4 Hz), 10.18 (1H, s)

Example 31

5-[(1-Methyl-4-piperidinyl)oxy]-2-[(phenylmethyl)oxy]-N-3-pyridinylbenzamide (E31)

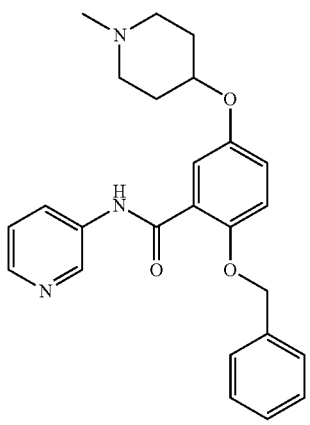 [SMILES: CN1CCC(Oc2ccc(OCc3ccccc3)c(C(=O)Nc3cccnc3)c2)CC1]

A solution of DIAD (0.30 ml, 1.56 mmol) in toluene (1 ml) was added dropwise to a solution of 5-hydroxy-2-[(phenylmethyl)oxy]-N-3-pyridinylbenzamide (may be prepared as described in Example 29; 200 mg, 0.624 mmol), 1-methyl-4-piperidinol (79 mg, 0.687 mmol) and Ph$_3$P (409 mg, 1.561 mmol) in toluene under nitrogen at 0° C. The reaction mixture was stirred at 115° C. overnight. The mixture was then cooled and concentrated. The residue was added to water and extracted with ethyl acetate (3×60 ml). The organic phase was washed with saturated brine (30 ml), dried over sodium sulphate and evaporated in vacuo to give the crude product. The crude product was purified by Pre-TCL (DCM:methanol=8:1) to yield the title compound as a yellow solid. 36 mg.

MS (electrospray): m/z [M+H]$^+$=418

1H NMR (CDCl3): 1.85 (2H, m), 2.05 (2H, m), 2.34 (5H, m), 2.74 (2H, m), 4.38 (1H, m), 5.19 (2H, s), 7.10 (2H, m), 7.19 (1H, dd, J=4.4 Hz, J=8.4 Hz), 7.51 (5H, m), 7.87 (1H, d, J=1.6 Hz), 7.98 (1H, d, J=2 Hz), 8.10 (1H, d, J=8.4 Hz), 8.26 (1H, d, J=3.6 Hz), 10.18 (1H, s)

Example 32

5-(4-Methyl-1-piperazinyl)-2-[(phenylmethyl)oxy]-N-3-pyridinylbenzamide (E32)

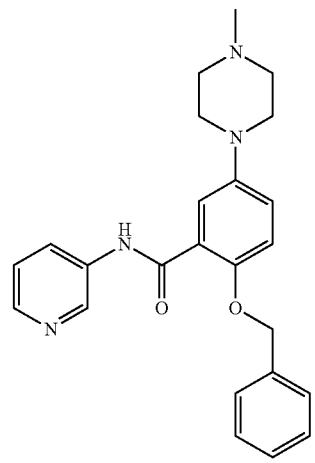 [SMILES: CN1CCN(c2ccc(OCc3ccccc3)c(C(=O)Nc3cccnc3)c2)CC1]

A solution of 5-(4-methyl-1-piperazinyl)-2-[(phenylmethyl)oxy]benzoic acid (may be prepared as described in Description 40; 50 mg, 0.15 mmol), 3-pyridinamine (14.42 mg, 0.15 mmol), EDC (29.4 mg, 0.15 mmol), HOBT (23.46 mg, 0.15 mmol) and triethylamine (0.02 ml, 0.15 mmol) dissolved in DMF (5 ml) was stirred for 3 h at 40° C. The mixture was then filtered and 10 ml water was added to the filtrate. The mixture was then extracted with ethyl acetate (30 ml) and concentrated. The residue was then purified by reverse phase HPLC using a gradient of acetonitrile and 0.1% aqueous ammonia as the eluent. Evaporation of the product-containing fractions gave the title compound as a white solid. 25 mg.

MS (electrospray): m/z [M+H]$^+$=403

1H NMR (CDCl3): 2.40 (3H, s), 2.64 (4H, t, J=4.8 Hz), 3.26 (4H, t, J=4.8 Hz), 5.21 (2H, s), 7.12-7.14 (2H, m), 7.21 (1H, dd, J=8.4 Hz, J=4.4 Hz), 7.53 (5H, m), 7.93 (1H, d, J=2.8 Hz), 8.00 (1H, d, J=2.4 Hz), 8.13 (1H, d, J=8.4 Hz), 8.28 (1H, d, J=4.4 Hz), 10.21 (1H, s).

Example 33

2-[(Phenylmethyl)oxy]-5-(1-piperidinyl)-N-3-pyridinylbenzamide (E33)

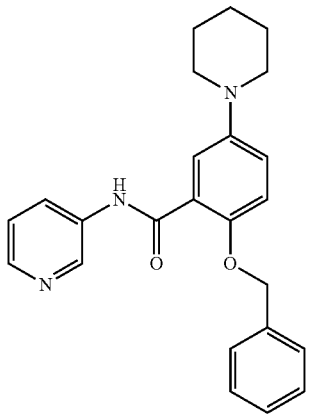 [SMILES: O=C(Nc1cccnc1)c1cc(N2CCCCC2)ccc1OCc1ccccc1]

A solution of 2-[(phenylmethyl)oxy]-5-(1-piperidinyl)benzoic acid (may be prepared as described in Description 42; 80 mg, 0.26 mmol), 3-pyridinamine (24.18 mg, 0.26 mmol), EDC (49.3 mg, 0.26 mmol), HOBT (39.3 mg, 0.26 mmol) and triethylamine (0.04 ml, 0.26 mmol) in DMF (5 ml) was stirred for 3 h at 40° C. The mixture was then filtered and 10 ml water was added to the filtrate. The mixture was extracted with ethyl acetate (30 ml) and concentrated. The residue was then purified by reverse phase HPLC using a gradient of acetonitrile and 0.1% aqueous trifluoroacetic acid as the eluent. Evaporation of the product-containing fractions gave the trifluoroacetate salt of the title compound as a light yellow solid., 48 mg.

$^1$H NMR (DMSO-d6)
MS (electrospray): m/z [M+H]$^+$=388

The trifluoroacetate salt was dissolved in water. 1N NaHCO3 solution was added and the mixture was extracted three times with ethyl acetate. The organic phase was concentrated to yield the title compound. 26 mg.

$^1$H NMR (DMSO-d6)
MS (electrospray): m/z [M+H]$^+$=388

1H NMR (DMSO-d6): 1.53 (2H, m), 1.64 (4H, m), 3.07 (4H, m), 5.19 (2H, s), 7.15 (2H, m), 7.27 (1H, d, J=2.8 Hz), 7.37 (4H, m), 7.52 (2H, d, J=6.8 Hz), 8.08 (1H, d, J=8.4 Hz), 8.27 (1H, d, J=4.4 Hz), 8.65 (1H, d, J=3.6 Hz), 10.35 (1H, s).

Example 34

5-Bromo-N-1,3-oxazol-2-yl-2-[(phenylmethyl)oxy]benzamide (E34)

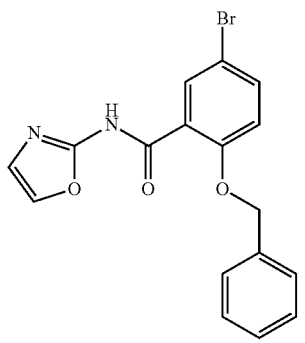 [SMILES: O=C(Nc1ncco1)c1cc(Br)ccc1OCc1ccccc1]

Solid 5-bromo-2-[(phenylmethyl)oxy]benzoic acid (may be prepared as described in Description 5; 200 mg, 0.65 mmol) was added to a stirred suspension of CDI (106 mg, 0.65 mmol) in tetrahydrofuran (10 ml) under nitrogen at 20° C. The reaction mixture was stirred at room temperature for 10 min. 1,3-Oxazol-2-amine (54.7 mg, 0.65 mmol) was then added and the reaction mixture was refluxed overnight. The reaction mixture was concentrated. Water (100 ml) was added to the residue followed by extraction with ethyl acetate (3×50 ml). The combined organic phase was washed with saturated brine (25 ml), dried over Na$_2$SO$_4$, and concentrated under reduced pressure. The crude product was purified by thin layer chromatography (petroleum ether:ethyl acetate=2:1) followed by Prep-HPLC (Gilson GX-281; Shimazu 15 μm; 250*19 mm; A: 10 mmol NH$_4$HCO$_3$/water, B: CH$_3$CN; 0-9 min, 70-80%; 9-9.3 min, 80-95%; 9.3-13 min, 95% CH$_3$CN; RT: 8.0 min) to yield the title compound as a white solid. 15 mg.

$^1$HNMR (400 MHz, CDCl$_3$): 5.31 (s, 2H), 6.90 (d, J=8.8 Hz, 1H), 7.02 (s, 1H), 7.42-7.46 (m, 6H), 8.42 (d, J=2.8 Hz, 1H), 10.51 (s, 1H)
MS (electrospray): m/z [M+H]$^+$=373

Example 35

5-[(4-Methyl-1-piperazinyl)carbonyl]-2-[(phenylmethyl)oxy]-N-3-pyridinylbenzamide (E35)

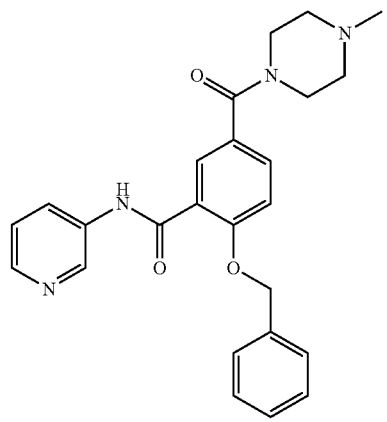 [SMILES: CN1CCN(C(=O)c2ccc(OCc3ccccc3)c(C(=O)Nc3cccnc3)c2)CC1]

To a solution of 5-[(4-methyl-1-piperazinyl)carbonyl]-2-[(phenylmethyl)oxy]benzoic acid (may be prepared as described in Description 51; 166 mg, 0.47 mmol), 3-pyridinamine (44.1 mg, 0.47 mmol), and EDC (90 mg, 0.47 mmol) in N,N-dimethylformamide (DMF) (4 mL) stirred under nitrogen at room temperature was added neat HOBT (71.7 mg, 0.47 mmol) in one charge. The reaction mixture was stirred at room temperature for 6 h. The mixture was diluted with water (50 ml), extracted with ethyl acetate (3×50 ml). The organic phase was washed with saturated brine (25 ml), dried over sodium sulfate, and evaporated in vacuo to give the crude product. The crude product was purified by Prep-HPLC (Gilson GX-281; Durashell 10 μm, 21.5*250 nm n; A: 10 mmol/water, B: MeCN, O-7.2 min, 35%-35%; 7.2-7.5 min, 35%-95%; 7.5-11.5 min, 95%; RT: 7.0 min) to yield the title compound as a white solid. 30 mg.

$^1$HNMR (400 MHz, CDCl$_3$): 2.34 (m, 4H), 3.55-3.80 (m, 4H), 5.28 (s, 2H), 7.19-7.21 (t, J=4.8 Hz, 1H), 7.23 (d, J=8.8 Hz, 1H), 7.53-7.55 (m, 5H), 7.70-7.73 (dd, J=2.4 Hz, J=9.0 Hz, 1H) 7.94 (s, 1H), 8.13 (m, 1H), 8.28 (m, 1H), 8.37 (d, J=2.4 Hz, 1H), 9.98 (s, 1H)
MS (electrospray): m/z [M+H]$^+$=431

Example 36

2-[(Phenylmethyl)oxy]-5-(1-piperidinylcarbonyl)-N-3-pyridinylbenzamide (E36)

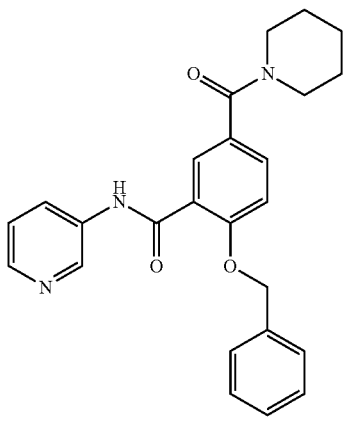 [SMILES: O=C(Nc1cccnc1)c1cc(C(=O)N2CCCCC2)ccc1OCc1ccccc1]

Neat HOBT (90 mg, 0.59 mmol) was added in one charge to a stirred solution of 2-[(phenylmethyl)oxy]-5-(1-piperidinylcarbonyl)benzoic acid (may be prepared as described in Description 53; 200 mg, 0.59 mmol), 3-pyridinamine (55.5 mg, 0.59 mmol), and EDC (113 mg, 0.59 mmol) in N,N-dimethylformamide (5 ml) under nitrogen at room temperature. The reaction mixture was stirred at room temperature for 4 h. The mixture was diluted with water (50 ml). The precipitate was collected by filtration, washed with ether (5 ml), and dried to yield the title compound as a white solid. 65 mg.

$^1$HNMR (400 MHz, CDCl$_3$): 1.61 (m, 4H), 1.70 (m, 2H), 3.14-3.72 (m, 2H), 5.28 (s, 1H), 7.19-7.22 (m, 2H), 7.52-7.55 (m, 5H), 7.68-7.71 (m, 1H), 7.97 (s, 1H), 8.11-8.14 (m, 1H), 8.28 (d, J=3.6 Hz, 1H), 8.36 (d, J=2.0 Hz, 1H), 10.00 (s, 1H)

MS (electrospray): m/z [M+H]$^+$=416

Example 37

2-[(Phenylmethyl)oxy]-N-3-pyridinyl-5-(1-pyrrolidinylcarbonyl)benzamide (E37)

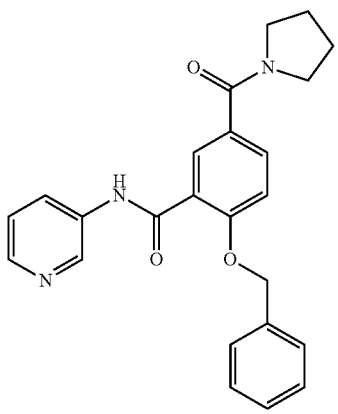 [SMILES: O=C(Nc1cccnc1)c1cc(C(=O)N2CCCC2)ccc1OCc1ccccc1]

Neat HOBT (94 mg, 0.62 mmol) was added in one charge to a stirred solution of 2-[(phenylmethyl)oxy]-5-(1-pyrrolidinylcarbonyl)benzoic acid (may be prepared as described in Description 55; 200 mg, 0.62 mmol), 3-pyridinamine (57.9 mg, 0.62 mmol) and EDC (118 mg, 0.62 mmol) in N,N-dimethylformamide (5 ml) under nitrogen at room temperature. The reaction mixture was stirred at room temperature for 4 h. The mixture was diluted with water (50 ml). The precipitate was collected by filtration, washed with ether (5 ml), and dried to yield the title compound as a white solid. 88 mg.

$^1$HNMR (400 MHz, CDCl$_3$): 1.90-1.99 (m, 4H), 3.53-3.68 (m, 4H), 5.28 (s, 1H), 7.19-7.22 (m, 2H), 7.51-7.57 (m, 5H), 7.64-7.86 (dd, J=2.0 Hz, J=8.4 Hz, 1H), 7.98-7.99 (d, J=2.8 Hz, 1H), 8.10-8.11 (m, 1H), 8.28 (d, J=3.6 Hz, 1H), 8.52 (d, J=2.0 Hz, 1H), 10.00 (s, 1H)

MS (electrospray): m/z [M-1-H]$^+$=402

Example 38

5-(4-Morpholinylcarbonyl)-2-[(phenylmethyl)oxy]-N-3-pyridinylbenzamide (E38)

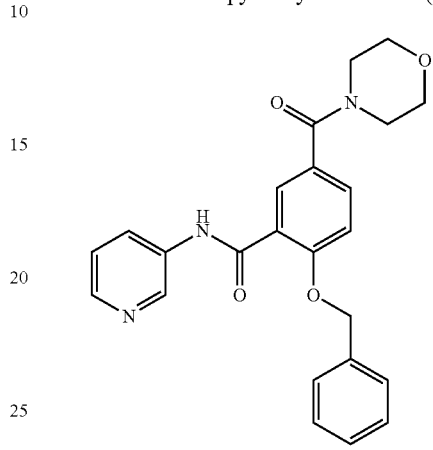

Neat HOBT (90 mg, 0.59 mmol) was added in one charge to a stirred solution of 5-(4-morpholinylcarbonyl)-2-[(phenylmethyl)oxy]benzoic acid (may be prepared as described in Description 57; 200 mg, 0.59 mmol), 3-pyridinamine (55.1 mg, 0.59 mmol) and EDC (112 mg, 0.59 mmol) in N,N-dimethylformamide (5 ml) under nitrogen at room temperature. The reaction mixture was stirred at room temperature for 4 h. The mixture was diluted with water (50 ml) and extracted with ethyl acetate (3×50 ml). The organic phase was washed with sodium hydroxide solution (1 mol/l, 25 ml), saturated brine (25 ml), dried over sodium sulfate, and evaporated in vacuo to give the crude product. The crude product was washed with ether (5 ml) and dried to yield the title compound as a white solid. 67 mg.

$^1$HNMR (400 MHz, CDCl$_3$): 3.72 (m, 8H), 5.28 (s, 1H), 7.19-7.25 (m, 2H), 7.52-7.54 (m, 5H), 7.71-7.73 (dd, J=2.0 Hz, J=8.4 Hz, 1H), 7.97 (m, 1H), 8.11-8.13 (m, 1H), 8.28 (d, J=3.6 Hz, 1H), 8.37 (d, J=2.0 Hz, 1H), 9.98 (s, 1H)

MS (electrospray): m/z [M+H]$^+$=418

Example 39

N$^1$,N$^1$-Dimethyl-4-[(phenylmethyl)oxy]-N$^3$-3-pyridinyl-1,3-benzenedicarboxamide (E40)

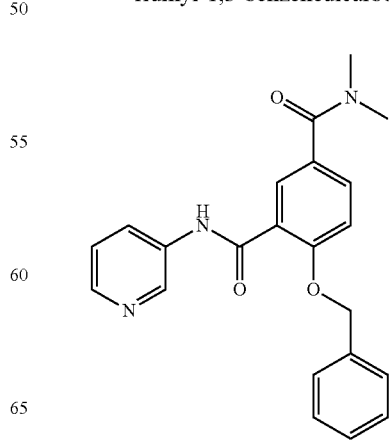

HOBT (102 mg, 0.67 mmol) was added in one charge to a stirred solution of 5-[(dimethylamino)carbonyl]-2-[(phenylmethyl)oxy]benzoic acid (may be prepared as described in Description 59; 200 mg, 0.67 mmol), 3-pyridinamine (62.9 mg, 0.67 mmol) and EDC (128 mg, 0.67 mmol) in N,N-dimethylformamide (5 ml) under nitrogen at room temperature. The reaction mixture was stirred at room temperature for 4 h. The mixture was diluted with water (50 ml). The precipitate was collected by filtration. The solid was dissolved in ethyl acetate (100 ml), and the organic phase was washed with NaOH (1 mol/l 25 ml), water (25 ml), saturated brine (25 ml), dried over sodium sulfate, and evaporated in vacuo to yield the title compound as a white solid. 78 mg.

$^1$HNMR (400 MHz, CDCl$_3$): 3.10 (t, J=1.0 Hz, J=6.8 Hz, 6H), 5.28 (s, 1H), 7.19-7.23 (m, 2H), 7.52-7.55 (m, 5H), 7.71-7.74 (d, J=2.0 Hz, J=8.8 Hz, 1H), 7.97 (s, 1H), 8.11-8.12 (m, 1H), 8.28 (d, J=3.2 Hz, 1H), 8.40 (d, J=2.0 Hz, 1H), 9.99 (s, 1H)

MS (electrospray): m/z [M+H]$^+$=376

Example 40

5-[(Dimethylamino)sulfonyl]-2-[(phenylmethyl)oxy]-N-3-pyridinylbenzamide (E40)

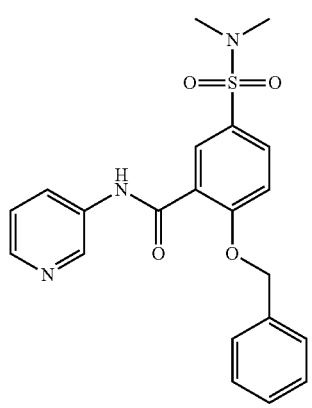 [SMILES: CN(C)S(=O)(=O)c1ccc(OCc2ccccc2)c(C(=O)Nc2cccnc2)c1]

A solution of oxalyl chloride (0.06 ml, 0.69 mmol) in dichloromethane (5 ml) was added dropwise over 1 minute to a stirred solution of 5-[(dimethylamino)sulfonyl]-2-[(phenylmethyl)oxy]benzoic acid (may be prepared as described in Description 63; 230 mg, 0.69 mmol) in dichloromethane (5 ml) at 0° C. The reaction mixture was stirred at 25° C. for 0.5 h, and then concentrated under reduced pressure to give the crude acyl chloride as a yellow solid. A solution of this crude acyl chloride in dichloromethane (5 ml) was added dropwise over 5 min to a stirred solution of 3-pyridinamine (64.5 mg, 0.69 mmol) and diisopropylethylamine (0.12 ml, 0.69 mmol) in dichloromethane (20 ml) under nitrogen at 0° C. The reaction mixture was stirred at 25° C. for 1 h. The organic phase was washed with water (25 ml) three times and saturated brine (10 mL) two times, dried over sodium sulfate, and evaporated in vacuo to give the crude product as a orange oil. The product was crystallized from methanol to yield the title compound as a white solid. 170 mg.

MS (electrospray): m/z [M+H]$^+$=412

$^1$H NMR (400 MHz, DMSO-d6): 2.64 (6H, s), 5.35 (2H, s), 7.35-7.40 (4H, m), 7.53-7.56 (3H, t), 7.90-7.95 (2H, m), 8.10 (1H, d, J=8.4), 8.30 (1H, dd, J=0.8, 1.2), 8.72 (1H, s), 10.52 (1H, s)

Example 41

5-(4-Morpholinylsulfonyl)-2-[(phenylmethyl)oxy]-N-3-pyridinylbenzamide (E41)

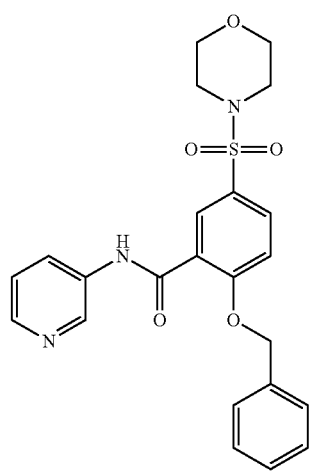 [SMILES: O=C(Nc1cccnc1)c1cc(S(=O)(=O)N2CCOCC2)ccc1OCc1ccccc1]

A solution of oxalyl chloride (0.06 ml, 0.66 mmol) in dichloromethane (5 ml) was added dropwise over 1 min to a stirred solution of 5-(4-morpholinylsulfonyl)-2-[(phenylmethyl)oxy]benzoic acid (may be prepared as described in Description 66; 250 mg, 0.66 mmol) in dichloromethane (5 ml) at 0° C. The reaction mixture was stirred at 25° C. for 0.5 h. The organic phase was evaporated in vacuo to give the crude acyl chloride as a yellow solid. A solution of this crude acyl chloride in dichloromethane (5 ml) was added dropwise over 5 min to a stirred solution of 3-pyridinamine (62.3 mg, 0.66 mmol) and diisopropylethylamine (0.12 ml, 0.66 mmol) in dichloromethane (20 ml) under nitrogen at 0° C. The reaction mixture was stirred at 25° C. for 1 h. The organic phase was washed with water (25 ml) three times and saturated brine (10 ml) two times, dried over sodium sulfate, and evaporated in vacuo to give the crude product as a orange oil.

The product was crystallized from methanol to yield the title compound as a white solid. 169 mg.

$^1$HNMR (400 MHz, DMSO-d6): 2.88-2.90 (4H, t), 3.64-3.67 (4H, t), 5.36 (2H, s), 7.35-7.40 (4H, m), 7.54-7.57 (3H, m), 7.89-7.94 (2H, m), 8.09-8.12 (1H, m), 8.30-8.32 (1H, m), 8.72 (1H, d, J=1.6), 10.53 (1H, s)

MS (electrospray): m/z [M+H]$^+$ 453.9

Example 42

2-[(Phenylmethyl)oxy]-5-(1-piperidinylsulfonyl)-N-3-pyridinylbenzamide (E42)

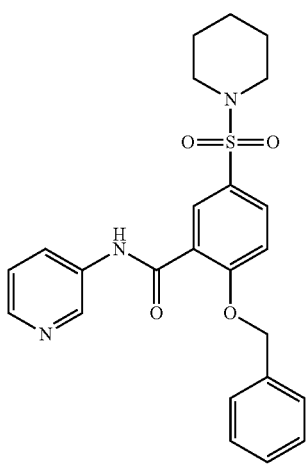 [SMILES: O=C(Nc1cccnc1)c1cc(S(=O)(=O)N2CCCCC2)ccc1OCc1ccccc1]

Oxalyl chloride (0.05 ml, 0.59 mmol) in dichloromethane (5 ml) was added dropwise over 1 min to a stirred solution of 2-[(phenylmethyl)oxy]-5-(1-piperidinylsulfonyl)benzoic acid (may be prepared as described in Description 69; 220 mg, 0.59 mmol) in dichloromethane (5 ml) at 0° C. The reaction mixture was stirred at 25° C. for 0.5 h, and then concentrated under reduced pressure to give crude acyl chloride. A solution of this crude acyl chloride in dichloromethane (5 ml) was added dropwise over 5 min to a stirred solution of 3-pyridinamine (55.1 mg, 0.59 mmol) and diisopropylethylamine (0.10 ml, 0.59 mmol) in dichloromethane (20 ml) under nitrogen at 0° C. The reaction mixture was stirred at 25° C. for 1 h. The organic phase was washed with water (25 ml) three times, saturated brine (10 ml) two times, dried over sodium sulfate, and evaporated in vacuo to give crude product as a orange oil. The product was crystallized from methanol to yield the title compound as a white solid. 125 mg.

$^1$HNMR (400 MHz, DMSO-d6): 1.38 (2H, d, J=4.4), 1.56 (4H, d, J=4.4), 2.89-2.92 (4H, t), 5.34 (2H, s), 7.34-7.41 (4H, m), 7.53-7.56 (3H, m), 7.87-7.93 (2H, m), 8.09-8.11 (1H, t), 8.31 (1H, s), 8.72 (1H, s), 10.50 (1H, s)

MS (electrospray): m/z [M+H]$^+$=451.9

Example 43

5-[(4-Methyl-1-piperazinyl)sulfonyl]-2-[(phenylmethyl)oxy]-N-3-pyridinylbenzamide (E43)

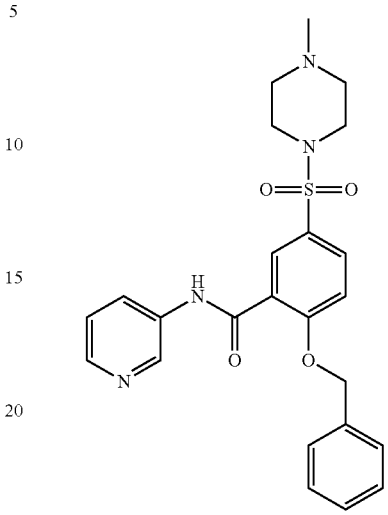

A solution of oxalyl chloride (0.03 ml, 0.31 mmol) in dichloromethane (5 ml) was added dropwise over 1 min to a stirred solution of 5-[(4-methyl-1-piperazinyl)sulfonyl]-2-[(phenylmethyl)oxy]benzoic acid (may be prepared as described in Description 72; 120 mg, 0.31 mmol) in dichloromethane (5 ml) at 0° C. The reaction mixture was stirred at 25° C. for 0.5 h, and then concentrated to give crude acyl chloride. A solution of this acyl chloride in dichloromethane (5 ml) was added dropwise over 5 min to a stirred solution of 3-pyridinamine (28.9 mg, 0.31 mmol) and diisopropylethylamine (0.05 ml, 0.31 mmol) in dichloromethane (20 ml) under nitrogen at 0° C. The reaction mixture was stirred at 25° C. for 1 h. The organic phase was washed with water (25 ml) three times, saturated brine (10 ml) two times, dried over sodium sulfate, and evaporated in vacuo to give crude product as an orange oil. The crude product was crystallized from methanol to yield the title compound as a white solid. 30 mg.

$^1$HNMR (400 MHz, DMSO-d6): 2.15 (3H, s), 2.38 (4H, d, J=4.4), 2.91 (4H, s), 5.36 (2H, s), 7.34-7.40 (4H, m), 7.53-7.55 (3H, d, J=8.8), 7.87-7.93 (2H, m), 8.08-8.11 (1H, m), 8.30-8.32 (1H, m), 8.72 (1H, d, J=1.6), 10.51 (1H, s)

MS (electrospray): m/z [M+H]$^+$=467

Example 44

2-[(Phenylmethyl)oxy]-N-3-pyridinyl-5-{[(2R)-2-pyrrolidinylmethyl]oxy}benzamide (E44)

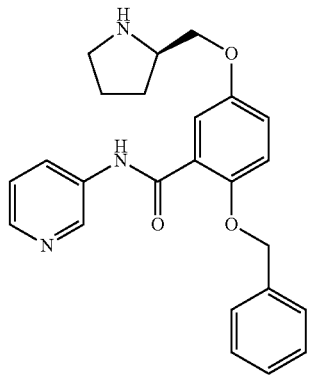 [SMILES: O=C(Nc1cccnc1)c1cc(OC[C@H]2CCCN2)ccc1OCc1ccccc1]

Trifluoroacetic acid (1.5 ml, 19.47 mmol) was added dropwise to an ice-cooled solution of 1,1-dimethylethyl (2R)-2-[({4-[(phenylmethyl)oxy]-3-[(3-pyridinylamino)carbonyl]phenyl}oxy)methyl]-1-pyrrolidinecarboxylate (may be prepared as described in Description 73; 500 mg, 0.99 mmol) in dichloromethane (15 ml). After stirring at 25° C. for 2 h, the pH of the solution was adjusted to 7-8 by adding aqueous $NaHCO_3$ solution. The mixture was extracted with dichloromethane. The dichloromethane layer was washed with brine, dried over $Na_2SO_4$, and concentrated to obtain a crude product. Half of the crude product was purified by pre-HPLC (Gilson GX-281, waters X-Bridge 5 μm, 100*19 mm; A: 0.04% $NH_3.H_2O$/water, B: $CH_3CN$; 0-7 min, 35%-50%; 7-14 min, 95%; RT=6.5 min) to yield the title compound as a light yellow solid. 70 mg.

$^1$HNMR (400 MHz, CDCl3): 10.20 (s, 1H), 8.27 (dd, 1H), 8.12 (d, 1H), 8.00 (t, 1H), 7.53 (m, 5H), 7.20 (m, 1H), 7.12 (m, 2H), 5.20 (s, 2H), 4.02 (m, 1H), 3.91 (m, 1H), 3.55 (m, 1H), 3.03 (m, 2H), 1.96 (m, 1H), 1.84 (m, 2H), 1.57 (m, 1H).

MS (electrospray): m/z $[M+H]^+$=404.2.

Example 45

5-({[(2R)-1-Methyl-2-pyrrolidinyl]methyl}oxy)-2-[(phenylmethyl)oxy]-N-3-pyridinylbenzamide (E45)

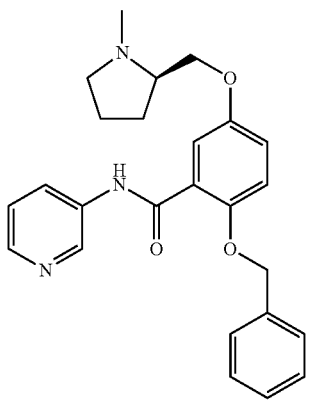 [SMILES: CN1CCC[C@@H]1COc1ccc(OCc2ccccc2)c(C(=O)Nc2cccnc2)c1]

2-[(Phenylmethyl)oxy]-N-3-pyridinyl-5-{[(2R)-2-pyrrolidinylmethyl]oxy}benzamide (may be prepared as described in Example 44; 250 mg, 0.62 mmol) was added to formic acid (4.5 ml) at 5° C., followed by 40% aqueous formaldehyde (2.4 ml). When the initial evolution of carbon dioxide had subsided, the mixture was refluxed for 2 h. After the solution was cooled, the pH of the solution was adjusted to 7-8 by adding aqueous $NaHCO_3$ solution. The mixture was extracted with dichloromethane. The organic layer was dried over $Na_2SO_4$, and concentrated to obtain a crude product, which was purified by prep-HPLC to yield the title compound as a white solid. 47 mg.

$^1$HNMR (400 MHz, CDCl3): δ: 10.20 (s, 1H), 8.27 (dd, 1H), 8.12 (d, 1H), 8.00 (t, 1H), 7.53 (m, 5H), 7.20 (m, 1H), 7.12 (m, 2H), 5.20 (s, 2H), 4.02 (m, 1H), 3.91 (m, 1H), 3.55 (m, 1H), 3.03 (m, 2H), 2.37 (s, 3H), 1.96 (m, 1H), 1.84 (m, 2H), 1.57 (m, 1H).

MS (electrospray): m/z $[M+H]^+$=418.2.

Example 46

2-[(Phenylmethyl)oxy]-N-3-pyridinyl-5-{[(2S)-2-pyrrolidinylmethyl]oxy}benzamide (E46)

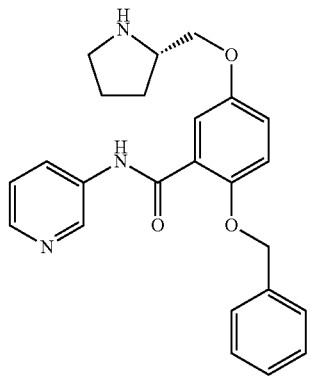 [SMILES: O=C(Nc1cccnc1)c1cc(OC[C@@H]2CCCN2)ccc1OCc1ccccc1]

To an ice-cooled solution of 1,1-dimethylethyl (2S)-2-[({4-[(phenylmethyl)oxy]-3-[(3-pyridinylamino)carbonyl]phenyl}oxy)methyl]-1-pyrrolidinecarboxylate (may be prepared as described in Description 74; 0.6 g, 1.19 mmol) in dichloromethane (15 ml) was added trifluoroacetic acid (2.0 ml, 26 mmol) dropwise. After stirred at 25° C. for 2 h, the pH of the solution was adjusted to 7-8 by adding aqueous $NaHCO_3$ solution. The mixture was extracted with dichloromethane. The dichloromethane layer was washed with brine, dried over $Na_2SO_4$, and concentrated to obtain a crude product. The crude product was purified by prep-HPLC (Gilson GX-281, waters X-Bridge 5 μm, 100*19 mm; A: 0.04% $NH_3.H_2O$/water, B: $CH_3CN$; 0-7 min, 35%-50%; 7-14 min, 95%; RT=7.0 min) to yield the title compound as a light yellow solid. 150 mg.

$^1$HNMR (400 MHz, CDCl3): 1.57 (m, 1H), 1.81 (m, 2H), 1.97 (m, 1H), 3.00 (m, 2H), 3.53 (m, 1H), 3.91 (m, 1H), 4.02 (m, 1H), 5.20 (s, 2H), 7.11-7.16 (m, 2H), 7.21 (m, 1H), 7.52 (m, 5H), 7.86 (s, 1H), 8.00 (s, 1H), 8.12 (m, 1H), 8.28 (d, J=4 Hz, 1H), 10.20 (s, 1H)

MS (electrospray): m/z $[M+H]^+$=404.3

Example 47

5-({[(2S)-1-Methyl-2-pyrrolidinyl]methyl}oxy)-2-[(phenylmethyl)oxy]-N-3-pyridinylbenzamide (E47)

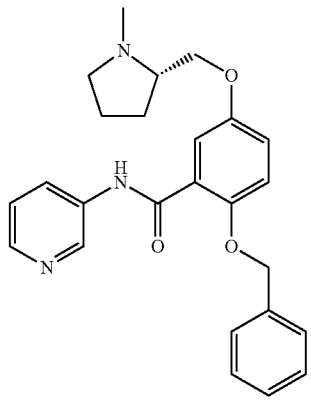 [SMILES: CN1CCC[C@H]1COc1ccc(OCc2ccccc2)c(C(=O)Nc2cccnc2)c1]

2-[(Phenylmethyl)oxy]-N-3-pyridinyl-5-{[(2S)-2-pyrrolidinylmethyl]oxy}benzamide (may be prepared as described in Example 46; 80 mg, 0.20 mmol) was added to formic acid (4 ml) at 5° C., followed by aqueous formaldehyde (40%, 2.0 ml). When the initial evolution of carbon dioxide had subsided, the mixture was refluxed for 2 h. After the solution was cooled, the pH of the solution was adjusted to 7-8 by adding aqueous $NaHCO_3$ solution. The mixture was extracted with dichloromethane. The organic layer was dried over $Na_2SO_4$, and concentrated to obtain a crude product. The crude product was purified by prep-HPLC (Gilson GX-281, waters X-Bridge 5 μm, 100*19 mm; A: 0.04% $NH_3.H_2O$/water, B: $CH_3CN$; 0-7.2 min, 40%-50%; 7.2-7.5 min, 50%-95%; 7.5-11.5 min, 95%, RT=4.0 min) to yield the title compound as a white solid. 68 mg.

$^1$HNMR (CDCl3, 400 MHz): 1.77-1.91 (m, 3H), 2.04-2.09 (m, 1H), 2.36 (m, 1H), 2.54 (s, 3H), 2.73 (m, 1H), 3.18 (t, 1H), 4.00-4.11 (m, 2H), 5.21 (s, 2H), 7.11-7.16 (m, 2H), 7.21 (m, 1H), 7.54 (m, 5H), 7.88 (d, J=2.4 Hz, 1H), 7.98 (d, J=2.4 Hz, 1H), 8.13 (m, 1H), 8.28 (d, J=4 Hz, 1H), 10.25 (s, 1H)

MS (electrospray): m/z [M+H]$^+$=418.2

Example 48

5-{[2-(Methylamino)ethyl]oxy}-2-[(phenylmethyl) oxy]-N-3-pyridinylbenzamide (E48)

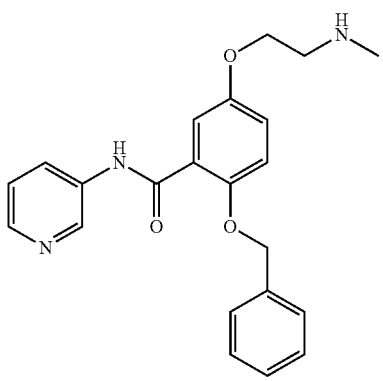 [SMILES: CNCCOc1ccc(OCc2ccccc2)c(C(=O)Nc2cccnc2)c1]

To the solution of 1,1-dimethylethyl methyl[2-({4-[(phenylmethyl)oxy]-3-[(3-pyridinylamino)carbonyl] phenyl}oxy)ethyl]carbamate (may be prepared as described in Description 75; 140 mg, 0.17 mmol) in dichloromethane (10 ml) was added trifluoroacetic acid (3.0 ml, 38.9 mmol) dropwise. After stirring at 30° C. for 2 h, the pH of the solution was adjusted to 7-8 by adding aqueous $NaHCO_3$ solution. The mixture was extracted with dichloromethane. The dichloromethane layer was washed with brine, dried over $Na_2SO_4$, and concentrated to obtain a crude product. The crude product was purified by prep-HPLC (Gilson GX-281, waters X-Bridge 5 μm, 100*30 mm; A: 0.04% $NH_3.H_2O$/water, B: $CH_3CN$; 0-6.0 min, 30%-55%; 6-12 min, 95%, RT=7.3 min) to yield the title compound as a white solid. 20 mg.

$^1$HNMR (400 MHz, CDCl3): 2.57 (s, 3H), 3.05 (t, 2H), 4.17 (t, 2H), 5.21 (s, 2H), 7.13 (m, 2H), 7.21 (m, 1H), 7.53 (m, 5H), 7.86 (d, J=2.4 Hz, 1H), 8.00 (d, J=2.4 Hz, 1H), 8.12 (m, 1H), 8.28 (d, J=4 Hz, 1H), 10.19 (s, 1H)

MS (electrospray): m/z [M+H]$^+$=378.1

Example 49

5-({2-[(2-Aminoethyl)oxy]ethyl}oxy)-2-[(phenylmethyl)oxy]-N-3-pyridinylbenzamide (E49)

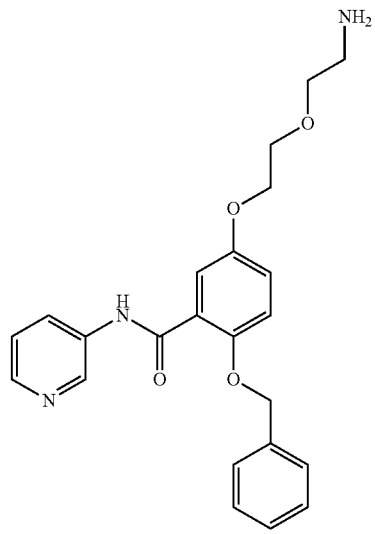 [SMILES: NCCOCCOc1ccc(OCc2ccccc2)c(C(=O)Nc2cccnc2)c1]

Bis(1,1-dimethylethyl) (2-{[2-({4-[(phenylmethyl)oxy]-3-[(3-pyridinylamino)carbonyl]phenyl}oxy)ethyl] oxy}ethyl)imidodicarbonate (may be prepared as described in Description 77; 340 mg, 0.56 mmol) was treated with trifluoroacetic acid/dichloromethane (v/v 40%, 10 ml). The mixture was stirred at 25° C. for 1 h. The solvent was removed under reduced pressure. The residue was purified twice by reverse phase HPLC using a gradient of acetonitrile and 0.1% aqueous ammonia as the eluent. Evaporation of the product-containing fractions yielded the title compound as a white solid. 86 mg.

$^1$HNMR (400 MHz, DMSO-d6): 3.00 (2H, s), 3.68 (2H, s), 3.86 (2H, s), 4.19 (2H, s), 5.18 (2H, s), 7.08-7.20 (3H, m), 7.50 (5H, s), 7.86 (1H, s), 8.01-8.08 (2H, t), 8.26 (1H, s), 10.17 (1H, s)

MS (electrospray): m/z [M+1-1]$^+$=408

Example 50

5-Bromo-N-(1-methyl-1H-pyrazol-4-yl)-2-[(phenylmethyl)oxy]benzamide (E50)

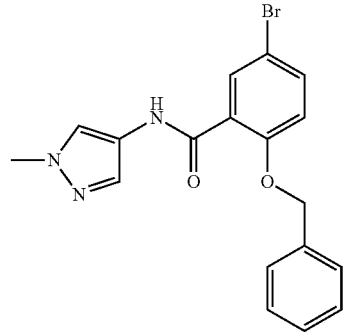 [SMILES: Cn1cc(NC(=O)c2cc(Br)ccc2OCc2ccccc2)cn1]

Neat 1-methyl-1H-pyrazol-4-amine (61.7 mg, 0.64 mmol) was added in one charge to a stirred suspension of 5-bromo-2-[(phenylmethyl)oxy]benzoic acid (may be prepared as described in Description 5; 150 mg, 0.49 mmol), EDC (281 mg, 1.47 mmol) and HOBT (224 mg, 1.47 mmol) in N,N-dimethylformamide (3 ml) in air at room temperature. The reaction mixture was stirred at room temperature overnight. 20 ml of water was added and the mixture was extracted with ethyl acetate (20 ml×2). The combined organic phases were dried over Na₂SO₄ and concentrated in vacuo to give crude product, which was purified by prep-HPLC (Gilson GX-281; waters X-Bridge 5 μm 30*100 mm; A: 0.1NH3*H2O/Water; B: CH₃CN) twice to yield the title compound as a white solid. 70 mg.

¹HNMR (400 MHz, DMSO-d6): 3.81 (s, 3H), 5.25 (s, 2H), 7.23 (d, 1H), 7.35-7.42 (m, 4H), 7.50 (d, 2H), 7.64-7.67 (m, 1H), 7.75 (d, 1H), 7.97 (s, 1H), 10.21 (s, 1H).

MS (electrospray): m/z [M+H]⁺=386

Example 51

5-Bromo-2-[(phenylmethyl)oxy]-N-1H-pyrazol-4-ylbenzamide (E51)

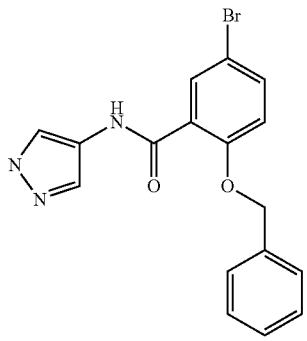 [SMILES: O=C(Nc1cn[nH]c1)c1cc(Br)ccc1OCc1ccccc1]

Neat 1H-pyrazol-4-amine (55.2 mg, 0.66 mmol) was added in one charge to a stirred solution of 5-bromo-2-[(phenylmethyl)oxy]benzoic acid (may be prepared as described in Description 5, method D; 170 mg, 0.55 mmol), EDC (318 mg, 1.66 mmol) and HOBT (254 mg, 1.66 mmol) in N,N-dimethylformamide (4 ml) in air at room temperature. The reaction mixture was stirred at room temperature overnight. Water (30 ml) was added, and the mixture was extracted with ethyl acetate (50 ml×2). The organic layers were combined, dried over MgSO₄, and concentrated in vacuo. The residue was washed with ethyl acetate yield the title compound as a brown solid. 180 mg.

¹HNMR (400 MHz, DMSO-d6): 5.26 (s, 2H), 7.24 (d, 1H), 7.35-7.45 (m, 4H), 7.52 (d, 2H), 7.65-7.68 (m, 1H), 7.77 (d, 1H), 7.93 (s, 1H), 10.21 (s, 1H), 12.66 (s, 1H).

MS (electrospray): m/z [M+H]⁺=372

Example 52

N-(4-Methyl-3-pyridinyl)-2-[(phenylmethyl)oxy]-5-(4-pyridinyl)benzamide (E52)

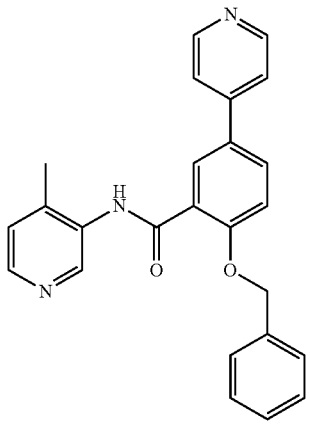 [SMILES: Cc1ccncc1NC(=O)c1cc(-c2ccncc2)ccc1OCc1ccccc1]

A solution of 2-[(phenylmethyl)oxy]-5-(4-pyridinyl)benzoic acid (may be prepared as described in Description 79; 110 mg, 0.33 mmol), EDC (126 mg, 0.66 mmol) and HOBT (101 mg, 0.66 mmol) in dimethylformamide (2 ml) stirred in air at room temperature for 1 h. 4-Methylpyridin-3-amine (35.6 mg, 0.33 mmol) was then added in one charge. The reaction mixture was stirred at 25° C. overnight. The reaction mixture was diluted with water (25 ml), and then extracted with ethyl acetate (60 ml×3). The organic phases were combined, washed with brine (50 ml×3), dried over anhydrous MgSO₄ and concentrated. The residue was purified by Prep-HPLC (instrument: Gilson GX-281, Column: Shimadzu 15 μm, 250×20 mm×2, Mobile Phase: A=10 mmol NH₄HCO₃/water B=CH₃CN, Flow rate: 30.0 ml/L method: B=55%-65%, 0.0-7.2 min; B=65%-95%, 7.2-7.5 min; B=95%-95%, 7.5 min-11.5 min, the RT=10.0 min) to yield the title compound as a pink solid. 94 mg.

¹HNMR (400 MHz, DMSO-d6): 9.92 (s, 1H), 8.77 (s, 1H), 8.63 (d, 2H, J=6.0), 8.26 (d, 1H, J=4.8), 8.20 (d, 1H, J=2.4), 8.01 (dd, 1H, J=2.4, 8.8), 7.76 (d, 2H, J=6.0), 7.56 (d, 2H, J=6.8), 7.48-7.37 (m, 4H), 7.26 (d, 1H, J=3.2, 5.39 (s, 2H), 2.02 (s, 3H).

MS (electrospray): m/z [M+H]⁺=396.1

Example 53

N-[2-(Methyloxy)-3-pyridinyl]-2-[(phenylmethyl)oxy]-5-(4-pyridinyl)benzamide (E53)

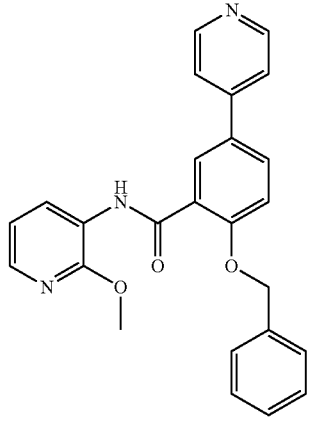 [SMILES: COc1ncccc1NC(=O)c1cc(-c2ccncc2)ccc1OCc1ccccc1]

A solution of 2-[(phenylmethyl)oxy]-5-(4-pyridinyl)benzoic acid (may be prepared as described in Description 79; 110 mg, 0.33 mmol), EDC (126 mg, 0.66 mmol) and HOBT (101 mg, 0.66 mmol) in dimethylformamide (2 ml) was stirred in air at room temperature for 1 h. 2-Methoxy-pyridin-3-amine (40.8 mg, 0.33 mmol) was then added in one charge. The reaction mixture was stirred at 25° C. overnight. The reaction mixture was diluted with water (25 ml) and then extracted with ethyl acetate (60 ml×3). The organic phases were combined, washed by brine (50 ml×3), dried over anhydrous MgSO₄, and concentrated. The residue was purified by Prep-HPLC (instrument: Gilson GX-281, Column: Shimadzu 15 μm, 250*20 mm*2, Mobile Phase: A=10 mmol NH₄HCO₃/water B=CH₃CN, Flow rate: 30.0 ml/L method: B=80%-90%, 0.0-7.2 min; B=90%-95%, 7.2-7.5 min; B=95%-95%, 7.5 min-11.5 min, the RT=11.0 min) to yield the title compound as a pink solid. 92 mg.

¹HNMR (400 MHz, DMSO-d6): 10.40 (s, 1H), 8.68 (d, 1H, J=7.6), 8.64 (d, 2H, J=5.2), 8.44 (d, 1H, J=2.8), 8.04 (dd, 1H, J=2.4, J=8.8), 7.89 (dd, 1H, J=1.2, 4.8), 7.73 (d, 2H, J=6.0), 7.60-7.54 (m, 3H), 7.45-7.38 (m, 3H), 7.04 (dd, 1H, J=5.2, 7.6), 5.54 (s, 2H), 3.65 (s, 3H).

MS (electrospray): m/z [M+H]⁺=412.20

Example 54

N-(2-Fluoro-3-pyridinyl)-2-[(phenylmethyl)oxy]-5-(4-pyridinyl)benzamide (E54)

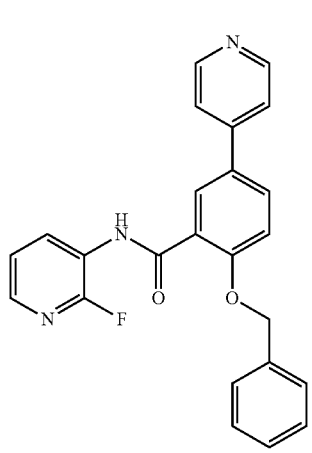 [SMILES: O=C(Nc1cccnc1F)c1cc(-c2ccncc2)ccc1OCc1ccccc1]

A solution of 2-[(phenylmethyl)oxy]-5-(4-pyridinyl)benzoic acid (may be prepared as described in Description 79; 0.12 g, 0.34 mmol), EDC (0.16 g, 0.84 mmol) and HOBT (0.13 g, 0.84 mmol) in dimethylformamide (2 ml) was stirred in air at room temperature for 1 h. 2-Fluoropyridin-3-amine (0.04 g, 0.37 mmol) was then added in one charge. The reaction mixture was stirred at 25° C. overnight. Another batch of HOBT (0.13 g, 0.84 mmol), EDC (0.161 g, 0.842 mmol) and 2-fluoropyridin-3-amine (0.04 g, 0.37 mmol) was added into the mixture and heating was continued at 40° C. for 38 hours. The reaction mixture was diluted with water (30 ml) and extracted with ethyl acetate (60 ml×3). The organic phases were combined, washed with brine (50 ml×3), dried over anhydrous MgSO$_4$, and concentrated. The residue was purified by chromatography (silica gel, 40 g, eluent: dichloromethane/methanol=50:1, 1 L). The solid was washed by methanol (3 ml×2) and dried in vacuo to yield the title compound as a grey solid. 31 mg.

$^1$HNMR (400 MHz, DMSO-d6): 10.31 (s, 1H), 8.64-8.61 (m, 3H), 8.26 (d, 1H, J=2.0), 8.04 (dd, 1H, J=2.4, 9.2), 7.97 (d, 1H, J=4.8), 7.74 (dd, 2H, J=1.6, 4.8), 7.56 (d, 2H, J=7.2), 7.50 (d, 1H, J=8.8), 7.43-7.36 (m, 4H), 5.42 (s, 2H).

MS (electrospray): m/z [M+H]$^+$=400.0

Example 55

N-[2-(Hydroxymethyl)-3-pyridinyl]-2-[(phenylmethyl)oxy]-5-(4-pyridinyl)benzamide (E55)

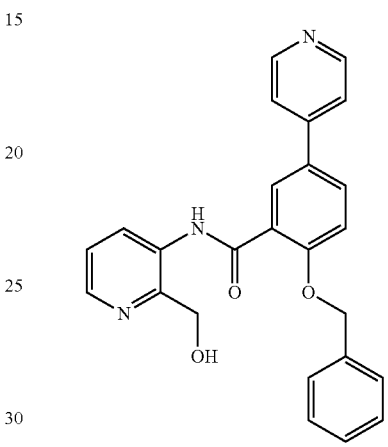

Neat (3-aminopyridin-2-yl)methanol (may be prepared as described in Description 80; 68 mg, 0.55 mmol) was added in one charge to a stirred suspension of 2-[(phenylmethyl)oxy]-5-(4-pyridinyl)benzoic acid (may be prepared as described in Description 79; 120 mg, 0.393 mmol), EDC (151 mg, 0.786 mmol), HOBT (120 mg, 0.79 mmol) and triethylamine (0.11 ml, 0.79 mmol) in N,N-dimethylformamide (1.5 ml) in air at 15° C. The reaction mixture was stirred at 15° C. overnight. Water (30 ml) was added and the reaction mixture extracted with ethyl acetate (30 ml×3). The organic phases were dried with Na$_2$SO$_4$ and concentrated. The residue was purified by pre-HPLC (instrument: Gilson-281, Column: WATERS XBRIDGE 30-100 MM 5 UM, Mobile Phase: A: 0.04% NH$_3$H$_2$O B: CH$_3$CN, Flow rate: 30.0 ml/L, Gradient: 0-10 min, B=30-38% RT=P1: 7.0 min; P2: 9.5 min) to yield the title compound as a white solid. 20 mg.

$^1$HNMR (400 MHz, DMSO-d6): 10.82 (s, 1H), 8.57-8.63 (m, 3H), 8.35-8.36 (m, 1H), 8.27-8.29 (m, 1H), 7.95-7.97 (m, 1H), 7.70-7.71 (m, 2H), 7.53-7.55 (m, 2H), 7.32-7.41 (m, 5H), 5.54 (s, 2H), 4.65 (s, 2H).

MS (electrospray): m/z [M+H]$^+$=412

Example 56

N-[4-(Hydroxymethyl)-3-pyridinyl]-2-[(phenylmethyl)oxy]-5-(4-pyridinyl)benzamide (E56)

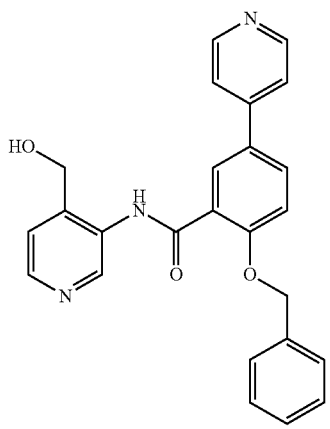 [SMILES: O=C(Nc1cnccc1CO)c1cc(-c2ccncc2)ccc1OCc1ccccc1]

Neat (3-aminopyridin-4-yl)methanol (may be prepared as described in Description 81; 103 mg, 0.83 mmol) was added in one charge to a stirred suspension of 2-[(phenylmethyl)oxy]-5-(4-pyridinyl)benzoic acid (may be prepared as described in Description 79; 180 mg, 0.59 mmol), EDC (226 mg, 1.18 mmol), HOBT (181 mg, 1.179 mmol) and triethylamine (0.16 ml, 1.18 mmol) in N,N-dimethylformamide (1.5 ml) in air at 15° C. The reaction mixture was stirred at 15° C. overnight. 100 ml of water was added. The solid was filtered, and then purified by prep-HPLC (instrument: Gilson-281, Column: Shimadzu 15 um: 250*20 mm*2, Mobile Phase: A: 10 mMol/LNH$_4$HCO$_3$, B: CH$_3$CN, Flow rate: 30.0 ml/L, Gradient: B: 43-55% in 0-7.2 RT=7.5 min, 10.5) to yield the title compound as a white solid. 57 mg.

$^1$H NMR (400 MHz, DMSO-d6): 10.29 (s, 1H), 8.90-8.92 (m, 2H), 8.62-8.63 (m, 2H), 8.39-8.40 (m, 1H), 8.24-8.25 (m, 1H), 7.96-7.99 (m, 1H), 7.73-7.75 (m, 2H), 7.53-7.55 (m, 2H), 7.47-7.48 (m, 1H), 7.33-7.42 (m, 4H), 5.56 (t, 1H, J=5.2), 5.46 (s, 2H), 4.53 (d, 2H, J=5.2).

MS (electrospray): m/z [M+H]$^+$=412.0

Example 57

5-Bromo-2-{[(3-fluorophenyl)methyl]oxy}-N-3-pyridinyl benzamide (E57)

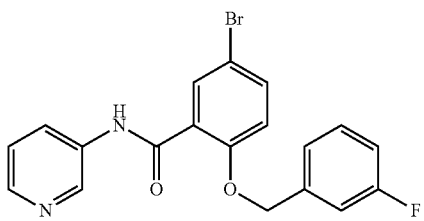 [SMILES: O=C(Nc1cccnc1)c1cc(Br)ccc1OCc1cccc(F)c1]

Neat pyridin-3-amine (116 mg, 1.23 mmol) was added in one charge to a stirred suspension of 5-bromo-2-{[(3-fluorophenyl)methyl]oxy}benzoic acid (may be prepared as described in Description 83; 200 mg, 0.62 mmol), EDC (354 mg, 1.85 mmol), HOBT (283 mg, 1.85 mmol) and triethylamine (0.26 ml, 1.85 mmol) in N,N-dimethylformamide (6 ml) in air at room temperature. The reaction mixture was stirred at 25° C. overnight. Water (25 ml) was added, and the mixture was extracted with ethyl acetate (20 ml×3). The organic phase was washed with saturated brine (10 ml), water (25 ml), dried over sodium sulfate, and evaporated in vacuo. The residue was purified with Prep-TLC (elute: dichloromethane:methanol=25:1) to obtain crude product which was washed with methanol (4 ml) to yield the title compound as a white solid. 33 mg.

HNMR (400 MHz, DMSO-d6): 9.85 (brs, 1H), 8.45 (d, 1H, J=2.4), 8.35 (brs, 1H), 8.15-8.18 (m, 2H), 7.65 (dd, 1H, J=2.4, J=8.8), 7.49-7.54 (m, 1H), 7.34-7.35 (m, 1H), 7.20-7.28 (m, 3H), 7.04 (d, 1H, J=8.8), 5.24 (s, 2H).

MS (electrospray): m/z [M+H]$^+$=401.0, 403.0

Example 58

5-Bromo-2-{[(2-fluorophenyl)methyl]oxy}-N-3-pyridinylbenzamide (E58)

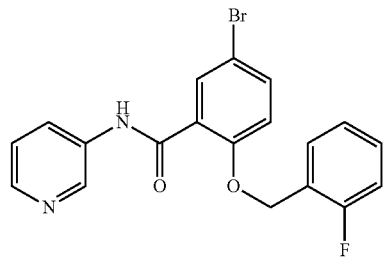 [SMILES: O=C(Nc1cccnc1)c1cc(Br)ccc1OCc1ccccc1F]

Neat pyridin-3-amine (82 mg, 0.87 mmol) was added in one charge to a stirred solution of 5-bromo-2-{[(2-fluorophenyl)methyl]oxy}benzoic acid (may be prepared as described in Description 85; 200 mg, 0.58 mmol), EDC (223 mg, 1.16 mmol) and HOBT (178 mg, 1.16 mmol) in dimethylformamide (3 ml) in air at room temperature. The reaction mixture was stirred at 25° C. overnight. Water (25 ml) was added into the reaction mixture. The precipitate was filtered, washed with water (15 ml), and dried in vacuum to obtain crude product, which was purified with Prep-TLC (eluate: dichloromethane:methanol=25:1) to yield the title compound as a white solid. 67 mg.

$^1$HNMR (400 MHz, CDCl$_3$): 9.85 (s, 1H), 8.42 (t, 1H, J=2.4), 8.31 (s, 1H), 8.23 (d, 1H, J=8.4), 8.06 (s, 1H), 7.64 (m, 1H), 7.51 (m, 2H), 7.26 (m, 3H), 7.08 (dd, 1H, J=2, J=8.4), 5.32 (s, 2H).

MS (electrospray): m/z [M+H]$^+$ 4 00.9

Example 59

5-Bromo-2-{[(4-fluorophenyl)methyl]oxy}-N-3-pyridinylbenzamide (E59)

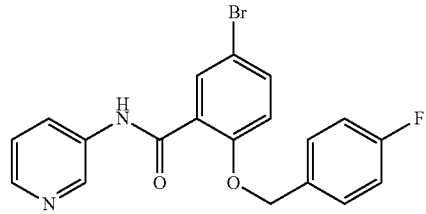 [SMILES: O=C(Nc1cccnc1)c1cc(Br)ccc1OCc1ccc(F)cc1]

Neat pyridin-3-amine (79 mg, 0.84 mmol) was added in one charge to a stirred solution of 5-bromo-2-{[(4-fluorophenyl)methyl]oxy}benzoic acid (may be prepared as described in Description 87; 200 mg, 0.56 mmol), EDC (213 mg, 1.11 mmol) and HOBT (170 mg, 1.11 mmol) in DMF (3 ml) at room temperature. The reaction mixture was stirred at 25° C. overnight. Water (25 ml) was added and the solid was filtered, washed with water (15 ml), and dried in vacuo. The residue was further purified with Prep-TLC (eluate: dichloromethane:methanol=25:1) to yield the title compound as a white solid. 76 mg.

$^1$HNMR (400 MHz, CDCl3): 9.89 (s, 1H), 8.45 (d, 1H, J=2.4), 8.33 (d, 1H, J=2.0), 8.15 (s, 1H), 8.09 (d, 1H, J=8.0), 7.64 (dd, 1H, J=2.4, 8.4), 7.54 (dd, 2H, J=5.2, 8.4), 7.27-7.20 (m, 3H), 7.05 (d, 1H, J=8.8), 5.22 (s, 2H).

MS (electrospray): m/z [M+H]$^+$=400.9

Method B

Diisopropylethylamine (1.34 ml, 7.69 mmol), 3-aminopyridine (0.43 g, 4.61 mmol) and HATU (2.19 g, 5.77 mmol) were added to a solution of 5-bromo-2-{[(4-fluorophenyl)methyl]oxy}benzoic acid (may be prepared as described in Description 87; 1.25 g, 3.84 mmol) in N,N-dimethylformamide (10 ml). The mixture was stirred for 2 hours. The solid was then filtered and washed with ethyl acetate to yield the title compound as a white solid. 650 mg.

MS (electrospray): m/z [M+H]$^+$=402/404

$^1$H NMR (DMSO-d$_6$): 5.22 (2H, s), 7.10-7.31 (3H, m), 7.37 (1H, dd, J=8.33, 4.82 Hz), 7.55 (2H, dd, J=8.55, 5.70 Hz), 7.69 (1H, dd, J=8.77, 2.63 Hz), 7.77 (1H, d, J=2.63 Hz), 8.08 (1H, dt, J=8.33, 1.97 Hz), 8.29 (1H, dd, J=4.71, 1.43 Hz), 8.70 (1H, d, J=2.19 Hz), 10.40 (1H, s)

Example 60

5-Bromo-2-{[(3,4-difluorophenyl)methyl]oxy}-N-3-pyridinylbenzamide (E60)

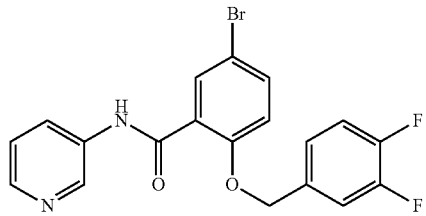 [SMILES: O=C(Nc1cccnc1)c1cc(Br)ccc1OCc1ccc(F)c(F)c1]

Method A

Neat pyridin-3-amine (105 mg, 1.11 mmol) was added in one charge to a stirred solution of 5-bromo-2-{[(3,4-difluorophenyl)methyl]oxy}benzoic acid (may be prepared as described in Description 89; 300 mg, 0.74 mmol), EDC (284 mg, 1.48 mmol), HOBT (227 mg, 1.48 mmol) in dimethylformamide (3 ml) in air at room temperature. The reaction mixture was stirred at 25° C. overnight. Water (50 ml) was added into reaction mixture. The precipitate was filtered, washed with water (15 ml), and dried in vacuo. The residue was washed with methanol/chloromethane (50:1, 8 ml), and dried in vacuo to yield the title compound as a white solid. 248 mg.

$^1$HNMR (400 MHz, CDCl3): 9.75 (s, 1H), 8.44 (d, 1H, J=2.4), 8.35 (s, 1H), 8.25 (s, 1H), 8.13 (d, 1H, J=8.0), 7.63 (dd, 1H, J=2.4, 8.4), 7.39-7.26 (m, 4H), 7.01 (d, 1H, J=8.8), 5.21 (s, 2H).

LCMS: MH+=419

Method B

3-Pyridinamine (0.28 g, 2.94 mmol), HATU (2.22 g, 5.83 mmol) and diisopropylethylamine (1.63 ml, 8.74 mmol) were added to a solution of 5-bromo-2-{[(3,4-difluorophenyl)methyl]oxy}benzoic acid (may be prepared as described in Description 89; 1 g, 2.91 mmol) in N,N-dimethylformamide (25 ml). The mixture was stirred at room temperature for 2 hours. The mixture was diluted with ethyl acetate (200 ml), shaken and allowed to stand for 5 min. The solid precipitate was filtered, washed with water (25 ml) and ethyl acetate (50 ml), and dried under vacuum to give a white solid. 380 mg.

MS (electrospray): m/z [M+H]$^+$=420

Example 61

N-(3-Methyl-4-isoxazolyl)-2-[(phenylmethyl)oxy]-5-(4-pyridinyl)benzamide (E61)

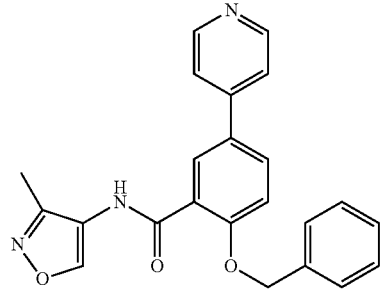 [SMILES: Cc1nocc1NC(=O)c1cc(-c2ccncc2)ccc1OCc1ccccc1]

A mixture of 2-[(phenylmethyl)oxy]-5-(4-pyridinyl)benzoic acid (may be prepared as described in Description 79; 0.12 g, 0.36 mmol), EDC (0.14 g, 0.72 mmol) and HOBT (0.11 g, 0.72 mmol) in N,N-dimethylformamide (2 ml) was stirred in air at room temperature for 1 h, then 3-methyl-4-isoxazolamine (may be prepared as described in Description 91; 100 mg, 1.02 mmol) was added in one charge. The reaction mixture was stirred at 25° C. overnight. The reaction mixture was diluted with water (25 ml). The solid was filtered, washed with water (30 ml) and methanol (5 ml×2), and dried in vacuo to yield the title compound as a grey solid. 72 mg.

$^1$HNMR (400 MHz, DMSO-d6): 9.97 (s, 1H), 9.19 (s, 1H), 8.63 (d, 2H, J=6.0), 8.18 (d, 1H, J=2.4), 8.04 (dd, 1H, J=2.4, J=8.8), 7.75 (d, 2H, J=6.0), 7.56 (d, 2H, J=6.8), 7.49-7.38 (m, 4H), 5.34 (s, 2H), 1.95 (s, 3H).

MS (electrospray): m/z [M+H]$^+$=386.00

Example 62

N-(5-Methyl-4-isoxazolyl)-2-[(phenylmethyl)oxy]-5-(4-pyridinyl)benzamide (E62)

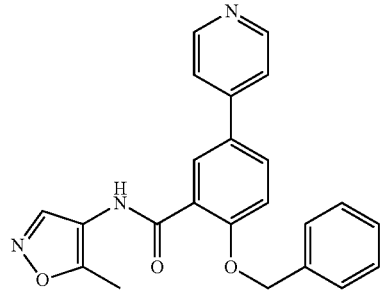 [SMILES: Cc1oncc1NC(=O)c1cc(-c2ccncc2)ccc1OCc1ccccc1]

A mixture of 2-[(phenylmethyl)oxy]-5-(4-pyridinyl)benzoic acid (may be prepared as described in Description 79; 100 mg, 0.30 mmol), EDC (115 mg, 0.60 mmol), and HOBT (92 mg, 0.60 mmol) in dimethylformamide (2 ml) was stirred in air at room temperature for 1 h, then 5-methyl-4-isoxazolamine (may be prepared as described in Description 93; 100 mg, 1.02 mmol) was added in one charge. The reaction mixture was stirred at 25° C. overnight. The solution was heated at 35° C. for 7 hours, then diluted with water (30 ml) and extracted with ethyl acetate (80 ml×3). The organic phase was washed with brine (60 ml×2), dried over anhydrous MgSO$_4$, and concentrated. The residue was purified by chromatography (silica gel, 20 g, eluent: dichloromethane/methanol=60:1, 600 ml). The crude product was washed with methanol (2 ml×2), filtered, and dried in vacuum to yield the title compound. 23 mg.

¹HNMR (400 MHz, DMSO-d6): 9.95 (s, 1H), 8.82 (s, 1H), 8.62 (d, 2H, J=6.4), 8.10 (d, 1H, J=2.4), 8.00 (dd, 1H, J=2.0, J=8.4), 7.74 (dd, 2H, J=1.2, 4.8), 7.54 (d, 2H, J=7.2), 7.44-7.34 (m, 4H), 5.33 (s, 2H), 2.22 (s, 3H).
MS (electrospray): m/z [M+H]⁺=386.1

Example 63

N-4-Isoxazolyl-2-[(phenylmethyl)oxy]-5-(4-pyridinyl)benzamide (E63)

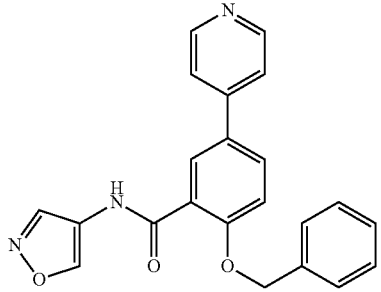 [SMILES: O=C(Nc1cnoc1)c1cc(-c2ccncc2)ccc1OCc1ccccc1]

A mixture of 2-[(phenylmethyl)oxy]-5-(4-pyridinyl)benzoic acid (may be prepared as described in Description 79; 100 mg, 0.30 mmol), EDC (172 mg, 0.90 mmol) and HOBT (137 mg, 0.90 mmol) in dimethylformamide (3 ml) was stirred in air at room temperature for 1 h, then 4-isoxazolamine (may be prepared as described in Description 95; 100 mg, 1.189 mmol) was added in one charge. The reaction mixture was stirred at room temperature overnight. The reaction mixture was diluted with water (30 ml). The solid was filtered and dried in vacuo to obtain crude product, which was purified with Prep-HPLC (Waters, X-Bridge, 5 μm; 30×100 mm; A=0.05% NH₃.H₂O/water, B: MeCN; v=30 ml/min; 0-7 min, 42%-54%; 7-12 min, 95%; t=8.0 min.) to yield the title compound as a white solid. 34 mg.
¹HNMR (400 MHz, DMSO-d6): 10.60 (s, 1H), 9.27 (s, 1H), 8.65 (s, 1H), 8.62 (d, 2H, J=5.6), 8.08 (d, 1H, J=2.0), 7.98 (dd, 1H, J=2.0, 8.4), 7.74 (d, 2H, J=5.6), 7.52 (d, 2H, J=7.6), 7.42-7.33 (m, 4H), 5.36 (s, 2H).
MS (electrospray): m/z [M+H]⁺=372.1

Example 64

2-[(Phenylmethyl)oxy]-N-1H-pyrazol-4-yl-5-(4-pyridinyl)benzamide (E64)

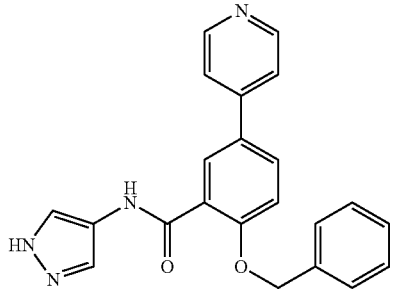 [SMILES: O=C(Nc1cn[nH]c1)c1cc(-c2ccncc2)ccc1OCc1ccccc1]

Neat 1H-pyrazol-4-amine (49.0 mg, 0.59 mmol) was added in one charge to a stirred solution of 2-[(phenylmethyl)oxy]-5-(4-pyridinyl)benzoic acid (may be prepared as described in Description 79; 150 mg, 0.49 mmol), EDC (283 mg, 1.47 mmol) and HOBT (226 mg, 1.47 mmol) in dimethylformamide (4 ml) in air at room temperature. The reaction mixture was stirred at room temperature overnight. 30 ml water was added, and the mixture was extracted with ethyl acetate (70 ml×2). The organic layers were combined, dried over MgSO₄, and concentrated in vacuo. The residue was further purified by pre-HPLC (Gilson GX-281; Shimadzu 15 μm 250*20 mm; A: 10 mMol NH₄HCO₃/Water; B: CH₃CN) to yield the title compound as a white solid. 50 mg.
¹HNMR (400 MHz, DMSO-d6): 5.34 (s, 2H), 7.34-7.44 (m, 4H), 7.55 (d, 2H), 7.74 (d, 4H), 7.95-7.98 (m, 1H), 8.09 (d, 1H), 8.62 (d, 2H), 10.25 (s, 1H), 12.65 (s, 1H).
MS (electrospray): m/z [M+H]⁺=371

Example 65

N-(1-Methyl-1H-pyrazol-4-yl)-2-[(phenylmethyl)oxy]-5-(4-pyridinyl)benzamide (E65)

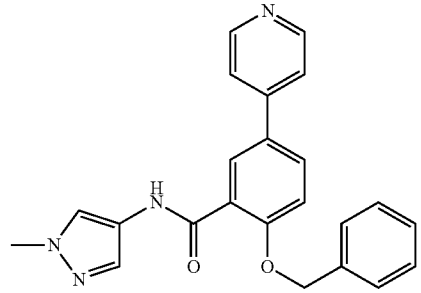 [SMILES: Cn1cc(NC(=O)c2cc(-c3ccncc3)ccc2OCc2ccccc2)cn1]

Neat 1-methyl-1H-pyrazol-4-amine (38.2 mg, 0.39 mmol) was added in one charge to a stirred solution of 2-[(phenylmethyl)oxy]-5-(4-pyridinyl)benzoic acid (may be prepared as described in Description 79; 100 mg, 0.33 mmol), EDC (188 mg, 0.98 mmol) and HOBT (150 mg, 0.983 mmol) in dimethylformamide (3 ml) in air at room temperature. The reaction mixture was stirred at room temperature overnight. Water (20 ml) was added, and the mixture was extracted with ethyl acetate (20 ml×2). The organic phase was dried over Na₂SO₄, and concentrated in vacuo to give crude product, which was purified by prep-HPLC (Gilson GX-281; waters X-Bridge 5 μm 30*100 mm; A: 0.1M NH₃.H₂O/Water; B: CH₃CN) twice to yield the title compound as a white solid. 58 mg.
¹HNMR (400 MHz, DMSO-d₆): 3.82 (s, 3H), 5.33 (s, 2H), 7.35-7.43 (m, 5H), 7.54 (d, 2H), 7.73 (d, 2H), 7.95-7.97 (m, 1H), 8.00 (s, 1H), 8.06 (d, 1H), 8.62 (d, 2H), 10.25 (s, 1H).
LCMS: MH+=385

Example 66

5-Formyl-2-[(phenylmethyl)oxy]-N-3-pyridinylbenzamide (E66)

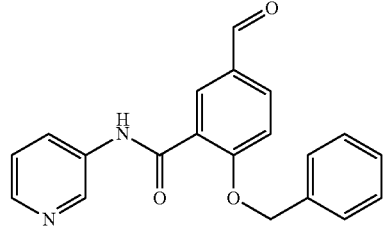 [SMILES: O=Cc1ccc(OCc2ccccc2)c(C(=O)Nc2cccnc2)c1]

Diisopropylethylamine (0.95 ml, 5.46 mmol), 3-aminopyridine (514 mg, 5.46 mmol) and HATU (1.56 g, 4.1 mmol)

were added to a solution of 5-formyl-2-[(phenylmethyl)oxy]benzoic acid (may be prepared as described in Description 97; 770 mg, 2.73 mmol) in dimethylformamide (10 ml). The solution was stirred for 72 hours. Ethyl acetate (40 ml) and H$_2$O (40 ml) were added and the organic layer was washed with H$_2$O (3×20 ml), dried and the solvent removed in vacuo to give a solid. The solid was purified by column chromatography (ethyl acetate) to yield the title compound as a white solid (300 mg).

MS (electrospray): m/z [M+H]$^+$=333

$^1$H NMR (DMSO-d$_6$): 5.37 (2H, s), 7.27-7.44 (4H, m), 7.47-7.61 (3H, m), 8.01-8.14 (2H, m), 8.18 (1H, d, J=1.97 Hz), 8.30 (1H, dd, J=4.71, 1.43 Hz), 8.72 (1H, d, J=2.41 Hz), 9.97 (1H, s), 10.47 (1H, s)

Example 67

5-[(E/Z)-(Hydroxyimino)methyl]-2-[(phenylmethyl)oxy]-N-3-pyridinylbenzamide (E67)

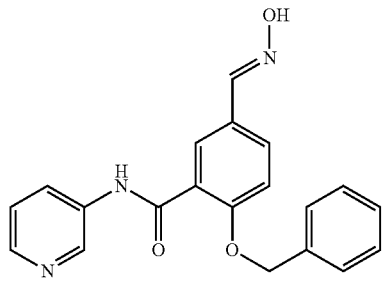 [SMILES: O=C(Nc1cccnc1)c1cc(/C=N/O)ccc1OCc1ccccc1]

Pyridine (0.24 ml, 3.01 mmol) and hydroxylamine hydrochloride (42 mg, 0.60 mmol) were added to a solution of 5-formyl-2-[(phenylmethyl)oxy]-N-3-pyridinylbenzamide (may be prepared as described in Example 66; 100 mg, 0.301 mmol) in methanol (5 ml). A solid came out of solution within 5 minutes and the mixture was stirred for a further 10 minutes. The solid was filtered and washed with methanol (1 ml) and water (1 ml) to yield the title compound as an off-white solid. 80 mg.

MS (electrospray): m/z [M+H]$^+$=348

$^1$H NMR (DMSO-d$_6$): 5.20-5.35 (2H, m), 7.25-7.44 (5H, m), 7.48-7.61 (2H, m), 7.74 (1H, dd, J=8.66, 2.08 Hz), 7.89 (1H, d, J=1.97 Hz), 8.03-8.20 (2H, m), 8.28 (1H, dd, J=4.71, 1.42 Hz), 8.69 (1H, d, J=2.41 Hz), 10.41 (1H, s), 11.15 (1H, s)

Example 68

Ethyl (2Z)-3-{4-[(phenylmethyl)oxy]-3-[(3-pyridinylamino)carbonyl]phenyl}-2-propenoate (E68)

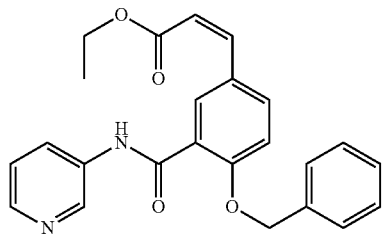 [SMILES: CCOC(=O)/C=C\c1ccc(OCc2ccccc2)c(C(=O)Nc2cccnc2)c1]

0.5N KHMDS (1.81 ml, 0.90 mmol) was added to a solution of triethyl phosphonoacetate (0.20 g, 0.90 mmol) in tetrahydrofuran (5 ml) at −78° C. The solution was stirred at −78° C. for 15 minutes, then a suspension of 5-formyl-2-[(phenylmethyl)oxy]-N-3-pyridinylbenzamide (may be prepared as described in Example 66; 200 mg, 0.60 mmol) in tetrahydrofuran (10 ml) was added dropwise over 3 minutes. The mixture was stirred at −78° C. for 15 minutes. It was then allowed to warm to room temperature and stirred for a further hour. The reaction was quenched with saturated NH$_4$Cl (10 ml) and extracted with ethyl acetate (2×10 ml). The combined organic layers were dried (MgSO$_4$) and the solvent removed in vacuo to give a brown solid. Trituration with 2:1 ethyl acetate/hexane yielded the title compound as a brown solid. 160 mg.

MS (electrospray): m/z [M+H]$^+$=403

$^1$H NMR (DMSO-d$_6$): 1.26 (3H, t, J=7.13 Hz), 4.18 (2H, q, J=7.16 Hz), 5.29 (2H, s), 6.61 (1H, d, J=16.00 Hz), 7.27-7.42 (5H, m), 7.51 (2H, d, J=6.58 Hz), 7.67 (1H, d, J=16.00 Hz), 7.90 (1H, dd, J=8.66, 2.30 Hz), 7.98 (1H, d, J=2.19 Hz), 8.12 (1H, dt, J=8.28, 1.89 Hz), 8.29 (1H, dd, J=4.71, 1.43 Hz), 8.74 (1H, d, J=2.19 Hz), 10.45 (1H, s)

Example 69

5-(4-Morpholinylmethyl)-2-[(phenylmethyl)oxy]-N-3-pyridinylbenzamide (E69)

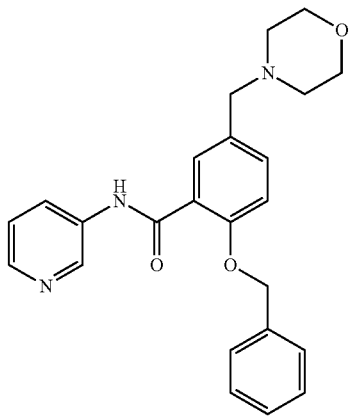 [SMILES: O=C(Nc1cccnc1)c1cc(CN2CCOCC2)ccc1OCc1ccccc1]

Morpholine (26 uL, 0.30 mmol) and acetic acid (17 ul, 0.30 mmol) were added to a solution of 5-formyl-2-[(phenylmethyl)oxy]-N-3-pyridinylbenzamide (may be prepared as described in Example 66; 100 mg, 0.301 mmol) in DCE (5 ml). The solution was stirred for 4 hours at 50° C. then sodium triacetoxyborohydride (96 mg, 0.45 mmol) was added. The reaction was stirred overnight. Saturated NaHCO$_3$ solution (5 ml) was added and the mixture stirred for 5 minutes. The organic layer was then diluted with dichloromethane (5 ml) before being separated and dried (MgSO$_4$). The solvent was removed in vacuo and the residue purified by MDAP to yield the title compound. 40 mg.

MS (electrospray): m/z [M+H]$^+$=418

$^1$H NMR (DMSO-d$_6$): 2.26-2.42 (4H, m), 3.34 (2H, br. s.), 3.57 (4H, t, J=4.38 Hz), 5.24 (2H, s), 7.20-7.49 (6H, m), 7.51-7.57 (2H, m), 7.63 (1H, d, J=1.97 Hz), 8.08 (1H, dd, J=8.33, 1.53 Hz), 8.27 (1H, dd, J=4.60, 1.53 Hz), 8.65 (1H, d, J=2.41 Hz), 10.33 (1H, s)

Example 70

2-[(Phenylmethyl)oxy]-N-3-pyridinyl-5-(1-pyrrolidinylmethyl)benzamide (E70)

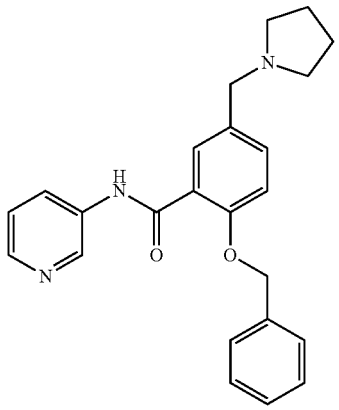 [SMILES: O=C(Nc1cccnc1)c1cc(CN2CCCC2)ccc1OCc1ccccc1]

Pyrrolidine (25 uL, 0.30 mmol) and acetic acid (17 uL, 0.30 mmol) were added to a solution of 5-formyl-2-[(phenylmethyl)oxy]-N-3-pyridinylbenzamide (may be prepared as described in Example 66; 100 mg, 0.30 mmol) in DCE (5 ml). The solution was stirred for 4 hours at 50° C. then sodium triacetoxyborohydride (96 mg, 0.45 mmol) was added. The reaction was stirred overnight then quenched with NaHCO₃ solution (7 ml) and extracted with dichloromethane (5 ml). The organic layer was dried (MgSO₄) and the solvent removed in vacuo to give a yellow solid. The residue purified by MDAP to yield the title compound as an opaque solid. 34 mg.

MS (electrospray): m/z [M+H]$^+$=388
$^1$H NMR (DMSO-d$_6$): 1.71 (4H, br. s.), 3.44 (6H, br. s.), 5.24 (2H, s), 7.18-7.42 (4H, m), 7.46 (1H, dd, J=8.44, 2.08 Hz), 7.54 (2H, d, J=6.36 Hz), 7.64 (1H, d, J=1.97 Hz), 8.03-8.12 (1H, m), 8.17-8.30 (2H, m), 8.65 (1H, d, J=2.19 Hz), 10.33 (1H, s)

Example 71

5-[(Dimethylamino)methyl]-2-[(phenylmethyl)oxy]-N-3-pyridinylbenzamide (E71)

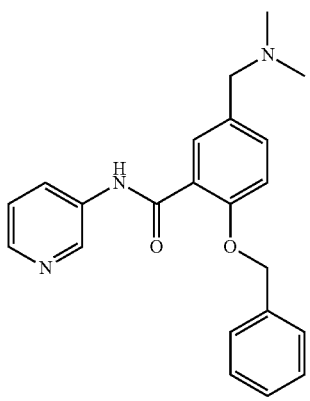 [SMILES: CN(C)Cc1ccc(OCc2ccccc2)c(C(=O)Nc2cccnc2)c1]

Dimethylamine (60 uL, 0.33 mmol) and acetic acid (19 uL, 0.33 mmol) were added to a solution of 5-formyl-2-[(phenylmethyl)oxy]-N-3-pyridinylbenzamide (may be prepared as described in Example 66; 100 mg, 0.33 mmol) in DCE (5 ml). The solution was stirred for 3 hours at 50° C. then sodium triacetoxyborohydride (105 mg, 0.50 mmol) was added. The mixture was stirred overnight. Saturated NaHCO₃ solution (5 ml) was then added and the mixture was stirred for 5 minutes. The organic layer was diluted with dichloromethane (5 ml), separated and dried (MgSO₄). The solvent was removed in vacuo and the residue purified by MDAP to yield the title compound as an opaque solid. 17 mg.

MS (electrospray): m/z [M+H]$^+$=362
$^1$H NMR (DMSO-d$_6$): 2.15 (6H, s), 3.50 (2H, br. s.), 5.24 (2H, s), 7.16-7.47 (6H, m), 7.50-7.66 (3H, m), 8.02-8.14 (1H, m), 8.27 (1H, dd, J=4.82, 1.32 Hz), 8.65 (1H, d, J=2.19 Hz), 10.33 (1H, s)

Example 72

5-Acetyl-2-[(phenylmethyl)oxy]-N-3-pyridinylbenzamide (E72)

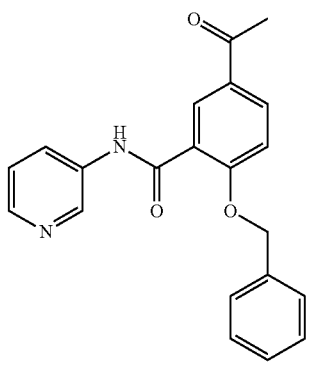 [SMILES: CC(=O)c1ccc(OCc2ccccc2)c(C(=O)Nc2cccnc2)c1]

Diisopropylethylamine (0.97 ml, 5.55 mmol), 3-aminopyridine (418 mg, 4.44 mmol) and HATU (1.27 g, 3.33 mmol) were added to a solution of 5-acetyl-2-[(phenylmethyl)oxy]benzoic acid (commercially available from Acros; 600 mg, 2.22 mmol) in dimethylformamide (10 ml). The solution was stirred for 2 hours. Ethyl acetate (40 ml) and H₂O (40 ml) were added and the organic layer washed with H₂O (3×20 ml), dried and the solvent removed in vacuo to give a solid. Trituration with 3:1 hexane/ethyl acetate yielded the title compound as a yellow solid. 541 mg.

MS (electrospray): m/z [M+H]$^+$=347
$^1$H NMR (DMSO-d$_5$): 2.58 (3H, s), 5.35 (2H, s), 7.28-7.46 (5H, m), 7.53 (2H, d, J=6.36 Hz), 8.06-8.18 (2H, m), 8.22 (1H, d, J=2.41 Hz), 8.29 (1H, dd, J=4.60, 1.32 Hz), 8.73 (1H, d, J=2.41 Hz), 10.46 (1H, s)

Example 73

5-(1-Methyl-1H-pyrazol-4-yl)-2-[(phenylmethyl)oxy]-N-4-pyridazinylbenzamide (E73)

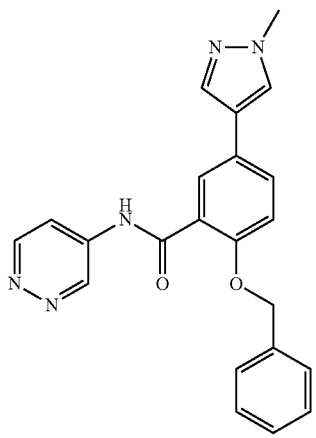 [SMILES: Cn1cc(-c2ccc(OCc3ccccc3)c(C(=O)Nc3ccnnc3)c2)cn1]

1-Methyl-4-(4,4,5,5-tetramethyl-1,3,2-dioxaborolan-2-yl)-1H-pyrazole (56.9 mg, 0.273 mmol), 1M Na$_2$CO$_3$ (0.52 ml, 0.52 mmol) and tetrakis(triphenylphosphine)palladium (0) (18 mg, 6 mol %) were added to a solution of 5-bromo-2-[(phenylmethyl)oxy]-N-4-pyridazinylbenzamide (may be prepared as described in Example 6; 100 mg, 0.26 mmol) in 1,2-dimethoxyethane (3 ml). The solution was heated at 140° C. in microwave for 35 minutes. The solvent was removed in vacuo to give a residue. Trituration with 1:1 dimethyl sulfoxide/methanol (0.6 ml) gave the product as a solid which was washed with methanol (2 ml) and ethyl acetate (5 ml) to yield the title compound as a grey solid. 45 mg.

MS (electrospray): m/z [M+H]$^+$=386

$^1$H NMR (DMSO-d$_6$): 3.85 (3H, s), 5.24 (2H, s), 7.21-7.41 (4H, m), 7.50 (2H, d, J=6.58 Hz), 7.71 (1H, dd, J=8.55, 1.97 Hz), 7.79 (1H, d, J=1.97 Hz), 7.86 (1H, s), 8.02 (1H, dd, J=5.81, 2.74 Hz), 8.14 (1H, s), 9.02 (1H, d, J=5.70 Hz), 9.22 (1H, br. s.), 10.84 (1H, br. s.)

Example 74

2-[(Phenylmethyl)oxy]-N-4-pyridazinyl-5-(4-pyridinyl)benzamide (E74)

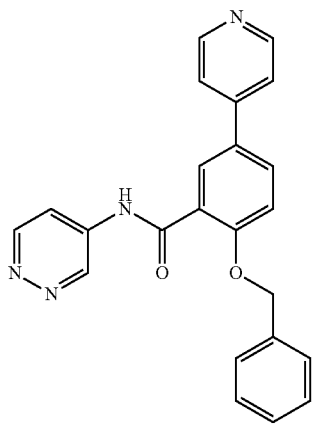 [SMILES: O=C(Nc1ccnnc1)c1cc(-c2ccncc2)ccc1OCc1ccccc1]

Pyridine 4-boronic acid (35.2 mg, 0.29 mmol), 1M Na$_2$CO$_3$ (0.52 ml, 0.52 mmol) and tetrakis(triphenylphosphine)palladium(0) (18 mg, 6 mol %) were added to a solution of 5-bromo-2-[(phenylmethyl)oxy]-N-4-pyridazinylbenzamide (may be prepared as described in Example 6; 100 mg, 0.26 mmol) in 1,2-dimethoxyethane (3 ml). The solution was heated at 140° C. in microwave for 25 minutes. The solvent was removed in vacuo and the residue purified by MDAP to yield the title compound as an off white solid. 22 mg.

MS (electrospray): m/z [m+H]$^+$=383

$^1$H NMR (DMSO-d$_6$): 5.32 (2H, s), 7.22-7.58 (6H, m), 7.70-7.82 (2H, m), 7.97-8.16 (3H, m), 8.56-8.69 (2H, m), 9.02-9.14 (1H, m), 9.29 (1H, d, J=1.97 Hz), 10.93 (1H, s)

Example 75

5-(1-Hydroxyethyl)-2-[(phenylmethyl)oxy]-N-3-pyridinylbenzamide (E75)

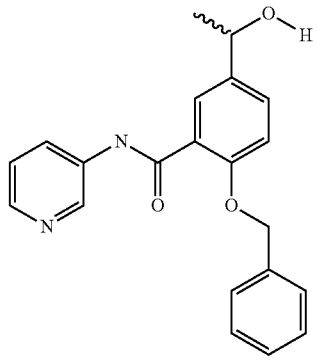 [SMILES: CC(O)c1ccc(OCc2ccccc2)c(C(=O)Nc2cccnc2)c1]

Sodium borohydride (32.8 mg, 0.87 mmol) and boric acid (53.6 mg, 0.87 mmol) were added to a suspension of 5-acetyl-2-[(phenylmethyl)oxy]-N-3-pyridinylbenzamide (may be prepared as described in Example 72; 100 mg, 0.29 mmol) in ethanol (5 ml). The mixture was stirred for one hour and then it was quenched using saturated NaHCO$_3$ solution (5 ml). The mixture was extracted with dichloromethane (3×5 ml). The organic layers were dried (MgSO$_4$) and the solvent removed in vacuo. The residue was purified by MDAP to yield the title compound as a golden solid. 62 mg.

MS (electrospray): m/z [M+H]$^+$=349

$^1$H NMR (DMSO-d$_6$): 1.33 (3H, d, J=6.58 Hz), 4.74 (1H, dd, J=6.14, 4.60 Hz), 5.20 (1H, d, J=4.38 Hz), 5.24 (2H, s), 7.25 (1H, d, J=8.55 Hz), 7.30-7.42 (4H, m), 7.43-7.59 (3H, m), 7.68 (1H, d, J=1.97 Hz), 8.02-8.15 (1H, m), 8.27 (1H, dd, J=4.82, 1.32 Hz), 8.66 (1H, d, J=2.41 Hz), 10.34 (1H, s)

Example 76

5-(1-Hydroxy-1-methylethyl)-2-[(phenylmethyl)oxy]-N-3-pyridinylbenzamide (E76)

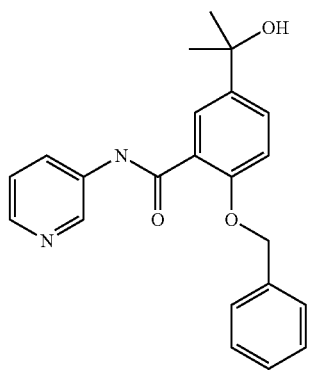 [SMILES: CC(C)(O)c1ccc(OCc2ccccc2)c(C(=O)Nc2cccnc2)c1]

3M Methylmagnesium bromide (0.10 ml, 0.29 mmol) was added to a solution of 5-acetyl-2-[(phenylmethyl)oxy]-N-3-pyridinylbenzamide (may be prepared as described in Example 72; 100 mg, 0.29 mmol) in tetrahydrofuran (3 ml) at 0° C. The solution was stirred for 45 minutes. Another 3 equivalents of 3M methylmagnesium bromide (300 ul) were added at 0° C. and solution was stirred for 18 hours. 1N H$_2$SO$_4$ (5 ml) was then added, the mixture was stirred for 3 minutes, then ethyl acetate (10 ml) was added. The acid layer was basified to pH 9 using saturated NaHCO$_3$ solution. The organic layer was washed with saturated NaHCO$_3$ solution (5 ml), dried (MgSO$_4$) and the solvent was removed in vacuo. The residue was purified by MDAP to give the title compound as a white solid. 61 mg.

MS (electrospray): m/z [M+H]$^+$=363

$^1$H NMR (DMSO-d$_6$): 1.43 (6H, s), 5.09 (1H, s), 5.24 (2H, s), 7.22 (1H, d, J=8.77 Hz), 7.28-7.43 (4H, m), 7.46-7.63 (3H, m), 7.79 (1H, d, J=2.19 Hz), 8.03-8.14 (1H, m), 8.27 (1H, dd, J=4.71, 1.42 Hz), 8.66 (1H, d, J=2.19 Hz), 10.34 (1H, s)

Example 77

5-Bromo-2-{[(4-fluorophenyl)methyl]oxy}-N-4-pyridazinylbenzamide (E77)

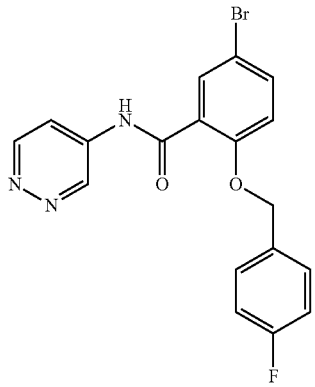 [SMILES: O=C(Nc1ccnnc1)c1cc(Br)ccc1OCc1ccc(F)cc1]

Diisopropylethylamine (1.61 ml, 9.23 mmol), 4-pyridazinamine (0.53 g, 5.54 mmol) and HATU (2.63 g, 6.92 mmol) were added to a solution of 5-bromo-2-{[(4-fluorophenyl) methyl]oxy}benzoic acid (may be prepared as described in Description 87; 1.5 g, 4.61 mmol) in N,N-dimethylformamide (10 ml). The mixture was stirred for 2 hours and the solid was filtered and washed with ethyl acetate to yield the title compound as a white solid. 658 mg.

MS (electrospray): m/z [M+H]$^+$=402/404

$^1$H NMR (DMSO-d$_6$): 5.21 (2H, s), 7.10-7.24 (2H, m), 7.27 (1H, d, J=8.99 Hz), 7.53 (2H, dd, J=8.66, 5.59 Hz), 7.67-7.82 (2H, m), 8.00 (1H, dd, J=5.92, 2.85 Hz), 9.07 (1H, d, J=5.92 Hz), 9.25 (1H, d, J=1.75 Hz), 10.85 (1H, s)

Example 78

5-Bromo-2-([(3,4-difluorophenyl)methyl]oxy)-N-4-pyridazinylbenzamide (E78)

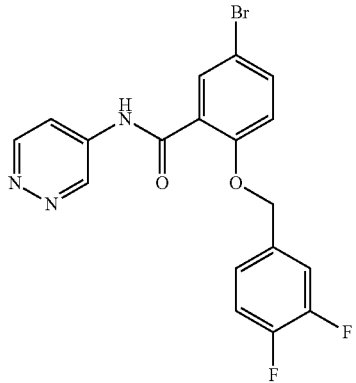 [SMILES: O=C(Nc1ccnnc1)c1cc(Br)ccc1OCc1ccc(F)c(F)c1]

4-Pyridazinamine (0.42 g, 4.37 mmol), HATU (2.22 g, 5.83 mmol) and diisopropylethylamine (1.53 ml, 8.74 mmol) were added to a solution of 5-bromo-2-{[(3,4-difluorophenyl)methyl]oxy}benzoic acid (may be prepared by Description 89; 1 g, 2.91 mmol) in N,N-dimethylformamide (25 ml). The mixture was stirred at room temperature for 2 hours. The mixture was diluted with ethyl acetate (200 ml), shaken and allowed to stand for 5 min. The precipitate was filtered, washed with water (25 ml) and ethyl acetate (50 ml), and dried under vacuum to yield the title compound as a white solid. No further purification was carried out. 900 mg.

MS (electrospray): m/z [M+H]$^+$=421

Example 79

2-{[(3,4-Difluorophenyl)methyl]oxy}-5-formyl-N-4-pyridazinylbenzamide (E79)

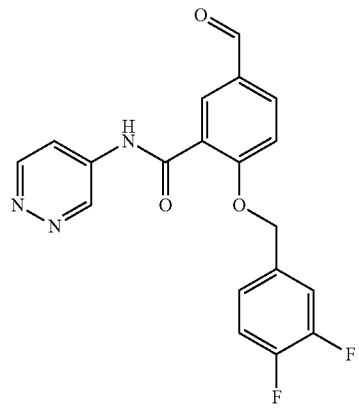 [SMILES: O=Cc1ccc(OCc2ccc(F)c(F)c2)c(C(=O)Nc2ccnnc2)c1]

EDC (0.79 g, 4.11 mmol), HOBT (0.84 g, 5.48 mmol), N-ethylmorpholine (0.87 mL, 6.84 mmol) and 4-pyridazinamine (0.49 g, 5.13 mmol) were added to a solution of 2-{[(3,4-difluorophenyl)methyl]oxy}-5-formylbenzoic acid (may be prepared by Description 101; 1 g, 3.42 mmol) in N,N-dimethylformamide (DMF; 25 ml) and the mixture was stirred at room temperature. The DMF was evaporated under reduced pressure and the residue was diluted with ethyl acetate (100 ml) and the organic layer washed with saturated sodium hydrogencarbonate (2×50 ml) and water (2×50 ml). The organic layer was dried (MgSO$_4$), filtered and evaporated under reduced pressure to yield the title compound as a dark yellow solid. 0.98 g.

MS (electrospray): m/z [M+H]; —370

Example 80

2-{[(3,4-Difluorophenyl)methyl]oxy}-5-formyl-N-3-pyridinylbenzamide (E80)

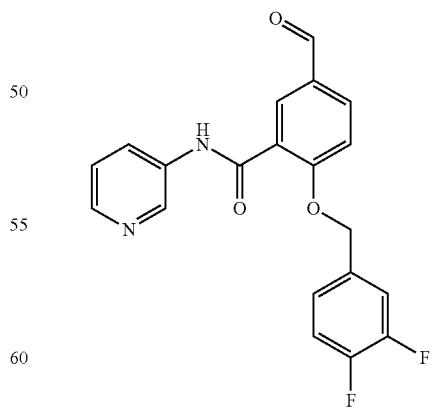

EDC (0.79 g, 4.11 mmol), HOBT (0.84 g, 5.48 mmol), N-ethylmorpholine (0.87 ml, 6.84 mmol) and 3-pyridinamine (0.48 g, 5.13 mmol) were added to a solution of 2-{[(3,4-difluorophenyl)methyl]oxy}-5-formylbenzoic acid (may be prepared as described in Description 101; 1 g, 3.42 mmol) in N,N-dimethylformamide (25 ml), and the mixture was stirred at room temperature. The N,N-dimethylformamide was evaporated under reduced pressure and the residue was diluted with ethyl acetate (100 ml). The organic layer was washed with saturated sodium hydrogencarbonate (2×50 ml) and water (2×50 ml). The organic layer was dried (MgSO$_4$), filtered and evaporated under reduced pressure to yield the title compound as a yellow solid. 1.19 g.

MS (electrospray): m/z [M+H]$^+$ 370

Example 81

5-Bromo-2-{[(2,4-difluorophenyl)methyl]oxy}-N-3-Pyridinylbenzamide (E81)

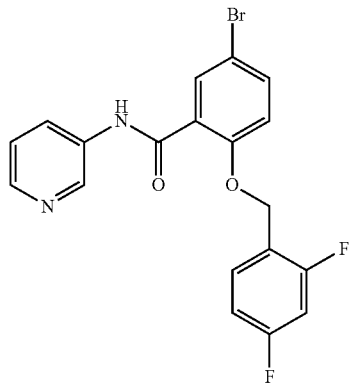 [SMILES: O=C(Nc1cccnc1)c1cc(Br)ccc1OCc1ccc(F)cc1F]

3-Pyridinamine (0.21 g, 2.19 mmol), EDC (0.34 g, 1.75 mmol), HOBT (0.36 g, 2.33 mmol) and N-ethylmorpholine (0.37 ml, 2.91 mmol) were added to a solution of 5-bromo-2-{[(2,4-difluorophenyl)methyl]oxy}benzoic acid (may be prepared by Description 103; 0.5 g, 1.46 mmol) in N,N-dimethylformamide (25 ml), and the mixture was stirred at room temperature for 4 hours. The N,N-dimethylformamide was removed on a buchi and the residue was diluted with ethyl acetate (50 ml) washed with saturated aqueous sodium hydrogencarbonate (1×25 ml) and water (1×25 ml) and dried (MgSO$_4$), filtered and evaporated to yield the title compound as a white solid. 0.6 g.

MS (electrospray): m/z [M+1-1]$^+$=420

Example 82

2-{[(4-Fluorophenyl)methyl]oxy}-5-formyl-N-3-pyridinylbenzamide (E82)

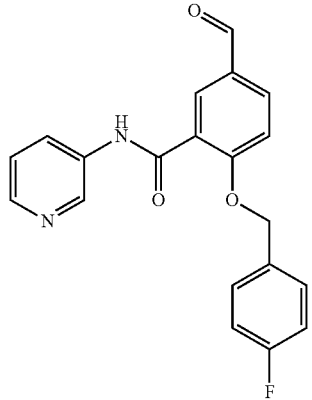 [SMILES: O=Cc1ccc(OCc2ccc(F)cc2)c(C(=O)Nc2cccnc2)c1]

3-Pyridinamine (0.52 g, 5.47 mmol), EDC (0.84 g, 4.38 mmol), HOBT (0.89 g, 5.83 mmol) and N-ethylmorpholine (0.92 ml, 7.29 mmol) were added to a solution of 2-{[(4-fluorophenyl)methyl]oxy}-5-formylbenzoic acid (may be prepared by Description 105; 1 g, 3.65 mmol) in N,N-dimethylformamide (25 ml), and the mixture was stirred at room temperature for 4 h. The N,N-dimethylformamide was evaporated on a buchi. Saturated aqueous sodium hydrogen carbonate (50 ml) and ethyl acetate (100 ml) were added to the residue and the mixture was stirred for 30 min. The organics were separated and washed with water (50 ml), dried (MgSO$_4$) and evaporated under reduced pressure to yield the title compound as a pale yellow solid. No further purification was carried out. 1.23 g.

MS (electrospray): m/z [M+H]$^+$ 351

Example 83

2-{[(4-Fluorophenyl)methyl]oxy}-5-[(Z)-(hydroxyimino)methyl]-N-3-pyridinylbenzamide (E83)

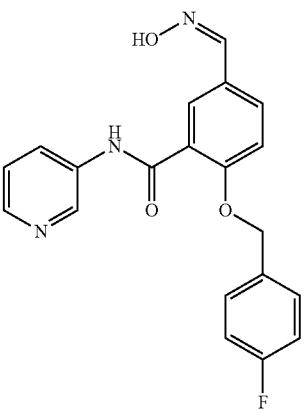 [SMILES: O=C(Nc1cccnc1)c1cc(/C=N\O)ccc1OCc1ccc(F)cc1]

Pyridine (0.69 ml, 8.56 mmol) and hydroxylamine hydrochloride (119 mg, 1.71 mmol) were added to a solution of 2-{[(4-fluorophenyl)methyl]oxy}-5-formyl-N-3-pyridinylbenzamide (may be prepared as described in Example 82; 300 mg, 0.86 mmol) in methanol (10 ml) and the mixture was stirred at room temperature for 30 min. The mixture was evaporated under reduced pressure to half volume. The mixture was diluted with water (20 ml) and filtered. The solid was washed with cold water (20 ml)/cold methanol (5 ml) and dried under vacuum to yield the title compound as a white solid. 220 mg.

MS (electrospray): m/z [M+H]$^+$=422

Example 84

2-{[(4-Fluorophenyl)methyl]oxy}-5-formyl-N-4-pyridazinylbenzamide (E84)

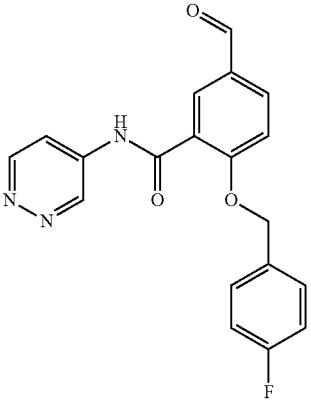 [SMILES: O=Cc1ccc(OCc2ccc(F)cc2)c(C(=O)Nc2ccnnc2)c1]

4-Pyridazinamine (0.52 g, 5.47 mmol), EDC (0.84 g, 4.38 mmol), HOBT (0.89 g, 5.83 mmol) and N-ethylmorpholine (0.92 ml, 7.29 mmol) were added to a solution of 2-{[(4-fluorophenyl)methyl]oxy}-5-formylbenzoic acid (may be prepared by Description 105; 1 g, 3.65 mmol) in N,N-dimethylformamide (25 ml), and the mixture was stirred at room temperature for 4 hrs. The N,N-dimethylformamide was evaporated under reduced pressure on a buchi. Saturated aqueous sodium hydrogen carbonate (50 ml) and ethyl acetate (100 ml) were added to the residue and the mixture was stirred for 30 mins. The organics were separated and washed with water (50 ml), dried (MgSO$_4$) and evaporated under reduced pressure to yield the title compound as a pale yellow solid. No further purification. No further purification carried out. 0.98 g.

MS (electrospray): m/z [M+H]$^+$=352

Example 85

2-{[(3,4-Difluorophenyl)methyl]oxy}-5-[(Z)-(hydroxyimino)methyl]-N-3-pyridinylbenzamide (E85)

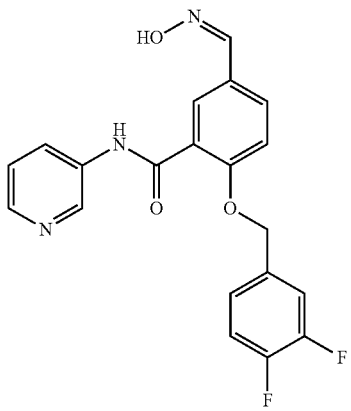 [SMILES: O=C(Nc1cccnc1)c1cc(/C=N\O)ccc1OCc1ccc(F)c(F)c1]

Pyridine (0.44 ml, 5.43 mmol) and hydroxylamine hydrochloride (75 mg, 1.09 mmol) were added to a solution of 2-([(3,4-difluorophenyl)methyl]oxy)-5-formyl-N-3-pyridinylbenzamide (may be prepared by Example 80; 200 mg, 0.54 mmol) in methanol (10 ml), and the mixture was stirred at room temperature for 30 min. The mixture was evaporated under reduced pressure to half volume. The mixture was diluted with water (20 ml) and filtered. The solid was washed with water (20 ml)/methanol (5 ml) and air dried under vacuum to yield the title compound as a white solid. 167 mg.

MS (electrospray): m/z [M+H]$^+$=384

Example 86

Methyl ({4-[(phenylmethyl)oxy]-3-[(3-pyridinylamino)carbonyl]phenyl}methyl)carbamate (E86)

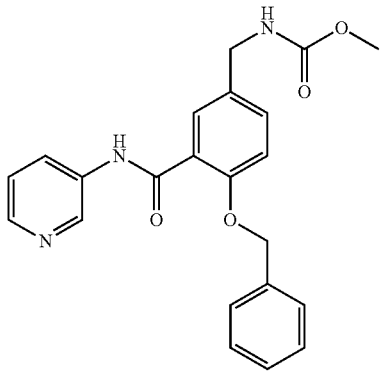 [SMILES: COC(=O)NCc1ccc(OCc2ccccc2)c(C(=O)Nc2cccnc2)c1]

2N HCl (2 ml) and zinc (152 mg, 2.33 mmol) were added to a suspension of 5-[(E/Z)-(hydroxyimino)methyl]-2-[(phenylmethyl)oxy]-N-3-pyridinylbenzamide (may be prepared as described in Example 67; 81 mg, 0.23 mmol) in tetrahydrofuran (5 ml). The mixture was heated at 60° C. for 15 minutes. The mixture was cooled and saturated NaHCO$_3$ solution was added to adjust the pH to 10. Methyl chloroformate (0.22 ml, 2.80 mmol) was added and the pH adjusted to pH 9-10 using saturated NaHCO$_3$ solution. The mixture was stirred for one hour and then the tetrahydrofuran was removed in vacuo. The aqueous layer was extracted with ethyl acetate (2×10 ml), dried (MgSO$_4$) and the solvent removed in vacuo to give an oil which was purified by MDAP to yield the title compound as a white solid. 20 mg.

MS (electrospray): m/z [M+H]$^+$=392

$^1$H NMR (DMSO-d$_6$): 3.54 (3H, s), 4.17 (2H, d, J=6.14 Hz), 5.24 (2H, s), 7.25 (1H, d, J=8.55 Hz), 7.28-7.44 (5H, m), 7.53 (2H, d, J=6.36 Hz), 7.59 (1H, d, J=2.19 Hz), 7.68-7.76 (1H, m), 8.05-8.12 (1H, m), 8.27 (1H, dd, J=4.71, 1.42 Hz), 8.66 (1H, d, J=2.41 Hz), 10.35 (1H, s)

Example 87

Ethyl 3-{-4-[(phenylmethyl)oxy]-3-[(3-pyridinylamino)carbonyl]phenyl}propanoate (E87)

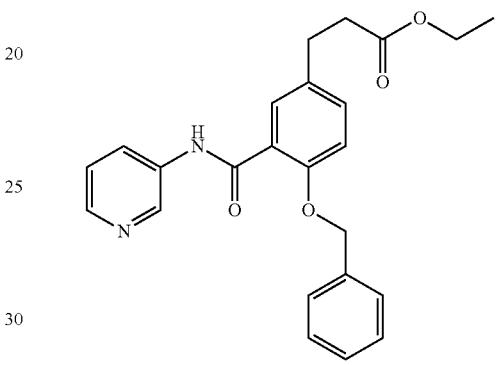

Cesium carbonate (171 mg, 0.53 mmol) and benzyl bromide (0.05 ml, 0.42 mmol) were added to a solution of ethyl 3-{4-hydroxy-3-[(3-pyridinylamino)carbonyl]phenyl}propanoate (may be prepared as described in Description 98; 110 mg, 0.35 mmol) in N,N-dimethylformamide (10 ml). The mixture was stirred for one hour and then ethyl acetate (10 ml) and water (10 ml) were added. The organic layer was separated, washed further with water (3×10 ml), dried (MgSO$_4$) and the solvent removed in vacuo to yield the title compound as a yellow solid. 126 mg.

MS (electrospray): m/z [M-1-H]$^+$=405

$^1$H NMR (DMSO-d$_6$): 1.07-1.26 (3H, m), 2.57-2.70 (2H, m), 2.79-2.97 (2H, m), 3.96-4.13 (2H, m), 5.22 (2H, s), 7.08-7.61 (9H, m), 8.00-8.15 (1H, m), 8.27 (1H, dd, J=4.71, 1.42 Hz), 8.66 (1H, d, J=2.41 Hz), 10.33 (1H, s)

Example 88

3-{4-[(phenylmethyl)oxy]-3-[(3-pyridinylamino)carbonyl]phenyl}propanoic acid (E88)

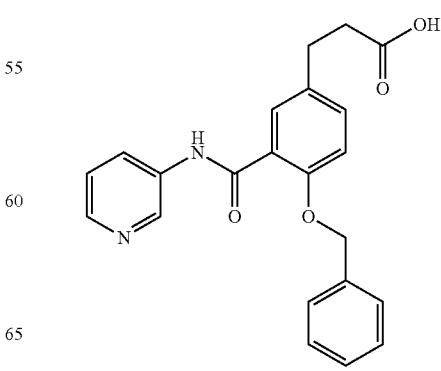

Lithium hydroxide (9.24 mg, 0.39 mmol) was added to a solution of ethyl 3-{4-[(phenylmethyl)oxy]-3-[(3-pyridinylamino)carbonyl]phenyl}propanoate (may be prepared as described in Example 87; 52 mg, 0.13 mmol) in tetrahydrofuran (2 ml) and water (0.5 ml) and the mixture was stirred overnight. The reaction mixture was purified by MDAP to yield the title compound as a golden solid. 62 mg.

MS (electrospray): m/z [M+H]$^+$=377

$^1$H NMR (DMSO-d$_6$): 2.53-2.59 (2H, m), 2.82 (2H, t, J=7.34 Hz), 5.22 (2H, s), 7.21 (1H, d, J=8.55 Hz), 7.28-7.45 (5H, m), 7.50-7.60 (3H, m), 8.09 (1H, br. s.), 8.26 (1H, d, J=3.73 Hz), 8.66 (1H, s), 10.32 (1H, s)

Example 89

2-{[(4-Fluorophenyl)methyl]oxy}-N-4-pyridazinyl-5-(4-pyridinyl)benzamide (E89)

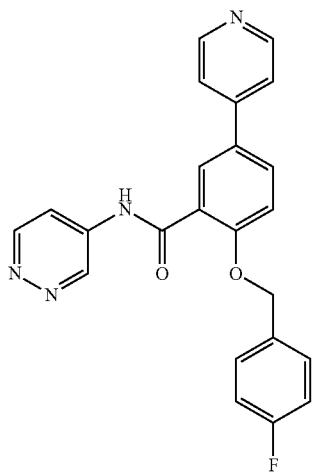 [SMILES: O=C(Nc1ccnnc1)c1cc(-c2ccncc2)ccc1OCc1ccc(F)cc1]

4-Pyridinylboronic acid (81 mg, 0.66 mmol), sodium carbonate (1.09 ml, 1.09 mmol) and tetrakis(triphenylphosphine)palladium(0) (37.9 mg, 0.03 mmol) were added to a solution of 5-bromo-2-{([(4-fluorophenyl)methyl]oxy}-N-4-pyridazinylbenzamide (may be prepared as described in Example 77; 220 mg, 0.55 mmol) in 1,2-dimethoxyethane (5 ml). The reaction was heated at 120° C. for one hour. The solvent was removed in vacuo, redissolved in 1:1 dimethylsulfoxide/methanol and purified by MDAP to yield the title compound as a white solid. 58 mg.

MS (electrospray): m/z [M+H]$^+$=401

$^1$H NMR (DMSO-d$_6$): 5.30 (2H, s), 7.10-7.28 (2H, m), 7.44 (1H, d, J=8.77 Hz), 7.57 (2H, dd, J=8.44, 5.59 Hz), 7.76 (2H, d, J=6.14 Hz), 7.96-8.16 (3H, m), 8.62 (2H, d, J=5.92 Hz), 9.08 (1H, d, J=5.70 Hz), 9.30 (1H, d, J=2.19 Hz), 10.90 (1H, s)

Example 90

2-{[(4-Fluorophenyl)methyl]oxy}-N-3-pyridinyl-5-(4-pyridinyl)benzamide (E90)

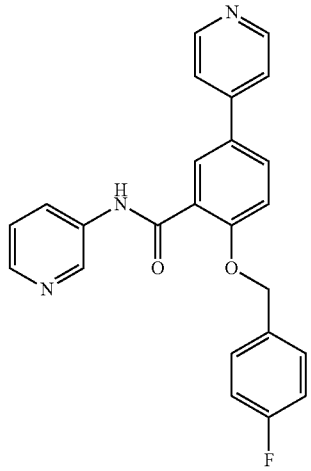 [SMILES: O=C(Nc1cccnc1)c1cc(-c2ccncc2)ccc1OCc1ccc(F)cc1]

To a solution of 5-bromo-2-{[(4-fluorophenyl)methyl]oxy}-N-3-pyridinylbenzamide (may be prepared as described in Example 59; 150 mg, 0.37 mmol) in 1,2-dimethoxyethane (5 ml) was added 4-pyridinylboronic acid (68.9 mg, 0.561 mmol), sodium carbonate (198 mg, 1.87 mmol) and bis(triphenylphosphine)palladium(II) chloride (15.74 mg, 0.02 mmol), followed by water (1 ml). The reaction was heated at 80° C. overnight. The reaction mixture was then placed in a microwave vial with another 0.5 eq of boronic acid and 5% catalyst and heated at 120° C. for 25 minutes. The solvent was removed in vacuo, redissolved in 1:1 DMSO/methanol and purified by MDAP to yield the title compound as white solid. 56 mg.

MS (electrospray): m/z [M+H]$^+$=400

$^1$H NMR (DMSO-d$_6$): 5.31 (2H, s), 7.21 (2H, t, J=8.88 Hz), 7.42 (2H, d, J=8.77 Hz), 7.60 (2H, dd, J=8.44, 5.59 Hz), 7.71-7.80 (2H, m), 7.94-8.24 (4H, m), 8.30 (1H, dd, J=4.71, 1.43 Hz), 8.56-8.65 (2H, m), 8.76 (1H, d, J=2.41 Hz), 10.47 (1H, s)

Example 91

2-{[(4-Fluorophenyl)methyl]oxy}-5-(1H-pyrazol-4-yl)-N-3-pyridinylbenzamide (E91)

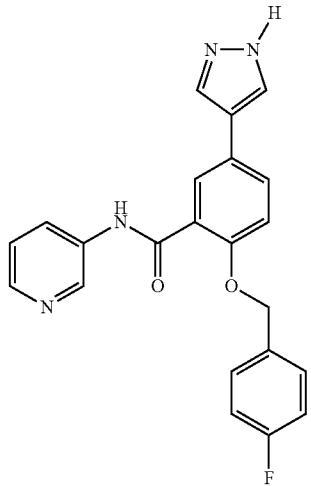 [SMILES: O=C(Nc1cccnc1)c1cc(-c2cn[nH]c2)ccc1OCc1ccc(F)cc1]

1,1-Dimethylethyl 4-(4,4,5,5-tetramethyl-1,3,2-dioxaborolan-2-yl)-1H-pyrazole-1-carboxylate (141 mg, 0.48 mmol), sodium carbonate (0.87 ml, 0.87 mmol) and Pd(Ph3P)4 (30.2 mg, 0.03 mmol) were added to a solution of 5-bromo-2-{[(4-fluorophenyl)methyl]oxy}-N-3-pyridinyl-benzamide (may be prepared as described in Example 59; 175 mg, 0.44 mmol) in 1,2-dimethoxyethane (5 ml). The reaction was heated at 120° C. for one hour. The solvent was removed in vacuo, triturated with 1:1 DMSO/methanol and washed with methanol (1 ml) and ethyl acetate (2 ml) to give a white solid (80 mg). Recrystallisation with hot 1:1 DMSO/ethyl acetate gave a white solid (45 mg). The filtrate was purified by MDAP to give a white solid (22 mg). The 2 batches were combined to yield the title compound. 67 mg.

MS (electrospray): m/z [m+H]$^+$=389

$^1$H NMR (DMSO-d$_6$): 5.23 (2H, s), 7.11-7.43 (5H, m), 7.58 (2H, dd, J=1333, 5.70 Hz), 7.86 (2H, d, J=2.19 Hz), 8.03-8.36 (3H, m), 8.73 (1H, d, J=2.41 Hz), 10.39 (1H, s), 12.91 (1H, br. s.)

Example 92

2-{[(4-Fluorophenyl)methyl]oxy}-5-(1H-pyrazol-4-yl)-N-4-pyridazinylbenzamide (E92)

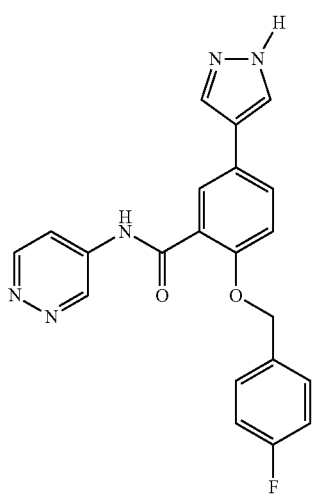 [SMILES: O=C(Nc1ccnnc1)c1cc(-c2cn[nH]c2)ccc1OCc1ccc(F)cc1]

1,1-Dimethylethyl 4-(4,4,5,5-tetramethyl-1,3,2-dioxaborolan-2-yl)-1H-pyrazole-1-carboxylate (110 mg, 0.37 mmol), sodium carbonate (0.75 ml, 0.75 mmol) and tetrakis(triphenylphosphine)palladium(0) (25.9 mg, 0.02 mmol) were added to a solution of 5-bromo-2-{[(4-fluorophenyl)methyl]oxy}-N-4-pyridazinylbenzamide (may be prepared as described in Example 77; 150 mg, 0.37 mmol) in 1,2-dimethoxyethane (5 ml). The reaction was heated at 120° C. for one hour. The solvent was removed in vacuo, triturated with 1:1 DMSO/methanol and washed with methanol (1 ml) and ethyl acetate (2 ml) to give a white solid. Recrystallisation with hot 1:1 DMSO/ethyl acetate yielded the title compound as a white solid. 48.6 mg.

MS (electrospray): m/z [M+H]$^+$=390

$^1$H NMR (DMSO-d$_6$): 5.09-5.29 (2H, s), 7.08-7.23 (2H, m), 7.29 (1H, d, J=8.77 Hz), 7.55 (2H, dd, J=8.66, 5.59 Hz), 7.71-7.88 (2H, m), 7.94-8.15 (3H, m), 9.06 (1H, d, J=5.70 Hz), 9.28 (1H, d, J=2.19 Hz), 10.83 (1H, br. s.), 12.92 (1H, br. s.)

Example 93

2-{[(4-Fluorophenyl)methyl]oxy}-5-(1-methyl-1H-pyrazol-4-yl)-N-3-pyridinylbenzamide (E93)

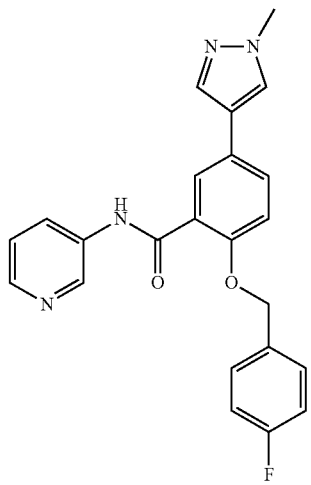 [SMILES: Cn1cc(-c2ccc(OCc3ccc(F)cc3)c(C(=O)Nc3cccnc3)c2)cn1]

1-Methyl-4-(4,4,5,5-tetramethyl-1,3,2-dioxaborolan-2-yl)-1H-pyrazole (78 mg, 0.37 mmol), 1M sodium carbonate (0.75 ml, 0.75 mmol) and tetrakis(triphenylphosphine)palladium(0) (25.9 mg, 0.02 mmol) were added to a solution of 5-bromo-2-{[(4-fluorophenyl)methyl]oxy}-N-3-pyridinyl-benzamide (may be prepared as described in Example 59; 150 mg, 0.37 mmol) in 1,2-dimethoxyethane (4 ml). The reaction was heated at 120° C. for one hour. The solvent was removed in vacuo to give a residue. Purification by MDAP yielded the title compound as a white solid. 70 mg.

MS (electrospray): m/z [M+1-1]$^+$=403

$^1$H NMR (DMSO-d$_5$): 3.85 (3H, s), 5.23 (2H, br. s.), 7.00-7.43 (4H, m), 7.49-7.94 (5H, m), 8.15 (2H, br. s.), 8.29 (1H, br. s.), 8.73 (1H, br. s.), 10.41 (1H, br. s.)

Example 94

2-{[(4-Fluorophenyl)methyl]oxy}-5-(1-methyl-1H-pyrazol-4-yl)-N-4-pyridazinylbenzamide (E94)

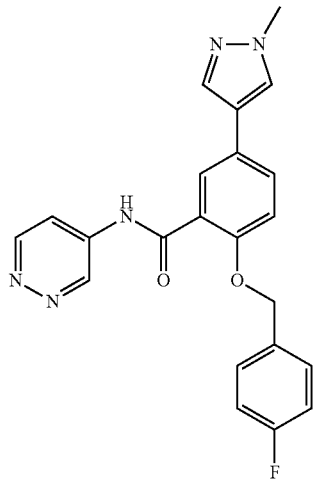 [SMILES: Cn1cc(-c2ccc(OCc3ccc(F)cc3)c(C(=O)Nc3ccnnc3)c2)cn1]

1-Methyl-4-(4,4,5,5-tetramethyl-1,3,2-dioxaborolan-2-yl)-1H-pyrazole (78 mg, 0.37 mmol), 1M sodium carbonate (0.75 ml, 0.75 mmol) and tetrakis(triphenylphosphine)palladium(0) (25.9 mg, 0.02 mmol) were added to a solution of 5-bromo-2-{[(4-fluorophenyl)methyl]oxy}-N-4-pyridazinylbenzamide (may be prepared as described in Example 77; 150 mg, 0.37 mmol) in 1,2-dimethoxyethane (4 ml). The reaction was heated at 120° C. for one hour. The solvent was removed in vacuo to give a residue. Purification by MDAP yielded the title compound as a white solid. 50 mg.

MS (electrospray): m/z [M+H]$^+$=404

$^1$H NMR (DMSO-d$_6$): 3.85 (3H, s), 5.22 (2H, br. s.), 7.08-7.36 (3H, m), 7.56 (2H, d, J=6.14 Hz), 7.68-7.92 (3H, m), 8.04 (1H, br. s.), 8.16 (1H, s), 9.07 (1H, d, J=5.70 Hz), 9.28 (1H, br. s.), 10.84 (1H, br. s.)

Example 95

2-{[(4-Fluorophenyl)methyl]oxy}-5-(1-methyl-1H-pyrazol-5-yl)-N-3-pyridinylbenzamide (E95)

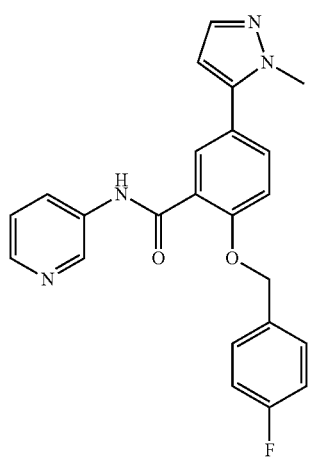 [SMILES: Cn1nccc1-c1ccc(OCc2ccc(F)cc2)c(C(=O)Nc2cccnc2)c1]

(1-Methyl-1H-pyrazol-5-yl)boronic acid (30.1 mg, 0.24 mmol), sodium carbonate (0.40 ml, 0.40 mmol) and tetrakis(triphenylphosphine)palladium(0) (13.82 mg, 0.01 mmol) were added to a solution of 5-bromo-2-{[(4-fluorophenyl)methyl]oxy}-N-3-pyridinylbenzamide (may be prepared as described in Example 59; 80 mg, 0.20 mmol) in 1,2-dimethoxyethane (3 ml). The mixture was heated at 120° C. for 1 hour. The solvent was removed in vacuo and purified by MDAP to yield the title compound as a brown gum. 13 mg.

MS (electrospray): m/z [M+H]$^+$=403

$^1$H NMR (DMSO-d$_6$): 3.86 (3H, s), 5.29 (2H, s), 6.42 (1H, d, J=1.75 Hz), 7.14-7.28 (2H, m), 7.33-7.43 (2H, m), 7.46 (1H, d, J=1.75 Hz), 7.60 (2H, dd, J=8.55, 5.70 Hz), 7.69 (1H, dd, J=8.55, 2.41 Hz), 7.75 (1H, d, J=2.41 Hz), 8.04-8.18 (1H, m), 8.29 (1H, dd, J=4.60, 1.32 Hz), 8.73 (1H, d, J=2.41 Hz), 10.42 (1H, s)

Example 96

5-(1-Methyl-1H-pyrazol-5-yl)-2-[(phenyl methyl)oxy]-N-3-pyridinylbenzamide (E96)

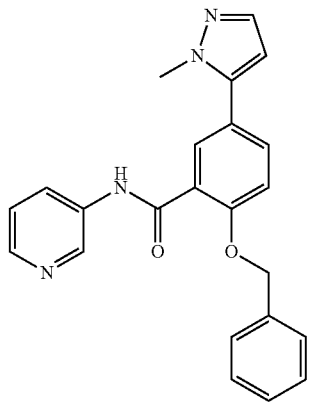 [SMILES: Cn1nccc1-c1ccc(OCc2ccccc2)c(C(=O)Nc2cccnc2)c1]

To a microwave vial was added 5-bromo-2-[(phenylmethyl)oxy]-N-3-pyridinylbenzamide (may be prepared as described in example 2; 100 mg, 0.26 mmol), 1-methyl-5-(4,4,5,5-tetramethyl-1,3,2-dioxaborolan-2-yl)-1H-pyrazole (59.7 mg, 0.29 mmol), 1,2-dimethoxyethane (2 ml), 1M sodium carbonate (0.52 ml, 0.52 mmol) and tetrakis(triphenylphosphine)palladium(0) (18.09 mg, 0.02 mmol). The vial was sealed and heated to 120° C. for 25 min under microwave conditions. The mixture was evaporated and water (5 ml) was added to the residue, the mixture was extracted with ethyl acetate (3×10 ml). The organics were combined and evaporated in vacuo and the residue was purified using the MDAP to yield the title compound. 22 mg.

MS (electrospray): m/z [M+H]$^+$=385

$^1$H NMR (400 MHz, CHLOROFORM-d) 3.93 (3H, s), 5.30 (2H, s), 6.35 (1H, d, J=1.75 Hz), 7.15-7.34 (2H, m), 7.45-7.68 (7H, m), 7.97 (1H, br. s.), 8.14 (1H, d, J=8.33 Hz), 8.24-8.34 (1H, m), 8.42 (1H, d, J=2.41 Hz), 10.03 (1H, s)

Example 97

5-(1-Methyl-1H-pyrazol-4-yl-2-[(phenylmethyl)oxy]-N-3-pyridinylbenzamide (E97)

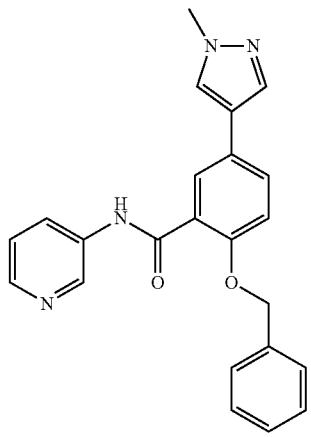 [SMILES: Cn1cc(-c2ccc(OCc3ccccc3)c(C(=O)Nc3cccnc3)c2)cn1]

To a microwave vial was added 5-bromo-2-[(phenylmethyl)oxy]-N-3-pyridinylbenzamide (may be prepared as described in example 2; 100 mg, 0.26 mmol), 1-methyl-4-(4,4,5,5-tetramethyl-1,3,2-dioxaborolan-2-yl)-1H-pyrazole (59.7 mg, 0.29 mmol), 1,2-dimethoxyethane (2 ml), 1M sodium carbonate (0.52 ml, 0.52 mmol) and tetrakis(triphenylphosphine)palladium(0) (18.09 mg, 0.02 mmol). The vial was sealed and heated to 120° C. for 25 min under microwave conditions. The mixture was evaporated under reduced pressure. Water (5 ml) was added to the residue and the mixture was extracted with ethyl acetate (3×10 ml). The organics were combined and evaporated and the residue was purified using MDAP to yield the title compound. 31 mg.

MS (electrospray): m/z [M+1-]⁺=385

¹H NMR (400 MHz, CHLOROFORM-d) 3.95 (3H, s), 5.25 (2H, s), 7.10-7.24 (2H, m), 7.44-7.59 (5H, m), 7.59-7.71 (2H, m), 7.79 (1H, s), 8.00 (1H, d, J=1.97 Hz), 8.12 (1H, d, J=8.55 Hz), 8.27 (1H, d, J=3.95 Hz), 8.41 (1H, d, J=2.41 Hz), 10.09 (1H, s)

Example 98

5-Bromo-N-(5-fluoro-3-pyridinyl)-2-[(phenylmethyl)oxy]benzamide (E98)

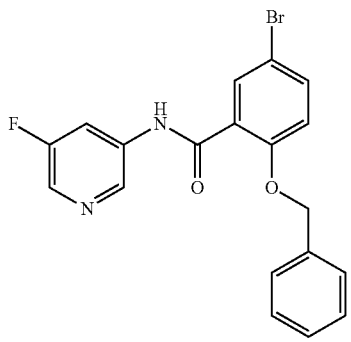 [SMILES: O=C(Nc1cncc(F)c1)c1cc(Br)ccc1OCc1ccccc1]

Diisopropylethylamine (0.28 ml, 1.63 mmol), 5-fluoro-3-pyridinamine (73.0 mg, 0.65 mmol) and HATU (371 mg, 0.98 mmol) were added to a solution of 5-bromo-2-[(phenylmethyl)oxy]benzoic acid (may be prepared as described in Description 5; 200 mg, 0.651 mmol) in N,N-dimethylformamide (50 ml) at room temperature. The mixture was stirred at room temperature for 3 hours. The mixture was then purified by chromatography on silica using 0-100% ethyl acetate/hexane. However a number of impurities persisted and the residue was re-purified by MDAP to yield the title compound. 45 mg.

MS (electrospray): m/z [M+H]⁺=402

¹H NMR (400 MHz, CHLOROFORM-d) 5.22 (2H, s) 7.07 (1H, d, J=8.77 Hz) 7.47-7.62 (6H, m) 7.65 (1H, dd, J=8.77, 2.63 Hz) 8.07 (1H, d, J=10.74 Hz) 8.14 (1H, br. s.) 8.43 (1H, d, J=2.63 Hz) 10.08 (1H, br. s.)

Example 99

2-[(Phenylmethyl)oxy]-5-(1H-pyrazol-4-yl)-N-3-pyridinylbenzamide (E99)

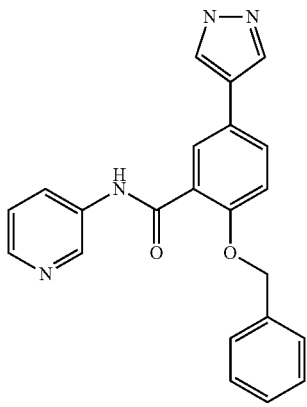 [SMILES: O=C(Nc1cccnc1)c1cc(-c2cn[nH]c2)ccc1OCc1ccccc1]

To a microwave vial was added 5-bromo-2-[(phenylmethyl)oxy]-N-3-pyridinylbenzamide (may be prepared as described in example 2; 310 mg, 0.81 mmol), 1,1-dimethylethyl 4-(4,4,5,5-tetramethyl-1,3,2-dioxaborolan-2-yl)-1H-pyrazole-1-carboxylate (262 mg, 0.89 mmol), 1,4-dioxane (3 ml), sodium carbonate (1.62 ml, 1.62 mmol) and tetrakis (triphenylphosphine)palladium(0) (56.1 mg, 0.05 mmol). The vial was sealed and heated to 120° C. for 25 min under microwave conditions. The mixture was evaporated under reduced pressure and water (5 ml) was added to the residue. The mixture was extracted with ethyl acetate (3×10 ml). The organics were combined and evaporated under reduced pressure, and the residue was purified using the MDAP to yield the title compound. 44 mg.

MS (electrospray): m/z [M+H]⁺=371

¹H NMR (400 MHz, DMSO-d₆) 5.26 (2H, s), 7.24-7.43 (5H, m), 7.52 (2H, s), 7.66-7.82 (1H, m), 7.87 (2H, d, J=2.41 Hz), 8.03-8.15 (1H, m), 8.13-8.25 (1H, m), 8.23-8.36 (1H, m), 8.61-8.81 (1H, m), 10.31-10.48 (1H, m), 12.76-13.08 (1H, m).

Example 100

2-[(Phenylmethyl)oxy]-N-3-pyridinyl-5-(4-pyridinyl)benzamide (E100)

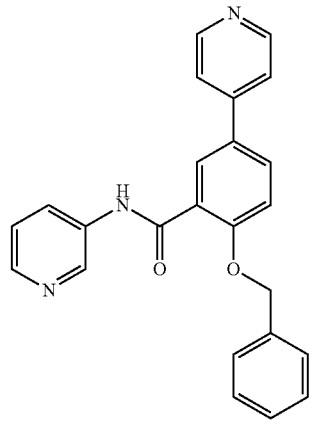 [SMILES: O=C(Nc1cccnc1)c1cc(-c2ccncc2)ccc1OCc1ccccc1]

To a microwave vial was added 5-bromo-2-[(phenylmethyl)oxy]-N-3-pyridinylbenzamide (may be prepared as described in example 2; 200 mg, 0.52 mmol), 1,4-dioxane (2 ml), 4-pyridinylboronic acid (64.1 mg, 0.52 mmol), 1M sodium carbonate (1.04 mL, 1.04 mmol) and tetrakis(triphenylphosphine)palladium(0) (36.2 mg, 0.03 mmol). The vial was sealed and heated to 100° C. for 30 min under microwave conditions. The mixture was evaporated under reduced pressure and the residue was purified using MDAP to yield the title compound. 41 mg.

MS (electrospray): m/z [M+H]⁺=382

¹H NMR (400 MHz, CHLOROFORM-d) 5.32 (2H, s), 7.23 (1H, d, J=4.82 Hz), 7.30 (1H, d, J=8.55 Hz), 7.51-7.62 (7H, m), 7.85 (1H, dd, J=8.55, 2.41 Hz), 7.99 (1H, d, J=2.63 Hz), 8.11-8.18 (1H, m), 8.29 (1H, dd, J=4.71, 1.43 Hz), 8.63-8.75 (3H, m), 10.04 (1H, s).

Example 101

2-[(Phenylmethyl)oxy]-N,5-di-3-pyridinylbenzamide (E101)

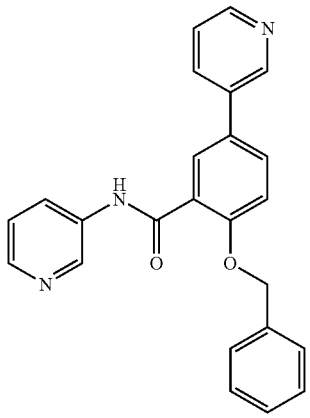 [SMILES: O=C(Nc1cccnc1)c1cc(-c2cccnc2)ccc1OCc1ccccc1]

To a microwave vial was added 5-bromo-2-[(phenylmethyl)oxy]-N-3-pyridinylbenzamide (may be prepared as described in example 2; 200 mg, 0.52 mmol), 1,4-dioxane (2 ml), 1M sodium carbonate (1.04 ml, 1.04 mmol), 3-(4,4,5,5-tetramethyl-1,3,2-dioxaborolan-2-yl)pyridine (107 mg, 0.52 mmol) and tetrakis(triphenylphosphine)palladium(0) (36.2 mg, 0.03 mmol). The vial was sealed and heated to 100° C. for 30 min under microwave conditions. The mixture was evaporated under reduced pressure and the residue was purified using the MDAP. Some impurities persisted and the mixture was re-purified using MDAP to yield the title compound. 17 mg.

MS (electrospray): m/z $[M+H]^+=382$ $^1$H NMR (400 MHz, CHLOROFORM-d) 5.30 (2H, s), 7.23 (1H, dd, J=8.44, 4.71 Hz), 7.25-7.33 (1H, m), 7.40 (1H, dd, J=7.78, 4.71 Hz), 7.49-7.62 (5H, m), 7.78 (1H, dd, J=8.55, 2.41 Hz), 7.96 (1H, dt, J=8.06, 1.89 Hz), 8.01 (1H, d, J=2.41 Hz), 8.14 (1H, dt, J=8.44, 1.92 Hz), 8.29 (1H, dd, J=4.60, 1.32 Hz), 8.53-8.67 (2H, m), 8.89 (1H, d, J=1.75 Hz), 10.07 (1H, s).

Example 102

N-(5-Fluoro-3-pyridinyl)-2-[(phenylmethyl)oxy]-5-(4-pyridinyl)benzamide (E102)

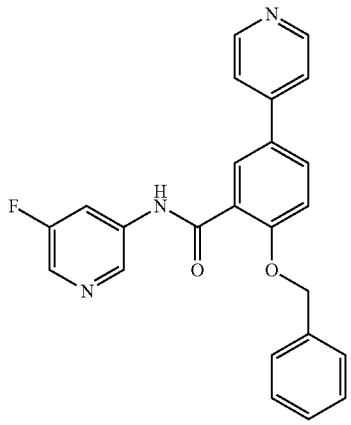 [SMILES: O=C(Nc1cncc(F)c1)c1cc(-c2ccncc2)ccc1OCc1ccccc1]

To a microwave vial was added 5-bromo-N-(5-fluoro-3-pyridinyl)-2-[(phenylmethyl)oxy]benzamide (may be prepared as described in Example 98; 200 mg, 0.50 mmol), 1,4-dioxane (2 ml), 4-pyridinylboronic acid (73.5 mg, 0.60 mmol), 1M sodium carbonate (1.00 ml, 1.00 mmol) and tetrakis(triphenylphosphine)palladium(0) (34.6 mg, 0.03 mmol). The vial was sealed and heated to 130° C. for 30 min under microwave conditions. The mixture was evaporated under reduced pressure and the residue was purified using MDAP (twice) to yield the title compound. 9 mg.

MS (electrospray): m/z $[M+H]^+=400$ $^1$H NMR (400 MHz, CHLOROFORM-d) 5.32 (2H, s), 7.33 (1H, d, J=8.55 Hz), 7.54-7.60 (5H, m), 7.62 (1H, s), 7.67 (2H, d, J=6.14 Hz), 7.89 (1H, dd, J=8.55, 2.63 Hz), 8.11 (1H, dd, J=10.74, 2.19 Hz), 8.16 (1H, d, J=2.63 Hz), 8.64-8.78 (3H, m), 10.16 (1H, s).

Example 103

2-[(Phenylmethyl)oxy]-N-3-pyridinyl-5-[(3R,5S)-3,4,5-trimethyl-1-piperazinyl]benzamide (E103)

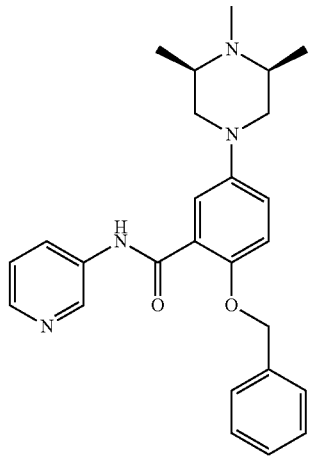 [SMILES: C[C@@H]1CN(c2ccc(OCc3ccccc3)c(C(=O)Nc3cccnc3)c2)C[C@H](C)N1C]

(2R,6S)-1,2,6-Trimethylpiperazine (105 mg, 0.52 mmol), cesium carbonate (680 mg, 2.09 mmol), BINAP (2.44 mg, 3.91 µmol) and Pd$_2$(dba)$_3$ (1.20 mg, 1.30 µmol) were added to 5-bromo-2-[(phenylmethyl)oxy]-N-3-pyridinylbenzamide (may be prepared as described in example 2; 200 mg, 0.52 mmol) in anhydrous toluene (5 ml), and the mixture was heated to reflux overnight. The reaction mixture was evaporated under reduced pressure. Water (50 ml) was added to the residue and the mixture was extracted with ethyl acetate (3×50 ml). The organics were combined and evaporated, and the residue purified by MDAP twice to yield the title compound. 180 mg.

MS (electrospray): m/z $[M+H]^+=431$ $^1$H NMR (400 MHz, METHANOL-d$_4$) 1.37 (6H, d, J=6.36 Hz), 2.72 (3H, s), 2.79 (2H, t, J=11.95 Hz), 3.13 (2H, br. s.), 3.64 (2H, d, J=12.50 Hz), 5.22 (2H, s), 7.24 (2H, s), 7.32 (1H, dd, J=8.00, 4.71 Hz), 7.37-7.47 (3H, m), 7.48-7.57 (2H, m), 7.92 (1H, d, J=8.33 Hz), 8.22 (1H, br. s.), 8.38 (1H, br. s.), 8.50-8.78 (1H, m), 8.51-8.86 (1H, m).

Example 104

5-(2-Fluoro-4-pyridinyl)-2-[(phenylmethyl)oxy]-N-3-pyridinylbenzamide (E104)

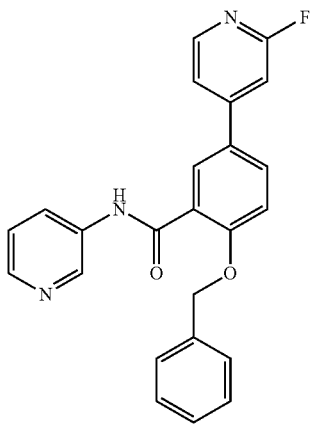 [SMILES: O=C(Nc1cccnc1)c1cc(-c2ccnc(F)c2)ccc1OCc1ccccc1]

(2-Fluoro-4-pyridinyl)boronic acid (425 mg, 3.02 mmol), bis(triphenylphosphine)palladium(II) chloride (70.6 mg, 0.10 mmol) and sodium carbonate (1066 mg, 10.06 mmol) as a solution in 2 ml of water was added to a solution of 5-bromo-2-[(phenylmethyl)oxy]-N-3-pyridinylbenzamide (may be prepared as described in example 2; 771 mg, 2.01 mmol) in 1,2-dimethoxyethane (20 ml). The mixture was heated to reflux for 2 hours. The mixture was diluted with ethyl acetate (50 ml) and water (50 ml). The organic layer was separated and the aqueous layer was extracted with ethyl acetate (2×50 ml). The organics were combined and evaporated. The residue was purified by chromatography on silica eluting with 0-10% methanol/dichloromethane 1% ammonia to yield the title compound as an off-white solid. 500 mg.

MS (electrospray): m/z [M+H]$^+$=400

$^1$H NMR (400 MHz, CHLOROFORM-d) 5.36 (2H, s), 7.18-7.32 (2H, m), 7.32-7.44 (2H, m), 7.49-7.66 (6H, m), 7.89 (1H, dd, J=8.55, 2.19 Hz), 8.01 (1H, d, J=7.45 Hz), 8.12 (1H, d, J=1.53 Hz), 8.25 (2H, t, J=5.04 Hz), 8.60 (1H, d, J=2.19 Hz).

Example 105

2-{[(3,4-Difluorophenyl)methyl]oxy}-5-(1-methyl-1H-pyrazol-4-yl)-N-4-pyridazinylbenzamide (E105)

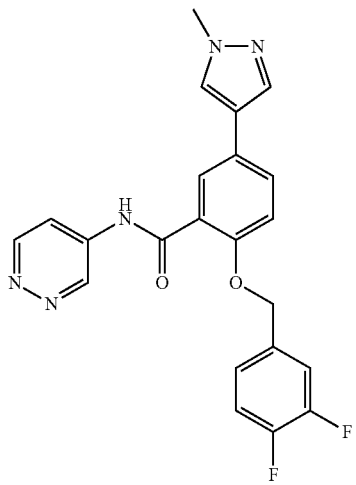 [SMILES: Cn1cc(-c2ccc(OCc3ccc(F)c(F)c3)c(C(=O)Nc3ccnnc3)c2)cn1]

To a microwave vial was added 5-bromo-2-{[(3,4-difluorophenyl)methyl]oxy}-N-4-pyridazinylbenzamide (may be prepared by Example 78; 150 mg, 0.36 mmol), 1-methyl-4-(4,4,5,5-tetramethyl-1,3,2-dioxaborolan-2-yl)-1H-pyrazole (75 mg, 0.36 mmol), 1,2-dimethoxyethane (2 nil), 1M sodium carbonate (0.71 ml, 0.71 mmol), and tetrakis(triphenylphosphine)palladium(0) (24.75 mg, 0.02 mmol). The vial was sealed and heated to 120° C. for 1 hour under microwave conditions. The mixture was evaporated under reduced pressure and water (5 ml) was added to the residue. The mixture was extracted with ethyl acetate (3×10 ml). The organics were combined and evaporated and the residue was purified using the MDAP to yield the title compound. 80 mg.

MS (electrospray): m/z [M+H]$^+$=422

$^1$H NMR (400 MHz, DMSO-d$_6$) 3.85 (3H, s), 5.23 (2H, s), 7.27 (1H, d, J=8.77 Hz), 7.35 (1H, d, J=5.26 Hz), 7.41 (1H, dd, J=10.74, 8.33 Hz), 7.57 (1H, ddd, J=11.56, 7.95, 1.75 Hz), 7.73 (1H, dd, J=8.55, 2.41 Hz), 7.80 (1H, d, J=2.41 Hz), 7.87 (1H, s), 8.05 (1H, dd, J=5.92, 2.63 Hz), 8.15 (1H, s), 9.08 (1H, d), 9.32 (1H, d, J=1.97 Hz), 10.85 (1H, br. s.).

Example 106

2-([(3,4-Difluorophenyl)methyl]oxy)-N-4-pyridazinyl-5-(4-pyridinyl)benzamide (E106)

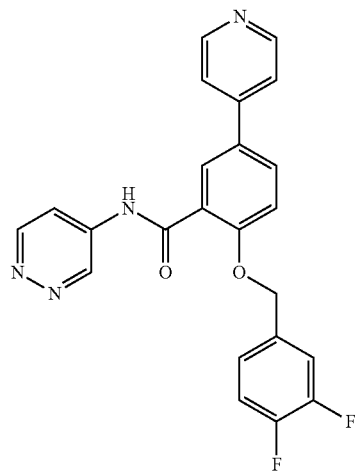 [SMILES: O=C(Nc1ccnnc1)c1cc(-c2ccncc2)ccc1OCc1ccc(F)c(F)c1]

To a microwave vial was added 5-bromo-2-([(3,4-difluorophenyl)methyl]oxy)-N-4-pyridazinylbenzamide (may be prepared as described in Example 78; 200 mg, 0.48 mmol), 4-pyridinylboronic acid (88 mg, 0.74 mmol), tetrakis(triphenylphosphine)palladium(0) (33.0 mg, 0.03 mmol), sodium carbonate (0.95 ml, 0.95 mmol) and 1,2-dimethoxyethane (3 ml). The mixture was sealed and heated to 120° C. for 1 hour under microwave conditions. The 1,2-dimethoxyethane was evaporated under reduced pressure and the residue was purified using MDAP to yield the title compound. 35 mg.

MS (electrospray): m/z [M+H]$^+$=419

$^1$H NMR (400 MHz, DMSO-d$_6$) 5.30 (2H, s), 7.32-7.50 (3H, m), 7.55-7.67 (1H, m), 7.74-7.86 (2H, m), 7.95-8.15 (3H, m), 8.48-8.73 (2H, m), 9.09 (1H, d, J=5.92 Hz), 9.34 (1H, d, J=1.75 Hz), 10.95 (1H, s).

Example 107

2-{[(3,4-Difluorophenyl)methyl]oxy}-5-(1H-pyrazol-5-yl)-N-3-pyridinylbenzamide (E107)

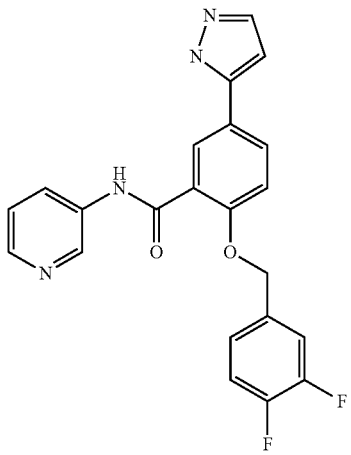 [SMILES: O=C(Nc1cccnc1)c1cc(-c2ccn[nH]2)ccc1OCc1ccc(F)c(F)c1]

To a microwave vial was added 5-bromo-2-{[(3,4-difluorophenyl)methyl]oxy}-N-3-pyridinylbenzamide (may be prepared as described in Example 60; 120 mg, 0.29 mmol), 1,1-dimethylethyl 4-(4,4,5,5-tetramethyl-1,3,2-dioxaborolan-2-yl)-1H-pyrazole-1-carboxylate (93 mg, 0.32 mmol), 1,2-dimethoxyethane (2 ml), 1M sodium carbonate (0.57 ml, 0.57 mmol) and tetrakis(triphenylphosphine)palladium(0) (19.85 mg, 0.02 mmol). The vial was sealed and heated to 120° C. for 25 min under microwave conditions. The mixture was evaporated under reduced pressure. Water (5 ml) was added to the residue and the mixture was extracted with ethyl acetate (3×10 ml). The organics were combined, evaporated under reduced pressure and the residue was purified using MDAP to yield the title compound. 65 mg.

MS (electrospray): m/z [M+H]$^+$=407

$^1$H NMR (400 MHz, DMSO-d$_6$) 5.23 (2H, s), 7.24 (1H, d, J=8.55 Hz), 7.33-7.48 (3H, m), 7.54-7.66 (1H, m), 7.74 (1H, dd, J=8.55, 2.41 Hz), 7.84 (1H, d, J=2.19 Hz), 7.88-8.01 (1H, m), 8.12-8.26 (2H, m), 8.29 (1H, dd, J=4.60, 1.32 Hz), 8.79 (1H, d, J=2.19 Hz), 10.42 (1H, s), 12.79-13.07 (1H, m).

Example 108

2-{[(3,4-Difluorophenyl)methyl]oxy}-5-(1H-pyrazol-4-yl)-N-4-pyridazinylbenzamide (E108)

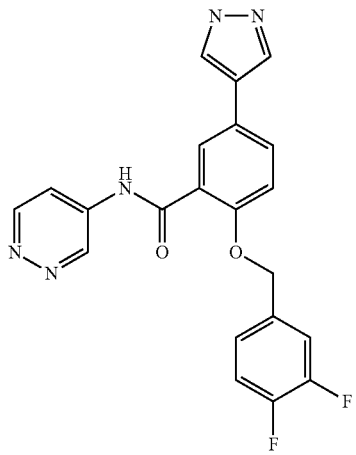 [SMILES: O=C(Nc1ccnnc1)c1cc(-c2cn[nH]c2)ccc1OCc1ccc(F)c(F)c1]

To a microwave vial was added 5-bromo-2-{[(3,4-difluorophenyl)methyl]oxy}-N-4-pyridazinylbenzamide (may be prepared as described in Example 78; 150 mg, 0.36 mmol), 1,1-dimethylethyl 4-(4,4,5,5-tetramethyl-1,3,2-dioxaborolan-2-yl)-1H-pyrazole-1-carboxylate (116 mg, 0.39 mmol), 1,2-dimethoxyethane (2 ml), 1M sodium carbonate (0.71 ml, 0.71 mmol) and tetrakis(triphenylphosphine)palladium(0) (24.75 mg, 0.02 mmol). The vial was sealed and heated to 120° C. for 25 min under microwave conditions. The mixture was evaporated under reduced pressure. Water (5 ml) was added to the residue and the mixture was extracted with ethyl acetate (3×10 ml). The organics were combined and evaporated under reduced pressure and the residue was purified using the MDAP to yield the title compound. 41 mg.

MS (electrospray): m/z [M+H]$^+$=408

$^1$H NMR (400 MHz, DMSO-d$_6$) 5.23 (2H, s), 7.27 (1H, d, J=8.55 Hz), 7.35 (1H, br. s.), 7.38-7.49 (1H, m), 7.53-7.63 (1H, m), 7.78 (1H, dd, J=8.66, 2.30 Hz), 7.84 (1H, d, J=2.19 Hz), 8.06 (3H, m), 9.08 (1H, d, J=5.92 Hz), 9.33 (1H, d, J=1.97 Hz), 10.73-11.06 (1H, m), 12.62-13.26 (1H, m).

Example 109

2-{[(3,4-Difluorophenyl)methyl]oxy}-N-3-pyridinyl-5-(4-pyridinyl)benzamide (E109)

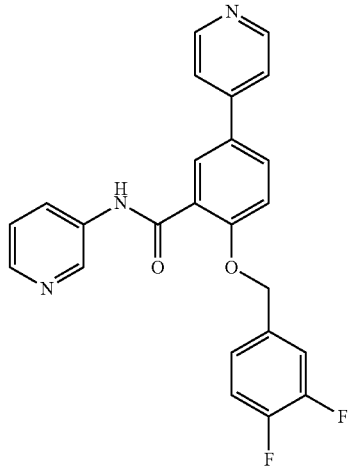 [SMILES: O=C(Nc1cccnc1)c1cc(-c2ccncc2)ccc1OCc1ccc(F)c(F)c1]

To a microwave vial was added 5-bromo-2-([(3,4-difluorophenyl)methyl]oxy)-N-3-pyridinylbenzamide (may be prepared as described in Example 60; 120 mg, 0.29 mmol), 4-pyridinylboronic acid (52.8 mg, 0.43 mmol), tetrakis(triphenylphosphine)palladium(0) (19.85 mg, 0.02 mmol), sodium carbonate (0.57 ml, 0.57 mmol) and 1,2-dimethoxyethane (3 ml). The mixture was sealed and heated to 120° C. for 1 hr under microwave conditions. The 1,2-dimethoxyethane was evaporated under reduced pressure and the residue was purified using MDAP to yield the title compound. 23.5 mg.

MS (electrospray): m/z [M+H]$^+$=418

$^1$H NMR (400 MHz, METHANOL-d$_4$) 5.32 (2H, s), 7.23-7.45 (4H, m), 7.45-7.55 (1H, m), 7.69-7.78 (2H, m), 7.96 (1H, dd, J=8.66, 2.52 Hz), 8.15 (1H, dd, J=8.33, 0.88 Hz), 8.23-8.32 (2H, m), 8.32-8.45 (1H, m), 8.57 (2H, d, J=6.14 Hz), 8.64 (1H, d, J=2.19 Hz).

Example 110

2-{[(3,4-Difluorophenyl)methyl]oxy)-5-(1-methyl-1H-pyrazol-4-yl)-N-3-pyridinylbenzamide (E110)

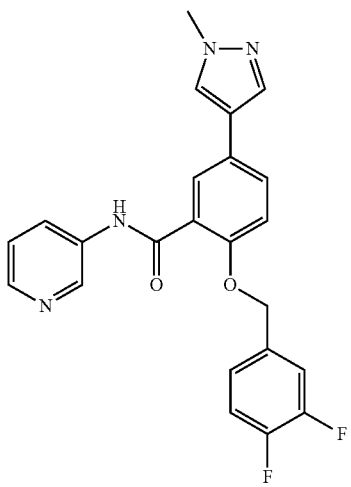 [SMILES: Cn1cc(-c2ccc(OCc3ccc(F)c(F)c3)c(C(=O)Nc3cccnc3)c2)cn1]

To a microwave vial was added 5-bromo-2-([(3,4-difluorophenyl)methyl]oxy}-N-3-pyridinylbenzamide (may be prepared as described in Example 60; 120 mg, 0.29 mmol), 1-methyl-4-(4,4,5,5-tetramethyl-1,3,2-dioxaborolan-2-yl)-1H-pyrazole (65.5 mg, 0.32 mmol), 1,2-dimethoxyethane (2 ml), 1M sodium carbonate (0.57 ml, 0.57 mmol) and tetrakis(triphenylphosphine)palladium(0) (19.85 mg, 0.017 mmol). The vial was sealed and heated to 120° C. for 1 hr under microwave conditions. The mixture was evaporated under reduced pressure. Water (5 ml) was added to the residue and the mixture was extracted with ethyl acetate (3×10 ml). The organics were combined, evaporated under reduced pressure and the residue was purified using the MDAP to yield the title compound. 28 mg.

MS (electrospray): m/z [M+H]$^+$=421

$^1$H NMR (400 MHz, METHANOL-d$_4$) 3.91 (3H, s), 5.22 (2H, s), 7.07-7.53 (6H, m), 7.66 (1H, dd, J=8.66, 2.08 Hz), 7.77 (1H, s), 7.90 (1H, s), 8.00 (1H, d, J=1.75 Hz), 8.05-8.16 (1H, m), 8.26 (1H, d, J=3.95 Hz), 8.53-8.71 (1H, m).

Example 111

2-{[(3,4-Difluorophenyl)methyl]oxy}-5-(4-morpholinylmethyl)-N-4-pyridazinylbenzamide (E111)

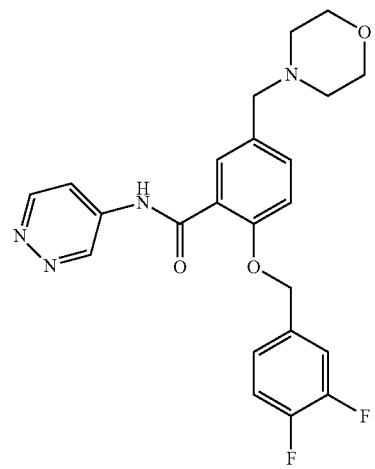 [SMILES: O=C(Nc1ccnnc1)c1cc(CN2CCOCC2)ccc1OCc1ccc(F)c(F)c1]

Morpholine (0.05 ml, 0.54 mmol) and acetic acid (0.03 ml, 0.54 mmol) were added to a solution of 2-{[(3,4-difluorophenyl)methyl]oxy}-5-formyl-N-4-pyridazinylbenzamide (may be prepared by Example 79; 200 mg, 0.54 mmol) in DCE (5 ml), and the mixture was stirred at room temperature for 10 min. Sodium triacetoxyborohydride (172 mg, 0.81 mmol) was then added and the mixture was stirred at 50° C. overnight. Saturated sodium hydrogencarbonate (10 ml) was added and the mixture stirred for 10 min before being diluted with dichloromethane (25 ml). The organic layer was separated and the aqueous phase was extracted with dichloromethane (25 ml). The organics were combined and evaporated under reduced pressure. The residue was purified by MDAP to yield the title compound. 147 mg.

MS (electrospray): m/z [M+H]$^+$=441

$^1$H NMR (400 MHz, DMSO-d$_6$) 2.27-2.42 (4H, m), 3.46 (2H, s), 3.51-3.65 (4H, m), 5.20 (2H, s), 7.24 (1H, d, J=8.55 Hz), 7.31-7.52 (3H, m), 7.53-7.66 (2H, m), 8.03 (1H, dd, J=5.92, 2.63 Hz), 8.40 (1H, s), 9.06 (1H, dd, J=5.92, 0.88 Hz), 9.23-9.35 (1H, m).

Example 112

2-{[(3,4-Difluorophenyl)methyl]oxy}-5-(4-morpholinylmethyl)-N-3-pyridinylbenzamide (E112)

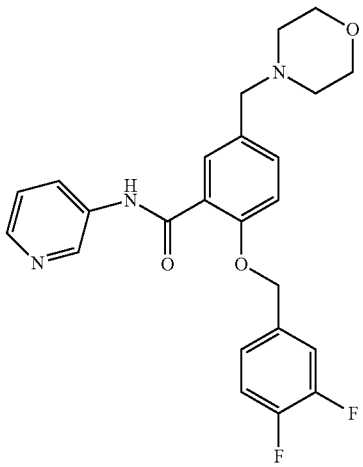 [SMILES: O=C(Nc1cccnc1)c1cc(CN2CCOCC2)ccc1OCc1ccc(F)c(F)c1]

Morpholine (0.05 ml, 0.54 mmol) and acetic acid (0.03 ml, 0.54 mmol) were added to solution of 2-([(3,4-difluorophenyl)methyl]oxy)-5-formyl-N-3-pyridinylbenzamide (may be prepared by Example 80; 200 mg, 0.54 mmol) in DCE (5 ml), and the mixture was stirred at room temperature for 10 min. Sodium triacetoxyborohydride (173 mg, 0.81 mmol) was then added and the mixture was warmed to 50° C. overnight. Saturated sodium hydrogencarbonate (10 ml) was added and the mixture stirred for 10 min before being diluted with dichloromethane (25 ml). The organic layer was separated and the aqueous phase was extracted with dichloromethane (25 ml), the organic were combined and evaporated under reduced pressure. The residue was purified by MDAP to yield the title compound. 82 mg.

MS (electrospray): m/z [M+H]$^+$=440

$^1$H NMR (400 MHz, DMSO-d$_6$) 2.36 (4H, d, J=3.95 Hz), 3.46 (2H, s), 3.50-3.68 (4H, m), 5.21 (2H, s), 7.22 (1H, d, J=8.33 Hz), 7.30-7.51 (4H, m), 7.58 (2H, d, J=1.97 Hz), 8.04-8.17 (1H, m), 8.28 (1H, dd, J=4.71, 1.42 Hz), 8.74 (1H, d, J=2.19 Hz), 10.33 (1H, s).

Example 113

2-{[(2-Cyanophenyl)methyl]oxy}-5-(1-methyl-1H-pyrazol-4-yl)-N-3-pyridinylbenzamide (E113)

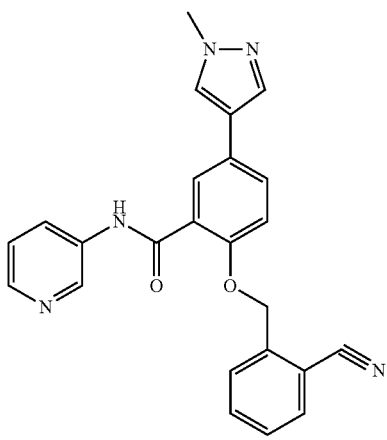 [SMILES: Cn1cc(-c2ccc(OCc3ccccc3C#N)c(C(=O)Nc3cccnc3)c2)cn1]

To a microwave vial was added 5-bromo-2-{[(2-cyanophenyl)methyl]oxy}-N-3-pyridinylbenzamide (may be prepared as described in example 23; 172 mg, 0.42 mmol), 1-methyl-4-(4,4,5,5-tetramethyl-1,3,2-dioxaborolan-2-yl)-1H-pyrazole (96 mg, 0.46 mmol), 1,2-dimethoxyethane (2 ml), 1M sodium carbonate (0.84 ml, 0.84 mmol) and tetrakis(triphenylphosphine)palladium(0) (29.2 mg, 0.025 mmol). The vial was sealed and heated to 120° C. for 1 hr under microwave conditions. The mixture was evaporated under reduced pressure. Water (5 ml) was added to the residue and the mixture was extracted with ethyl acetate (3×10 ml). The organics were combined, evaporated under reduced pressure and the residue was purified using MDAP to yield the title compound. 58 mg.

MS (electrospray): m/z [M+H]$^+$=410

$^1$H NMR (400 MHz, DMSO-d$_6$) 3.86 (3H, s), 5.42 (2H, s), 7.32 (2H, d, J=8.77 Hz), 7.55 (1H, d, J=1.10 Hz), 7.70 (2H, dd, J=4.28, 1.86 Hz), 7.77-7.84 (2H, m), 7.85-7.92 (2H, m), 8.06-8.12 (1H, m), 8.16 (1H, s), 8.28 (1H, dd, J=4.71, 1.43 Hz), 8.71 (1H, d, J=2.41 Hz), 10.35 (1H, s).

Example 114

2-({[2-(Methyloxy)phenyl]methyl}oxy)-5-(1-methyl-1H-pyrazol-4-yl)-N-3-pyridinylbenzamide (E114)

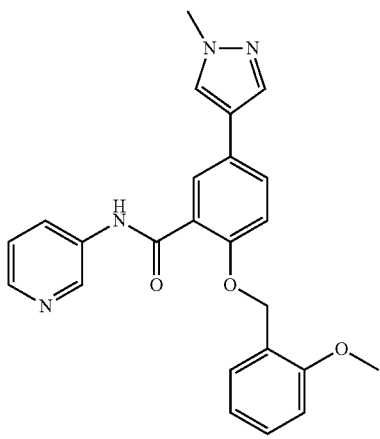 [SMILES: COc1ccccc1COc1ccc(-c2cnn(C)c2)cc1C(=O)Nc1cccnc1]

To a microwave vial was added 5-bromo-2-({[2-(methyloxy)phenyl]methyl}oxy)-N-3-pyridinylbenzamide (may be prepared as described in example 21; 115 mg, 0.28 mmol), 1-methyl-4-(4,4,5,5-tetramethyl-1,3,2-dioxaborolan-2-yl)-1H-pyrazole (63.7 mg, 0.31 mmol), 1,2-dimethoxyethane (2 ml), 1M sodium carbonate (0.56 ml, 0.56 mmol) and tetrakis(triphenylphosphine)palladium(0) (19.29 mg, 0.02 mmol). The vial was sealed and heated to 120° C. for 1 hr under microwave conditions. The mixture was evaporated under reduced pressure. Water (5 ml) was added to the residue and the mixture was extracted with ethyl acetate (3×10 ml). The organics were combined, evaporated under reduced pressure and the residue was purified using MDAP to yield the title compound. 10 mg.

MS (electrospray): m/z [M+H]$^+$=415

$^1$H NMR (400 MHz, CHLOROFORM-d) 3.79 (3H, s), 3.95 (3H, s), 5.31 (2H, s), 6.99-7.10 (2H, m), 7.18-7.25 (2H, m), 7.46 (2H, dd, J=7.67, 1.75 Hz), 7.60-7.69 (2H, m), 7.79 (1H, s), 8.04 (1H, d, J=2.63 Hz), 8.16-8.23 (1H, m), 8.28 (1H, dd, J=4.82, 1.32 Hz), 8.39 (1H, d, J=2.41 Hz), 10.24 (1H, s).

Example 115

2-({[3-(Methyloxy)phenyl]methyl}oxy)-5-(1-methyl-1H-pyrazol-4-yl)-N-3-pyridinylbenzamide (E115)

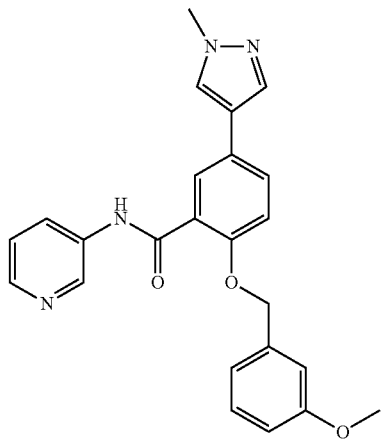 [SMILES: COc1cccc(COc2ccc(-c3cnn(C)c3)cc2C(=O)Nc2cccnc2)c1]

To a microwave vial was added 5-bromo-2-({[3-(methyloxy)phenyl]methyl}oxy)-N-3-pyridinylbenzamide ((may be prepared as described in Example 18; 120 mg, 0.29 mmol), 1-methyl-4-(4,4,5,5-tetramethyl-1,3,2-dioxaborolan-2-yl)-1H-pyrazole (66.5 mg, 0.32 mmol), 1,2-dimethoxyethane (2 ml), 1M sodium carbonate (0.58 ml, 0.58 mmol) and tetrakis(triphenylphosphine)palladium(0) (20.13 mg, 0.02 mmol). The vial was sealed and heated to 120° C. for 1 hr under microwave conditions. The mixture was evaporated under reduced pressure. Water (5 ml) was added to the residue and the mixture was extracted with ethyl acetate (3×10 ml). The organics were combined, evaporated under reduced pressure and the residue was purified using MDAP to yield the title compound. 24 mg.

MS (electrospray): m/z [M+H]$^+$=415

$^1$H NMR (400 MHz, METHANOL-d$_4$) 3.79 (3H, s), 3.94 (3H, s), 5.25 (2H, s), 7.01 (1H, dd, J=8.22, 2.08 Hz), 7.08-7.17 (2H, m), 7.24 (1H, d, J=8.55 Hz), 7.31 (1H, dd, J=8.11, 4.82 Hz), 7.39 (1H, t, J=7.78 Hz), 7.64-7.72 (1H, m), 7.78 (1H, s), 7.83 (1H, s), 7.96 (1H, d, J=8.33 Hz), 8.19-8.27 (2H, m), 8.35 (1H, s).

Example 116

2-{[(2,4-Difluorophenyl)methyl]oxy}-5-(1-methyl-1H-pyrazol-4-yl)-N-3-pyridinylbenzamide (E116)

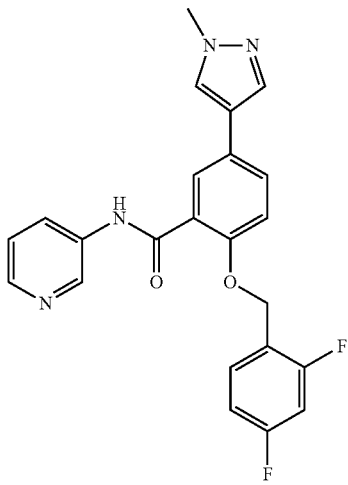 [SMILES: Cn1cc(-c2ccc(OCc3ccc(F)cc3F)c(C(=O)Nc3cccnc3)c2)cn1]

1-Methyl-4-(4,4,5,5-tetramethyl-1,3,2-dioxaborolan-2-yl)-1H-pyrazole (112 mg, 0.54 mmol), tetrakis(triphenylphosphine)palladium(0) (24.81 mg, 0.02 mmol) and sodium carbonate (0.72 ml, 0.72 mmol) were added to a solution of 5-bromo-2-{[(2,4-difluorophenyl)methyl]oxy}-N-3-pyridinylbenzamide (may be prepared by Example 81; 150 mg, 0.36 mmol) in 1,2-dimethoxyethane (3 ml), and the mixture was heated to 120° C. for 1 hr under microwave conditions. The mixture was evaporated under reduced pressure and the residue was purified by MDAP to yield the title compound. 58 mg.

MS (electrospray): m/z [M+H]$^+$=421

$^1$H NMR (400 MHz, METHANOL-d$_4$) 3.91 (3H, s), 5.31 (2H, s), 6.95-7.08 (2H, m), 7.28 (1H, d, J=8.55 Hz), 7.37 (1H, dd, J=8.33, 4.82 Hz), 7.62 (1H, d, J=6.36 Hz), 7.69 (1H, dd, J=8.66, 2.30 Hz), 7.78 (1H, s), 7.90 (1H, s), 8.02-8.11 (2H, m), 8.25 (1H, dd, J=4.71, 1.21 Hz), 8.53 (1H, d, J=2.19 Hz).

Example 117

2-{[(4-Fluorophenyl)methyl]oxy}-5-(4-morpholinylmethyl)-N-3-pyridinylbenzamide (E117)

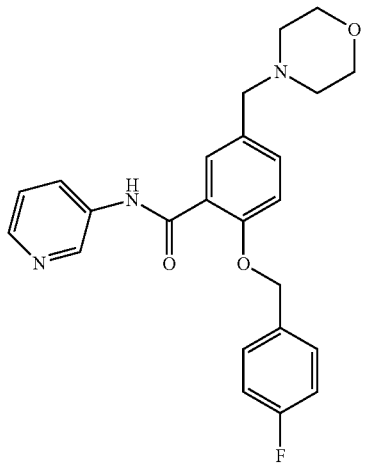 [SMILES: O=C(Nc1cccnc1)c1cc(CN2CCOCC2)ccc1OCc1ccc(F)cc1]

Morpholine (0.05 ml, 0.57 mmol) and acetic acid (0.03 ml, 0.57 mmol) were added to a solution of 2-{[(4-fluorophenyl)methyl]oxy}-5-formyl-N-3-pyridinylbenzamide (may be prepared Example 82; 200 mg, 0.57 mmol) in DCE (5 ml) and the mixture was stirred at room temperature for 10 min. Sodium triacetoxyborohydride (181 mg, 0.86 mmol) was then added and the mixture was warmed to 50° C. overnight. Saturated sodium hydrogencarbonate (10 ml) was added and the mixture was stirred for 10 min before being diluted with dichloromethane (25 ml). The organic layer was separated and the aqueous phase was extracted with dichloromethane (25 ml). The organics were combined and evaporated under reduced pressure. The residue was purified by MDAP to yield the title compound. 150 mg.

MS (electrospray): m/z [M+H]$^+$=422

$^1$H NMR (400 MHz, METHANOL-d$_4$) 2.40-2.56 (4H, m), 3.56 (2H, s), 3.64-3.77 (4H, m), 5.28 (2H, s), 7.15 (2H, t, J=8.77 Hz), 7.29 (1H, d, J=8.33 Hz), 7.34-7.41 (1H, m), 7.52-7.63 (3H, m), 7.93 (1H, d, J=1.97 Hz), 8.00-8.07 (1H, m), 8.24 (1H, dd, J=4.82, 1.32 Hz), 8.48 (1H, d, J=2.41 Hz).

Example 118

Methyl ({4-{[(4-fluorophenyl)methyl]oxy}-3-[(3-pyridinylamino)carbonyl]phenyl}methyl)carbamate (E118)

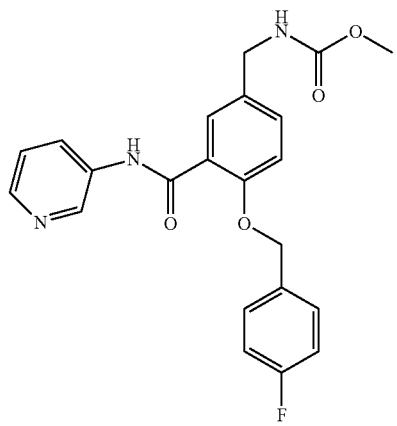 [SMILES: COC(=O)NCc1ccc(OCc2ccc(F)cc2)c(C(=O)Nc2cccnc2)c1]

To a suspension of 2-{[(4-fluorophenyl)methyl]oxy}-5-[(Z)-(hydroxyimino)methyl]-N-3-pyridinylbenzamide (may be prepared by Example 83; 215 mg, 0.57 mmol) in tetrahydrofuran (5 ml) was added 2M aqueous hydrochloric acid (1.72 ml, 56.7 mmol) followed by zinc (371 mg, 5.67 mmol) at room temperature. After stirring at room temperature for 30 min the mixture was heated to 60° C. for 30 min. On cooling, the mixture was treated with saturated sodium hydrogen carbonate (excess). A small amount of the solution was put aside to generate the amine. Methyl chloroformate (0.53 ml, 6.80 mmol) was added to the remainder and the pH was adjusted with further NaHCO$_3$ to pH 9-10. The mixture was then stirred at room temperature for 1 hour. The tetrahydrofuran was evaporated under reduced pressure, and the resulting aqueous layer was extracted with ethyl acetate (2×30 ml), dried (MgSO$_4$) and evaporated under reduced pressure. The residue was purified twice using MDAP to yield the title compound. 12 mg.

MS (electrospray): m/z [M+H]$^+$=422

$^1$H NMR (400 MHz, METHANOL-d$_4$) 3.66 (3H, s), 4.28 (2H, s), 5.26 (2H, s), 5.48 (2H, s), 7.14 (2H, t, J=8.77 Hz), 7.27 (1H, s), 7.33-7.39 (1H, m), 7.45-7.51 (1H, m), 7.53-7.62 (2H, m), 7.88 (1H, d, J=2.19 Hz), 7.99-8.06 (1H, m), 8.24 (1H, dd, J=4.82, 1.32 Hz), 8.47 (1H, d, J=2.41 Hz).

Example 119

2-{[(4-Fluorophenyl)methyl]oxy}-5-(4-morpholinyl-methyl)-N-4-pyridazinyl benzamide (E119)

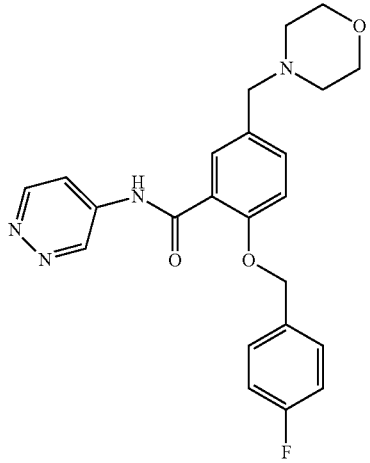 [SMILES: O=C(Nc1ccnnc1)c1cc(CN2CCOCC2)ccc1OCc1ccc(F)cc1]

Morpholine (0.07 ml, 0.85 mmol) followed by acetic acid (0.03 ml, 0.57 mmol) were added to a suspension of 2-([(4-fluorophenyl)methyl]oxy)-5-formyl-N-4-pyridazinylbenzamide (may be prepared as described in Example 84; 200 mg, 0.57 mmol) in DCE (10 ml). The mixture was stirred at room temperature for 10 min and then sodium triacetoxyborohydride (133 mg, 0.63 mmol) was added. The mixture was warmed to 50° C. for 3 hrs. The reaction mixture was diluted with dichloromethane (25 ml) and saturated sodium hydrogen carbonate was added to this mixture until no effevervesence was observed. The mixture was separated and the organic layer was evaporated under reduced pressure. The residue was purified using MDAP to yield the title compound. 180 mg.

MS (electrospray): m/z [M+H]$^+$=423

$^1$H NMR (400 MHz, METHANOL-d$_4$) 2.42-2.55 (4H, m), 3.56 (2H, s), 3.64-3.75 (4H, m), 5.28 (2H, s), 7.11-7.21 (2H, m), 7.30 (1H, d, J=8.55 Hz), 7.52-7.63 (3H, m), 7.91 (1H, d, J=2.41 Hz), 8.07 (1H, dd, J=6.03, 2.74 Hz), 8.91 (1H, dd, J=2.85, 0.88 Hz), 8.97 (1H, dd, J=5.92, 0.88 Hz).

Example 120

5-(Aminomethyl)-2-{[(3,4-difluorophenyl)methyl]oxy}-N-3-pyridinylbenzamide (E120A) and Methyl ({4-{[(3,4-difluorophenyl)methyl]oxy}-3-[(3-pyridinylamino)carbonyl]phenyl}methyl)carbamate (E120B)

A
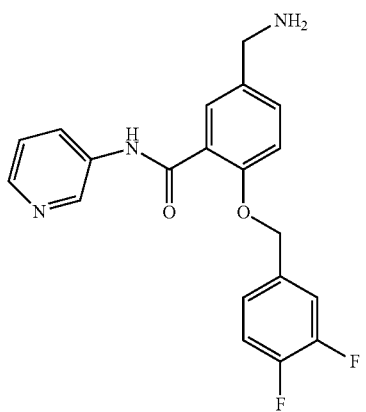 [SMILES: CC(O)c1ccc(OCc2ccc(F)c(F)c2)c(C(=O)Nc2cccnc2)c1]

B
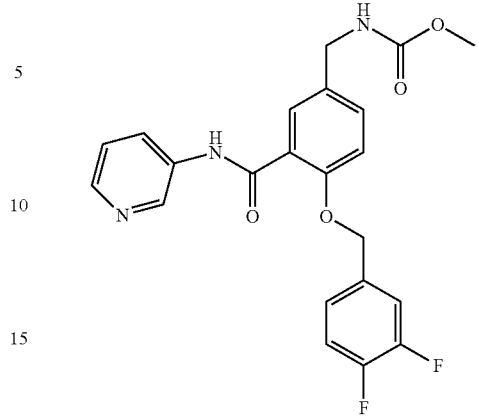

To a suspension of 2-{[(3,4-difluorophenyl)methyl]oxy}-5-[(Z)-(hydroxyimino)methyl]-N-3-pyridinylbenzamide (may be prepared as described in Example 85; 167 mg, 0.42 mmol) in tetrahydrofuran (5 ml) was added 2M aqueous hydrochloric acid (3.60 ml, 119 mmol) followed by zinc (275 mg, 4.20 mmol) at room temperature. After stirring at room temperature for 30 min the mixture was heated to 60° C. for 30 min. On cooling the mixture was treated with saturated sodium hydrogen carbonate (excess).

5-(Aminomethyl)-2-{[(3,4-difluorophenyl)methyl]oxy}-N-3-pyridinylbenzamide (E120A)

An aliquot (10 ml) was extracted with ethyl acetate (4×15 ml). The organics were combined, dried (MgSO$_4$) and evaporated under reduced pressure to give a residue which was purified using MDAP to give 16 mg of 5-(aminomethyl)-2-{[(3,4-difluorophenyl)methyl]oxy}-N-3-pyridinylbenzamide (E120A).

MS (electrospray): m/z [M+H]$^+$=370

$^1$H NMR (400 MHz, METHANOL-d$_4$) 4.14 (2H, s), 5.29 (2H, s), 7.19-7.54 (5H, m), 7.65 (1H, dd, J=8.55, 2.19 Hz), 7.98 (1H, s), 8.11 (1H, d, J=8.11 Hz), 8.28 (1H, d, J=4.60 Hz), 8.49 (1H, br. s.), 8.64 (1H, br. s.)

Methyl ({4-{[(3,4-difluorophenyl)methyl]oxy}-3-[(3-pyridinylamino)carbonyl]phenyl}methyl)carbamate (120B)

Methyl chloroformate (0.39 ml, 5.04 mmol) was added to the remainder of the cooled mixture and the pH adjusted with further NaHCO$_3$ to pH 9-10. The mixture was then stirred at room temperature for 1 hour. The tetrahydrofuran was removed under reduced pressure on a buchi and the aqueous layer was extracted with ethyl acetate (2×30 ml), dried (MgSO$_4$) and evaporated under reduced pressure. The residue was columned using the isolera eluting with 0-10% methanol/dichloromethane/ammonia. The mixture was then purified by MDAP to give 41 mg of methyl ({4-{[(3,4-difluorophenyl)methyl]oxy}-3-[(3-pyridinylamino)carbonyl]phenyl}methyl) carbamate (E120B)

MS (electrospray): m/z [M+H]$^+$=428

$^1$H NMR (400 MHz, METHANOL-d$_4$) 3.65 (3H, 5), 4.28 (2H, s), 5.24 (2H, s), 7.18-7.36 (3H, m), 7.36-7.42 (1H, m), 7.47 (2H, dd, J=8.77, 1.97 Hz), 7.80 (1H, s), 8.06-8.16 (1H, m), 8.26 (1H, d, J=4.60 Hz), 8.59 (1H, br. s.).

Example 121

2-{[(3,4-Difluorophenyl)methyl]oxy}-5-(1-hydroxyethyl)-N-3-pyridinylbenzamide (E121)

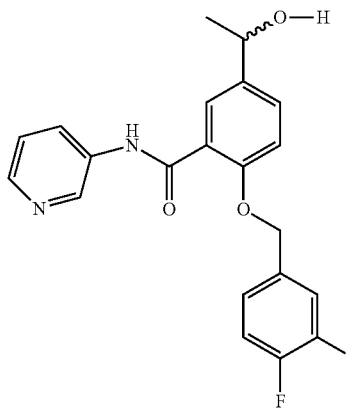

A solution of 2-{[(3,4-difluorophenyl)methyl]oxy}-5-formyl-N-3-pyridinylbenzamide (may be prepared as described in Example 80; 100 mg, 0.27 mmol) in tetrahydrofuran (5 ml) was cooled to 0° C. and methylmagnesium bromide (0.18 ml, 0.54 mmol) was added. The mixture was allowed to warm to room temperature and stirred overnight. An additional 3 eq of methylmagnesium bromide was added and the mixture was stirred at room temperature. 5 ml of 1M aqueous sulphuric acid was then added. After stirring for 30 min the mixture was extracted with ethyl acetate (3×10 ml). The organics were combined, evaporated under reduced pressure and the residue was purified by MDAP to yield the title compound. 48 mg.

MS (electrospray): m/z [M+H]$^+$=428

$^1$H NMR (400 MHz, METHANOL-d$_4$) 1.45 (3H, d, J=6.36 Hz), 4.86 (1H, d, J=6.58 Hz), 5.26 (2H, s), 7.24 (3H, d, J=8.55 Hz), 7.37-7.43 (1H, m), 7.43-7.51 (1H, m), 7.55 (1H, s), 7.90 (1H, d, J=2.19 Hz), 8.06-8.18 (1H, m), 8.26 (1H, dd, J=4.82, 1.32 Hz), 8.59 (1H, d, J=2.19 Hz)

Example 122

5-(2-Amino-4-pyridinyl)-2-[(phenylmethyl)oxy]-N-3-pyridinylbenzamide (E122)

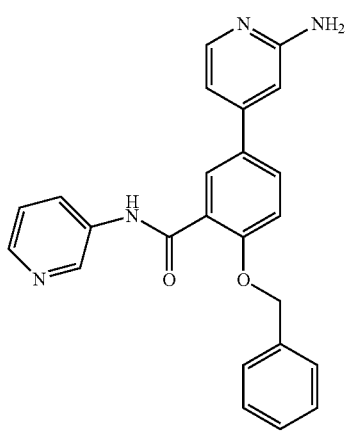 [SMILES: Nc1cc(-c2ccc(OCc3ccccc3)c(C(=O)Nc3cccnc3)c2)ccn1]

To a microwave vial was added 5-bromo-2-[(phenylmethyl)oxy]-N-3-pyridinylbenzamide (may be prepared as described in example 2; 200 mg, 0.52 mmol), 1,4-dioxane (2 ml), 4-(4,4,5,5-tetramethyl-1,3,2-dioxaborolan-2-yl)-2-pyridinamine (201 mg, 0.78 mmol), 1M sodium carbonate (1.04 ml, 1.04 mmol) and tetrakis(triphenylphosphine)palladium (0) (36.2 mg, 0.03 mmol). The vial was sealed and heated to 100° C. for 30 minutes under microwave conditions. The mixture was evaporated in vacuo and the residue was purified using the MDAP to yield the title compound. 41 mg.

MS (electrospray): m/z [M+H]$^+$=382

$^1$H NMR (400 MHz, CHLOROFORM-d) δ ppm 5.32 (2H, s) 7.23 (1H, d, J=4.82 Hz) 7.25-7.32 (1H, m) 7.51-7.61 (7H, m) 7.85 (1H, dd, J=8.55, 2.41 Hz) 7.99 (1H, d, J=2.63 Hz) 8.12-8.19 (1H, m) 8.29 (1H, dd, J=4.71, 1.43 Hz) 8.64-8.73 (3H, m) 10.04 (1H, s)

Example 123

2-{[(4-Fluorophenyl)methyl]oxy}-N-(2-fluoro-3-pyridinyl)-5-(4-morpholinylcarbonyl)benzamide (E123)

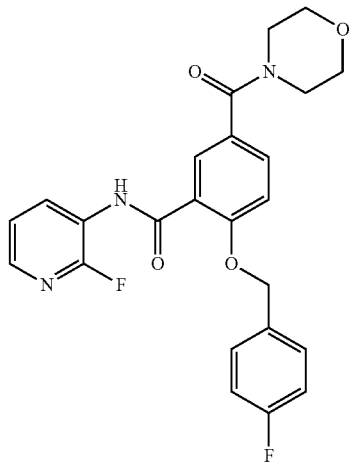 [SMILES: O=C(Nc1cccnc1F)c1cc(C(=O)N2CCOCC2)ccc1OCc1ccc(F)cc1]

To a solution of methyl 2-{[(4-fluorophenyl)methyl]oxy}-5-(4-morpholinylcarbonyl)benzoate (may be prepared as described in Description 109, 93 mg, 0.25 mmol) in tetrahydrofuran (4 ml) was added lithium hydroxide (19 mg, 0.79 mmol) and water (1 ml). The mixture was stirred at 50° C. for one hour, cooled and 2M hydrochloric acid (0.40 ml, 0.80 mmol) was added and the solvent removed in vacuo The residue was redissolved in N,N-dimethylformamide (4 ml) and diisopropylethylamine (0.11 ml, 0.62 mmol), 2-fluoro-3-pyridinamine (36.3 mg, 0.32 mmol) and HATU (284 mg, 0.75 mmol) were added. The solvent was removed in vacuo and the residue purified by MDAP to yield the title compound as an off-white solid. 5 mg.

MS (electrospray): m/z, [M+H]$^+$=454

$^1$H NMR (400 MHz, DMSO-d$_6$); 3.41-3.71 (8H, m), 5.35 (2H, s), 7.23 (3H, t, J=8.91 Hz), 7.33-7.45 (2H, m), 7.52-7.72 (3H, m), 7.86-7.98 (2H, m), 8.61 (1H, br. s.), 10.19 (1H, s).

Example 124

2-{[(4-Fluorophenyl)methyl]oxy}-N-(3-methyl-4-isoxazolyl)-5-(4-morpholinylcarbonyl)benzamide
(E124)

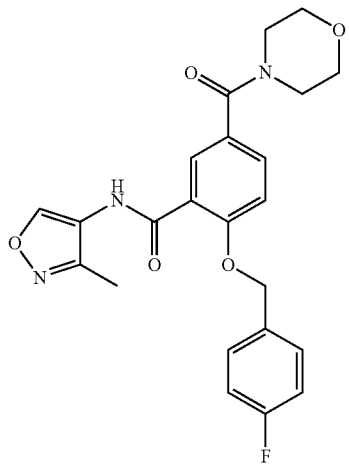 [SMILES: Cc1nocc1NC(=O)c1cc(C(=O)N2CCOCC2)ccc1OCc1ccc(F)cc1]

3-Methyl-4-isoxazolamine hydrochloride (44.9 mg, 0.33 mmol), 1-hydroxy-7-azabenzotriazole (41.7 mg, 0.31 mmol), diisopropylethylamine (0.10 ml, 0.56 mmol) and EDC (80 mg, 0.42 mmol) were added to a solution of 2-{[(4-fluorophenyl)methyl]oxy}-5-(4-morpholinylcarbonyl)benzoic acid (100 mg, 0.28 mmol) in N,N-dimethylformamide (5 ml). The solution was stirred for 18 hours before the solvent was removed in vacuo. The residue purified by column chromatography (silica gel; 10% 7M $NH_3$ in methanol/dichloromethane). Trituration with methanol yielded the title compound as a white solid. 21 mg.

MS (electrospray): m/z, $[M+H]^+$=440

$^1$H NMR (400 MHz, DMSO-$d_6$); 3.61 (8H, br. s.), 5.28 (3H, s), 5.75 (2H, s), 7.25 (2H, t, J=8.78 Hz), 7.38 (1H, d, J=8.78 Hz), 7.52-7.66 (3H, m), 7.79 (1H, d, J=2.26 Hz), 9.15 (1H, s), 9.86 (1H, s).

Example 125

2-{[(2,4-Difluorophenyl)methyl]oxy)-N-(2-fluoro-3-pyridinyl)-5-(4-morpholinylcarbonyl)benzamide
(E125)

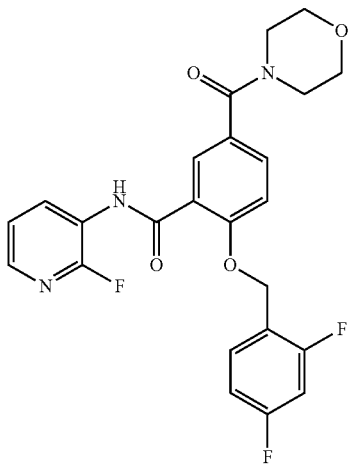 [SMILES: O=C(Nc1cccnc1F)c1cc(C(=O)N2CCOCC2)ccc1OCc1ccc(F)cc1F]

To a solution of methyl 2-([(2,4-difluorophenyl)methyl]oxy}-5-(4-morpholinylcarbonyl)benzoate (may be prepared as described in Description 110, 100 mg, 0.26 mmol) in tetrahydrofuran (THF) (4 ml) was added lithium hydroxide (26 mg, 1.09 mmol) and water (1 ml). The mixture was heated at 50° C. for one hour, cooled and 2M hydrochloric acid (0.54 ml, 1.09 mmol) was added. The solvent removed in vacuo and the residue was redissolved in N,N-dimethylformamide (4 ml). Diisopropylethylamine (0.09 ml, 0.51 mmol), 2-fluoro-3-pyridinamine (34.4 mg, 0.31 mmol) and HATU (243 mg, 0.64 mmol) were added and the mixture stirred overnight. The solvent was removed in vacuo and the residue purified by column chromatography (silicon, 10% methanol/dichloromethane) to give an oil. Purification by MDAP yielded the title compound as an off-white solid. 22 mg.

MS (electrospray): m/z, $[M+H]^+$=472

$^1$H NMR (400 MHz, DMSO-$d_6$); 3.61 (8H, br. s.), 5.40 (2H, s), 7.15 (1H, td, J=8.60, 2.13 Hz), 7.29-7.43 (2H, m), 7.49 (1H, d, J=8.53 Hz), 7.63-7.81 (2H, m), 7.83-8.03 (2H, m), 8.56-8.71 (1H, m), 10.11 (1H, s).

Example 126

2-{[(2,4-Difluorophenyl)methyl]oxy}-N-(3-methyl-4-isoxazolyl)-5-(4-morpholinylcarbonyl)benzamide
(D126)

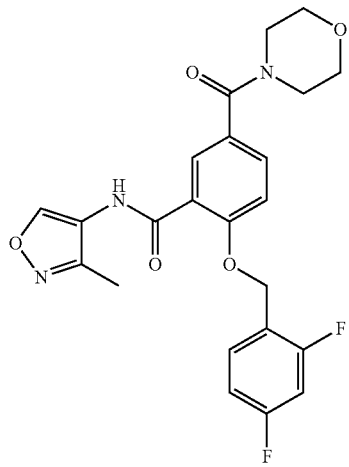 [SMILES: Cc1nocc1NC(=O)c1cc(C(=O)N2CCOCC2)ccc1OCc1ccc(F)cc1F]

To a solution of methyl 2-{[(2,4-difluorophenyl)methyl]oxy}-5-(4-morpholinylcarbonyl)benzoate acid (may be prepared as described in Description 110; 100 mg, 0.26 mmol) in tetrahydrofuran (4 ml) was added lithium hydroxide (26 mg, 109 mmol) and water (1 ml). The mixture was heated at 50° C. for one hour, cooled and 2 M hydrochloric acid (0.54 ml, 1.09 mmol) was added. The solvent was removed in vacuo and the residue was redissolved in N,N-dimethylformamide (5 ml). 3-Methyl-4-isoxazolamine hydrochloride (42.8 mg, 0.32 mmol), 1-hydroxy-7-azabenzotriazole (39.7 mg, 0.29 mmol), diisopropylethylamine (0.09 ml, 0.53 mmol) and EDC (76 mg, 0.40 mmol) were added. The solution was stirred for 18 hours. Water (3 ml) was added and a pale brown solid precipitated which was filtered. Recrystallisation with 1:1 methanol/DMSO yielded the title compound as a white solid. 9.5 mg.

MS (electrospray): m/z, $[M+H]^+$=458

$^1$H NMR (400 MHz, DMSO-$d_6$); 1.86-1.99 (3H, s), 3.41-3.66 (8H, m), 5.29 (2H, s), 7.12 (1H, td, J=8.47, 1.88 Hz), 7.22-7.34 (1H, m), 7.40 (1H, d, J=8.53 Hz), 7.53-7.79 (3H, m), 9.10 (1H, s), 9.78 (1H, s).

Example 127

2-{[(4-Fluorophenyl)methyl]oxy}-5-(4-morpholinylcarbonyl)-N-3-pyridinylbenzamide (E127)

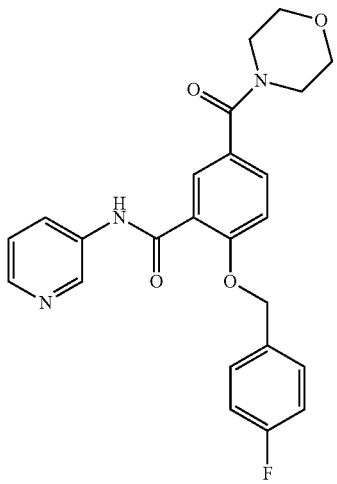 [SMILES: O=C(Nc1cccnc1)c1cc(C(=O)N2CCOCC2)ccc1OCc1ccc(F)cc1]

To a solution of crude 4-{[(4-fluorophenyl)methyl]oxy}-3-[(3-pyridinylamino)carbonyl]benzoic acid (may be prepared as described in Description 111; 62 mg, 0.17 mmol) in N,N-dimethylformamide (DMF) (5 ml) was added morpholine (0.03 ml, 0.34 mmol), EDC (38.9 mg, 0.20 mmol), HOBT (41.5 mg, 0.27 mmol) and N-ethylmorpholine (0.04 ml, 0.34 mmol). The mixture was stirred at room temperature overnight. The mixture was evaporated and the residue was purified by MDAP.

MS (electrospray): m/z [M+H]$^+$=436

$^1$H NMR (400 MHz, METHANOL-d$_4$) δ ppm 3.70 (8H, br. s.) 5.31 (2H, s) 7.09-7.21 (2H, m) 7.32-7.42 (2H, m) 7.58 (2H, dd, J=8.66, 5.37 Hz) 7.65 (1H, dd, J=8.66, 2.30 Hz) 8.00 (1H, d, J=2.19 Hz) 8.02-8.09 (1H, m) 8.25 (1H, d, J=4.17 Hz) 8.51 (1H, d, J=1.53 Hz).

Example 128

2-{[(4-Fluorophenyl)methyl]oxy}-5-{1-[2-(4-morpholinyl)ethyl]-1H-pyrazol-4-yl}-N-3-pyridinylbenzamide (E128)

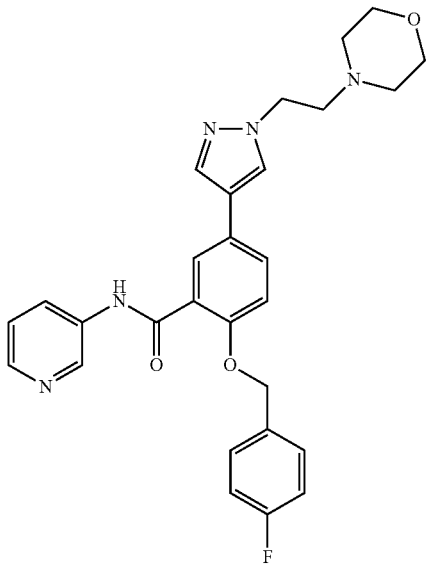 [SMILES: O=C(Nc1cccnc1)c1cc(-c2cnn(CCN3CCOCC3)c2)ccc1OCc1ccc(F)cc1]

3-Pyridinamine (26.5 mg, 0.28 mmol), 1-hydroxy-7-azabenzotriazole (30.7 mg, 0.23 mmol), EDC (43.3 mg, 0.23 mmol) and diisopropylethylamine (0.07 ml, 0.38 mmol) were added to a solution of 2-{[(4-fluorophenyl)methyl]oxy}-5-{1-[2-(4-morpholinyl)ethyl]-1H-pyrazol-4-yl}benzoic acid (may be prepared as described in Description 114; 80 mg, 0.19 mmol) in N,N-dimethylformamide (2 ml), and the reaction was stirred at room temperature overnight. The DMF was removed on a buchi. The residue was taken up into ethyl acetate (50 ml), washed with water (1×25 ml). The ethyl acetate layer was evaporated on a buchi under reduced pressure and the residue was purified using the MDAP to yield the title compound. 45 mg.

MS (electrospray): m/z [M+H]$^+$=502

$^1$H NMR (400 MHz, METHANOL-d$_4$) δ ppm 2.41-2.54 (4H, m) 2.82 (2H, t, J=6.53 Hz) 3.59-3.71 (4H, m) 4.28 (2H, t, J=6.53 Hz) 5.23 (2H, s) 7.07-7.18 (2H, m) 7.25 (1H, d, J=8.78 Hz) 7.34 (1H, dd, J=8.28, 4.77 Hz) 7.56 (2H, dd, J=8.53, 5.52 Hz) 7.68 (1H, dd, J=8.53, 2.26 Hz) 7.80 (1H, s) 7.91-8.04 (2H, m) 8.01-8.13 (1H, m) 8.22 (1H, dd, J=4.89, 1.38 Hz) 8.40-8.55 (1H, m).

Example 129

2-([(4-Fluorophenyl)methyl]oxy)-N-(3-methyl-4-isoxazolyl)-5-{1-[2-(4-morpholinyl)ethyl]-1H-pyrazol-4-yl}benzamide (E129)

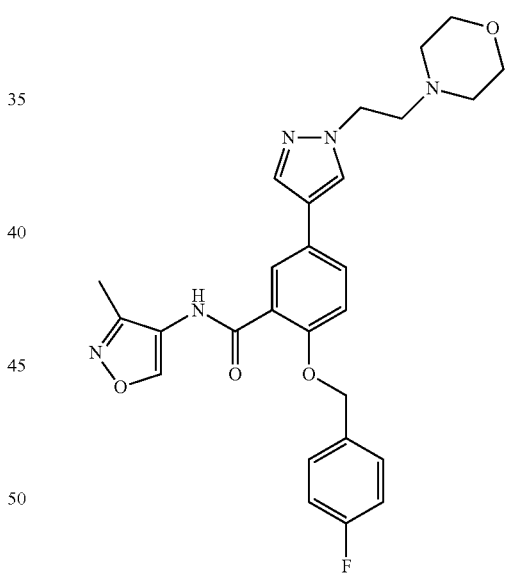

3-Methyl-4-isoxazolamine (38.0 mg, 0.28 mmol), 1-hydroxy-7-azabenzotriazole (30.7 mg, 0.23 mmol), EDC (43.3 mg, 0.23 mmol) and diisopropylethylamine (0.10 ml, 0.56 mmol) were added to a solution of 2-{[(4-fluorophenyl)methyl]oxy}-5-{1-[2-(4-morpholinyl)ethyl]-1H-pyrazol-4-yl}benzoic acid (may be prepared as described in Description 114; 80 mg, 0.19 mmol) in N,N-dimethylformamide (2 ml) and the reaction mixture was stirred at room temperature overnight. The DMF was removed on a buchi. The residue was taken up into ethyl acetate (50 ml) and washed with water (1×25 ml). The ethyl acetate layer was evaporated on a buchi under reduced pressure and the residue was purified using the MDAP. The solid obtained after concentrating the appropriate sample was taken up into ethyl acetate (50 ml) and washed with saturated bicarbonate (10 ml). The organic phase was dried (MgSO₄) and evaporated to yield the title compound as a white solid. 15 mg.

MS (electrospray): m/z [M+H]⁺=506

¹H NMR (400 MHz, CHLOROFORM-d) δ ppm 1.57 (3H, s) 2.47-2.60 (4H, m) 2.87 (2H, t, J=6.65 Hz) 3.66-3.79 (4H, m) 4.29 (2H, t, J=6.65 Hz) 5.20 (2H, s) 7.13-7.23 (3H, m) 7.54 (2H, dd, J=8.53, 5.27 Hz) 7.66 (1H, dd, J=8.53, 2.26 Hz) 7.79 (2H, d, J=13.80 Hz) 8.42 (1H, d, J=2.26 Hz) 9.11 (1H, s)

Example 130

2-{[(4-Fluorophenyl)methyl]oxy}-5-{1-[2-(methyloxy)ethyl]-1H-pyrazol-4-yl}-N-3-pyridinylbenzamide (E130)

3-Pyridinamine (49.0 mg, 0.52 mmol), HATU (148 mg, 0.39 mmol) and diisopropylethylamine (0.11 ml, 0.65 mmol) were added to a solution of methyl 2-{[(4-fluorophenyl)methyl]oxy}-5-{1-[2-(methyloxy)ethyl]-1H-pyrazol-4-yl}benzoate (may be prepared as described in Description 116; 100 mg, 0.26 mmol) in N,N-dimethylformamide (5 ml) and the mixture was stirred at room temperature overnight. The DMF was evaporated under reduced pressure on a buchi. Water (5 ml) and ethyl acetate (10 ml) were added to the residue. The organics were separated and the aqueous layer was further extracted with ethyl acetate (3×10 ml). The organics were combined and evaporated. The residue was purified using MDAP to yield the title compound. 36 mg.

MS (electrospray): m/z [M+H]⁺=447

¹H NMR (400 MHz, METHANOL-d₄) δ ppm 3.33 (3H, s) 3.75 (2H, t, J=5.14 Hz) 4.31 (2H, t, J=5.27 Hz) 5.23 (2H, s) 7.14 (2H, t, J=8.78 Hz) 7.25 (1H, d, J=8.78 Hz) 7.31-7.39 (1H, m) 7.56 (2H, dd, J=8.53, 5.52 Hz) 7.64-7.70 (1H, m) 7.80 (1H, s) 7.95 (2H, s) 8.08 (1H, d, J=2.26 Hz) 8.17-8.29 (1H, m) 8.41-8.55 (1H, m)

Example 131

2-{[(4-Fluorophenyl)methyl]oxy}-N-3-pyridinyl-5-(trifluoromethyl)benzamide (E131)

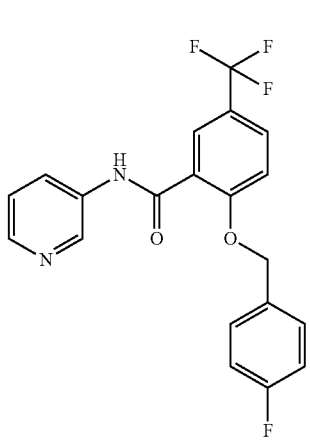 [SMILES: O=C(Nc1cccnc1)c1cc(C(F)(F)F)ccc1OCc1ccc(F)cc1]

EDC (122 mg, 0.64 mmol), 3-pyridinamine (59.9 mg, 0.64 mmol), HOBT (63.4 mg, 0.41 mmol) and diisopropylethylamine (0.11 ml, 0.64 mmol) were added to a solution of 2-{[(4-fluorophenyl)methyl]oxy}-5-(trifluoromethyl)benzoic acid (may be prepared as described in Description 119; 100 mg, 0.32 mmol) in N,N-dimethylformamide (5 ml) and the mixture was stirred at room temperature overnight. The mixture was then heated to 70° C. for 5 hours. The mixture was diluted with water (25 ml) and extracted with ethyl acetate (3×25 ml). The organics were combined, evaporated under reduced pressure on a buchi and the residue was purified using an MDAP to yield the title compound. 85 mg.

MS (electrospray): m/z [M+11]⁺=391

¹H NMR (400 MHz, METHANOL-d₄) δ ppm 5.34 (2H, s) 7.15 (2H, t, J=8.78 Hz) 7.34-7.41 (1H, m) 7.47 (1H, d, J=8.78 Hz) 7.59 (2H, dd, J=8.53, 5.52 Hz) 7.80-7.88 (1H, m) 8.00-8.10 (1H, m) 8.18 (1H, d, J=1.76 Hz) 8.25 (1H, d, J=3.76 Hz) 8.50 (1H, d, J=2.26 Hz)

Example 132

2-{[(4-Fluorophenyl)methyl]oxy}-N-4-pyridazinyl-5-(trifluoromethyl)benzamide

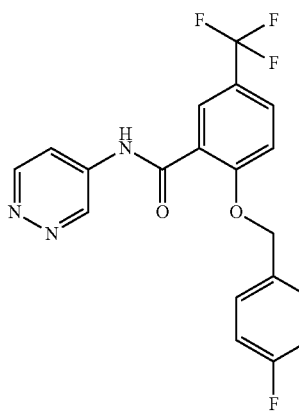

4-Pyridazinamine (60.5 mg, 0.64 mmol), EDC (122 mg, 0.64 mmol), HOBT (63.4 mg, 0.41 mmol) and diisopropylethylamine (0.11 ml, 0.64 mmol) were added to a solution of 2-{[(4-fluorophenyl)methyl]oxy}-5-(trifluoromethyl)benzoic acid (may be prepared as described in Description 119; 100 mg, 0.32 mmol) in N,N-dimethylformamide (20 ml) and the mixture was stirred at room temperature overnight. The mixture was then heated to 70° C. overnight (NOTE: it would be better to prepare the acid chloride and react this with the amine). The mixture was diluted with water (25 ml) and extracted with ethyl acetate (3×25 ml). The organics were combined, evaporated under reduced pressure on a buchi and the residue was purified using an MDAP to yield the title compound. 70 mg.

MS (electrospray): m/z [M+H]⁺=392

¹H NMR (400 MHz, METHANOL-d₄) δ ppm 5.34 (2H, s) 715 (2H, t, J=8.78 Hz) 7.48 (1H, d, J=8.78 Hz) 7.57 (2H, dd, J=8.53, 5.52 Hz) 7.80-7.93 (1H, m) 8.08 (1H, dd, J=5.90, 2.64 Hz) 8.15 (1H, d, J=2.01 Hz) 8.92-9.05 (2H, m)

Example 133

2-{[(4-fluorophenyl)methyl]oxy}-N-(3-methyl-4-isoxazolyl)-5-(trifluoromethyl)benzamide (E133)

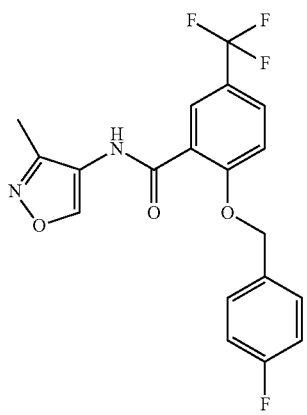 [SMILES: Cc1nocc1NC(=O)c1cc(C(F)(F)F)ccc1OCc1ccc(F)cc1]

To a solution of 2-{[(4-fluorophenyl)methyl]oxy}-5-(trifluoromethyl)benzoic acid (may be prepared as described in Description 119; 100 mg, 0.32 mmol in N,N-dimethylformamide (4 ml) was added EDC (122 mg, 0.64 mmol), HOBT (63.4 mg, 0.41 mmol), 3-methyl-4-isoxazolamine (86 mg, 0.64 mmol), DIPEA (0.22 ml, 1.27 mmol) and the mixture was stirred at room temperature overnight. The mixture was then heated to 70° C. overnight (NOTE: it would be better to prepare the acid chloride and react this with the amine). The mixture was diluted with water (25 ml) and extracted with ethyl acetate (3×25 ml). The organics were combined, evaporated under reduced pressure on a buchi and the residue was purified using an MDAP to yield the title compound. 33 mg.

MS (electrospray): m/z [M+H]⁺=395

¹H NMR (400 MHz, METHANOL-d₄) δ ppm 1.72 (3H, s) 5.34 (2H, s) 7.19 (2H, s) 7.48-7.56 (1H, m) 7.57-7.67 (2H, m) 7.83-7.91 (1H, m) 8.24-8.34 (1H, m) 9.05 (1H, s)

Example 134

2-{[(4-Fluorophenyl)methyl]oxy}-N-4-isoxazolyl-5-(1-methyl-1H-pyrazol-4-yl)benzamide (E134)

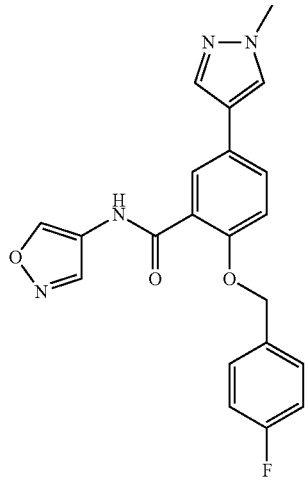 [SMILES: Cn1cc(-c2ccc(OCc3ccc(F)cc3)c(C(=O)Nc3cnoc3)c2)cn1]

A mixture of 2-{[(4-fluorophenyl)methyl]oxy}-5-(1-methyl-1H-pyrazol-4-yl)benzoic acid (may be prepared as described in Description 121; 100 mg, 0.31 mmol), isoxazol-4-amine (38.6 mg, 0.46 mmol), HOBT (70.4 mg, 0.46 mmol) and EDC (88 mg, 0.46 mmol) in N,N-dimethylformamide (5 ml) was stirred at room temperature for 16 hours. Water (50 ml) was added. The mixture was extracted with ethyl acetate (50 ml×3). The combined organic layers were washed with brine (50 ml), dried over Na₂SO₄, and concentrated to give the crude product. The crude product was purified by a prep-HPLC (instrument: Gilson GX-281; Column: Shimadzu PRC-ODS, 15.0 um, 19 mm*250 mm; Mobile Phase: A: 0.05% NH₃H₂O/H₂O; B: CH₃CN; Gradient 0-8 min 42-54% B; 8-12 min 95%; Flow Rate (ml/min) 30.00; Detective Wavelength (nm) 214; Retention Time (min) 7.5) to yield the title compound as a white solid. 17 mg.

¹HNMR (400 MHz, DMSO-d6): 3.85 (3H, s), 5.25 (2H, s), 7.20-7.26 (3H, m), 7.53-7.55 (2H, q), 7.67-7.70 (1H, dd, J=2.4 Hz, J=8.8 Hz), 7.79 (1H, d, J=2.4 Hz), 7.85 (1H, s), 8.13 (1H, s), 8.63 (1H, s), 9.24 (1H, s), 10.49 (1H, s)

MS (electrospray): m/z [M+H]⁺=393.1

Example 135

2-{[(4-Fluorophenyl)methyl]oxy}-N-(5-methyl-4-isoxazolyl)-5-(1-methyl-1H-pyrazol-4-yl)benzamide (E135)

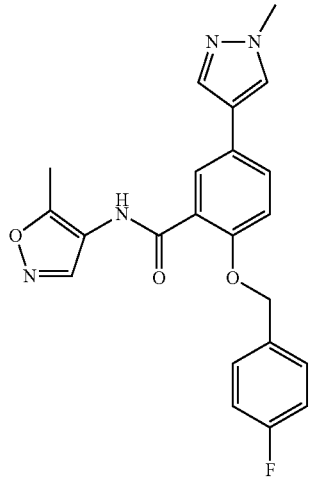 [SMILES: Cc1oncc1NC(=O)c1cc(-c2cnn(C)c2)ccc1OCc1ccc(F)cc1]

A mixture of 2-{[(4-fluorophenyl)methyl]oxy}-5-(1-methyl-1H-pyrazol-4-yl)benzoic acid (may be prepared as described in Description 121; 80 mg, 0.25 mmol), 3-methyl-isoxazol-4-amine (49.5 mg, 0.37 mmol), HOBT (56.3 mg, 0.37 mmol) and EDC (70.5 mg, 0.37 mmol) in N,N-dimethylformamide (2 ml) was stirred at room temperature for 16 hours. Water (50 ml) was added. A white precipitate was filtered, washed with ethyl acetate, and dried in vacuo to yield the title compound as a white solid. 54 mg, ¹HNMR (400 MHz, DMSO-d6): 1.99 (3H, s), 3.86 (3H, s), 5.25 (2H, s), 7.25 (2H, t, J=8.8 Hz), 7.32 (2H, d, J=8.4 HZ), 7.59-7.62 (1H, q, J=2.8, J=8.8), 7.73-7.75 (1H, dd, J=2.4 Hz, J=8.4 Hz), 7.88 (1H, s), 7.92 (1H, d, J=2.4), 8.16 (1H, s), 9.17 (1H, s), 9.88 (1H, s)

MS (electrospray): m/z [M+H]⁺=407.1

Example 136

2-{[(4-Fluorophenyl)methyl]oxy}-5-[3-(4-morpholinyl)propyl]-N-3-pyridinylbenzamide (E136)

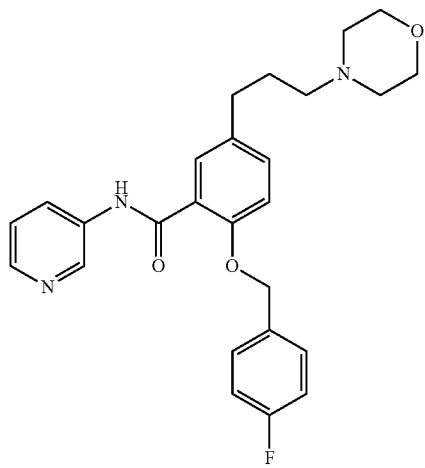 [SMILES: O=C(Nc1cccnc1)c1cc(CCCN2CCOCC2)ccc1OCc1ccc(F)cc1]

To a solution of methyl 2-{[(4-fluorophenyl)methyl]oxy}-5-[3-(4-morpholinyl)propyl]benzoate (may be prepared as described in Description 124; 166 mg, 0.43 mmol) in tetrahydrofuran (6 ml) was added lithium hydroxide (61.6 mg, 2.57 mmol) and water (1.5 ml). The mixture was stirred at 50° C. for 3 hours, cooled and the acidified with 2M hydrochloric acid (1.29 ml, 2.57 mmol). The solvent was removed in vacuo to give a residue. The residue was redissolved in N,N-dimethylformamide (3 ml) and diisopropylethylamine (0.15 ml, 0.86 mmol), 3-aminopyridine (52.4 mg, 0.56 mmol), 1-hydroxy-7-azabenzotriazole (70.0 mg, 0.51 mmol) and EDC (140 mg, 0.73 mmol). The solution was stirred overnight, the solvent removed in vacuo and the residue was purified by MDAP to yield the title compound as a white solid. 25 mg.

MS (electrospray): m/z [M+H]⁺450

¹H NMR (DMSO-d6): 1.72 (2H, quin, J=7.47 Hz), 2.19-2.40 (6H, m), 2.60 (2H, t, J=7.53 Hz), 3.57 (4H, t, J=4.52 Hz), 5.20 (2H, s), 7.09-7.27 (3H, m), 7.31-7.42 (2H, m), 7.49-7.64 (3H, m), 7.97-8.12 (1H, m), 8.27 (1H, dd, J=4.64, 1.38 Hz), 8.66 (1H, d, J=2.26 Hz), 10.29 (1H, s).

Example 137

2-{[(4-Fluorophenyl)methyl]oxy)-5-(1-[2-(4-morpholinyl)ethyl]-1H-pyrazol-4-yl}-N-4-pyridazinyl-benzamide (E137)

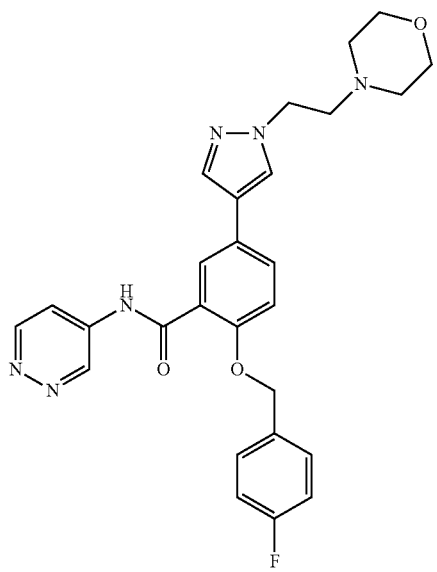 [SMILES: O=C(Nc1ccnnc1)c1cc(-c2cnn(CCN3CCOCC3)c2)ccc1OCc1ccc(F)cc1]

To a solution of 2-{[(4-fluorophenyl)methyl]oxy}-5-{1-[2-(4-morpholinyl)ethyl]-1H-pyrazol-4-yl}benzoic acid (may be prepared as described in Description 114; 220 mg, 0.52 mmol) in N,N-dimethylformamide (10 ml) was added diisopropylethylamine (0.18 ml, 1.03 mmol), 1-hydroxy-7-azabenzotriazole (84 mg, 0.62 mmol), 4-pyridazinamine (59.0 mg, 0.62 mmol) and EDC (149 mg, 0.78 mmol). The solution was stirred for 3 hours, then N,N-dimethylformamide was removed in vacuo and redissolved in ethyl acetate (10 ml). The solution was washed with water (3×10 ml), dried (MgSO₄) and the solvent removed in vacuo. Trituration with 1:1 methanol/dimethyl sulfoxide gave the product as a brown solid (12 mg, 5% yield). The filtrate was purified by MDAP to give a brown solid which was partitioned between NaHCO₃ solution (5 ml) and ethyl acetate (10 ml). The organic layer was dried (MgSO₄) and the solvent removed in vacuo to give an oil which was lyophilised to give a white solid. This was combined with the previous crop to yield the title compound as a white solid. 27 mg.

MS (electrospray): m/z [M-1-H]⁺ 503

¹H NMR (DMSO-d6): 2.33-2.44 (4H, m), 2.73 (2H, t, J=6.65 Hz), 3.49-3.63 (4H, m), 4.23 (2H, t, J=6.53 Hz), 5.23 (2H, s), 7.12-7.26 (2H, m), 7.30 (1H, d, J=8.78 Hz), 7.55 (2H, dd, J=8.41, 5.65 Hz), 7.74 (1H, dd, J=8.66, 2.38 Hz), 7.81 (1H, d, J=2.26 Hz), 7.88 (1H, s), 8.02 (1H, dd, J=5.77, 2.76 Hz), 8.21 (1H, s), 9.06 (1H, d, J=5.77 Hz), 9.27 (1H, d, J=2.01 Hz), 10.80 (1H, s).

Biological Data

Production of 6His-Tev-LRRK2 (1326-2527)

A LRRK2 cDNA encoding residues 1326-2527 was received from Dundee University (described in M. Jaleel et al., 2007, Biochem J, 405: 407-417). This gene fragment was subcloned into pFB-HTb (Invitrogen) using BamHI and NotI restriction sites. The LRRK2 plasmid was recombined into the baculovirus genome according to the BAC-to-BAC protocol described by Invitrogen. Transfection into *Spodoptera frugiperda* (Sf9) insect cells was performed using Cellfectin (Invitrogen), according to the manufacturer's protocol.

Sf9 cells were grown in Excell 420 (SAFC Biosciences) growth media at 27° C., 80 rpm in shake flask until of a sufficient volume to inoculate a bioreactor. The cells were grown in a 100 liter working volume bioreactor (Applikon) at 27° C., 40% dissolved oxygen and an agitation rate of 60-150 rpm until the required volume was achieved with a cell concentration of approximately 4×e6 cells/ml. The insect cells were infected with Baculovirus at a multiplicity of infection (MOI) of 3. The cultivation was continued for a 48 hour expression phase. The infected cells were removed from the growth media by centrifugation at 2500 g using a Viafuge (Carr) continuous centrifuge at a flow rate of 80 liters/hour. The cell pellet was immediately frozen and subsequently supplied for purification.

A 100 g pellet was allowed to thaw in a water bath at 27° C. with 200 ml lysis buffer/buffer A (50 mm Tris-HCl pH8.5, 300 mm NaCl, 1 mm DTT, 10% glycerol, 1 ml/L calbiochem complete protease inhibitor cocktail and benzonase (20 ul/300 ml)) before being dounce homogenised on ice using 20 strokes per 100 ml. The suspension was then centrifuged at 100,000 g for 90 min, at 4° C.

The lysate was decanted from the insoluble pellet and loaded (at 1.5 ml/min over one cycle volume) onto 5 ml hisHP column that had been pre-equilibrated with 10 column volumes buffer A. The column was then washed with 10 column volumes buffer A, 10 column volumes buffer B (buffer A+1M NaCl) and 10 column volumes buffer C (buffer A+20 mm imidazole). The column was then eluted with 15 column volumes buffer D (buffer A+300 mm imidazole) collecting 2.5 ml fractions. All washes and elution were conducted at 2.5 ml/min.

Fractions identified by SDS-PAGE as containing protein of interest were pooled and loaded directly onto a 320 ml SEC Superdex 200 pg column that was pre-equilibrated with buffer E (50 mM Tris-HCl pH8.5, 300 mM NaCl, 10% glycerol, 1 mM DTT). The column was loaded and eluted with 1.2 column volumes buffer E at 3 ml/min collecting 2 ml fractions.

Fractions identified by SDS-PAGE as containing protein of interest were tested for activity.

Production of Biotin-LRRKtide

The peptide (biotin-RLGRDKYKTLRQIRQGNTKQR-OH) was assembled at a 0.2 mM scale using FMOC solid phase peptide synthesis on an ACT 357 MPS automated peptide synthesizer. The resulting crude peptide was cleaved from the resin using a 95:2.5:2.5 mix of trifluoroacetic acid: triisopropylsilane:water. The crude cleaved peptide was purified by reverse phase HPLC, eluting with a 5-35% gradient of 0.1% trifluoroacetic acid/acetonitrile in 0.1% trifluoroacetic acid/water.

Production of GST-PS-Moesin (400-577)

A fragment of human moesin (400-577) was amplified by PCR using a full length cDNA clone encoding human moesin (described in M. Jaleel et al., 2007, Biochem J, 405: 407-417) as a template. The fragment was subcloned into pGEX6P1 (Amersham) using BamHI and XhoI restriction sites. The moesin plasmid was transformed into BL21*(DE3) competent cells (Invitrogen) for expression.

The transformed cells were cultured in LB medium (10 g/L tryptone, 5 g/L yeast extract, 10 g/L NaCl) at 37° C. Once the culture had reached an optical density (600 nm) of 0.5, it was induced with 0.1 mM IPTG and cultured at 30° C. for 20 h. The cells were then collected by centrifugation at 4,400 rpm in for 20 mins at 4° C. and the cell pellets were stored at −80° C.

70 g of cell pellet was thawed at room temperature in 280 ml pre-chilled lysis buffer (50 mM Tris-HCl pH 7.5, 1% Triton X-100, 0.27 M Sucrose, 5 mM beta-mercaptoethanol, 1 ml/L Calbiochem complete protease inhibitor cocktail, 500 mM NaCl, 1 mM Sodium orthovanadate, 10 mM sodium 2-glycerophosphate, 50 mM NaF, 5 mM Sodium pyrophosphate, 0.1 mg/L Lysozyme, 0.1 ml/L) for 30 minutes with constant stirring. The suspension was then sonicated in a pyrex beaker in an ice-water bath at 40% amplitude for 5 minutes, using a pulse of 9.9 sec on/9.9 sec off. Following sonication, the lysate was clarified by centrifugation at 100,000 g for 60 min.

Four 5 ml GST-HP columns were connected in series and were pre-equilibrated with 10 column volumes Buffer F (50 mM Tris/HCl pH 7.5, 0.27 M Sucrose, 5 mM beta-mercaptoethanol, 1 ml/L calbiochem complete protease inhibitor, 500 mM NaCl). The clarified lysate was loaded onto the column at 1 ml/min. The non absorbed fraction was retained. The column was then washed with 10 column volumes Buffer F at 3 ml/min (the non-absorbed fraction was retained). The column was then eluted at 2 ml/min using Buffer G (Buffer F plus 20 mM reduced glutathione) collecting 10 ml fractions. Fractions containing protein of interest were identified using SDS-PAGE and pooled.

A 500 ml SEC Superdex 200 pg column was pre-equilibrated in Buffer H (50 mM Tris-HCl pH 6.4, 0.27 M Sucrose, 5 mM Beta-mercaptoethanol. 150 mM NaCl). The pooled fractions were loaded onto the column at 2 ml/min. The column was then eluted over 1.2 column volumes Buffer H at 2 ml/min, collecting 2 ml fractions. Fractions containing protein of interest were identified by SDS-PAGE and pooled and tested for activity.

Compounds of formula (I) may be tested for in vitro kinase activity in accordance with the following assays, using the non natural, in vitro, substrates moesin and the Longer Biotin-LRRKtide. Moesin and a shorter version of the peptide were identified as substrates in Jaleel et al, (2007, Biochem J, 405: 307-317).

LRRK2 Peptide Substrate Assay a) 100 nl of a 1:4 serial dilution of test compound with a top final assay concentration of 30 μM is added to certain wells in a low volume 384 well black plate. 100 nl of DMSO is used in certain wells as controls.

b) 3 μl enzyme solution (80 nM purified recombinant 6His-Tev-LRRK2 (1326-2527) in assay buffer: 50 mM Hepes (pH 7.2), 10 mM $MgCl_2$, 150 mM NaCl, 5% glycerol, 0.0025% triton X-100 and 1 mM DTT) is added to certain wells. 3 μl assay buffer is added to certain wells as a 100% inhibition (no enzyme) control.

c) After incubation at room temperature for 30 minutes, 3 μl substrate solution (2 μM Biotin-LRRKtide peptide substrate and ATP at $K_m$ in assay buffer) is added to each well. Plates are then incubated for a further 1-2 hours at room temperature (incubation time varies depending upon rate and linearity of reaction with differing enzyme batches).

d) 6 μl detection solution (50 nM Streptavidin SureLight® APC (PerkinElmer), 4 nM Eu-W1024 labelled anti-rabbit IgG antibody (PerkinElmer), 1:500 dilution (dilution determined on a batch to batch basis) of Phospho-Ezrin (Thr567)/Radixin (Thr564)/Moesin (Thr558) Polyclonal Antibody (New England Biolabs) and 60 mM EDTA in buffer: 40 mM Hepes (pH 7.2), 150 mM NaCl, 0.03% BSA) is added to each well. Plates are then incubated for a further 2 hours at room temperature before reading on a suitable plate reader (Excitation 330 nm, emission 620 nm (Eu) and 665 nm (APC)). Data is analysed using ActivityBase software (IDBS).

LRRK2 AlphaScreen Protein Substrate Assay a) 100 nl of a 1:4 serial dilution of test compound with a top final assay concentration of 30 μM is added to certain wells in a low volume 384 well black plate. 100 nl of DMSO is used in certain wells as controls.

b) 3 μl enzyme solution (80 nM purified recombinant 6His-Tev-LRRK2 (1326-2527) in assay buffer: 50 mM Hepes (pH 7.2), 10 mM $MgCl_2$, 150 mM NaCl, 5% glycerol, 0.0025% triton X-100 and 1 mM DTT) is added to certain wells. 3 μl assay buffer is added to certain wells as a 100% inhibition (no enzyme) control.

c) After incubation at room temperature for 30 minutes, 3 μl substrate solution (200 nM GST-PS-Moesin (400-577) and ATP at $K_m$ in assay buffer) is added to each well. Plates are then incubated for a further 1-2 hours at room temperature (incubation time varies depending upon rate and linearity of reaction with differing enzyme batches).

d) 6 μl detection solution (1:250 dilution of AlphaLisa Protein A Acceptor beads (PerkinElmer), 1:64 dilution of AlphaLisa Gluthathione Donor beads (PerkinElmer) and 1:600 dilution (dilution determined on a batch to batch basis) of Phospho-Ezrin (Thr567)/Radixin (Thr564)/Moesin (Thr558) Polyclonal Antibody (New England Biolabs) in a buffer: 50 mM Hepes (pH 7.5), 250 mM NaCl, 60 mM EDTA, 1% PEG and 0.01% Brij 35) is added to each well. Plates are then incubated for a further 2 hours at room temperature in the dark before reading on an EnVision™ plate reader with AlphaScreen HTS turbo option module and AlphaScreen settings. Data is analysed using ActivityBase software (IDBS).

LRRK2 AlphaScreen Desensitised Protein Substrate Assay

This is conducted as described for the LRRK2 alphascreen protein substrate assay, with the following differences:
1. The concentration of ATP in the substrate solution was 2 mM.
2. The plates were incubated for 20 minutes at room temperature following addition of the substrate solution.

Pharmacological Data

The compounds of examples 1-28, 28A, 28B, 29-51, 53, 57-61, 63, 65, 69-71, 73-76, 86-119, 122-130 and 132-137 were tested in the LRRK2 peptide substrate assay and exhibited a pIC50≥5.6. More particularly, the compounds of examples 1-16, 26, 28, 28A, 29-33, 37-38, 44-49, 51, 57-61, 63, 69-71, 73-76, 86-110, 112, 113, 115-119, 122, 123, 125, 127-131 and 134-136 were tested in the LRRK2 peptide substrate assay and exhibited a pIC50≥7.0. Most particularly, the compounds of examples 32, 44-45, 47, 49, 58-59, 61, 73-76, 86-87, 89-93, 97, 99-101, 103-104, 107, 116, 118, 128 and 130 were tested in the LRRK2 peptide substrate assay and exhibited a pIC50≥8.0. The compounds of examples 1-21, 23-28 and 29-33 were tested in the LRRK2 alphascreen protein substrate assay and exhibited a pIC50≥5.1. More particularly, the compounds of examples 1-15, 26 and 28-33 were tested in the LRRK2 alphascreen protein substrate assay and exhibited a pIC50≥7.0.

The compound of example 22 was tested in the LRRK2 alphascreen protein substrate assay and exhibited a pIC50<4.6.

The compounds of examples 1-6, 8-10, 12, 14, 16, 21, 23, 28, 28A, 28B, 29-33, 35-39, 44-51, 54, 58, 61, 63-65, 69-71, 73-76, 86, 87, 89-97, 99-101, 103-119, 122, 123, 125-128, 130-132, 134 and 136 were tested in the LRRK2 alphascreen desensitised protein substrate assay and exhibited a pIC50≥4.7 (excess of ATP present). More particularly, the compounds of examples 91, 93, 97, 99-101, 104, 116 and 130 were tested in the LRRK2 alphascreen desensitised protein substrate assay and exhibited a pIC50 z 7.0 (excess of ATP present).

The compounds of examples 7, 11, 13, 15, 17-20, 22, 24, 27, 34, 40-43, 52, 53, 55-57, 59-60, 62, 88, 98, 102, 120A, 120B, 124, 129 and 133 were tested in the LRRK2 alphascreen desensitised protein substrate assay and exhibited a pIC50<4.6 (excess of ATP present).

The compounds of examples 38, 69, 93, 94, 117, 123, 127, 128, 129, 130, 131 and 136 were tested in the LRRK2 peptide substrate assay and in the LRRK2 alphascreen desensitised protein substrate assay. Mean pIC50 values for each compound are indicated in the attached table:

| Example Number | LRRK2 peptide substrate assay (pIC50) | LRRK2 alphascreen desensitised protein substrate assay (pIC50) |
|---|---|---|
| 38 | 7.1 | 5.1 |
| 69 | 7.8 | 6.3 |
| 93 | 8.2 | 6.6 |
| 94 | 7.9 | 7.0 |
| 117 | 7.7 | 6.1 |
| 123 | 7.4 | 5.6 |
| 127 | 7.2 | 5.0 |
| 128 | 8.1 | 6.9 |
| 129 | 7.9 | <4.6 |
| 130 | 8.5 | 7.5 |
| 131 | 7.4 | 6.3 |
| 136 | 7.0 | 6.4 |

The invention claimed is:
1. A compound of formula (I) or a salt thereof

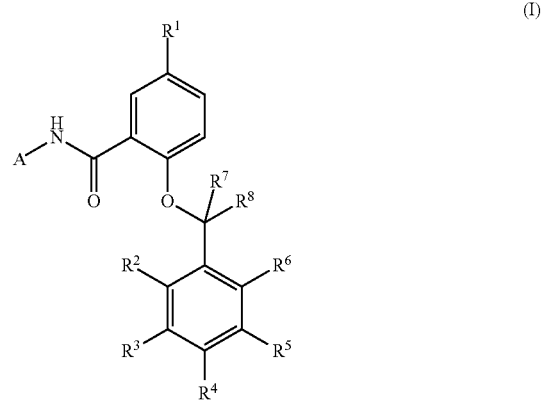

(I)

wherein
A represents pyridin-2-yl, pyridin-3-yl, pyridazin-3-yl, pyridazin-4-yl, pyrimidin-5-yl, 1,3-oxazol-2-yl, 1H-pyrazol-4-yl or isoxazol-4-yl or a group of formula (a) wherein * represents the point of attachment:

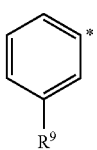

(a)

wherein when A represents pyridin-3-yl, the pyridinyl ring may optionally be substituted at the 2 position by fluoro, methoxy or $CH_2OH$, at the 4 position by methyl or $CH_2OH$, or at the 5 position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl;

$R^1$ represents halo, halo$C_{1-3}$alkyl, hydroxy, CN, —O(CH_2)_2O(CH_2)_2NH_2, —CNOH, $(O)_n(CH_2)_pR^{10}$, —(CO)$R^{16}$, $R^{13}$, —(SO_2)$R_{13}$, ($C_{1-3}$alkylene)(CO)$_q$$R^{14}$, (CH=CH)(CO)$R^{14}$, ($C_{1-3}$alkylene)NHCOR$^{14}$, —O-nitrogen containing monoheterocyclic ring with the proviso that the atom directly attached to the oxygen is not nitrogen, or a nitrogen containing heteroaryl ring, wherein the nitrogen containing monoheterocyclic ring is optionally substituted with one, two or three methyl groups and wherein the nitrogen containing heteroaryl ring is optionally substituted by one two or three groups selected from $NH_2$, $(C_{1-3}$ alkylene)$R^{13}$, $(C_{1-3}$alkylene)$(CO)_qR^{14}$, $C_{1-3}$alkyl and halo;

n and q independently represent 0 or 1;

p represents 1, 2 or 3;

$R^2$, $R^3$, $R^4$, $R^5$ and $R^6$ independently represent hydrogen, halo, CN, $C_{1-3}$alkyl or $C_{1-3}$alkoxy;

$R^7$ and $R^8$ independently represent hydrogen or $C_{1-2}$ alkyl;

$R^9$ represents halo, $C^{1-2}$alkyl, $C^{1-2}$alkoxy, —$CH_2CO_2H$ or —$CONHCH_3$;

$R^{10}$ represents hydrogen, $C_{1-3}$alkyl, —$NR^{11}R^{12}$, or a nitrogen containing monoheterocyclic ring which ring is optionally substituted with one, two or three methyl groups;

$R^{11}$ and $R^{12}$ are independently selected from hydrogen and $C_{1-3}$ alkyl, wherein said $C_{1-3}$ alkyl group is optionally substituted with one, two or three halo, hydroxy, cyano or $C_{1-2}$alkoxy groups;

$R^{13}$ represents —$NR^{11}R^{12}$, or a nitrogen containing monoheterocyclic ring which ring is optionally substituted with one, two or three methyl groups and wherein the nitrogen containing monoheterocyclic ring is attached via a nitrogen atom; and $R^{14}$ represents hydroxy or $C_{1-3}$alkoxy;

with the proviso that the compound of formula (I) is not:
2-[(phenylmethyl)oxy]-N-3-pyridinyl-5-(1-pyrrolidinylsulfonyl)benzamide;
2-{[(3,4-difluorophenyl)methyl]oxy}-5-(1-hydroxyethyl)-N-4-pyridazinylbenzamide;
5-bromo-2-(2-chlorobenzyloxy)-N-(pyridin-3-yl)benzamide;
5-chloro-2-[(phenylmethyl)oxy]-N-3-pyridinylbenzamide;
5-bromo-N-{3-[(methylamino)carbonyl]phenyl}-2-[(phenylmethyl)oxy]benzamide; or
5-chloro-2-[(2-cyanophenyl)methoxy]-N-phenylbenzamide.

2. A compound or formula (I) or a salt thereof according to claim 1, wherein $R^1$ represents —$(O)_n(CH_2)_pR^{10}$ or —$(CO)R^{10}$ wherein $R^{10}$ represents hydrogen, $C_{1-3}$alkyl, —$NR^{11}R^{12}$, or a nitrogen containing monoheterocyclic ring which ring is optionally substituted with one, two or three methyl groups and wherein n represents 0 or 1 and wherein p represents 1, 2 or 3.

3. A compound of formula (I) or a salt thereof according to claim 1, wherein one or two of $R^2$, $R^3$, $R^4$, $R^5$ and $R^6$ represent fluoro and the remaining groups represent hydrogen.

4. A compound of formula (I) or a salt thereof according to claim 1, wherein $R^2$, $R^3$, $R^5$ and $R^6$ each represent hydrogen and $R^4$ represents fluoro.

5. A compound of formula (I) or a salt thereof according to claim 1, wherein $R^7$ and $R^8$ each represent hydrogen.

6. A compound of formula (I) or a salt thereof according to claim 1, wherein A represents pyridin-3-yl, wherein the pyridinyl ring may optionally be substituted at the 2 position by fluoro, pyridazin-4-yl, 1H-pyrazol-4-yl, wherein the pyrazolyl ring may optionally be substituted at the 1 position by methyl, or isoxazol-4-yl, wherein the isoxazolyl ring may optionally be substituted at the 3 position by methyl or at the 5 position by methyl.

7. A compound of formula (I) or a salt thereof according to claim 1, wherein:
A represents pyridin-3-yl, pyridazin-4-yl, 1H-pyrazol-4-yl or isoxazol-4-yl, wherein when A represents pyridin-3-yl, the pyridinyl ring may optionally be substituted at the 2 position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl;

$R^1$ represents —$(O)_n(CH_2)_pR^{10}$, —$(CO)R^{10}$, $R^{13}$, —$(SO_2)R^{13}$ or a nitrogen containing heteroaryl ring which nitrogen containing heteroaryl ring is optionally substituted by one, two or three groups selected from $NH_2$, $(C_{1-3}$ alkylene)$R^{13}$, $(C_{1-3}$alkylene)$(CO)_qR^{14}$, $C_{1-3}$alkyl and halo;

$R^2$, $R^3$, $R^4$, $R^5$, $R^6$ independently represent hydrogen or fluoro;

$R^7$ and $R^8$ represent hydrogen;

$R^{10}$ represents hydrogen, $C_{1-3}$alkyl, —$NR^{11}R^{12}$, or a nitrogen containing monoheterocyclic ring which ring is optionally substituted with one, two or three methyl groups;

$R^{11}$ and $R^{12}$ independently represent hydrogen or $C_{1-3}$ alkyl;

$R^{13}$ represents —$NR^{11}R^{12}$, or a nitrogen containing monoheterocyclic ring which ring is optionally substituted with one, two or three methyl groups and wherein the nitrogen containing monoheterocyclic ring is attached via a nitrogen atom;

$R^{14}$ represents hydroxy or $C_{1-3}$alkoxy; and n and q independently represent 0 or 1 and p represents 1, 2 or 3;

with the proviso that the compound of formula (I) is not 2-[(phenylmethyl)oxy]-N-3-pyridinyl-5-(1-pyrrolidinylsulfonyl)benzamide.

8. A compound of formula (I) or a salt thereof according to claim 1, which is a compound of examples 1 to 137 or a salt thereof.

9. A pharmaceutical composition which comprises the compound of formula (I) as defined in claim 1 or a pharmaceutically acceptable salt thereof and a pharmaceutically acceptable carrier or excipient.

10. A method of treatment of Parkinson's Disease which comprises administering to a host in need thereof an effective amount of a compound of formula (I) or a pharmaceutically acceptable salt thereof, wherein formula (I) is

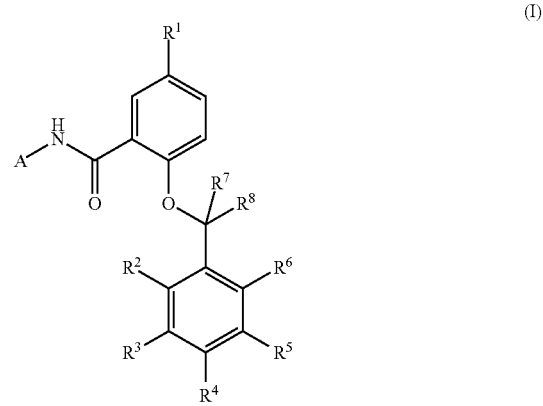

wherein:
A represents pyridin-2-yl, pyridin-3-yl, pyridazin-3-yl, pyridazin-4-yl, pyrimidin-5-yl, 1,3-oxazol-2-yl, 1H-pyrazol-4-yl or isoxazol-4-yl or a group of formula (a) wherein * represents the point of attachment:

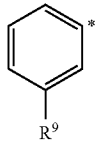

(a)

wherein when A represents pyridin-3-yl, the pyridinyl ring may optionally be substituted at the 2 position by fluoro, methoxy or $CH_2OH$, at the 4 position by methyl or $CH_2OH$, or at the 5 position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl;
$R^1$ represents halo, halo$C_{1-3}$alkyl, hydroxy, CN, —O(CH$_2$)$_2$O(CH$_2$)$_2$NH$_2$, —CNOH, (O)$_n$(C$t_2$)$_p$R$^{10}$, —(CO)R$^{10}$, R$^{13}$, —(SO$_2$)R$^{13}$, (C$_{1-3}$alkylene)(CO)$_q$R$^{14}$, (CH=CH)(CO)R$^{14}$, (C$_{1-3}$alkylene)NHCOR$^{14}$, —O-nitrogen containing monoheterocyclic ring with the proviso that the atom directly attached to the oxygen is not nitrogen, or a nitrogen containing heteroaryl ring, wherein the nitrogen containing monoheterocyclic ring is optionally substituted with one, two or three methyl groups and wherein the nitrogen containing heteroaryl ring is optionally substituted by one two or three groups selected from NH$_2$, (C$_{1-3}$ alkylene)R$^{13}$, (C$_{1-3}$alkylene)(CO)$_q$R$^{14}$, C$_{1-3}$alkyl and halo;
n and q independently represent 0 or 1;
p represents 1, 2 or 3;
$R^2, R^3, R^4, R^5$ and $R^6$ independently represent hydrogen, halo, CN, C$_{1-3}$alkyl or C$_{1-3}$alkoxy;
$R^7$ and $R^8$ independently represent hydrogen or C$_{1-2}$ alkyl;
$R^9$ represents hydrogen, halo, C$_{1-2}$alkyl, C$_{1-2}$alkoxy, —CH$_2$CO$_2$H or —CONHCH$_3$;
$R^{10}$ represents hydrogen, C$_{1-3}$alkyl, —NR$^{11}$R$^{12}$, or a nitrogen containing monoheterocyclic ring which ring is optionally substituted with one, two or three methyl groups;
$R^{11}$ and $R^{12}$ are independently selected from hydrogen and C$_{1-3}$alkyl, wherein said C$_{1-2}$ alkyl group is optionally substituted with one, two or three halo, hydroxy, cyano or C$_{1-2}$alkoxy groups;
$R^{13}$ represents —NR$^{11}$R$^{12}$, or a nitrogen containing monoheterocyclic ring which ring is optionally substituted with one, two or three methyl groups and wherein the nitrogen containing monoheterocyclic ring is attached via a nitrogen atom; and
$R^{14}$ represents hydroxy or C$_{1-3}$alkoxy;
with the proviso that the compound of formula (I) is not:
2-[(phenylmethyl)oxy]-N-3-pyridinyl-5-(1-pyrrolidinylsulfonyl)benzamide;
2-{[(3,4-difluorophenyl)methyl]oxy}-5-(1-hydroxyethyl)-N-4-pyridazinylbenzamide;
5-bromo-2-(2-chlorobenzyloxy)-N-(pyridin-3-yl)benzamide;
5-chloro-2-[(phenylmethyl)oxy]-N-3-pyridinylbenzamide;
5-bromo-N-{3-[(methylamino)carbonyl]phenyl}-2-[(phenylmethyl)oxy]benzamide; or
5-chloro-2-[(2-cyanophenyl)methoxy]-N-phenylbenzamide.

11. A method of treatment of Parkinson's Disease according to claim 10, wherein the host is human.

12. A method of treatment of Parkinson's Disease which comprises administering to a host in need thereof an effective amount of a compound of formula (I) defined below or a pharmaceutically acceptable salt thereof,

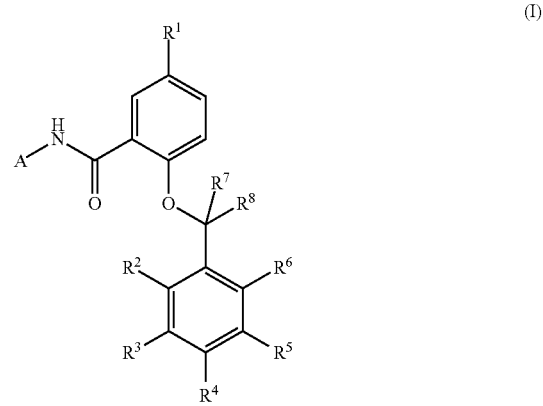

(I)

wherein:
A represents pyridin-2-yl, pyridin-3-yl, pyridazin-3-yl, pyridazin-4-yl, pyrimidin-5-yl, 1,3-oxazol-2-yl, 1H-pyrazol-4-yl or isoxazol-4-yl or a group of formula (a) wherein * represents the point of attachment:

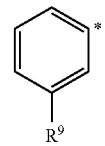

(a)

wherein when A represents pyridin-3-yl, the pyridinyl ring may optionally be substituted at the 2 position by fluoro, methoxy or $CH_2OH$, at the 4 position by methyl or $CH_2OH$, or at the 5 position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl;
$R^1$ represents halo, halo$C_{1-3}$alkyl, hydroxy, CN, —O(CH$_2$)$_2$O(CH$_2$)$_2$NH$_2$, —CNOH, (O)$_n$(CH$_2$)$_p$R$^{10}$, —(CO)R$^{10}$, R$^{13}$, —(SO$_2$)R$^{13}$, (C$_{1-3}$alkylene)(CO)$_q$R$^{14}$, (CH=CH)(CO)R$^{14}$, (C$_{1-3}$alkylene)NHCOR$^{14}$, —O-nitrogen containing monoheterocyclic ring with the proviso that the atom directly attached to the oxygen is not nitrogen, or a nitrogen containing heteroaryl ring, wherein the nitrogen containing monoheterocyclic ring is optionally substituted with one, two or three methyl groups and wherein the nitrogen containing heteroaryl ring is optionally substituted by one two or three groups selected from NH$_2$, (C$_{1-3}$ alkylene)R$^{13}$, (C$_{1-3}$alkylene)(CO)$_q$R$_{14}$, C$_{1-3}$alkyl and halo;
n and q independently represent 0 or 1;
p represents 1, 2 or 3;
$R^2, R^3, R^4, R^5$ and $R^6$ independently represent hydrogen, halo, CN, C$_{1-3}$alkyl or C$_{1-3}$alkoxy;
$R^7$ and $R^8$ independently represent hydrogen or $C_{1-2}$alkyl;

$R^9$ represents hydrogen, halo, $C_{1-2}$alkyl, $C_{1-2}$alkoxy, —$CH_2CO_2H$ or —$CONHCH_3$;

$R^{10}$ represents hydrogen, $C_{1-3}$alkyl, —$NR^{11}R^{12}$, or a nitrogen containing monoheterocyclic ring which ring is optionally substituted with one, two or three methyl groups;

$R^{11}$ and $R^{12}$ are independently selected from hydrogen and $C_{1-3}$alkyl, wherein said $C_{1-3}$alkyl group is optionally substituted with one, two or three halo, hydroxy, cyano or $C_{1-2}$alkoxy groups;

$R^{13}$ represents —$NR^{11}R^{12}$, or a nitrogen containing monoheterocyclic ring which ring is optionally substituted with one, two or three methyl groups and wherein the nitrogen containing monoheterocyclic ring is attached via a nitrogen atom; and $R^{14}$ represents hydroxy or $C_{1-3}$alkoxy;

with the proviso that the compound of formula (I) is not:

2-[(phenylmethyl)oxy]-N-3-pyridinyl-5-(1-pyrrolidinylsulfonyl)benzamide; or

2-{[(3,4-difluorophenyl)methyl]oxy}-5-(1-hydroxyethyl)-N-4-pyridazinylbenzamide.

13. A pharmaceutical composition for use in the treatment or prophylaxis of Parkinson's disease which comprises the compound of formula (I) as defined in claim 12 or a pharmaceutically acceptable salt thereof and a pharmaceutically acceptable carrier.

* * * * *